US010954536B2

(12) United States Patent
Jendresen et al.

(10) Patent No.: US 10,954,536 B2
(45) Date of Patent: Mar. 23, 2021

(54) MODIFIED *ESCHERICHIA COLI* HAVING AN INCREASED EXPRESSION OF A CYSP TRANSPORTER, AN ATP SULFURYLASE, AN APS KINASE AND A PAP PHOSPHATASE

(71) Applicant: CysBio ApS, Kgs. Lyngby (DK)

(72) Inventors: Christian Bille Jendresen, Copenhagen Ø (DK); Alex Toftgaard Nielsen, Rungsted Kyst (DK)

(73) Assignee: CysBio ApS, Kgs. Lyngby (DK)

( * ) Notice: Subject to any disclaimer, the term of this patent is extended or adjusted under 35 U.S.C. 154(b) by 0 days.

(21) Appl. No.: 16/079,502

(22) PCT Filed: Feb. 24, 2017

(86) PCT No.: PCT/EP2017/054346
§ 371 (c)(1),
(2) Date: Aug. 23, 2018

(87) PCT Pub. No.: WO2017/144671
PCT Pub. Date: Aug. 31, 2017

(65) Prior Publication Data
US 2019/0284590 A1 Sep. 19, 2019

(30) Foreign Application Priority Data
Feb. 24, 2016 (EP) .................................... 16157231

(51) Int. Cl.
*C12P 11/00* (2006.01)
*C12N 9/10* (2006.01)
*C12P 5/00* (2006.01)

(52) U.S. Cl.
CPC .............. *C12P 11/00* (2013.01); *C12N 9/13* (2013.01); *C12P 5/005* (2013.01); *C12Y 208/02001* (2013.01)

(58) Field of Classification Search
None
See application file for complete search history.

(56) References Cited

U.S. PATENT DOCUMENTS 10,590,440 B2 * 3/2020 Jendresen ...... C12Y 208/02001

FOREIGN PATENT DOCUMENTS

| WO | WO 98/03636 A1 | 1/1998 |
| WO | WO 2016/008886 A1 | 1/2016 |
| WO | WO 2016/026976 A1 | 2/2016 |

OTHER PUBLICATIONS

Mansilla et al. Microbiology. Apr. 2000;146 ( Pt 4):815-821 (Year: 2000).*
Burkart et al. J Org Chem. Sep. 8, 2000;65(18):5565-74 (Year: 2000).*
Sekowska et al. J. Mol. Microbiol. Biotechnol. (2000) 2(2): 145-177 (Year: 2000).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Purchartova et al. Appl Microbiol Biotechnol. Dec. 2013;97(24):10391-8. Epub Mar. 14, 2013. (Year: 2013).*
Accession P17988. Nov. 1, 1990. (Year: 1990).*
Accession O34734. Jun. 16, 2009 (Year: 2009).*
Accession B7LEH0. Jul. 28, 2009 (Year: 2009).*
Accession B7NT95. Apr. 14, 2009 (Year: 2009).*
Accession A7ZQJ4. Feb. 5, 2008 (Year: 2008).*
Accession P22255. Aug. 1, 1991 (Year: 1991).*
Accession F1NMA2. May 3, 2011 (Year: 2011).*
Accession Q90WR6. Dec. 1, 2001 (Year: 2001).*
Accession B1PXA8. Apr. 29, 2008 (Year: 2008).*
Accession Q9M1V2. May 16, 2012 (Year: 2012).*
Burnell, J.N. et al., "A New, Rapid, and Sensitive Assay for Adenosine 5'-Phosphosulphate (APS) Kinase" Analytical Biochemistry, 1975, pp. 281-288, vol. 68.
Fukuda, Chikako et al., "NADP(H) Phosphatase Activities of Archaeal Inositol Monophosphatase and Eubacterial 3'-Phosphoadenosine 5'-Phosphate Phosphatase" Applied and Environmental Microbiology, Sep. 2007, pp. 5447-5452, vol. 73, No. 17.
Hommes, Frits A. et al., "The Assay of ATP-Sulfurylase" Analytical Biochemistry, 1986, pp. 100-103, vol. 154.
Jensen, Niels B. et al., "EasyClone: method for iterative chromosomal integration of multiple genes in *Saccharomyces cerevisiae*" FEMS Yeast Res, 2014, pp. 238-248, vol. 14.
Kawai, Yoshifumi et al., "p-Hydroxycinnamic acid production directly from cellulose using endoglucanase- and tyrosine ammonia lyase-expressing Streptomyces lividans" Microbial Cell Factories, 2013, vol. 12, No. 45.
Li, Hao et al., "The Isolation and Characterization of cDNA Encoding the Mouse Bifunctional ATP Sulfurylase-Adenosine 5'-Phosphosulfate Kinase" The Journal of Biological Chemistry, Dec. 1995, pp. 29453-29459, vol. 270, No. 49.
Logan, Helen M. et al., "Cloning of a cDNA Encoded by a Member of the *Arabidopsis thaliana* ATP Sulfurylase Multigene Family" The Journal of Biological Chemistry, May 1996, pp. 12227-12233, vol. 271, No. 21.

(Continued)

*Primary Examiner* — Christian L Fronda
(74) *Attorney, Agent, or Firm* — Knobbe Martens Olson & Bear LLP

(57) ABSTRACT

The present invention generally relates to the field of biotechnology as it applies to the production of aryl sulfates using recombinant host cells. More particularly, the present invention pertains to recombinant host cells comprising (e.g., expressing) a polypeptide having aryl sulfotransferase activity, wherein said recombinant host cells have been modified to have an increased uptake of sulfate compared to identical host cells that does not carry said modification. Further provided are processes for the production of aryl sulfates, such as zosteric acid, employing such recombinant host cells.

18 Claims, 7 Drawing Sheets

Specification includes a Sequence Listing.

(56) References Cited

OTHER PUBLICATIONS

Mansilla, Maria Cecilia et al., "The *Bacillus subtilis* cysP gene encodes a novel sulphate permease related to the inorganic phosphate transporter (Pit) family" Microbiology, 2000, pp. 815-821, vol. 146.
Reuveny, Ziva et al., "A New Assay for ATP Sulfurylase Based on Differential Solubility of the Sodium Salts of Adenosine Y-Phosphosulfate and Sulfate" Analytical Biochemistry, 1976, pp. 410-428, vol. 75.
Wong, Chi Chun et al., "Inhibition of hydroxycinnamic acid sulfation by flavonoids and their conjugated metabolites" BioFactors, Nov./Dec. 2013, pp. 644-651, vol. 39, XP-002734418.
Yanagisawa, Ken et al., "cDNA Cloning, Expression, and Characterization of the Human Bifunctional ATP Sulfurylase / Adenosine 5'-Phosphosulfate Kinase Enzyme" Bioscience, Biotechnology and Biochemistry, 1998, pp. 1037-1040, vol. 62, No. 5.
Zolotarev, Alexander S. et al., "Increased sulfate uptake by *E. coli* overexpressing the SLC26-related SuIP protein Rv1739c from *Mycobacterium tuberculosis*" Comparative Biochemistry and Physiology, Part A, 2008, pp. 255-266, vol. 149.
International Search Report for PCT/EP2017/054346 dated May 9, 2017.

\* cited by examiner pRSFDuet-1 MCS2::cysDNC-Q

SEQUENCE LISTING

<160> NUMBER OF SEQ ID NOS: 105

<210> SEQ ID NO 1
<211> LENGTH: 291
<212> TYPE: PRT
<213> ORGANISM: Rattus norvegicus

<400> SEQUENCE: 1

Met Glu Phe Ser Arg Pro Pro Leu Val His Val Lys Gly Ile Pro Leu
1               5                   10                  15

Ile Lys Tyr Phe Ala Glu Thr Ile Gly Pro Leu Gln Asn Phe Thr Ala
            20                  25                  30

Trp Pro Asp Asp Leu Leu Ile Ser Thr Tyr Pro Lys Ser Gly Thr Thr
        35                  40                  45

Trp Met Ser Glu Ile Leu Asp Met Ile Tyr Gln Gly Gly Lys Leu Glu
    50                  55                  60

Lys Cys Gly Arg Ala Pro Ile Tyr Ala Arg Val Pro Phe Leu Glu Phe
65                  70                  75                  80

Lys Cys Pro Gly Val Pro Ser Gly Leu Glu Thr Leu Glu Glu Thr Pro
                85                  90                  95

Ala Pro Arg Leu Leu Lys Thr His Leu Pro Leu Ser Leu Leu Pro Gln
            100                 105                 110

Ser Leu Leu Asp Gln Lys Val Lys Val Ile Tyr Ile Ala Arg Asn Ala
        115                 120                 125

Lys Asp Val Val Val Ser Tyr Tyr Asn Phe Tyr Asn Met Ala Lys Leu
    130                 135                 140

His Pro Asp Pro Gly Thr Trp Asp Ser Phe Leu Glu Asn Phe Met Asp
145                 150                 155                 160

Gly Glu Val Ser Tyr Gly Ser Trp Tyr Gln His Val Lys Glu Trp Trp
                165                 170                 175

Glu Leu Arg His Thr His Pro Val Leu Tyr Leu Phe Tyr Glu Asp Ile
            180                 185                 190

Lys Glu Asn Pro Lys Arg Glu Ile Lys Lys Ile Leu Glu Phe Leu Gly
        195                 200                 205

Arg Ser Leu Pro Glu Glu Thr Val Asp Ser Ile Val His His Thr Ser
    210                 215                 220

Phe Lys Lys Met Lys Glu Asn Cys Met Thr Asn Tyr Thr Thr Ile Pro
225                 230                 235                 240

```
Thr Glu Ile Met Asp His Asn Val Ser Pro Phe Met Arg Lys Gly Thr
                245                 250                 255

Thr Gly Asp Trp Lys Asn Thr Phe Thr Val Ala Gln Asn Glu Arg Phe
            260                 265                 270

Asp Ala His Tyr Ala Lys Thr Met Thr Asp Cys Asp Phe Lys Phe Arg
        275                 280                 285

Cys Glu Leu
    290

<210> SEQ ID NO 2
<211> LENGTH: 295
<212> TYPE: PRT
<213> ORGANISM: Homo sapiens

<400> SEQUENCE: 2

Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
                20                  25                  30

Ser Phe Gln Ala Arg Pro Asp Asp Leu Leu Ile Ser Thr Tyr Pro Lys
            35                  40                  45

Ser Gly Thr Thr Trp Val Ser Gln Ile Leu Asp Met Ile Tyr Gln Gly
    50                  55                  60

Gly Asp Leu Glu Lys Cys His Arg Ala Pro Ile Phe Met Arg Val Pro
65                  70                  75                  80

Phe Leu Glu Phe Lys Ala Pro Gly Ile Pro Ser Gly Met Glu Thr Leu
                85                  90                  95

Lys Asp Thr Pro Ala Pro Arg Leu Leu Lys Thr His Leu Pro Leu Ala
            100                 105                 110

Leu Leu Pro Gln Thr Leu Leu Asp Gln Lys Val Lys Val Val Tyr Val
        115                 120                 125

Ala Arg Asn Ala Lys Asp Val Ala Val Ser Tyr Tyr His Phe Tyr His
    130                 135                 140

Met Ala Lys Val His Pro Glu Pro Gly Thr Trp Asp Ser Phe Leu Glu
145                 150                 155                 160

Lys Phe Met Val Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Asp Phe Met Val
    210                 215                 220

Gln His Thr Ser Phe Lys Glu Met Lys Lys Asn Pro Met Thr Asn Tyr
225                 230                 235                 240

Thr Thr Val Pro Gln Glu Phe Met Asp His Ser Ile Ser Pro Phe Met
                245                 250                 255

Arg Lys Gly Met Ala Gly Asp Trp Lys Thr Thr Phe Thr Val Ala Gln
            260                 265                 270

Asn Glu Arg Phe Asp Ala Asp Tyr Ala Glu Lys Met Ala Gly Cys Ser
        275                 280                 285

Leu Ser Phe Arg Ser Glu Leu
    290                 295
```

```
<210> SEQ ID NO 3
<211> LENGTH: 295
<212> TYPE: PRT
<213> ORGANISM: Equus caballus

<400> SEQUENCE: 3
```

Met Glu Leu Ile Gln Asp Thr Ser Arg Pro Pro Leu Lys Tyr Val Lys
 1               5                  10                  15

Gly Val Pro Leu Ile Lys Tyr Phe Ala Glu Ala Leu Gly Pro Leu Gln
             20                  25                  30

Ser Phe Gln Ala Arg Pro Asp Asp Leu Leu Ile Ser Thr Tyr Pro Lys
         35                  40                  45

Ser Gly Thr Thr Trp Val Ser Glu Ile Leu Asp Met Ile Tyr His Gly
     50                  55                  60

Gly Asp Leu Glu Lys Cys Arg Arg Ala Pro Ile Phe Ile Arg Val Pro
 65                  70                  75                  80

Phe Leu Glu Phe Lys Ala Pro Glu Ile Pro Ser Gly Val Glu Val Leu
                 85                  90                  95

Lys Asp Thr Pro Ala Pro Arg Leu Leu Lys Thr His Leu Pro Leu Ser
            100                 105                 110

Leu Leu Pro Gln Thr Leu Leu Asp Gln Lys Val Lys Val Val Tyr Leu
        115                 120                 125

Ala Arg Asn Ala Lys Asp Val Ala Val Ser Tyr Tyr His Phe Tyr Arg
    130                 135                 140

Met Ala Lys Val His Pro Asp Pro Gly Thr Trp Asp Ser Phe Leu Glu
145                 150                 155                 160

Lys Phe Met Ala Gly Glu Val Ser Tyr Gly Ser Trp Tyr Lys His Val
                165                 170                 175

Gln Glu Trp Trp Glu Leu Ser His Thr His Pro Val Leu Tyr Leu Phe
            180                 185                 190

Tyr Glu Asp Met Lys Glu Asn Pro Lys Lys Glu Ile Gln Lys Ile Leu
        195                 200                 205

Glu Phe Val Gly Arg Ser Leu Pro Glu Glu Thr Leu Asp Arg Ile Val
    210                 215                 220

Gln His Thr Ser Phe Lys Glu Met Lys Lys Asn Pro Met Ala Asn Tyr
225                 230                 235                 240

Ser Thr Ile Pro Cys Asp Ile Met Asp His Asn Ile Ser Ala Phe Met
                245                 250                 255

Arg Lys Gly Ile Ala Gly Asp Trp Lys Asn Thr Phe Thr Val Ala Gln
            260                 265                 270

Asn Glu His Phe Asp Thr Asp Tyr Ala Glu Lys Met Ala Gly Cys Lys
        275                 280                 285

Leu Ser Phe Arg Ser Glu Val
        290                 295

```
<210> SEQ ID NO 4
<211> LENGTH: 295
<212> TYPE: PRT
<213> ORGANISM: Sus scrofa

<400> SEQUENCE: 4
```

Met Glu Pro Val Gln Asp Thr Tyr Arg Pro Pro Leu Glu Tyr Val Lys
 1               5                  10                  15

Gly Val Pro Leu Ile Lys Tyr Phe Ala Glu Ala Leu Gly Pro Leu Glu
             20                  25                  30

Ser Phe Gln Ala Trp Pro Asp Asp Val Leu Ile Ser Thr Tyr Pro Lys

```
                35                  40                  45
Ser Gly Thr Thr Trp Val Ser Glu Ile Leu Asp Leu Ile Tyr Gln Gly
     50                  55                  60

Gly Asp Leu Gln Lys Cys Gln Arg Ala Pro Ile Phe Val Arg Val Pro
 65                  70                  75                  80

Phe Leu Glu Phe Lys Ile Pro Gly Cys Pro Thr Gly Phe Glu Leu Leu
                 85                  90                  95

Lys Asp Thr Pro Ala Pro Arg Leu Leu Lys Thr His Leu Pro Leu Ala
            100                 105                 110

Leu Leu Pro Gln Thr Leu Leu Asp Gln Lys Val Lys Val Val Tyr Val
        115                 120                 125

Ala Arg Asn Ala Lys Asp Val Ala Val Ser Tyr Tyr His Phe Tyr Arg
    130                 135                 140

Met Ala Lys Val His Pro Asn Pro Gly Thr Trp Asp Ser Phe Leu Glu
145                 150                 155                 160

Asp Phe Met Ala Gly Glu Val Ser Tyr Gly Ser Trp Tyr Gln His Val
                165                 170                 175

Gln Glu Trp Trp Glu Leu Arg His Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Glu Asp Ile Val
    210                 215                 220

Gln His Thr Ser Phe Gln Glu Met Lys Asn Asn Ala Met Thr Asn Tyr
225                 230                 235                 240

Arg Thr Leu Pro Ser Asp Leu Asp His Ser Ile Ser Ala Phe Met
                245                 250                 255

Arg Lys Gly Ile Thr Gly Asp Trp Lys Ser Thr Phe Thr Val Ala Gln
            260                 265                 270

Asn Glu Arg Phe Glu Ala Asp Tyr Ala Glu Lys Met Ala Gly Cys Asn
        275                 280                 285

Leu Arg Phe Arg Ser Glu Leu
    290                 295

<210> SEQ ID NO 5
<211> LENGTH: 295
<212> TYPE: PRT
<213> ORGANISM: Canis lupus

<400> SEQUENCE: 5

Met Glu Asp Ile Pro Asp Thr Ser Arg Pro Pro Leu Lys Tyr Val Lys
 1               5                  10                  15

Gly Ile Pro Leu Ile Lys Tyr Phe Ala Glu Ala Leu Glu Ser Leu Gln
             20                  25                  30

Asp Phe Gln Ala Gln Pro Asp Asp Leu Leu Ile Ser Thr Tyr Pro Lys
         35                  40                  45

Ser Gly Thr Thr Trp Val Ser Glu Ile Leu Asp Met Ile Tyr Gln Asp
     50                  55                  60

Gly Asp Val Glu Lys Cys Arg Arg Ala Pro Val Phe Ile Arg Val Pro
 65                  70                  75                  80

Phe Leu Glu Phe Lys Ala Pro Gly Ile Pro Thr Gly Leu Glu Val Leu
                 85                  90                  95

Lys Asp Thr Pro Ala Pro Arg Leu Ile Lys Thr His Leu Pro Leu Ala
            100                 105                 110
```

Leu Leu Pro Gln Thr Leu Leu Asp Gln Lys Val Lys Val Tyr Val
            115                 120                 125

Ala Arg Asn Ala Lys Asp Val Ala Val Ser Tyr Tyr His Phe Tyr Arg
130                 135                 140

Met Ala Lys Val His Pro Asp Pro Asp Thr Trp Asp Ser Phe Leu Glu
145                 150                 155                 160

Lys Phe Met Ala Gly Glu Val Ser Tyr Gly Ser Trp Tyr Gln His Val
                165                 170                 175

Gln Glu Trp Trp Glu Leu Ser His Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Lys Phe Val Gly Arg Ser Leu Pro Glu Glu Thr Val Asp Leu Ile Val
    210                 215                 220

Gln His Thr Ser Phe Lys Glu Met Lys Asn Asn Ser Met Ala Asn Tyr
225                 230                 235                 240

Thr Thr Leu Ser Pro Asp Ile Met Asp His Ser Ile Ser Ala Phe Met
                245                 250                 255

Arg Lys Gly Ile Ser Gly Asp Trp Lys Thr Thr Phe Thr Val Ala Gln
            260                 265                 270

Asn Glu Arg Phe Asp Ala Asp Tyr Ala Lys Lys Met Glu Gly Cys Gly
        275                 280                 285

Leu Ser Phe Arg Thr Gln Leu
    290                 295

<210> SEQ ID NO 6
<211> LENGTH: 294
<212> TYPE: PRT
<213> ORGANISM: Gallus gallus

<400> SEQUENCE: 6

Met Gly Asn Asp Glu Val Ile Arg Gln Asp Leu Gly Cys Leu Tyr Asp
1               5                   10                  15

Ile Pro Leu Tyr Lys Cys Phe Val Ala Gly Trp Pro Gln Val Glu Ala
            20                  25                  30

Phe Gln Ala Arg Pro Asp Asp Leu Leu Ile Ala Thr Tyr Pro Lys Ser
        35                  40                  45

Gly Thr Thr Trp Leu Ser Glu Ile Leu Asp Ala Ile Tyr His Asp Gly
    50                  55                  60

Asp Leu Glu Lys Cys Arg Arg Asp Ala Ile Tyr Asn Arg Val Pro Phe
65                  70                  75                  80

Leu Glu Met Lys Ala Pro Gly Ile Leu Ser Gly Val Glu Gln Leu Glu
                85                  90                  95

Lys Ile Pro Ser Pro Arg Leu Val Lys Thr His Leu Pro Val His Leu
            100                 105                 110

Leu Pro Ala Ser Phe Gln Glu Lys Asp Cys Lys Val Ile Tyr Met Ala
        115                 120                 125

Arg Asn Ala Lys Asp Val Val Ile Ser Tyr Tyr Tyr Phe Tyr Gln Met
    130                 135                 140

Ala Lys Ile His Pro Asp Pro Gly Thr Leu Ser Glu Phe Leu Gln Ala
145                 150                 155                 160

Phe Met Asp Gly Lys Val Ala Tyr Gly Ser Trp Tyr Lys His Val Lys
                165                 170                 175

Gly Trp Trp Glu Lys Arg His Glu Lys Arg Leu Leu Tyr Leu Phe Tyr
            180                 185                 190

Glu Asp Met Lys Lys Asp Pro Arg Arg Glu Ile Gln Lys Ile Leu Gln
            195                 200                 205

Phe Leu Gly Lys Glu Val Ala Glu Glu Thr Val Ala Arg Ile Leu His
210                 215                 220

His Thr Ser Phe Gln Glu Met Lys Lys Asn Pro Ala Thr Asn Tyr Glu
225                 230                 235                 240

Thr Met Pro Thr Glu Leu Met Asp His Ser Leu Ser Pro Phe Met Arg
                245                 250                 255

Lys Gly Ile Ser Gly Asp Trp Ala Asn His Phe Thr Val Ala Gln Asn
                260                 265                 270

Glu Arg Phe Asp Gln His Tyr Gln Gln Gln Met Ala Gly Ser Asp Leu
            275                 280                 285

Cys Phe Gln Met Glu Ala
        290

<210> SEQ ID NO 7
<211> LENGTH: 307
<212> TYPE: PRT
<213> ORGANISM: Gallus gallus

<400> SEQUENCE: 7

Met Ala Leu Asp Lys Met Glu Asn Leu Ser Leu Glu Glu Asn Met Leu
1               5                   10                  15

Arg Ser Glu Met Gly Glu Val Gln Gly Ile Pro Val Thr Lys Pro Thr
            20                  25                  30

Cys Asp Ile Trp Asp Gln Val Trp Asn Phe Lys Ala Arg Pro Asp Asp
        35                  40                  45

Leu Leu Val Ala Thr Tyr Ala Lys Ala Gly Thr Thr Trp Thr Gln Glu
    50                  55                  60

Ile Val Asp Met Ile Gln Gln Asn Gly Asp Ile Glu Lys Cys Arg Arg
65                  70                  75                  80

Ala Ser Thr Tyr Lys Arg His Pro Phe Leu Glu Trp Tyr Ile Pro Asp
                85                  90                  95

Ser Ser Pro Leu Gly Tyr Ser Gly Leu Lys Leu Ala Glu Ala Met Pro
            100                 105                 110

Ser Pro Arg Thr Met Lys Thr His Leu Pro Val Gln Leu Val Pro Pro
        115                 120                 125

Ser Phe Trp Glu Gln Asn Cys Lys Ile Ile Tyr Val Ala Arg Asn Ala
    130                 135                 140

Lys Asp Asn Leu Val Ser Tyr Tyr His Phe His Arg Met Asn Lys Val
145                 150                 155                 160

Leu Pro Asp Pro Gly Thr Ile Glu Glu Phe Thr Glu Lys Phe Met Asn
                165                 170                 175

Gly Glu Val Leu Trp Gly Ser Trp Tyr Asp His Val Lys Gly Trp Trp
            180                 185                 190

Lys Ala Lys Asp Lys His Arg Ile Leu Tyr Leu Phe Tyr Glu Asp Met
        195                 200                 205

Lys Glu Asn Pro Lys Arg Glu Ile Gln Lys Ile Met Lys Phe Leu Glu
    210                 215                 220

Lys Asp Leu Asp Glu Val Leu Asn Lys Ile Ile Tyr Asn Thr Ser
225                 230                 235                 240

Phe Glu Ile Met Lys Asp Asn Pro Met Thr Asn Tyr Thr Lys Asp Phe
                245                 250                 255

Val Gly Val Met Asp His Ser Val Ser Pro Phe Met Arg Lys Gly Ser

```
            260                 265                 270
Val Gly Asp Trp Lys Asn Tyr Phe Thr Val Ala Leu Asn Lys Lys Phe
            275                 280                 285

Asp Gln Asp Tyr Lys Lys Lys Met Ala Asp Thr Ser Leu Val Phe Arg
            290                 295                 300

Met Glu Leu
305

<210> SEQ ID NO 8
<211> LENGTH: 301
<212> TYPE: PRT
<213> ORGANISM: Danio rerio

<400> SEQUENCE: 8

Met Asp Leu Pro Asp Ile Ser Ser Ile Lys Leu Pro Ser Arg Pro Lys
1               5                   10                  15

Ile Phe Glu Phe Glu Gly Ile Ser Met Ile Ser Tyr Phe Thr Asp Asn
            20                  25                  30

Trp Glu Lys Leu Lys Asn Phe Gln Ala Arg Pro Asp Ile Leu Ile
            35                  40                  45

Ala Thr Tyr Pro Lys Ala Gly Thr Thr Trp Val Ser Tyr Ile Leu Asp
50                  55                  60

Leu Leu Tyr Phe Gly Lys Val Glu Pro Asn Gly Gln Ser Ser Leu Pro
65                  70                  75                  80

Ile Tyr Met Arg Val Pro Phe Leu Glu Ser Cys Phe Pro Gly Met Pro
            85                  90                  95

Ser Gly Thr Glu Leu Ala Asp Asn Leu Pro Asn Ser Pro Arg Leu Ile
            100                 105                 110

Lys Thr His Leu Pro Val Gln Leu Val Pro Lys Ser Phe Trp Gly Gln
            115                 120                 125

Asn Ser Lys Val Val Tyr Val Ala Arg Asn Ala Lys Asp Asn Val Val
130                 135                 140

Ser Phe Phe His Phe Asp Arg Met Asn His Gly Gln Pro Glu Pro Gly
145                 150                 155                 160

Asp Trp Asp Thr Phe Leu Gln Ala Phe Ile Lys Gly Glu Arg Val Phe
            165                 170                 175

Gly Ser Trp Phe Asp His Val Cys Gly Trp Trp Glu Lys Lys Lys Thr
            180                 185                 190

Tyr Pro Asn Leu His Tyr Met Phe Tyr Glu Asp Ile Ala Lys Asp Ile
            195                 200                 205

Asn Gly Glu Val Glu Ser Leu Cys Thr Phe Leu Lys Leu Ser Arg Ser
210                 215                 220

Asp Glu Glu Lys Glu Lys Ile Ile Asn Gly Val Gln Phe Asp Ala Met
225                 230                 235                 240

Lys Gln Asn Val Met Thr Asn Tyr Ser Thr Ile Pro Thr Met Asp Phe
            245                 250                 255

Thr Ile Ser Pro Phe Met Arg Lys Gly Lys Val Gly Asp Trp Lys Asn
            260                 265                 270

His Phe Thr Val Ala Gln Asn Glu Gln Phe Asp Glu Asp Tyr Lys Glu
            275                 280                 285

Lys Met Lys Asn Thr Thr Leu Asn Phe Arg Thr Lys Ile
            290                 295                 300

<210> SEQ ID NO 9
<211> LENGTH: 300
```

<212> TYPE: PRT
<213> ORGANISM: Danio rerio

<400> SEQUENCE: 9

Met Glu Ile Gln Gly Lys Ser Ser Thr Asp Leu Pro Asp Arg Pro Glu
1               5                   10                  15

Ile Phe Glu Phe Glu Gly Ile Ser Met Val His Phe Thr Lys Asn
            20                  25                  30

Trp Glu Asn Val Lys Asn Phe Gln Ala Arg Pro Asp Asp Ile Leu Ile
            35                  40                  45

Ala Thr Tyr Pro Lys Ala Gly Thr Thr Trp Val Ser Asn Ile Leu Asp
    50                  55                  60

Leu Leu Tyr Phe Gly Lys Glu Asp Pro Lys Arg Gln Thr Thr Lys Pro
65                  70                  75                  80

Ile Tyr Lys Arg Val Pro Phe Leu Glu Ser Cys Phe Pro Glu Met Gln
                85                  90                  95

Ser Gly Thr Glu Leu Ala Asn Asn Leu Pro Thr Ser Pro Arg Leu Ile
            100                 105                 110

Lys Thr His Leu Pro Val Gln Leu Val Pro Gln Ser Phe Trp Glu Lys
        115                 120                 125

Asn Ser Arg Val Ala Tyr Val Ala Arg Asn Ala Lys Asp Asn Ala Val
    130                 135                 140

Ser Tyr Phe His Phe Asn Arg Met Asn Lys Ala Gln Pro Glu Pro Gly
145                 150                 155                 160

Asp Trp Asn Thr Phe Leu Glu Glu Phe Met Lys Gly Lys Met Val Phe
                165                 170                 175

Gly Ser Trp Phe Asp His Val Cys Gly Trp Trp Glu Lys Lys Lys Thr
            180                 185                 190

Tyr Pro Asn Leu His Tyr Met Leu Tyr Glu Asp Met Ala Lys Asp Ile
        195                 200                 205

Lys Gly Glu Val Glu Ser Leu Cys Thr Phe Leu Lys Leu Ser Arg Ser
    210                 215                 220

Asp Glu Glu Lys Glu Lys Ile Ile Asn Gly Ile Gln Phe Asp Ala Met
225                 230                 235                 240

Lys Gln Asn Lys Met Thr Asn Tyr Ser Thr Val Leu Val Met Asp Phe
                245                 250                 255

Thr Ile Ser Pro Phe Met Arg Lys Gly Lys Val Gly Asp Trp Lys Asn
            260                 265                 270

His Phe Thr Val Ala Gln Asn Glu Gln Phe Asn Glu Asp Tyr Lys Gln
        275                 280                 285

Lys Met Lys Asn Ser Thr Leu Lys Phe Pro Thr Glu
    290                 295                 300

<210> SEQ ID NO 10
<211> LENGTH: 338
<212> TYPE: PRT
<213> ORGANISM: Drosophila melanogaster

<400> SEQUENCE: 10

Met Pro Gln Ser Ser Phe Phe Ala Lys Ser Val Pro Phe Glu Gln Ile
1               5                   10                  15

Asp Lys Leu Ala Ile Ser Gly Gly Tyr Ser Ser Ile Phe Ala Ser Ser
            20                  25                  30

Lys Pro Ser Val Pro Val Val Gly Asn Trp Glu Gln Arg Phe Cys Arg
        35                  40                  45

```
Leu Ala Asp Thr Phe Gln Pro Val Leu Asp Arg Val Tyr Asp Phe Glu
        50                  55                  60

Val Arg Asp Asp Val Trp Ile Val Thr Leu Pro Lys Cys Gly Thr
65                  70                  75                  80

Thr Trp Met Gln Glu Leu Ala Trp Leu Val Ile Asn Glu Cys Asp Phe
                    85                  90                  95

Glu Thr Ala Lys Ser Val Asp Leu Thr His Arg Ser Pro Phe Leu Glu
                100                 105                 110

Phe Asn Gly Val Val Pro Asn Val Pro His Asp Thr Ile Ala Ala Ala
                115                 120                 125

Asn Ala Leu Pro Ser Pro Arg Leu Ile Lys Ser His Leu Pro Ala Trp
130                 135                 140

Met Leu Pro Arg Gln Ile Trp Ser Lys Arg Pro Lys Ile Ile Tyr Val
145                 150                 155                 160

Tyr Arg Asn Pro Lys Asp Ala Ala Ile Ser Tyr Phe His His Trp Arg
                165                 170                 175

Gly Met Val Gly Tyr Gln Gly Thr Lys Ser Asp Phe Met His Ser Phe
                180                 185                 190

Ile Asp Gly Tyr Val Asn Phe Thr Pro Cys Trp Pro His Ile Leu Asp
                195                 200                 205

Phe Trp Gln Leu Arg His Glu Pro Asn Ile Phe Phe Thr Ser Tyr Glu
210                 215                 220

Arg Met Lys Gly Gln Leu Gly Gln Val Ile Ser Glu Val Ala Gln Phe
225                 230                 235                 240

Leu Glu Arg Ser Val Ser Gln Glu Gln Met Gln Gln Met Gln Arg His
                245                 250                 255

Leu Ser Phe Glu Ser Met Arg Asp Asn Pro Ala Cys Asn His Val Lys
                260                 265                 270

Glu Phe Glu Ser Met Lys Ala Ala Gly Arg Glu Val Glu Glu Phe
                275                 280                 285

Arg Phe Val Arg Arg Gly Val Val Gly Ser His Lys Asp Glu Leu Thr
                290                 295                 300

Ala Asp Ile Ile Arg Glu Phe Asp Leu Trp Ser Asp Ser Asn Leu Arg
305                 310                 315                 320

Asp Phe Lys Leu Asn Met Asp Asp Phe Ala Asn Tyr Ser Lys Phe Ala
                325                 330                 335

Ser Thr

<210> SEQ ID NO 11
<211> LENGTH: 313
<212> TYPE: PRT
<213> ORGANISM: Drosophila melanogaster

<400> SEQUENCE: 11

Met Asn Arg Val Gln Val Thr Pro Arg Ser Tyr Pro Thr Asn Leu Ile
1                   5                   10                  15

Asp Lys Asp Trp Gly Asn Arg Lys Leu Phe Tyr Thr Lys Asp Ser Glu
                20                  25                  30

Asn Phe Leu Arg Leu Val His Asp Met Lys Leu Arg Asp Asp Val
            35                  40                  45

Trp Ile Val Thr Leu Pro Lys Cys Gly Thr Thr Trp Met Gln Glu Leu
    50                  55                  60

Leu Trp Leu Leu Leu Asn Asn Cys Asp Phe Glu Gly Ala Leu Ala Lys
65                  70                  75                  80
```

```
Asp Gln Glu Leu Arg Thr Pro Phe Leu Glu Phe Gly Tyr Ser Val Phe
                85                  90                  95

His Asp Pro Asn Arg Ser Phe Gly Pro Ile Glu Asp Leu Lys Ser Pro
            100                 105                 110

Arg Leu Ile Lys Ser His Leu Ser Leu Ala Leu Leu Pro Ser Lys Leu
        115                 120                 125

Trp Glu Gly Lys Asn Lys Val Ile Tyr Val Ser Arg Asn Pro Leu Asp
    130                 135                 140

Ser Tyr Val Ser Arg Tyr Tyr His Gly Val Ser Phe Gly Phe Asn Tyr
145                 150                 155                 160

Gly Lys Ser Leu His Gln Tyr Phe Asp Glu Val Leu Ala Ser Asp Asp
                165                 170                 175

Phe Pro Thr Glu Phe Ile Glu His Ala His Glu Phe Tyr Gln Leu Arg
            180                 185                 190

Asn Glu Pro Trp Val Phe Tyr Thr Ser Phe Glu Met Met Lys Lys Asp
        195                 200                 205

Leu Arg Gly Val Ile Asn Asp Val Ser Arg Phe Leu Asn Lys Pro Ile
    210                 215                 220

Asn Asp Gln Gln Met Glu Lys Leu Leu Lys His Leu Ser Phe Ala Glu
225                 230                 235                 240

Met Lys Lys Asn Pro Thr Thr Asn His Leu Trp Glu Leu Ala Gln Val
                245                 250                 255

Gln His Glu Asn Ala Gly Lys Glu Met His Pro Phe Val Arg Arg Gly
            260                 265                 270

Asp Val Asn Gly Tyr Lys Asp Glu Leu Lys Pro Glu Gln Ile Glu Lys
        275                 280                 285

Ala Asn Val Arg Ile Gln Glu Val Leu Ala Lys Asn Gly Val Thr Leu
    290                 295                 300

Asp Glu Leu Leu Leu Leu Lys Asp Gln
305                 310

<210> SEQ ID NO 12
<211> LENGTH: 346
<212> TYPE: PRT
<213> ORGANISM: Drosophila melanogaster

<400> SEQUENCE: 12

Met Glu Asn Thr Pro Leu Lys Phe Pro His Glu Ile Arg Asp Val Glu
1               5                   10                  15

Glu Ser Thr Asn Ala Glu Leu Leu Asp His Phe His Gly Glu Arg Thr
            20                  25                  30

Gly Phe Val Gln Val Gly Ser Glu Gly Tyr Phe Phe Pro His Lys Tyr
        35                  40                  45

Lys Asp Glu Ala Glu Arg Tyr Tyr Asn Phe Glu Ala Arg Pro Asp Asp
    50                  55                  60

Val Trp Ile Ala Thr Val Pro Arg Ser Gly Thr Thr Trp Thr Gln Glu
65                  70                  75                  80

Leu Ile Trp Leu Val Ala Asn Gly Leu Asp Phe Glu His Ala Gln Glu
                85                  90                  95

Arg Pro Leu Thr Glu Arg Phe Pro Phe Phe Gly Phe Pro Leu Phe Val
            100                 105                 110

His Pro Lys Ile Lys Glu Glu Leu Gln Glu Glu Asn Arg Asp Ser Ala
        115                 120                 125

Glu Ala Leu Glu Phe Ile Glu Lys Ile Ala Arg Pro Gly Tyr Glu Ala
    130                 135                 140
```

-continued

```
Leu Ser Glu Ile Pro Arg Ser Gln Arg Phe Ile Lys Thr His Phe
145                 150                 155                 160

Pro Phe Ser Leu Met Pro Pro Ser Val Leu Glu Lys Lys Cys Lys Val
                165                 170                 175

Ile Tyr Val Val Arg Asp Pro Lys Asp Val Ala Val Ser Tyr Tyr His
            180                 185                 190

Leu Asn Arg Leu Phe Arg Thr Gln Gly Tyr Val Gly Asp Phe Glu Arg
        195                 200                 205

Tyr Trp His Tyr Phe Gln Asn Gly Leu Asn Pro Trp Leu Pro Tyr Tyr
    210                 215                 220

Ser His Val Lys Glu Ala Arg Glu His Ala His Leu Ser Asn Val Leu
225                 230                 235                 240

Phe Leu Arg Tyr Glu Asp Met Leu Ala Asp Leu Pro Gly Ala Ile Asn
                245                 250                 255

Ser Ile Ala Ser Phe Leu Glu Cys Pro Pro Lys Pro Glu Asp Met Asp
            260                 265                 270

Arg Leu Leu Asp His Leu Ser Ile Arg Ser Phe Arg Glu Asn Lys Ser
        275                 280                 285

Val Asn Met His Glu Met Ala Ser Val Gly Val Leu Asn Lys Gly Glu
    290                 295                 300

Ala Gly Phe Val Arg Ser Gly Ala Lys Thr Ala Tyr Gln Pro Gln Gln
305                 310                 315                 320

Glu Phe Val Glu Asn Pro Lys Leu Leu Lys Ser Ala Asn Glu Trp Val
                325                 330                 335

Glu Gln Asn Ile Lys Ser Phe Lys Thr Ile
                340                 345

<210> SEQ ID NO 13
<211> LENGTH: 323
<212> TYPE: PRT
<213> ORGANISM: Arabidopsis thaliana

<400> SEQUENCE: 13

Met Glu Met Asn Leu Arg Ile Glu Asp Leu Asn Glu Glu Thr Lys Thr
1               5                   10                  15

Leu Ile Ser Ser Leu Pro Ser Asp Lys Asp Phe Thr Gly Lys Thr Ile
            20                  25                  30

Cys Lys Tyr Gln Gly Cys Trp Tyr Thr His Asn Val Leu Gln Ala Val
        35                  40                  45

Leu Asn Phe Gln Lys Ser Phe Lys Pro Gln Asp Thr Asp Ile Ile Val
    50                  55                  60

Ala Ser Phe Pro Lys Cys Gly Thr Thr Trp Leu Lys Ala Leu Thr Phe
65                  70                  75                  80

Ala Leu Leu His Arg Ser Lys Gln Pro Ser His Asp Asp His Pro
                85                  90                  95

Leu Leu Ser Asn Asn Pro His Val Leu Val Pro Tyr Phe Glu Ile Asp
                100                 105                 110

Leu Tyr Leu Arg Ser Glu Asn Pro Asp Leu Thr Lys Phe Ser Ser Ser
        115                 120                 125

Pro Arg Leu Phe Ser Thr His Val Pro Ser His Thr Leu Gln Glu Gly
    130                 135                 140

Leu Lys Gly Ser Thr Cys Lys Ile Val Tyr Ile Ser Arg Asn Val Lys
145                 150                 155                 160

Asp Thr Leu Val Ser Tyr Trp His Phe Phe Thr Lys Lys Gln Thr Asp
```

```
                        165                 170                 175
Glu Lys Ile Ile Ser Ser Phe Glu Asp Thr Phe Glu Met Phe Cys Arg
                180                 185                 190

Gly Val Ser Ile Phe Gly Pro Phe Trp Asp His Val Leu Ser Tyr Trp
            195                 200                 205

Arg Gly Ser Leu Glu Asp Pro Asn His Val Leu Phe Met Lys Phe Glu
        210                 215                 220

Glu Met Lys Ala Glu Pro Arg Asp Gln Ile Lys Lys Phe Ala Glu Phe
225                 230                 235                 240

Leu Gly Cys Pro Phe Thr Lys Glu Glu Glu Ser Gly Ser Val Asp
                245                 250                 255

Glu Ile Ile Asp Leu Cys Ser Leu Arg Asn Leu Ser Ser Leu Glu Ile
                260                 265                 270

Asn Lys Thr Gly Lys Leu Asn Ser Gly Arg Glu Asn Lys Met Phe Phe
                275                 280                 285

Arg Lys Gly Glu Val Gly Asp Trp Lys Asn Tyr Leu Thr Pro Glu Met
            290                 295                 300

Glu Asn Lys Ile Asp Met Ile Ile Gln Glu Lys Leu Gln Asn Ser Gly
305                 310                 315                 320

Leu Lys Phe

<210> SEQ ID NO 14
<211> LENGTH: 253
<212> TYPE: PRT
<213> ORGANISM: Escherichia coli

<400> SEQUENCE: 14

Met Val Ser Ser Phe Thr Ser Ala Pro Arg Ser Gly Phe Tyr Tyr Phe
1               5                   10                  15

Ala Gln Gly Trp Lys Leu Val Ser Gln Pro Gly Ile Arg Arg Phe Val
                20                  25                  30

Ile Leu Pro Leu Leu Val Asn Ile Leu Met Gly Gly Ala Phe Trp
            35                  40                  45

Trp Leu Phe Thr Gln Leu Asp Val Trp Ile Pro Thr Leu Met Ser Tyr
        50                  55                  60

Val Pro Asp Trp Leu Gln Trp Leu Ser Tyr Leu Leu Trp Pro Leu Ala
65                  70                  75                  80

Val Ile Ser Val Leu Leu Val Phe Gly Tyr Phe Ser Thr Ile Ala
                85                  90                  95

Asn Trp Ile Ala Ala Pro Phe Asn Gly Leu Leu Ala Glu Gln Leu Glu
                100                 105                 110

Ala Arg Leu Thr Gly Ala Thr Pro Pro Asp Thr Gly Ile Phe Gly Ile
            115                 120                 125

Met Lys Asp Val Pro Arg Ile Met Lys Arg Glu Trp Gln Lys Phe Ala
130                 135                 140

Trp Tyr Leu Pro Arg Ala Ile Val Leu Leu Ile Leu Tyr Phe Ile Pro
145                 150                 155                 160

Gly Ile Gly Gln Thr Val Ala Pro Val Leu Trp Phe Leu Phe Ser Ala
                165                 170                 175

Trp Met Leu Ala Ile Gln Tyr Cys Asp Tyr Pro Phe Asp Asn His Lys
                180                 185                 190

Val Pro Phe Lys Glu Met Arg Thr Ala Leu Arg Thr Arg Lys Ile Thr
            195                 200                 205

Asn Met Gln Phe Gly Ala Leu Thr Ser Leu Phe Thr Met Ile Pro Leu
```

```
                210                 215                 220
Leu Asn Leu Phe Ile Met Pro Val Ala Val Cys Gly Ala Thr Ala Met
225                 230                 235                 240

Trp Val Asp Cys Tyr Arg Asp Lys His Ala Met Trp Arg
                245                 250
```

<210> SEQ ID NO 15
<211> LENGTH: 309
<212> TYPE: PRT
<213> ORGANISM: Corynebacterium glutamicum

<400> SEQUENCE: 15

```
Met Gln Thr Leu Ile Phe Ile Ala Ile Ala Gly Val Ala Ala Gln Leu
1               5                   10                  15

Val Asp Gly Gly Leu Gly Met Gly Phe Gly Val Thr Ser Thr Thr Ile
            20                  25                  30

Leu Ile Met Leu Ala Gly Leu Gly Pro Ala Gln Ala Ser Ala Val Val
        35                  40                  45

His Thr Ala Glu Val Gly Thr Thr Leu Val Ser Gly Leu Ser His Trp
    50                  55                  60

Lys Phe Gly Asn Val Asp Trp Lys Val Val Arg Leu Gly Ile Pro
65                  70                  75                  80

Gly Ala Ile Gly Ala Phe Ala Gly Ala Thr Phe Leu Ser Asn Ile Ser
                85                  90                  95

Thr Glu Ala Ala Ala Pro Ile Thr Ser Leu Ile Leu Ala Leu Ile Gly
            100                 105                 110

Met Asn Leu Val Trp Arg Phe Ser Lys Gly Arg Ile Arg Arg Asp Tyr
        115                 120                 125

Ser Asp Arg Pro His Ser Arg Gly Phe Leu Gly Gly Leu Gly Ile Val
    130                 135                 140

Gly Gly Phe Val Asp Ala Ser Gly Gly Gly Trp Gly Pro Val Thr
145                 150                 155                 160

Thr Ser Thr Leu Leu Ser Leu Gly Arg Thr Glu Pro Arg Lys Val Val
                165                 170                 175

Gly Thr Val Asn Thr Ala Glu Phe Leu Val Ser Leu Ala Ala Thr Leu
            180                 185                 190

Gly Phe Val Val Gly Leu Trp Asp Asp Leu Val Ala Asn Leu Ser Ala
        195                 200                 205

Val Leu Ala Leu Leu Ile Gly Gly Ala Ile Ala Pro Ile Gly Ala
    210                 215                 220

Trp Met Ile Ser Arg Val Asn Ala Thr Val Leu Gly Gly Phe Val Gly
225                 230                 235                 240

Thr Leu Ile Val Thr Leu Asn Leu Pro Lys Val Leu Asn Val Val Gly
                245                 250                 255

Leu Asp Phe Ile Pro Thr Gly Leu Ile Gln Val Thr Val Leu Leu Ile
            260                 265                 270

Gly Leu Pro Leu Thr Tyr Leu Gly Phe Arg Arg Tyr Arg Lys Asn Leu
        275                 280                 285

Leu Asn Glu Thr Ile Ser Ser Glu Val Val Ser Glu Pro Lys Gly Gln
    290                 295                 300

Lys Ile Lys Ser Thr
305
```

<210> SEQ ID NO 16
<211> LENGTH: 277

```
<212> TYPE: PRT
<213> ORGANISM: Escherichia coli

<400> SEQUENCE: 16

Met Phe Ala Val Ser Ser Arg Arg Val Leu Pro Gly Phe Thr Leu Ser
1               5                   10                  15

Leu Gly Thr Ser Leu Leu Phe Val Cys Leu Ile Leu Leu Pro Leu
                20                  25                  30

Ser Ala Leu Val Met Gln Leu Ala Gln Met Ser Trp Ala Gln Tyr Trp
                35                  40                  45

Glu Val Ile Thr Asn Pro Gln Val Val Ala Ala Tyr Lys Val Thr Leu
            50                  55                  60

Leu Ser Ala Phe Val Ala Ser Ile Phe Asn Gly Val Phe Gly Leu Leu
65                  70                  75                  80

Met Ala Trp Ile Leu Thr Arg Tyr Arg Phe Pro Gly Arg Thr Leu Leu
                85                  90                  95

Asp Ala Leu Met Asp Leu Pro Phe Ala Leu Pro Thr Ala Val Ala Gly
                100                 105                 110

Leu Thr Leu Ala Ser Leu Phe Ser Val Asn Gly Phe Tyr Gly Glu Trp
                115                 120                 125

Leu Ala Lys Phe Asp Ile Lys Val Thr Tyr Thr Trp Leu Gly Ile Ala
            130                 135                 140

Val Ala Met Ala Phe Thr Ser Ile Pro Phe Val Val Arg Thr Val Gln
145                 150                 155                 160

Pro Val Leu Glu Glu Leu Gly Pro Glu Tyr Glu Glu Ala Ala Glu Thr
                165                 170                 175

Leu Gly Ala Thr Arg Trp Gln Ser Phe Cys Lys Val Val Leu Pro Glu
                180                 185                 190

Leu Ser Pro Ala Leu Val Ala Gly Val Ala Leu Ser Phe Thr Arg Ser
            195                 200                 205

Leu Gly Glu Phe Gly Ala Val Ile Phe Ile Ala Gly Asn Ile Ala Trp
            210                 215                 220

Lys Thr Glu Val Thr Ser Leu Met Ile Phe Val Arg Leu Gln Glu Phe
225                 230                 235                 240

Asp Tyr Pro Ala Ala Ser Ala Ile Ala Ser Val Ile Leu Ala Ala Ser
                245                 250                 255

Leu Leu Leu Leu Phe Ser Ile Asn Thr Leu Gln Ser Arg Phe Gly Arg
                260                 265                 270

Arg Val Val Gly His
            275

<210> SEQ ID NO 17
<211> LENGTH: 291
<212> TYPE: PRT
<213> ORGANISM: Escherichia coli

<400> SEQUENCE: 17

Met Ala Glu Val Thr Gln Leu Lys Arg Tyr Asp Ala Arg Pro Ile Asn
1               5                   10                  15

Trp Gly Lys Trp Phe Leu Ile Gly Ile Gly Met Leu Val Ser Ala Phe
                20                  25                  30

Ile Leu Leu Val Pro Met Ile Tyr Ile Phe Val Gln Ala Phe Ser Lys
                35                  40                  45

Gly Leu Met Pro Val Leu Gln Asn Leu Ala Asp Pro Asp Met Leu His
            50                  55                  60
```

-continued

```
Ala Ile Trp Leu Thr Val Met Ile Ala Leu Ile Ala Val Pro Val Asn
 65                  70                  75                  80

Leu Val Phe Gly Ile Leu Leu Ala Trp Leu Val Thr Arg Phe Asn Phe
                 85                  90                  95

Pro Gly Arg Gln Leu Leu Leu Thr Leu Leu Asp Ile Pro Phe Ala Val
            100                 105                 110

Ser Pro Val Val Ala Gly Leu Val Tyr Leu Leu Phe Tyr Gly Ser Asn
        115                 120                 125

Gly Pro Leu Gly Gly Trp Leu Asp Glu His Asn Leu Gln Ile Met Phe
130                 135                 140

Ser Trp Pro Gly Met Val Leu Val Thr Ile Phe Val Thr Cys Pro Phe
145                 150                 155                 160

Val Val Arg Glu Leu Val Pro Val Met Leu Ser Gln Gly Ser Gln Glu
                165                 170                 175

Asp Glu Ala Ala Ile Leu Leu Gly Ala Ser Gly Trp Gln Met Phe Arg
            180                 185                 190

Arg Val Thr Leu Pro Asn Ile Arg Trp Ala Leu Leu Tyr Gly Val Val
        195                 200                 205

Leu Thr Asn Ala Arg Ala Ile Gly Glu Phe Gly Ala Val Ser Val Val
210                 215                 220

Ser Gly Ser Ile Arg Gly Glu Thr Leu Ser Leu Pro Leu Gln Ile Glu
225                 230                 235                 240

Leu Leu Glu Gln Asp Tyr Asn Thr Val Gly Ser Phe Thr Ala Ala Ala
                245                 250                 255

Leu Leu Thr Leu Met Ala Ile Ile Thr Leu Phe Leu Lys Ser Met Leu
            260                 265                 270

Gln Trp Arg Leu Glu Asn Gln Glu Lys Arg Ala Gln Gln Glu Glu His
        275                 280                 285

His Glu His
290

<210> SEQ ID NO 18
<211> LENGTH: 365
<212> TYPE: PRT
<213> ORGANISM: Escherichia coli

<400> SEQUENCE: 18

Met Ser Ile Glu Ile Ala Asn Ile Lys Lys Ser Phe Gly Arg Thr Gln
  1               5                  10                  15

Val Leu Asn Asp Ile Ser Leu Asp Ile Pro Ser Gly Gln Met Val Ala
             20                  25                  30

Leu Leu Gly Pro Ser Gly Ser Gly Lys Thr Thr Leu Leu Arg Ile Ile
         35                  40                  45

Ala Gly Leu Glu His Gln Thr Ser Gly His Ile Arg Phe His Gly Thr
     50                  55                  60

Asp Val Ser Arg Leu His Ala Arg Asp Arg Lys Val Gly Phe Val Phe
 65                  70                  75                  80

Gln His Tyr Ala Leu Phe Arg His Met Thr Val Phe Asp Asn Ile Ala
                 85                  90                  95

Phe Gly Leu Thr Val Leu Pro Arg Glu Arg Pro Asn Ala Ala
            100                 105                 110

Ile Lys Ala Lys Val Thr Lys Leu Leu Glu Met Val Gln Leu Ala His
        115                 120                 125

Leu Ala Asp Arg Tyr Pro Ala Gln Leu Ser Gly Gly Gln Lys Gln Arg
130                 135                 140
```

Val Ala Leu Ala Arg Ala Leu Ala Val Glu Pro Gln Ile Leu Leu Leu
145                 150                 155                 160

Asp Glu Pro Phe Gly Ala Leu Asp Ala Gln Val Arg Lys Glu Leu Arg
                165                 170                 175

Arg Trp Leu Arg Gln Leu His Glu Glu Leu Lys Phe Thr Ser Val Phe
            180                 185                 190

Val Thr His Asp Gln Glu Glu Ala Thr Glu Val Ala Asp Arg Val Val
        195                 200                 205

Val Met Ser Gln Gly Asn Ile Glu Gln Ala Asp Ala Pro Asp Gln Val
    210                 215                 220

Trp Arg Glu Pro Ala Thr Arg Phe Val Leu Phe Met Gly Glu Val
225                 230                 235                 240

Asn Arg Leu Gln Gly Thr Ile Arg Gly Gly Gln Phe His Val Gly Ala
                245                 250                 255

His Arg Trp Pro Leu Gly Tyr Thr Pro Ala Tyr Gln Gly Pro Val Asp
            260                 265                 270

Leu Phe Leu Arg Pro Trp Glu Val Asp Ile Ser Arg Thr Ser Leu
        275                 280                 285

Asp Ser Pro Leu Pro Val Gln Val Leu Glu Ala Ser Pro Lys Gly His
290                 295                 300

Tyr Thr Gln Leu Val Val Gln Pro Leu Gly Trp Tyr Asn Glu Pro Leu
305                 310                 315                 320

Thr Val Val Met His Gly Asp Asp Ala Pro Gln Arg Gly Glu Arg Leu
                325                 330                 335

Phe Val Gly Leu Gln His Ala Arg Leu Tyr Asn Gly Asp Glu Arg Ile
            340                 345                 350

Glu Thr Arg Asp Glu Glu Leu Ala Leu Ala Gln Ser Ala
            355                 360                 365

<210> SEQ ID NO 19
<211> LENGTH: 338
<212> TYPE: PRT
<213> ORGANISM: Escherichia coli

<400> SEQUENCE: 19

Met Ala Val Asn Leu Leu Lys Lys Asn Ser Leu Ala Leu Val Ala Ser
1               5                   10                  15

Leu Leu Leu Ala Gly His Val Gln Ala Thr Glu Leu Leu Asn Ser Ser
            20                  25                  30

Tyr Asp Val Ser Arg Glu Leu Phe Ala Ala Leu Asn Pro Pro Phe Glu
        35                  40                  45

Gln Gln Trp Ala Lys Asp Asn Gly Gly Asp Lys Leu Thr Ile Lys Gln
    50                  55                  60

Ser His Ala Gly Ser Ser Lys Gln Ala Leu Ala Ile Leu Gln Gly Leu
65                  70                  75                  80

Lys Ala Asp Val Val Thr Tyr Asn Gln Val Thr Asp Val Gln Ile Leu
                85                  90                  95

His Asp Lys Gly Lys Leu Ile Pro Ala Asp Trp Gln Ser Arg Leu Pro
            100                 105                 110

Asn Asn Ser Ser Pro Phe Tyr Ser Thr Met Gly Phe Leu Val Arg Lys
        115                 120                 125

Gly Asn Pro Lys Asn Ile His Asp Trp Asn Asp Leu Val Arg Ser Asp
    130                 135                 140

Val Lys Leu Ile Phe Pro Asn Pro Lys Thr Ser Gly Asn Ala Arg Tyr 145                 150                 155                 160
Thr Tyr Leu Ala Ala Trp Gly Ala Ala Asp Lys Ala Asp Gly Gly Asp
                    165                 170                 175
Lys Gly Lys Thr Glu Gln Phe Met Thr Gln Phe Leu Lys Asn Val Glu
                    180                 185                 190
Val Phe Asp Thr Gly Gly Arg Gly Ala Thr Thr Thr Phe Ala Glu Arg
                    195                 200                 205
Gly Leu Gly Asp Val Leu Ile Ser Phe Glu Ser Glu Val Asn Asn Ile
                    210                 215                 220
Arg Lys Gln Tyr Glu Ala Gln Gly Phe Glu Val Val Ile Pro Lys Thr
225                 230                 235                 240
Asn Ile Leu Ala Glu Phe Pro Val Ala Trp Val Asp Lys Asn Val Gln
                    245                 250                 255
Ala Asn Gly Thr Glu Lys Ala Ala Lys Ala Tyr Leu Asn Trp Leu Tyr
                    260                 265                 270
Ser Pro Gln Ala Gln Thr Ile Ile Thr Asp Tyr Tyr Tyr Arg Val Asn
                    275                 280                 285
Asn Pro Glu Val Met Asp Lys Leu Lys Asp Lys Phe Pro Gln Thr Glu
                    290                 295                 300
Leu Phe Arg Val Glu Asp Lys Phe Gly Ser Trp Pro Glu Val Met Lys
305                 310                 315                 320
Thr His Phe Thr Ser Gly Gly Glu Leu Asp Lys Leu Leu Ala Ala Gly
                    325                 330                 335
Arg Asn

<210> SEQ ID NO 20
<211> LENGTH: 329
<212> TYPE: PRT
<213> ORGANISM: Escherichia coli

<400> SEQUENCE: 20

Met Asn Lys Trp Gly Val Gly Leu Thr Phe Leu Leu Ala Ala Thr Ser
1                   5                   10                  15
Val Met Ala Lys Asp Ile Gln Leu Leu Asn Val Ser Tyr Asp Pro Thr
                    20                  25                  30
Arg Glu Leu Tyr Glu Gln Tyr Asn Lys Ala Phe Ser Ala His Trp Lys
                    35                  40                  45
Gln Gln Thr Gly Asp Asn Val Val Ile Arg Gln Ser His Gly Gly Ser
                    50                  55                  60
Gly Lys Gln Ala Thr Ser Val Ile Asn Gly Ile Glu Ala Asp Val Val
65                  70                  75                  80
Thr Leu Ala Leu Ala Tyr Asp Val Asp Ala Ile Ala Glu Arg Gly Arg
                    85                  90                  95
Ile Asp Lys Glu Trp Ile Lys Arg Leu Pro Asp Asn Ser Ala Pro Tyr
                    100                 105                 110
Thr Ser Thr Ile Val Phe Leu Val Arg Lys Gly Asn Pro Lys Gln Ile
                    115                 120                 125
His Asp Trp Asn Asp Leu Ile Lys Pro Gly Val Ser Val Ile Thr Pro
                    130                 135                 140
Asn Pro Lys Ser Ser Gly Gly Ala Arg Trp Asn Tyr Leu Ala Ala Trp
145                 150                 155                 160
Gly Tyr Ala Leu His His Asn Asn Asp Gln Ala Lys Ala Gln Asp
                    165                 170                 175
Phe Val Arg Ala Leu Tyr Lys Asn Val Glu Val Leu Asp Ser Gly Ala

```
                    180                 185                 190
Arg Gly Ser Thr Asn Thr Phe Val Glu Arg Gly Ile Gly Asp Val Leu
            195                 200                 205

Ile Ala Trp Glu Asn Glu Ala Leu Leu Ala Ala Asn Glu Leu Gly Lys
210                 215                 220

Asp Lys Phe Glu Ile Val Thr Pro Ser Glu Ser Ile Leu Ala Glu Pro
225                 230                 235                 240

Thr Val Ser Val Val Asp Lys Val Val Glu Lys Lys Gly Thr Lys Glu
            245                 250                 255

Val Ala Glu Ala Tyr Leu Lys Tyr Leu Tyr Ser Pro Glu Gly Gln Glu
            260                 265                 270

Ile Ala Ala Lys Asn Tyr Tyr Arg Pro Arg Asp Ala Glu Val Ala Lys
            275                 280                 285

Lys Tyr Glu Asn Ala Phe Pro Lys Leu Lys Leu Phe Thr Ile Asp Glu
            290                 295                 300

Glu Phe Gly Gly Trp Thr Lys Ala Gln Lys Glu His Phe Ala Asn Gly
305                 310                 315                 320

Gly Thr Phe Asp Gln Ile Ser Lys Arg
                    325

<210> SEQ ID NO 21
<211> LENGTH: 277
<212> TYPE: PRT
<213> ORGANISM: Salmonella typhimurium

<400> SEQUENCE: 21

Met Leu Ala Val Ser Ser Arg Arg Val Leu Pro Gly Phe Thr Leu Ser
1               5                   10                  15

Leu Gly Thr Ser Leu Leu Phe Val Cys Leu Ile Leu Leu Leu Pro Leu
            20                  25                  30

Ser Ala Leu Val Met Gln Leu Ser Gln Met Ser Trp Ala Gln Tyr Trp
        35                  40                  45

Asp Val Val Thr Asn Pro Gln Val Val Ala Ala Tyr Lys Val Thr Leu
    50                  55                  60

Leu Ala Ala Phe Val Ala Ser Ile Phe Asn Gly Val Phe Gly Leu Leu
65                  70                  75                  80

Met Ala Trp Ile Leu Thr Arg Tyr Arg Phe Pro Gly Arg Thr Leu Leu
                85                  90                  95

Asp Ala Leu Met Asp Leu Pro Phe Ala Leu Pro Thr Ala Val Ala Gly
            100                 105                 110

Leu Thr Leu Ala Ser Leu Phe Ser Val Asn Gly Phe Tyr Gly Gln Phe
        115                 120                 125

Leu Ala Gln Phe Asp Ile Lys Val Thr Tyr Thr Trp Leu Gly Ile Ala
    130                 135                 140

Val Ala Met Ala Phe Thr Ser Ile Pro Phe Val Val Arg Thr Val Gln
145                 150                 155                 160

Pro Val Leu Glu Glu Leu Gly Pro Glu Tyr Glu Glu Ala Ala Gln Thr
                165                 170                 175

Leu Gly Ala Thr Arg Leu Gln Ser Phe Arg Lys Val Val Leu Pro Glu
            180                 185                 190

Leu Ser Pro Ala Leu Ile Ala Gly Val Ala Leu Ser Phe Thr Arg Ser
        195                 200                 205

Leu Gly Glu Phe Gly Ala Val Ile Phe Ile Ala Gly Asn Ile Ala Trp
    210                 215                 220
```

```
Lys Thr Glu Val Thr Ser Leu Met Ile Phe Val Arg Leu Gln Glu Phe
225                 230                 235                 240

Asp Tyr Pro Ala Ala Ser Ala Ile Ala Ser Val Ile Leu Ala Ala Ser
            245                 250                 255

Leu Leu Leu Leu Phe Ser Ile Asn Thr Leu Gln Ser Arg Phe Gly Arg
            260                 265                 270

Arg Val Val Gly His
        275

<210> SEQ ID NO 22
<211> LENGTH: 291
<212> TYPE: PRT
<213> ORGANISM: Salmonella typhimurium

<400> SEQUENCE: 22

Met Ala Glu Val Thr Gln Leu Lys Arg Tyr Asp Val Pro Arg Ile Asn
1               5                   10                  15

Trp Gly Lys Trp Phe Leu Ile Gly Val Gly Met Leu Val Ser Ala Phe
            20                  25                  30

Ile Leu Leu Val Pro Met Ile Tyr Ile Phe Val Gln Ala Phe Ser Lys
        35                  40                  45

Gly Leu Met Pro Val Leu Gln Asn Leu Ala Asp Pro Asp Met Leu His
    50                  55                  60

Ala Ile Trp Leu Thr Val Leu Ile Ala Leu Ile Ala Val Pro Val Asn
65                  70                  75                  80

Leu Val Phe Gly Ile Leu Leu Ala Trp Leu Val Thr Arg Phe Asn Phe
                85                  90                  95

Pro Gly Arg Gln Leu Leu Leu Thr Leu Leu Asp Ile Pro Phe Ala Val
            100                 105                 110

Ser Pro Val Val Ala Gly Leu Val Tyr Leu Leu Phe Tyr Gly Ser Asn
        115                 120                 125

Gly Pro Leu Gly Gly Trp Leu Asp Glu His Asn Leu Gln Met Met Phe
    130                 135                 140

Ser Trp Pro Gly Met Val Leu Val Thr Ile Phe Val Thr Cys Pro Phe
145                 150                 155                 160

Val Val Arg Glu Leu Val Pro Val Met Leu Ser Gln Gly Ser Gln Glu
                165                 170                 175

Asp Glu Ala Ala Ile Leu Leu Gly Ala Ser Gly Trp Gln Met Phe Arg
            180                 185                 190

Arg Val Thr Leu Pro Asn Ile Arg Trp Ala Leu Leu Tyr Gly Val Val
        195                 200                 205

Leu Thr Asn Ala Arg Ala Ile Gly Glu Phe Gly Ala Val Ser Val Val
    210                 215                 220

Ser Gly Ser Ile Arg Gly Glu Thr Leu Ser Leu Pro Leu Gln Ile Glu
225                 230                 235                 240

Leu Leu Glu Gln Asp Tyr Asn Thr Val Gly Ser Phe Thr Ala Ala Ala
            245                 250                 255

Leu Leu Thr Leu Met Ala Ile Ile Thr Leu Phe Leu Lys Ser Met Leu
            260                 265                 270

Gln Trp Arg Leu Glu Asn Gln Glu Lys Arg Ala Gln Gln Glu Glu Asn
        275                 280                 285

His Glu His
    290

<210> SEQ ID NO 23
```

```
<211> LENGTH: 365
<212> TYPE: PRT
<213> ORGANISM: Salmonella typhimurium

<400> SEQUENCE: 23

Met Ser Ile Glu Ile Ala Arg Ile Lys Lys Ser Phe Gly Arg Thr Gln
1               5                   10                  15

Val Leu Asn Asp Ile Ser Leu Asp Ile Pro Ser Gly Gln Met Val Ala
            20                  25                  30

Leu Leu Gly Pro Ser Gly Ser Gly Lys Thr Thr Leu Leu Arg Ile Ile
        35                  40                  45

Ala Gly Leu Glu His Gln Ser Ser Gly His Ile Arg Phe His Gly Thr
    50                  55                  60

Asp Val Ser Arg Leu His Ala Arg Glu Arg Lys Val Gly Phe Val Phe
65                  70                  75                  80

Gln His Tyr Ala Leu Phe Arg His Met Thr Val Phe Asp Asn Ile Ala
                85                  90                  95

Phe Gly Leu Thr Val Leu Pro Arg Arg Asp Arg Pro Thr Ala Ala Ala
            100                 105                 110

Ile Lys Thr Lys Val Thr Gln Leu Leu Glu Met Val Gln Leu Ala His
        115                 120                 125

Leu Ala Asp Arg Phe Pro Ala Gln Leu Ser Gly Gly Gln Lys Gln Arg
    130                 135                 140

Val Ala Leu Ala Arg Ala Leu Ala Val Glu Pro Gln Ile Leu Leu Leu
145                 150                 155                 160

Asp Glu Pro Phe Gly Ala Leu Asp Ala Gln Val Arg Lys Glu Leu Arg
                165                 170                 175

Arg Trp Leu Arg Gln Leu His Glu Glu Leu Lys Phe Thr Ser Val Phe
            180                 185                 190

Val Thr His Asp Gln Glu Glu Ala Thr Glu Val Ala Asp Arg Val Val
        195                 200                 205

Val Met Ser Gln Gly Asn Ile Glu Gln Ala Asp Ala Pro Asp Arg Val
    210                 215                 220

Trp Arg Glu Pro Ala Thr Arg Phe Val Leu Glu Phe Met Gly Glu Val
225                 230                 235                 240

Asn Arg Leu Thr Gly Thr Val Arg Gly Gly Gln Phe His Val Gly Ala
                245                 250                 255

His Arg Trp Pro Leu Gly Tyr Thr Pro Ala Tyr Gln Gly Pro Val Asp
            260                 265                 270

Leu Phe Leu Arg Pro Trp Glu Val Asp Ile Ser Arg Arg Thr Ser Leu
        275                 280                 285

Asp Ser Pro Leu Pro Val Gln Val Ile Glu Ala Ser Pro Lys Gly His
    290                 295                 300

Tyr Thr Gln Leu Val Val Gln Pro Leu Gly Trp Tyr His Asp Pro Leu
305                 310                 315                 320

Thr Val Val Met Ala Gly Glu Asp Val Pro Val Arg Gly Glu Arg Leu
                325                 330                 335

Phe Val Gly Leu Gln Lys Ala Arg Leu Tyr Asn Gly Asp Gln Arg Ile
            340                 345                 350

Glu Thr Arg Glu Glu Glu Leu Ala Leu Ala Gln Ser Ala
        355                 360                 365

<210> SEQ ID NO 24
<211> LENGTH: 338
<212> TYPE: PRT
```

<213> ORGANISM: Salmonella typhimurium

<400> SEQUENCE: 24

```
Met Ala Val Asn Leu Leu Lys Lys Arg Pro Leu Thr Leu Ala Ala Met
1               5                   10                  15
Leu Leu Leu Ala Gly Gln Ala Gln Ala Thr Glu Leu Leu Asn Ser Ser
            20                  25                  30
Tyr Asp Val Ser Arg Glu Leu Phe Ala Ala Leu Asn Pro Pro Phe Glu
        35                  40                  45
Gln Gln Trp Ala Lys Asp Asn Gly Asp Lys Leu Thr Ile Lys Gln
    50                  55                  60
Ser His Ala Gly Ser Ser Lys Gln Ala Leu Ala Ile Leu Gln Gly Leu
65                  70                  75                  80
Lys Ala Asp Val Val Thr Tyr Asn Gln Val Thr Asp Val Gln Ile Leu
                85                  90                  95
His Asp Lys Gly Lys Leu Ile Pro Ala Asp Trp Gln Ser Arg Leu Pro
            100                 105                 110
Asn Asn Ser Ser Pro Phe Tyr Ser Thr Met Gly Phe Leu Val Arg Lys
        115                 120                 125
Gly Asn Pro Lys Asn Ile His Asp Trp Ser Asp Leu Val Arg Ser Asp
    130                 135                 140
Val Lys Leu Ile Phe Pro Asn Pro Lys Thr Ser Gly Asn Ala Arg Tyr
145                 150                 155                 160
Thr Tyr Leu Ala Ala Trp Gly Ala Ala Asp Asn Ala Asp Gly Gly Asp
                165                 170                 175
Lys Ala Lys Thr Glu Gln Phe Met Thr Gln Phe Leu Lys Asn Val Glu
            180                 185                 190
Val Phe Asp Thr Gly Gly Arg Gly Ala Thr Thr Thr Phe Ala Glu Arg
        195                 200                 205
Gly Leu Gly Asp Val Leu Ile Ser Phe Glu Ser Glu Val Asn Asn Ile
    210                 215                 220
Arg Lys Gln Tyr Glu Ala Gln Gly Phe Glu Val Val Ile Pro Lys Thr
225                 230                 235                 240
Asn Ile Leu Ala Glu Phe Pro Val Ala Trp Val Asp Lys Asn Val Gln
                245                 250                 255
Ala Asn Gly Thr Glu Lys Ala Ala Lys Ala Tyr Leu Asn Trp Leu Tyr
            260                 265                 270
Ser Pro Gln Ala Gln Thr Ile Ile Thr His Tyr Tyr Arg Val Asn
        275                 280                 285
Asn Pro Glu Ile Met Gly Lys Gln Ala Asp Lys Phe Pro Gln Thr Glu
    290                 295                 300
Leu Phe Arg Val Glu Lys Phe Gly Ser Trp Pro Glu Val Met Lys
305                 310                 315                 320
Thr His Phe Ala Ser Gly Gly Glu Leu Asp Lys Leu Leu Ala Ala Gly
                325                 330                 335
Arg Lys
```

<210> SEQ ID NO 25
<211> LENGTH: 329
<212> TYPE: PRT
<213> ORGANISM: Salmonella typhimurium

<400> SEQUENCE: 25

```
Met Lys Lys Trp Gly Val Gly Phe Thr Leu Leu Leu Ala Ser Thr Ser
1               5                   10                  15
```

-continued

Ile Leu Ala Lys Asp Ile Gln Leu Leu Asn Val Ser Tyr Asp Pro Thr
            20                  25                  30

Arg Glu Leu Tyr Glu Gln Tyr Asn Lys Ala Phe Ser Ala His Trp Lys
        35                  40                  45

Gln Glu Thr Gly Asp Asn Val Val Ile Arg Gln Ser His Gly Gly Ser
    50                  55                  60

Gly Lys Gln Ala Thr Ser Val Ile Asn Gly Ile Glu Ala Asp Val Val
65                  70                  75                  80

Thr Leu Ala Leu Ala Tyr Asp Val Asp Ala Ile Ala Glu Arg Gly Arg
                85                  90                  95

Ile Asp Lys Asn Trp Ile Lys Arg Leu Pro Asp Asn Ser Ala Pro Tyr
            100                 105                 110

Thr Ser Thr Ile Val Phe Leu Val Arg Lys Gly Asn Pro Lys Gln Ile
        115                 120                 125

His Asp Trp Asn Asp Leu Ile Lys Pro Gly Val Ser Val Ile Thr Pro
    130                 135                 140

Asn Pro Lys Ser Ser Gly Gly Ala Arg Trp Asn Tyr Leu Ala Ala Trp
145                 150                 155                 160

Gly Tyr Ala Leu His His Asn Asn Asn Asp Gln Ala Lys Ala Gln Asp
                165                 170                 175

Phe Val Lys Ala Leu Phe Lys Asn Val Glu Val Leu Asp Ser Gly Ala
            180                 185                 190

Arg Gly Ser Thr Asn Thr Phe Val Glu Arg Gly Ile Gly Asp Val Leu
        195                 200                 205

Ile Ala Trp Glu Asn Glu Ala Leu Leu Ala Thr Asn Glu Leu Gly Lys
    210                 215                 220

Asp Lys Phe Glu Ile Val Thr Pro Ser Glu Ser Ile Leu Ala Glu Pro
225                 230                 235                 240

Thr Val Ser Val Val Asp Lys Val Val Glu Lys Lys Asp Thr Lys Ala
                245                 250                 255

Val Ala Glu Ala Tyr Leu Lys Tyr Leu Tyr Ser Pro Glu Gly Gln Glu
            260                 265                 270

Ile Ala Ala Lys Asn Phe Tyr Arg Pro Arg Asp Ala Asp Val Ala Lys
        275                 280                 285

Lys Tyr Asp Asp Ala Phe Pro Lys Leu Lys Leu Phe Thr Ile Asp Glu
    290                 295                 300

Val Phe Gly Gly Trp Ala Lys Ala Gln Lys His Phe Ala Asn Gly
305                 310                 315                 320

Gly Thr Phe Asp Gln Ile Ser Lys Arg
                325

<210> SEQ ID NO 26
<211> LENGTH: 560
<212> TYPE: PRT
<213> ORGANISM: Mycobacterium tuberculosis

<400> SEQUENCE: 26

Met Ile Pro Thr Met Thr Ser Ala Gly Trp Ala Pro Gly Val Val Gln
1               5                   10                  15

Phe Arg Glu Tyr Gln Arg Arg Trp Leu Arg Gly Asp Val Leu Ala Gly
            20                  25                  30

Leu Thr Val Ala Ala Tyr Leu Ile Pro Gln Ala Met Ala Tyr Ala Thr
        35                  40                  45

Val Ala Gly Leu Pro Pro Ala Ala Gly Leu Trp Ala Ser Ile Ala Pro

```
             50                  55                  60
Leu Ala Ile Tyr Ala Leu Leu Gly Ser Ser Arg Gln Leu Ser Ile Gly
 65                  70                  75                  80

Pro Glu Ser Ala Thr Ala Leu Met Thr Ala Ala Val Leu Ala Pro Met
                 85                  90                  95

Ala Ala Gly Asp Leu Arg Arg Tyr Ala Val Leu Ala Ala Thr Leu Gly
                100                 105                 110

Leu Leu Val Gly Leu Ile Cys Leu Leu Ala Gly Thr Ala Arg Leu Gly
                115                 120                 125

Phe Leu Ala Ser Leu Arg Ser Arg Pro Val Leu Val Gly Tyr Met Ala
                130                 135                 140

Gly Ile Ala Leu Val Met Ile Ser Ser Gln Leu Gly Thr Ile Thr Gly
145                 150                 155                 160

Thr Ser Val Glu Gly Asn Glu Phe Phe Ser Glu Val His Ser Phe Ala
                165                 170                 175

Thr Ser Val Thr Arg Val His Trp Pro Thr Phe Val Leu Ala Met Ser
                180                 185                 190

Val Leu Ala Leu Leu Thr Met Leu Thr Arg Trp Ala Pro Arg Ala Pro
                195                 200                 205

Gly Pro Ile Ile Ala Val Leu Ala Ala Thr Met Leu Val Ala Val Met
210                 215                 220

Ser Leu Asp Ala Lys Gly Ile Ala Ile Val Gly Arg Ile Pro Ser Gly
225                 230                 235                 240

Leu Pro Thr Pro Gly Val Pro Pro Val Ser Val Glu Asp Leu Arg Ala
                245                 250                 255

Leu Ile Ile Pro Ala Ala Gly Ile Ala Ile Val Thr Phe Thr Asp Gly
                260                 265                 270

Val Leu Thr Ala Arg Ala Phe Ala Ala Arg Arg Gly Gln Glu Val Asn
                275                 280                 285

Ala Asn Ala Glu Leu Arg Ala Val Gly Ala Cys Asn Ile Ala Ala Gly
                290                 295                 300

Leu Thr His Gly Phe Pro Val Ser Ser Ser Ser Arg Thr Ala Leu
305                 310                 315                 320

Ala Asp Val Val Gly Arg Thr Gln Leu Tyr Ser Leu Ile Ala Leu
                325                 330                 335

Gly Leu Val Val Ile Val Met Val Phe Ala Ser Gly Leu Leu Ala Met
                340                 345                 350

Phe Pro Ile Ala Ala Leu Gly Ala Leu Val Val Tyr Ala Ala Leu Arg
                355                 360                 365

Leu Ile Asp Leu Ser Glu Phe Arg Arg Leu Ala Arg Phe Arg Arg Ser
370                 375                 380

Glu Leu Met Leu Ala Leu Ala Thr Thr Ala Ala Val Leu Gly Leu Gly
385                 390                 395                 400

Val Phe Tyr Gly Val Leu Ala Ala Val Ala Leu Ser Ile Leu Glu Leu
                405                 410                 415

Leu Arg Arg Val Ala His Pro His Asp Ser Val Leu Gly Phe Val Pro
                420                 425                 430

Gly Ile Ala Gly Met His Asp Ile Asp Asp Tyr Pro Gln Ala Lys Arg
                435                 440                 445

Val Pro Gly Leu Val Val Tyr Arg Tyr Asp Ala Pro Leu Cys Phe Ala
450                 455                 460

Asn Ala Glu Asp Phe Arg Arg Arg Ala Leu Thr Val Val Asp Gln Asp
465                 470                 475                 480
```

```
Pro Gly Gln Val Glu Trp Phe Val Leu Asn Ala Glu Ser Asn Val Glu
            485                 490                 495

Val Asp Leu Thr Ala Leu Asp Ala Leu Asp Gln Leu Arg Thr Glu Leu
            500                 505                 510

Leu Arg Arg Gly Ile Val Phe Ala Met Ala Arg Val Lys Gln Asp Leu
            515                 520                 525

Arg Glu Ser Leu Arg Ala Ala Ser Leu Leu Asp Lys Ile Gly Glu Asp
            530                 535                 540

His Ile Phe Met Thr Leu Pro Thr Ala Val Gln Ala Phe Arg Arg Arg
545                 550                 555                 560

<210> SEQ ID NO 27
<211> LENGTH: 354
<212> TYPE: PRT
<213> ORGANISM: Bacillus subtilis

<400> SEQUENCE: 27

Met Glu Leu Ala Ala Ile Leu Phe Ser Leu Phe Phe Ala Met Asn Ile
1               5                   10                  15

Gly Ala Ser Gly Ala Ala Ser Met Gly Val Ala Tyr Gly Ser Gly
            20                  25                  30

Ala Ile Lys Lys Lys Thr Tyr Ala Leu Ile Leu Cys Ala Val Gly Val
            35                  40                  45

Phe Ala Gly Ala Val Ile Gly Gly Glu Val Val Lys Thr Ile Ser
        50                  55                  60

Ser Gly Ile Ile Pro Glu Gln Thr Ile Thr Leu Thr Val Cys Ile
65              70                  75                  80

Ile Ile Gly Ala Ala Leu Ser Leu Phe Thr Ala Asn Leu Leu Gly
            85                  90                  95

Ile Pro Leu Ser Thr Ser Glu Val Thr Val Gly Ala Val Val Gly Val
            100                 105                 110

Gly Val Ala Tyr Lys Val Leu Phe Val Asn Asn Leu Leu Ile Ile Val
            115                 120                 125

Ser Phe Trp Val Phe Val Pro Leu Phe Ala Phe Gly Phe Thr Tyr Phe
130                 135                 140

Val Ser Lys Leu Phe Arg Tyr Phe Lys Ile Glu Val Lys Ser Ser Lys
145                 150                 155                 160

Lys Gln Lys Ile Leu Gly Ile Val Leu Leu Val Ala Gly Phe Phe Glu
            165                 170                 175

Ala Phe Ser Ala Gly Met Asn Asn Val Ala Asn Ala Val Gly Pro Leu
            180                 185                 190

Val Ala Ala Gly Val Leu Asp Val Gly Lys Gly Thr Leu Tyr Gly Gly
            195                 200                 205

Ala Phe Val Ala Leu Gly Ala Leu Leu Leu Gly Arg Arg Val Leu Glu
210                 215                 220

Thr Asn Gly Lys Lys Ile Thr Arg Phe Ser Lys Gly Glu Gly Ile Leu
225                 230                 235                 240

Leu Ser Gly Thr Gly Ala Gly Leu Val Ile Ile Ser Ser Val Phe Gly
            245                 250                 255

Met Pro Val Pro Leu Ala Gln Val Thr Ser Ser Ile Ile Gly Ile
            260                 265                 270

Gly Met Ala Lys Asn Gly Pro Asn Val Phe His Lys Gln Val Val Gln
            275                 280                 285

Thr Met Leu Lys Val Trp Ile Val Ser Pro Phe Leu Ser Leu Ser Ile
```

```
            290                 295                 300
Ser Tyr Leu Leu Val Ser Leu Phe Leu Lys Ala Asp Tyr Tyr Ser Ile
305                 310                 315                 320

Phe Ile Met Val Ser Val Leu Leu Ala Ala Gly Gly Ala Ile Ser Leu
                325                 330                 335

Thr Lys Ala Ile Arg Lys Glu Arg Arg Ser Val His Glu Gln Gly Gly
            340                 345                 350

Gly Ile

<210> SEQ ID NO 28
<211> LENGTH: 302
<212> TYPE: PRT
<213> ORGANISM: Escherichia coli

<400> SEQUENCE: 28

Met Asp Gln Ile Arg Leu Thr His Leu Arg Gln Leu Glu Ala Glu Ser
1               5                   10                  15

Ile His Ile Ile Arg Glu Val Ala Ala Glu Phe Ser Asn Pro Val Met
                20                  25                  30

Leu Tyr Ser Ile Gly Lys Asp Ser Ser Val Met Leu His Leu Ala Arg
            35                  40                  45

Lys Ala Phe Tyr Pro Gly Thr Leu Pro Phe Pro Leu Leu His Val Asp
50                  55                  60

Thr Gly Trp Lys Phe Arg Glu Met Tyr Glu Phe Arg Asp Arg Thr Ala
65                  70                  75                  80

Lys Ala Tyr Gly Cys Glu Leu Leu Val His Lys Asn Pro Glu Gly Val
                85                  90                  95

Ala Met Gly Ile Asn Pro Phe Val His Gly Ser Ala Lys His Thr Asp
            100                 105                 110

Ile Met Lys Thr Glu Gly Leu Lys Gln Ala Leu Asn Lys Tyr Gly Phe
        115                 120                 125

Asp Ala Ala Phe Gly Gly Ala Arg Arg Asp Glu Glu Lys Ser Arg Ala
    130                 135                 140

Lys Glu Arg Ile Tyr Ser Phe Arg Asp Arg Phe His Arg Trp Asp Pro
145                 150                 155                 160

Lys Asn Gln Arg Pro Glu Leu Trp His Asn Tyr Asn Gly Gln Ile Asn
                165                 170                 175

Lys Gly Glu Ser Ile Arg Val Phe Pro Leu Ser Asn Trp Thr Glu Gln
            180                 185                 190

Asp Ile Trp Gln Tyr Ile Trp Leu Glu Asn Ile Asp Ile Val Pro Leu
        195                 200                 205

Tyr Leu Ala Ala Glu Arg Pro Val Leu Glu Arg Asp Gly Met Leu Met
    210                 215                 220

Met Ile Asp Asp Asn Arg Ile Asp Leu Gln Pro Gly Glu Val Ile Lys
225                 230                 235                 240

Lys Arg Met Val Arg Phe Arg Thr Leu Gly Cys Trp Pro Leu Thr Gly
                245                 250                 255

Ala Val Glu Ser Asn Ala Gln Thr Leu Pro Glu Ile Ile Glu Glu Met
            260                 265                 270

Leu Val Ser Thr Thr Ser Glu Arg Gln Gly Arg Val Ile Asp Arg Asp
        275                 280                 285

Gln Ala Gly Ser Met Glu Leu Lys Lys Arg Gln Gly Tyr Phe
    290                 295                 300
```

<210> SEQ ID NO 29
<211> LENGTH: 475
<212> TYPE: PRT
<213> ORGANISM: Escherichia coli

<400> SEQUENCE: 29

```
Met Asn Thr Ala Leu Ala Gln Gln Ile Ala Asn Glu Gly Gly Val Glu
 1               5                  10                  15

Ala Trp Met Ile Ala Gln Gln His Lys Ser Leu Leu Arg Phe Leu Thr
            20                  25                  30

Cys Gly Ser Val Asp Asp Gly Lys Ser Thr Leu Ile Gly Arg Leu Leu
        35                  40                  45

His Asp Thr Arg Gln Ile Tyr Glu Asp Gln Leu Ser Ser Leu His Asn
    50                  55                  60

Asp Ser Lys Arg His Gly Thr Gln Gly Glu Lys Leu Asp Leu Ala Leu
65                  70                  75                  80

Leu Val Asp Gly Leu Gln Ala Glu Arg Glu Gln Gly Ile Thr Ile Asp
                85                  90                  95

Val Ala Tyr Arg Tyr Phe Ser Thr Glu Lys Arg Lys Phe Ile Ile Ala
            100                 105                 110

Asp Thr Pro Gly His Glu Gln Tyr Thr Arg Asn Met Ala Thr Gly Ala
        115                 120                 125

Ser Thr Cys Glu Leu Ala Ile Leu Leu Ile Asp Ala Arg Lys Gly Val
    130                 135                 140

Leu Asp Gln Thr Arg Arg His Ser Phe Ile Ser Thr Leu Leu Gly Ile
145                 150                 155                 160

Lys His Leu Val Val Ala Ile Asn Lys Met Asp Leu Val Asp Tyr Ser
                165                 170                 175

Glu Glu Thr Phe Thr Arg Ile Arg Glu Asp Tyr Leu Thr Phe Ala Gly
            180                 185                 190

Gln Leu Pro Gly Asn Leu Asp Ile Arg Phe Val Pro Leu Ser Ala Leu
        195                 200                 205

Glu Gly Asp Asn Val Ala Ser Gln Ser Glu Ser Met Pro Trp Tyr Ser
    210                 215                 220

Gly Pro Thr Leu Leu Glu Val Leu Glu Thr Val Glu Ile Gln Arg Val
225                 230                 235                 240

Val Asp Ala Gln Pro Met Arg Phe Pro Val Gln Tyr Val Asn Arg Pro
                245                 250                 255

Asn Leu Asp Phe Arg Gly Tyr Ala Gly Thr Leu Ala Ser Gly Arg Val
            260                 265                 270

Glu Val Gly Gln Arg Val Lys Val Leu Pro Ser Gly Val Glu Ser Asn
        275                 280                 285

Val Ala Arg Ile Val Thr Phe Asp Gly Asp Arg Glu Glu Ala Phe Ala
    290                 295                 300

Gly Glu Ala Ile Thr Leu Val Leu Thr Asp Glu Ile Asp Ile Ser Arg
305                 310                 315                 320

Gly Asp Leu Leu Leu Ala Ala Asp Glu Ala Leu Pro Ala Val Gln Ser
                325                 330                 335

Ala Ser Val Asp Val Val Trp Met Ala Glu Gln Pro Leu Ser Pro Gly
            340                 345                 350

Gln Ser Tyr Asp Ile Lys Ile Ala Gly Lys Lys Thr Arg Ala Arg Val
        355                 360                 365

Asp Gly Ile Arg Tyr Gln Val Asp Ile Asn Asn Leu Thr Gln Arg Glu
    370                 375                 380
```

-continued

```
Val Glu Asn Leu Pro Leu Asn Gly Ile Gly Leu Val Asp Leu Thr Phe
385                 390                 395                 400

Asp Glu Pro Leu Val Leu Asp Arg Tyr Gln Gln Asn Pro Val Thr Gly
            405                 410                 415

Gly Leu Ile Phe Ile Asp Arg Leu Ser Asn Val Thr Val Gly Ala Gly
            420                 425                 430

Met Val His Glu Pro Val Ser Gln Ala Thr Ala Pro Ser Glu Phe
            435                 440                 445

Ser Ala Phe Glu Leu Glu Leu Asn Ala Leu Val Arg Arg His Phe Pro
450                 455                 460

His Trp Gly Ala Arg Asp Leu Leu Gly Asp Lys
465                 470                 475
```

<210> SEQ ID NO 30
<211> LENGTH: 511
<212> TYPE: PRT
<213> ORGANISM: Saccharomyces cerevisiae

<400> SEQUENCE: 30

```
Met Pro Ala Pro His Gly Gly Ile Leu Gln Asp Leu Ile Ala Arg Asp
1               5                   10                  15

Ala Leu Lys Lys Asn Glu Leu Leu Ser Glu Ala Gln Ser Ser Asp Ile
                20                  25                  30

Leu Val Trp Asn Leu Thr Pro Arg Gln Leu Cys Asp Ile Glu Leu Ile
            35                  40                  45

Leu Asn Gly Gly Phe Ser Pro Leu Thr Gly Phe Leu Asn Glu Asn Asp
        50                  55                  60

Tyr Ser Ser Val Val Thr Asp Ser Arg Leu Ala Asp Gly Thr Leu Trp
65              70                  75                  80

Thr Ile Pro Ile Thr Leu Asp Val Asp Glu Ala Phe Ala Asn Gln Ile
                85                  90                  95

Lys Pro Asp Thr Arg Ile Ala Leu Phe Gln Asp Asp Glu Ile Pro Ile
            100                 105                 110

Ala Ile Leu Thr Val Gln Asp Val Tyr Lys Pro Asn Lys Thr Ile Glu
        115                 120                 125

Ala Glu Lys Val Phe Arg Gly Asp Pro Glu His Pro Ala Ile Ser Tyr
130                 135                 140

Leu Phe Asn Val Ala Gly Asp Tyr Tyr Val Gly Gly Ser Leu Glu Ala
145                 150                 155                 160

Ile Gln Leu Pro Gln His Tyr Asp Tyr Pro Gly Leu Arg Lys Thr Pro
                165                 170                 175

Ala Gln Leu Arg Leu Glu Phe Gln Ser Arg Gln Trp Asp Arg Val Val
            180                 185                 190

Ala Phe Gln Thr Arg Asn Pro Met His Arg Ala His Arg Glu Leu Thr
        195                 200                 205

Val Arg Ala Ala Arg Glu Ala Asn Ala Lys Val Leu Ile His Pro Val
210                 215                 220

Val Gly Leu Thr Lys Pro Gly Asp Ile Asp His His Thr Arg Val Arg
225                 230                 235                 240

Val Tyr Gln Glu Ile Ile Lys Arg Tyr Pro Asn Gly Ile Ala Phe Leu
                245                 250                 255

Ser Leu Leu Pro Leu Ala Met Arg Met Ser Gly Asp Arg Glu Ala Val
            260                 265                 270

Trp His Ala Ile Ile Arg Lys Asn Tyr Gly Ala Ser His Phe Ile Val
        275                 280                 285
```

Gly Arg Asp His Ala Gly Pro Gly Lys Asn Ser Lys Gly Val Asp Phe
            290                 295                 300

Tyr Gly Pro Tyr Asp Ala Gln Glu Leu Val Glu Ser Tyr Lys His Glu
305                 310                 315                 320

Leu Asp Ile Glu Val Val Pro Phe Arg Met Val Thr Tyr Leu Pro Asp
                325                 330                 335

Glu Asp Arg Tyr Ala Pro Ile Asp Gln Ile Asp Thr Thr Lys Thr Arg
            340                 345                 350

Thr Leu Asn Ile Ser Gly Thr Glu Leu Arg Arg Leu Arg Val Gly
            355                 360                 365

Gly Glu Ile Pro Glu Trp Phe Ser Tyr Pro Val Val Lys Ile Leu
370                 375                 380

Arg Glu Ser Asn Pro Pro Arg Pro Lys Gln Gly Phe Ser Ile Val Leu
385                 390                 395                 400

Gly Asn Ser Leu Thr Val Ser Arg Glu Gln Leu Ser Ile Ala Leu Leu
                405                 410                 415

Ser Thr Phe Leu Gln Phe Gly Gly Arg Tyr Tyr Lys Ile Phe Glu
                420                 425                 430

His Asn Asn Lys Thr Glu Leu Leu Ser Leu Ile Gln Asp Phe Ile Gly
            435                 440                 445

Ser Gly Ser Gly Leu Ile Ile Pro Asn Gln Trp Glu Asp Asp Lys Asp
450                 455                 460

Ser Val Val Gly Lys Gln Asn Val Tyr Leu Leu Asp Thr Ser Ser Ser
465                 470                 475                 480

Ala Asp Ile Gln Leu Glu Ser Ala Asp Glu Pro Ile Ser His Ile Val
                485                 490                 495

Gln Lys Val Val Leu Phe Leu Glu Asp Asn Gly Phe Phe Val Phe
            500                 505                 510

<210> SEQ ID NO 31
<211> LENGTH: 389
<212> TYPE: PRT
<213> ORGANISM: Bacillus subtilis

<400> SEQUENCE: 31

Met Asn Gly Asn Glu Pro His Gly Gly Val Leu Ile Asn Arg Cys Asp
1               5                   10                  15

Pro Ala Cys His Phe Glu Gly Cys Ala Cys Gln Ala Glu Leu Asp Gln
                20                  25                  30

Leu Ala Leu Ser Asp Leu Glu Leu Ile Ala Ile Gly Gly Tyr Ser Pro
            35                  40                  45

Leu Thr Gly Phe Leu Gly Glu Lys Asp Tyr His Ser Val Val Lys Glu
50                  55                  60

Met Arg Leu Ala Asn Gly Leu Pro Trp Ser Leu Pro Ile Thr Leu Pro
65                  70                  75                  80

Val Gly Glu Lys Thr Ala Arg Gln Leu Ser Ala Gly Asp His Val Lys
                85                  90                  95

Leu Val Lys Asp Gly Val Thr Tyr Gly Met Ile Thr Val Thr Asp Ile
            100                 105                 110

Tyr Gln Pro Asp Lys Thr Gln Glu Ala Leu Ser Val Phe Lys Thr Asn
            115                 120                 125

Asp Pro Ala His Pro Gly Val Lys Lys Leu Leu Ala Arg Pro Asp Tyr
            130                 135                 140

Tyr Ile Gly Gly Pro Ile Thr Val Ser Ser Leu Pro Asp Lys Ser Phe

```
                   145                 150                 155                 160
          Glu Gln Phe Tyr Ala Thr Pro Ala Glu Thr Arg Ala Ala Phe Gln Lys
                           165                 170                 175

Leu Gly Trp Lys Thr Ile Val Gly Phe Gln Thr Arg Asn Pro Val His
                           180                 185                 190

Arg Ala His Glu Tyr Ile Gln Lys Thr Ala Leu Glu Thr Val Asp Gly
                           195                 200                 205

Leu Leu Leu His Pro Leu Val Gly Glu Thr Lys Ser Asp Asp Ile Pro
                           210                 215                 220

Ser Asp Ile Arg Met Glu Ser Tyr Gln Ala Leu Leu Asn His Tyr Tyr
          225                 230                 235                 240

Pro Lys Asp Arg Val Met Leu Ser Val Phe Pro Ala Ala Met Arg Tyr
                              245                 250                 255

Ala Gly Pro Arg Glu Ala Ile Phe His Ala Leu Val Arg Lys Asn Tyr
                              260                 265                 270

Gly Cys Thr His Phe Ile Val Gly Arg Asp His Ala Gly Val Gly Ser
                              275                 280                 285

Tyr Tyr Gly Thr Tyr Asp Ala Gln Asn Ile Phe Gln Ser Phe Thr Glu
                  290                 295                 300

Glu Glu Leu Gly Ile Lys Pro Leu Phe Phe Glu His Ser Phe Tyr Cys
          305                 310                 315                 320

Arg Lys Cys Gly Asn Met Gly Thr Ser Lys Thr Cys Pro His Ser Pro
                              325                 330                 335

Arg Asp His Ile His Leu Ser Gly Thr Lys Val Arg Glu Leu Leu Arg
                              340                 345                 350

Gln Gly Lys Lys Pro Pro Lys Glu Phe Ser Arg Pro Glu Val Ala Ala
                              355                 360                 365

Val Leu Ile Lys Gly Leu His Gln Gln Pro Val Ala Ile Lys Gln Asn
                  370                 375                 380

Ser Gly Glu Leu Gln
          385

<210> SEQ ID NO 32
          <211> LENGTH: 201
          <212> TYPE: PRT
          <213> ORGANISM: Escherichia coli

<400> SEQUENCE: 32

Met Ala Leu His Asp Glu Asn Val Val Trp His Ser His Pro Val Thr
          1               5                   10                  15

Val Gln Gln Arg Glu Leu His His Gly His Arg Gly Val Val Leu Trp
                          20                  25                  30

Phe Thr Gly Leu Ser Gly Ser Gly Lys Ser Thr Val Ala Gly Ala Leu
                      35                  40                  45

Glu Glu Ala Leu His Lys Leu Gly Val Ser Thr Tyr Leu Leu Asp Gly
              50                  55                  60

Asp Asn Val Arg His Gly Leu Cys Ser Asp Leu Gly Phe Ser Asp Ala
          65                  70                  75                  80

Asp Arg Lys Glu Asn Ile Arg Arg Val Gly Glu Val Ala Asn Leu Met
                          85                  90                  95

Val Glu Ala Gly Leu Val Val Leu Thr Ala Phe Ile Ser Pro His Arg
                      100                 105                 110

Ala Glu Arg Gln Met Val Arg Glu Arg Val Gly Glu Gly Arg Phe Ile
                      115                 120                 125
```

```
Glu Val Phe Val Asp Thr Pro Leu Ala Ile Cys Glu Ala Arg Asp Pro
            130                 135                 140

Lys Gly Leu Tyr Lys Lys Ala Arg Ala Gly Glu Leu Arg Asn Phe Thr
145                 150                 155                 160

Gly Ile Asp Ser Val Tyr Glu Ala Pro Glu Ser Ala Glu Ile His Leu
                165                 170                 175

Asn Gly Glu Gln Leu Val Thr Asn Leu Val Gln Gln Leu Leu Asp Leu
                180                 185                 190

Leu Arg Gln Asn Asp Ile Ile Arg Ser
                195                 200

<210> SEQ ID NO 33
<211> LENGTH: 581
<212> TYPE: PRT
<213> ORGANISM: Rattus norvegicus

<400> SEQUENCE: 33

Met Glu Ile Pro Gly Ser Leu Cys Lys Lys Val Lys Leu Ser Asn Asn
1               5                   10                  15

Ala Gln Asn Trp Gly Met Gln Arg Ala Thr Asn Val Thr Tyr Gln Ala
                20                  25                  30

His His Val Ser Arg Asn Lys Arg Gly Gln Val Val Gly Thr Arg Gly
            35                  40                  45

Gly Phe Arg Gly Cys Thr Val Trp Leu Thr Gly Leu Ser Gly Ala Gly
        50                  55                  60

Lys Thr Thr Val Ser Met Ala Leu Glu Glu Tyr Leu Val Cys His Gly
65                  70                  75                  80

Ile Pro Cys Tyr Thr Leu Asp Gly Asp Asn Ile Arg Gln Gly Leu Asn
                85                  90                  95

Lys Asn Leu Gly Phe Ser Pro Glu Asp Arg Glu Asn Val Arg Arg
                100                 105                 110

Ile Ala Glu Val Ala Lys Leu Phe Ala Asp Ala Gly Leu Val Cys Ile
            115                 120                 125

Thr Ser Phe Ile Ser Pro Tyr Thr Gln Val Arg Gln Gly Phe Thr Gly
        130                 135                 140

Ile Asp Ser Glu Tyr Glu Lys Pro Glu Ala Pro Glu Leu Val Leu Lys
145                 150                 155                 160

Thr Asp Ser Cys Asp Val Asn Asp Cys Val Gln Gln Val Val Glu Leu
                165                 170                 175

Leu Gln Glu Arg Asp Ile Val Pro Val Asp Ala Ser Tyr Glu Val Lys
                180                 185                 190

Glu Leu Tyr Val Pro Glu Asn Lys Leu His Leu Ala Lys Thr Asp Ala
            195                 200                 205

Glu Ala Leu Pro Ala Leu Lys Ile Asn Lys Val Asp Met Gln Trp Val
        210                 215                 220

Gln Val Leu Ala Glu Gly Trp Ala Thr Pro Leu Asn Gly Phe Met Arg
225                 230                 235                 240

Glu Arg Glu Tyr Leu Gln Cys Leu His Phe Asp Cys Leu Leu Asp Gly
                245                 250                 255

Gly Val Ile Asn Leu Ser Val Pro Ile Val Leu Thr Ala Thr Gln Glu
                260                 265                 270

Asp Lys Glu Arg Leu Asp Gly Cys Thr Ala Phe Ala Leu Val Tyr Glu
            275                 280                 285

Gly Arg Arg Val Ala Ile Leu Arg Asn Pro Glu Phe Phe Glu His Arg
        290                 295                 300
```

```
Lys Glu Glu Arg Cys Ala Arg Gln Trp Gly Thr Thr Cys Arg Ser His
305                 310                 315                 320

Pro Tyr Ile Lys Met Ile Leu Glu Gln Gly Asp Trp Leu Ile Gly Gly
            325                 330                 335

Asp Leu Gln Val Leu Asp Arg Ile Tyr Trp Asn Asp Gly Leu Asp Gln
                340                 345                 350

Tyr Arg Leu Thr Pro Ala Glu Leu Lys Gln Lys Phe Lys Asp Met Asn
            355                 360                 365

Ala Asp Ala Val Phe Ala Phe Gln Leu Arg Asn Pro Val His Asn Gly
370                 375                 380

His Ala Leu Leu Met Gln Asp Thr His Lys Gln Leu Leu Glu Arg Gly
385                 390                 395                 400

Tyr Arg Arg Pro Val Leu Leu Leu His Pro Leu Gly Gly Trp Thr Lys
                405                 410                 415

Asp Asp Asp Val Pro Leu Met Trp Arg Met Lys Gln His Ala Ala Val
                420                 425                 430

Leu Glu Glu Gly Ile Leu Asn Pro Glu Thr Thr Val Ala Ile Phe
            435                 440                 445

Pro Ser Pro Met Met Tyr Ala Gly Pro Thr Glu Val Gln Trp His Cys
450                 455                 460

Arg Ala Arg Met Val Ala Gly Ala Asn Phe Tyr Ile Val Gly Arg Asp
465                 470                 475                 480

Pro Ala Gly Met Pro His Pro Glu Thr Gly Lys Asp Leu Tyr Glu Pro
                485                 490                 495

Thr His Gly Ala Lys Val Leu Thr Met Ala Pro Gly Leu Ile Thr Leu
            500                 505                 510

Glu Ile Val Pro Phe Arg Val Ala Ala Tyr Asn Lys Lys Lys Lys Arg
            515                 520                 525

Met Asp Tyr Tyr Asp Ser Asp His His Glu Asp Phe Glu Phe Ile Ser
    530                 535                 540

Gly Thr Arg Met Arg Lys Leu Ala Arg Glu Gly Gln Lys Pro Pro Glu
545                 550                 555                 560

Gly Phe Met Ala Pro Lys Ala Trp Thr Val Leu Val Glu Tyr Tyr Lys
                565                 570                 575

Ser Leu Glu Lys Ala
            580

<210> SEQ ID NO 34
<211> LENGTH: 614
<212> TYPE: PRT
<213> ORGANISM: Rattus norvegicus

<400> SEQUENCE: 34

Met Ser Glu Ile Lys Lys Gln Lys Thr Asp Gln Gln Lys Ser Thr Asn
1               5                   10                  15

Val Val Tyr Gln Ala His His Val Ser Arg Asn Lys Arg Gly Gln Val
            20                  25                  30

Val Gly Thr Arg Gly Gly Phe Arg Gly Cys Thr Val Trp Leu Thr Gly
        35                  40                  45

Leu Ser Gly Ala Gly Lys Thr Thr Ile Ser Phe Ala Leu Glu Glu Tyr
    50                  55                  60

Leu Val Ser His Ala Ile Pro Cys Tyr Ser Leu Asp Gly Asp Asn Val
65                  70                  75                  80

Arg His Gly Leu Asn Lys Asn Leu Gly Phe Ser Ala Gly Asp Arg Glu
```

```
                    85                  90                  95
Glu Asn Ile Arg Arg Ile Ala Glu Val Ala Lys Leu Phe Ala Asp Ala
                100                 105                 110
Gly Leu Val Cys Ile Thr Ser Phe Ile Ser Pro Phe Ala Lys Asp Arg
                115                 120                 125
Glu Asn Ala Arg Lys Ile His Glu Ser Ala Gly Leu Pro Phe Phe Glu
                130                 135                 140
Ile Phe Val Asp Ala Pro Leu Asn Ile Cys Glu Ser Arg Asp Val Lys
145                 150                 155                 160
Gly Leu Tyr Lys Arg Ala Arg Ala Gly Glu Ile Lys Gly Phe Thr Gly
                165                 170                 175
Ile Asp Ser Asn Tyr Glu Lys Pro Glu Thr Pro Glu Cys Val Leu Lys
                180                 185                 190
Thr Asn Leu Ser Ser Val Ser Asp Cys Val Gln Gln Val Val Glu Leu
                195                 200                 205
Leu Gln Glu Gln Ser Ile Val Pro His Thr Thr Ile Lys Gly Ile His
                210                 215                 220
Glu Leu Phe Val Pro Glu Asn Lys Ile Asp Gln Ile Arg Ala Glu Leu
225                 230                 235                 240
Glu Thr Leu Pro Ser Leu Pro Ile Thr Lys Leu Asp Leu Gln Trp Val
                245                 250                 255
Gln Ile Leu Ser Glu Gly Trp Ala Thr Pro Leu Lys Gly Phe Met Arg
                260                 265                 270
Glu Lys Glu Tyr Leu Gln Thr Leu His Phe Asp Thr Leu Leu Asp Asp
                275                 280                 285
Gly Val Ile Asn Met Ser Ile Pro Ile Val Leu Pro Val Ser Gly Asp
                290                 295                 300
Asp Lys Ala Arg Leu Glu Gly Cys Ser Lys Phe Ala Leu Met Tyr Glu
305                 310                 315                 320
Gly Arg Arg Val Ala Leu Leu Gln Asp Pro Glu Phe Tyr Glu His Arg
                325                 330                 335
Lys Glu Glu Arg Cys Ser Arg Val Trp Gly Thr Ala Ser Ala Lys His
                340                 345                 350
Pro His Ile Lys Met Val Met Glu Gly Gly Asp Trp Leu Val Gly Gly
                355                 360                 365
Asp Leu Gln Val Leu Glu Arg Ile Arg Trp Asn Asp Gly Leu Asp Gln
                370                 375                 380
Tyr Arg Leu Thr Pro Leu Glu Leu Lys Gln Lys Cys Lys Asp Met Asp
385                 390                 395                 400
Ala Asp Ala Val Phe Ala Phe Gln Leu Arg Asn Pro Val His Asn Gly
                405                 410                 415
His Ala Leu Leu Met Gln Asp Thr Arg Arg Leu Leu Glu Arg Gly
                420                 425                 430
Tyr Lys His Pro Val Leu Leu Leu His Pro Leu Gly Gly Trp Thr Lys
                435                 440                 445
Asp Asp Asp Val Pro Leu Asp Trp Arg Met Lys Gln His Ala Ala Val
                450                 455                 460
Leu Glu Glu Gly Ile Leu Asp Pro Lys Ser Thr Ile Val Ala Ile Phe
465                 470                 475                 480
Pro Ser Pro Met Leu Tyr Ala Gly Pro Thr Glu Val Gln Trp His Cys
                485                 490                 495
Arg Cys Arg Met Ile Ala Gly Ala Asn Phe Tyr Ile Val Gly Arg Asp
                500                 505                 510
```

```
Pro Ala Gly Met Pro His Pro Glu Thr Lys Lys Asp Leu Tyr Glu Pro
            515                 520                 525

Thr His Gly Gly Lys Val Leu Ser Met Ala Pro Gly Leu Thr Ser Val
    530                 535                 540

Glu Ile Ile Pro Phe Arg Val Ala Ala Tyr Asn Lys Ile Lys Lys Ala
545                 550                 555                 560

Met Asp Phe Tyr Asp Pro Ala Arg His Asp Glu Phe Asp Phe Ile Ser
                565                 570                 575

Gly Thr Arg Met Arg Lys Leu Ala Arg Glu Gly Glu Asp Pro Pro Asp
            580                 585                 590

Gly Phe Met Ala Pro Lys Ala Trp Lys Val Leu Thr Asp Tyr Tyr Arg
        595                 600                 605

Ser Leu Glu Lys Ile Asn
    610
```

<210> SEQ ID NO 35
<211> LENGTH: 202
<212> TYPE: PRT
<213> ORGANISM: Saccharomyces cerevisiae

<400> SEQUENCE: 35

```
Met Ala Thr Asn Ile Thr Trp His Pro Asn Leu Thr Tyr Asp Glu Arg
1               5                   10                  15

Lys Ala Leu Arg Lys Gln Asp Gly Cys Thr Ile Trp Leu Thr Gly Leu
            20                  25                  30

Ser Ala Ser Gly Lys Ser Thr Ile Ala Cys Ala Leu Glu Gln Leu Leu
        35                  40                  45

Leu Gln Lys Asn Leu Ser Ala Tyr Arg Leu Asp Gly Asp Asn Ile Arg
    50                  55                  60

Phe Gly Leu Asn Lys Asp Leu Gly Phe Ser Glu Lys Asp Arg Asn Glu
65                  70                  75                  80

Asn Ile Arg Arg Ile Ser Glu Val Ser Lys Leu Phe Ala Asp Ser Cys
                85                  90                  95

Ala Ile Ser Ile Thr Ser Phe Ile Ser Pro Tyr Arg Val Asp Arg Asp
            100                 105                 110

Arg Ala Arg Glu Leu His Lys Glu Ala Gly Leu Lys Phe Ile Glu Ile
        115                 120                 125

Phe Val Asp Val Pro Leu Glu Val Ala Glu Gln Arg Asp Pro Lys Gly
    130                 135                 140

Leu Tyr Lys Lys Ala Arg Glu Gly Val Ile Lys Glu Phe Thr Gly Ile
145                 150                 155                 160

Ser Ala Pro Tyr Glu Ala Pro Lys Ala Pro Glu Leu His Leu Arg Thr
                165                 170                 175

Asp Gln Lys Thr Val Glu Glu Cys Ala Thr Ile Ile Tyr Glu Tyr Leu
            180                 185                 190

Ile Ser Glu Lys Ile Ile Arg Lys His Leu
        195                 200
```

<210> SEQ ID NO 36
<211> LENGTH: 199
<212> TYPE: PRT
<213> ORGANISM: Bacillus subtilis

<400> SEQUENCE: 36

```
Met Thr His Asn Pro Asn Ile Ile Trp His Pro Ala Ala Ile Ser Lys
1               5                   10                  15
```

```
Ser Asp Arg Gln Ser Leu Asn Gly His Lys Ser Cys Val Leu Trp Phe
             20                  25                  30

Thr Gly Leu Ser Gly Ser Gly Lys Ser Val Leu Ala Asn Ala Val Asp
             35                  40                  45

Glu Lys Leu Tyr Arg Lys Gly Ile Gln Ser Tyr Val Leu Asp Gly Asp
 50                  55                  60

Asn Ile Arg His Gly Leu Asn Lys Asp Leu Gly Phe Gln Thr Gly Asp
 65                  70                  75                  80

Arg Ile Glu Asn Ile Arg Arg Ile Gly Glu Val Ala Lys Leu Phe Val
                 85                  90                  95

Asp Ser Gly Gln Met Ile Leu Thr Ala Phe Ile Ser Pro Phe Arg Glu
                100                 105                 110

Asp Arg Asp Met Val Arg Ala Leu Phe Pro Lys Gly Glu Phe Phe Glu
            115                 120                 125

Ile Tyr Val Lys Cys Pro Leu His Val Cys Glu Gln Arg Asp Pro Lys
130                 135                 140

Gly Leu Tyr Lys Lys Ala Arg Asn Gly Glu Ile Lys His Phe Thr Gly
145                 150                 155                 160

Ile Asp Ser Pro Tyr Glu Ala Pro Leu Ser Pro Asp Phe Ile Ile Glu
                165                 170                 175

Ser Asp Gln Thr Ser Ile Ser Asp Gly Ala Asp Leu Ile Ile Asn Ala
            180                 185                 190

Leu Gln Asn Arg Gly Ile Ile
        195

<210> SEQ ID NO 37
<211> LENGTH: 246
<212> TYPE: PRT
<213> ORGANISM: Escherichia coli

<400> SEQUENCE: 37

Met Leu Asp Gln Val Cys Gln Leu Ala Arg Asn Ala Gly Asp Ala Ile
 1               5                  10                  15

Met Gln Val Tyr Asp Gly Thr Lys Pro Met Asp Val Val Ser Lys Ala
             20                  25                  30

Asp Asn Ser Pro Val Thr Ala Ala Asp Ile Ala Ala His Thr Val Ile
             35                  40                  45

Met Asp Gly Leu Arg Thr Leu Thr Pro Asp Val Pro Val Leu Ser Glu
 50                  55                  60

Glu Asp Pro Pro Gly Trp Glu Val Arg Gln His Trp Gln Arg Tyr Trp
 65                  70                  75                  80

Leu Val Asp Pro Leu Asp Gly Thr Lys Glu Phe Ile Lys Arg Asn Gly
                 85                  90                  95

Glu Phe Thr Val Asn Ile Ala Leu Ile Asp His Gly Lys Pro Ile Leu
                100                 105                 110

Gly Val Val Tyr Ala Pro Val Met Asn Val Met Tyr Ser Ala Ala Glu
            115                 120                 125

Gly Lys Ala Trp Lys Glu Glu Cys Gly Val Arg Lys Gln Ile Gln Val
130                 135                 140

Arg Asp Ala Arg Pro Pro Leu Val Val Ile Ser Arg Ser His Ala Asp
145                 150                 155                 160

Ala Glu Leu Lys Glu Tyr Leu Gln Gln Leu Gly Glu His Gln Thr Thr
                165                 170                 175

Ser Ile Gly Ser Ser Leu Lys Phe Cys Leu Val Ala Glu Gly Gln Ala
```

```
                    180                 185                 190
Gln Leu Tyr Pro Arg Phe Gly Pro Thr Asn Ile Trp Asp Thr Ala Ala
            195                 200                 205

Gly His Ala Val Ala Ala Ala Gly Ala His Val His Asp Trp Gln
        210                 215                 220

Gly Lys Pro Leu Asp Tyr Thr Pro Arg Glu Ser Phe Leu Asn Pro Gly
225                 230                 235                 240

Phe Arg Val Ser Ile Tyr
                245

<210> SEQ ID NO 38
<211> LENGTH: 357
<212> TYPE: PRT
<213> ORGANISM: Saccharomyces cerevisiae

<400> SEQUENCE: 38

Met Ala Leu Glu Arg Glu Leu Val Ala Thr Gln Ala Val Arg Lys
1               5                   10                  15

Ala Ser Leu Leu Thr Lys Arg Ile Gln Ser Glu Val Ile Ser His Lys
            20                  25                  30

Asp Ser Thr Thr Ile Thr Lys Asn Asp Asn Ser Pro Val Thr Thr Gly
        35                  40                  45

Asp Tyr Ala Ala Gln Thr Ile Ile Ile Asn Ala Ile Lys Ser Asn Phe
    50                  55                  60

Pro Asp Asp Lys Val Val Gly Glu Glu Ser Ser Ser Gly Leu Ser Asp
65                  70                  75                  80

Ala Phe Val Ser Gly Ile Leu Asn Glu Ile Lys Ala Asn Asp Glu Val
                85                  90                  95

Tyr Asn Lys Asn Tyr Lys Lys Asp Asp Phe Leu Phe Thr Asn Asp Gln
            100                 105                 110

Phe Pro Leu Lys Ser Leu Glu Asp Val Arg Gln Ile Ile Asp Phe Gly
        115                 120                 125

Asn Tyr Glu Gly Gly Arg Lys Gly Arg Phe Trp Cys Leu Asp Pro Ile
    130                 135                 140

Asp Gly Thr Lys Gly Phe Leu Arg Gly Glu Gln Phe Ala Val Cys Leu
145                 150                 155                 160

Ala Leu Ile Val Asp Gly Val Val Gln Leu Gly Cys Ile Gly Cys Pro
                165                 170                 175

Asn Leu Val Leu Ser Ser Tyr Gly Ala Gln Asp Leu Lys Gly His Glu
            180                 185                 190

Ser Phe Gly Tyr Ile Phe Arg Ala Val Arg Gly Leu Gly Ala Phe Tyr
        195                 200                 205

Ser Pro Ser Ser Asp Ala Glu Ser Trp Thr Lys Ile His Val Arg His
    210                 215                 220

Leu Lys Asp Thr Lys Asp Met Ile Thr Leu Glu Gly Val Glu Lys Gly
225                 230                 235                 240

His Ser Ser His Asp Glu Gln Thr Ala Ile Lys Asn Lys Leu Asn Ile
                245                 250                 255

Ser Lys Ser Leu His Leu Asp Ser Gln Ala Lys Tyr Cys Leu Leu Ala
            260                 265                 270

Leu Gly Leu Ala Asp Val Tyr Leu Arg Leu Pro Ile Lys Leu Ser Tyr
        275                 280                 285

Gln Glu Lys Ile Trp Asp His Ala Ala Gly Asn Val Ile Val His Glu
    290                 295                 300
```

```
Ala Gly Gly Ile His Thr Asp Ala Met Glu Asp Val Pro Leu Asp Phe
305                 310                 315                 320

Gly Asn Gly Arg Thr Leu Ala Thr Lys Gly Val Ile Ala Ser Ser Gly
            325                 330                 335

Pro Arg Glu Leu His Asp Leu Val Val Ser Thr Ser Cys Asp Val Ile
            340                 345                 350

Gln Ser Arg Asn Ala
            355

<210> SEQ ID NO 39
<211> LENGTH: 313
<212> TYPE: PRT
<213> ORGANISM: Bacillus subtilis

<400> SEQUENCE: 39

Met Lys Thr Glu Leu Ile Arg Thr Ile Ser Leu Tyr Asp Thr Ile Ile
1               5                   10                  15

Leu His Arg His Val Arg Pro Asp Pro Asp Ala Tyr Gly Ser Gln Cys
            20                  25                  30

Gly Leu Thr Glu Ile Leu Arg Glu Thr Tyr Pro Glu Lys Asn Ile Phe
        35                  40                  45

Ala Val Gly Thr Pro Glu Pro Ser Leu Ser Phe Leu Tyr Ser Leu Asp
    50                  55                  60

Glu Val Asp Asn Glu Thr Tyr Glu Gly Ala Leu Val Ile Val Cys Asp
65                  70                  75                  80

Thr Ala Asn Gln Glu Arg Ile Asp Asp Gln Arg Tyr Pro Ser Gly Ala
            85                  90                  95

Lys Leu Met Lys Ile Asp His His Pro Asn Glu Asp Pro Tyr Gly Asp
            100                 105                 110

Leu Leu Trp Val Asp Thr Ser Ala Ser Val Ser Glu Met Ile Tyr
            115                 120                 125

Glu Leu Tyr Leu Glu Gly Lys Glu His Gly Trp Lys Leu Asn Thr Lys
130                 135                 140

Ala Ala Glu Leu Ile Tyr Ala Gly Ile Val Gly Asp Thr Gly Arg Phe
145                 150                 155                 160

Leu Phe Pro Asn Thr Thr Glu Lys Thr Leu Lys Tyr Ala Gly Glu Leu
            165                 170                 175

Ile Gln Tyr Pro Phe Ser Ser Ser Glu Leu Phe Asn Gln Leu Tyr Glu
            180                 185                 190

Thr Lys Leu Asn Val Val Lys Leu Asn Gly Phe Ile Phe Gln Asn Val
            195                 200                 205

Ser Leu Ser Glu Asn Gly Ala Ala Ser Val Phe Ile Lys Lys Asp Thr
210                 215                 220

Leu Glu Lys Phe Gly Thr Thr Ala Ser Glu Ala Ser Gln Leu Val Gly
225                 230                 235                 240

Thr Leu Gly Asn Ile Ser Gly Ile Arg Ala Trp Val Phe Phe Val Glu
            245                 250                 255

Glu Asp Asp Gln Ile Arg Val Arg Phe Arg Ser Lys Gly Pro Val Ile
            260                 265                 270

Asn Gly Leu Ala Arg Lys Tyr Asn Gly Gly His Pro Leu Ala Ser
            275                 280                 285

Gly Ala Ser Ile Tyr Ser Trp Asp Glu Ala Asp Arg Ile Leu Ala Asp
    290                 295                 300

Leu Glu Thr Leu Cys Lys Glu His Glu
305                 310
```

<210> SEQ ID NO 40
<211> LENGTH: 506
<212> TYPE: PRT
<213> ORGANISM: Flavobacterium johnsoniae

<400> SEQUENCE: 40

```
Met Asn Thr Ile Asn Glu Tyr Leu Ser Leu Glu Glu Phe Glu Ala Ile
1               5                   10                  15

Ile Phe Gly Asn Gln Lys Val Thr Ile Ser Asp Val Val Asn Arg
            20                  25                  30

Val Asn Glu Ser Phe Asn Phe Leu Lys Glu Phe Ser Gly Asn Lys Val
        35                  40                  45

Ile Tyr Gly Val Asn Thr Gly Phe Gly Pro Met Ala Gln Tyr Arg Ile
    50                  55                  60

Lys Glu Ser Asp Gln Ile Gln Leu Gln Tyr Asn Leu Ile Arg Ser His
65                  70                  75                  80

Ser Ser Gly Thr Gly Lys Pro Leu Ser Pro Val Cys Ala Lys Ala Ala
                85                  90                  95

Ile Leu Ala Arg Leu Asn Thr Leu Ser Leu Gly Asn Ser Gly Val His
            100                 105                 110

Pro Ser Val Ile Asn Leu Met Ser Glu Leu Ile Asn Lys Asp Ile Thr
        115                 120                 125

Pro Leu Ile Phe Glu His Gly Val Gly Ala Ser Gly Asp Leu Val
    130                 135                 140

Gln Leu Ser His Leu Ala Leu Val Leu Ile Gly Glu Gly Glu Val Phe
145                 150                 155                 160

Tyr Lys Gly Glu Arg Arg Pro Thr Pro Glu Val Phe Glu Ile Glu Gly
                165                 170                 175

Leu Lys Pro Ile Gln Val Glu Ile Arg Glu Gly Leu Ala Leu Ile Asn
            180                 185                 190

Gly Thr Ser Val Met Thr Gly Ile Gly Val Val Asn Val Tyr His Ala
        195                 200                 205

Lys Lys Leu Leu Asp Trp Ser Leu Lys Ser Ser Cys Ala Ile Asn Glu
    210                 215                 220

Leu Val Gln Ala Tyr Asp Asp His Phe Ser Ala Glu Leu Asn Gln Thr
225                 230                 235                 240

Lys Arg His Lys Gly Gln Gln Glu Ile Ala Leu Lys Met Arg Gln Asn
                245                 250                 255

Leu Ser Asp Ser Thr Leu Ile Arg Lys Arg Glu Asp His Leu Tyr Ser
            260                 265                 270

Gly Glu Asn Thr Glu Glu Ile Phe Lys Glu Lys Val Gln Glu Tyr Tyr
        275                 280                 285

Ser Leu Arg Cys Val Pro Gln Ile Leu Gly Pro Val Leu Glu Thr Ile
    290                 295                 300

Asn Asn Val Ala Ser Ile Leu Glu Asp Glu Phe Asn Ser Ala Asn Asp
305                 310                 315                 320

Asn Pro Ile Ile Asp Val Lys Asn Gln His Val Tyr His Gly Asn
                325                 330                 335

Phe His Gly Asp Tyr Ile Ser Leu Glu Met Asp Lys Leu Lys Ile Val
            340                 345                 350

Ile Thr Lys Leu Thr Met Leu Ala Glu Arg Gln Leu Asn Tyr Leu Leu
        355                 360                 365

Asn Ser Lys Ile Asn Glu Leu Leu Pro Pro Phe Val Asn Leu Gly Thr
```

```
            370                 375                 380
Leu Gly Phe Asn Phe Gly Met Gln Gly Val Gln Phe Thr Ala Thr Ser
385                 390                 395                 400

Thr Thr Ala Glu Ser Gln Met Leu Ser Asn Pro Met Tyr Val His Ser
                405                 410                 415

Ile Pro Asn Asn Asn Asp Asn Gln Asp Ile Val Ser Met Gly Thr Asn
                420                 425                 430

Ser Ala Val Ile Thr Ser Lys Val Ile Glu Asn Ala Phe Glu Val Leu
                435                 440                 445

Ala Ile Glu Met Ile Thr Ile Val Gln Ala Ile Asp Tyr Leu Gly Gln
                450                 455                 460

Lys Asp Lys Ile Ser Ser Val Ser Lys Lys Trp Tyr Asp Glu Ile Arg
465                 470                 475                 480

Asn Ile Ile Pro Thr Phe Lys Glu Asp Gln Val Met Tyr Pro Phe Val
                485                 490                 495

Gln Lys Val Lys Asp His Leu Ile Asn Asn
                500                 505

<210> SEQ ID NO 41
<211> LENGTH: 552
<212> TYPE: PRT
<213> ORGANISM: Herpetosiphon aurantiacus

<400> SEQUENCE: 41

Met Ser Thr Thr Leu Ile Leu Thr Gly Glu Gly Leu Gly Ile Asp Asp
1               5                   10                  15

Val Val Arg Val Ala Arg His Gln Asp Arg Val Glu Leu Thr Thr Asp
                20                  25                  30

Pro Ala Ile Leu Ala Gln Ile Glu Ala Ser Cys Ala Tyr Ile Asn Gln
            35                  40                  45

Ala Val Lys Glu His Gln Pro Val Tyr Gly Val Thr Thr Gly Phe Gly
        50                  55                  60

Gly Met Ala Asn Val Ile Ile Ser Pro Glu Glu Ala Ala Glu Leu Gln
65              70                  75                  80

Asn Asn Ala Ile Trp Tyr His Lys Thr Gly Ala Gly Lys Leu Leu Pro
                85                  90                  95

Phe Thr Asp Val Arg Ala Ala Met Leu Leu Arg Ala Asn Ser His Met
            100                 105                 110

Arg Gly Ala Ser Gly Ile Arg Leu Glu Ile Ile Gln Arg Met Val Thr
        115                 120                 125

Phe Leu Asn Ala Asn Val Thr Pro His Val Arg Glu Phe Gly Ser Ile
130             135                 140

Gly Ala Ser Gly Asp Leu Val Pro Leu Ser Ile Thr Gly Ala Leu Leu
145             150                 155                 160

Leu Gly Thr Asp Gln Ala Phe Met Val Asp Phe Asn Gly Glu Thr Leu
                165                 170                 175

Asp Cys Ile Ser Ala Leu Glu Arg Gly Leu Pro Arg Leu Arg Leu
            180                 185                 190

Gln Pro Lys Glu Gly Leu Ala Met Met Asn Gly Thr Ser Val Met Thr
        195                 200                 205

Gly Ile Ala Ala Asn Cys Val His Asp Ala Arg Ile Leu Leu Ala Leu
    210                 215                 220

Ala Leu Glu Ala His Ala Leu Met Ile Gln Gly Leu Gln Gly Thr Asn
225             230                 235                 240
```

Gln Ser Phe His Pro Phe Ile His Arg His Lys Pro His Thr Gly Gln
                245                 250                 255

Val Trp Ala Ala Asp His Met Leu Glu Leu Leu Gln Gly Ser Gln Leu
            260                 265                 270

Ser Arg Asn Glu Leu Asp Gly Ser His Asp Tyr Arg Asp Gly Asp Leu
        275                 280                 285

Ile Gln Asp Arg Tyr Ser Leu Arg Cys Leu Pro Gln Phe Leu Gly Pro
    290                 295                 300

Ile Ile Asp Gly Met Ala Phe Ile Ser His His Leu Arg Val Glu Ile
305                 310                 315                 320

Asn Ser Ala Asn Asp Asn Pro Leu Ile Asp Thr Ala Ser Ala Ala Ser
                325                 330                 335

Tyr His Gly Gly Asn Phe Leu Gly Gln Tyr Ile Gly Val Gly Met Asp
            340                 345                 350

Gln Leu Arg Tyr Tyr Met Gly Leu Met Ala Lys His Leu Asp Val Gln
        355                 360                 365

Ile Ala Leu Leu Val Ser Pro Gln Phe Asn Asn Gly Leu Pro Ala Ser
    370                 375                 380

Leu Val Gly Asn Ile Gln Arg Lys Val Asn Met Gly Leu Lys Gly Leu
385                 390                 395                 400

Gln Leu Thr Ala Asn Ser Ile Met Pro Ile Leu Thr Phe Leu Gly Asn
                405                 410                 415

Ser Leu Ala Asp Arg Phe Pro Thr His Ala Glu Gln Phe Asn Gln Asn
            420                 425                 430

Ile Asn Ser Gln Gly Phe Gly Ser Ala Asn Leu Ala Arg Gln Thr Ile
        435                 440                 445

Gln Thr Leu Gln Gln Tyr Ile Ala Ile Thr Leu Met Phe Gly Val Gln
    450                 455                 460

Ala Val Asp Leu Arg Thr His Lys Leu Ala Gly His Tyr Asn Ala Ala
465                 470                 475                 480

Glu Leu Leu Ser Pro Leu Thr Ala Lys Ile Tyr His Ala Val Arg Ser
                485                 490                 495

Ile Val Lys His Pro Pro Ser Pro Glu Arg Pro Tyr Ile Trp Asn Asp
            500                 505                 510

Asp Glu Gln Val Leu Glu Ala His Ile Ser Ala Leu Ala His Asp Ile
        515                 520                 525

Ala Asn Asp Gly Ser Leu Val Ser Ala Val Glu Gln Thr Leu Ser Gly
    530                 535                 540

Leu Arg Ser Ile Ile Leu Phe Arg
545                 550

<210> SEQ ID NO 42
<211> LENGTH: 552
<212> TYPE: PRT
<213> ORGANISM: Herpetosiphon aurantiacus

<400> SEQUENCE: 42

Met Arg His Gln Val Thr Leu Thr Gly Ala Gly Leu Thr Ile Glu Asp
1               5                   10                  15

Val Val Arg Val Ala Arg His His Gln Pro Val Gly Leu Thr Asp Asn
            20                  25                  30

Pro Glu Ile Leu Gln Arg Ile Glu Asp Ser Cys Ala Tyr Ile Asn Asp
        35                  40                  45

Ala Val Lys Ala Ser Lys Pro Val Tyr Gly Val Thr Thr Gly Phe Gly
    50                  55                  60

```
Gly Met Ala Asp Val Val Ile Ser Ser Glu Glu Ala Ala Asp Leu Gln
 65                  70                  75                  80

Asn Asn Ala Ile Trp Tyr His Lys Thr Gly Ala Gly Lys Leu Leu Pro
                 85                  90                  95

Leu Ala Asp Val Arg Ala Ala Met Leu Leu Arg Ala Asn Ser His Met
            100                 105                 110

Arg Gly Val Ser Gly Ile Arg Leu Glu Ile Ile Gln Arg Met Met Thr
        115                 120                 125

Phe Leu Asn Ala Asn Val Thr Pro His Val Arg Glu Phe Gly Ser Ile
130                 135                 140

Gly Ala Ser Gly Asp Leu Val Pro Leu Ile Ser Ile Thr Gly Ala Leu
145                 150                 155                 160

Leu Gly Thr Asp Pro Ala Phe Arg Val Asp Phe Asp Gly Glu Asn Ile
                165                 170                 175

Asp Cys Leu Glu Ala Leu Glu Arg Leu Asn Leu Pro Arg Leu Glu Leu
            180                 185                 190

Leu Pro Lys Glu Gly Leu Ala Met Met Asn Gly Thr Ser Val Met Thr
        195                 200                 205

Gly Ile Ala Ser Asn Val Leu His Asp Ala Arg Ile Leu Leu Gly Leu
210                 215                 220

Ala Leu Asn Ile His Gly Leu Met Ile Gln Gly Leu Gln Gly Thr Asn
225                 230                 235                 240

Gln Ser Phe His Pro Phe Ile His Gln His Lys Ala His Thr Gly Gln
                245                 250                 255

Val Trp Ala Ala Asp His Met Leu Gln Ile Leu Glu Gly Ser Ala Leu
            260                 265                 270

Ser Arg Asp Glu Leu Asp Gly Arg His Glu Tyr Arg Glu Gly Asp Leu
        275                 280                 285

Ile Gln Asp Arg Tyr Ser Leu Arg Cys Leu Pro Gln Phe Leu Gly Pro
290                 295                 300

Ile Ile Asp Gly Met Ala Tyr Ile Thr His His Leu Arg Val Glu Ile
305                 310                 315                 320

Asn Ser Ala Asn Asp Asn Pro Leu Ile Asn Thr Glu Ala Gly Ala Ser
                325                 330                 335

Tyr His Gly Gly Asn Phe Leu Gly Gln Tyr Ile Gly Val Gly Met Asp
            340                 345                 350

Gln Leu Arg Tyr Tyr Met Gly Leu Met Ala Lys His Leu Asp Val Gln
        355                 360                 365

Ile Ala Leu Leu Val Ser Pro Gln Phe Asn Asn Gly Leu Ser Ala Ser
370                 375                 380

Leu Val Gly Asn Thr Asp Arg Lys Val Asn Met Gly Leu Lys Gly Leu
385                 390                 395                 400

Gln Ile Ser Gly Asn Ser Ile Met Pro Ile Leu Gly Phe Leu Gly Asn
                405                 410                 415

Ser Leu Ala Asp Arg Phe Pro Thr His Ala Glu Gln Phe Asn Gln Asn
            420                 425                 430

Ile Asn Ser Gln Gly Phe Gly Ser Ala Asn Leu Ala Arg Gln Thr Ile
        435                 440                 445

Glu Thr Leu Gln Gln Tyr Ile Ala Ile Ala Leu Ile Phe Gly Val Gln
450                 455                 460

Ala Val Asp Leu Arg Thr Phe Lys Arg Thr Gly His Tyr Asn Ala Val
465                 470                 475                 480
```

```
Glu Thr Leu Ser Pro Met Thr Ala Lys Leu Tyr Ser Ala Met Arg Glu
                485                 490                 495

Val Val Gly Lys Pro Ile Ser His Glu Arg Pro Tyr Ile Trp Asn Asp
            500                 505                 510

Asn Glu Gln Ala Leu Glu Gln His Ile Ser Ala Ile Val Ser Asp Ile
            515                 520                 525

Thr Asn Asp Gly Ile Ile Pro Gln Ala Ile Gln Glu Thr Leu Asp Ser
            530                 535                 540

Leu Arg Ser Ile Ile Leu Phe Ala
545                 550

<210> SEQ ID NO 43
<211> LENGTH: 523
<212> TYPE: PRT
<213> ORGANISM: Rhodobacter sphaeroides

<400> SEQUENCE: 43

Met Leu Ala Met Ser Pro Pro Lys Pro Ala Val Glu Leu Asp Arg His
1               5                   10                  15

Ile Asp Leu Asp Glu Ala His Ser Val Ala Ser Gly Ala Arg Ile
                20                  25                  30

Val Leu Ala Pro Pro Ala Arg Asp Arg Cys Arg Ala Ser Glu Ala Arg
            35                  40                  45

Leu Gly Ala Val Ile Arg Glu Ala Arg His Val Tyr Gly Leu Thr Thr
        50                  55                  60

Gly Phe Gly Pro Leu Ala Asn Arg Leu Val Ser Gly Glu Asn Val Arg
65                  70                  75                  80

Thr Leu Gln Ala Asn Leu Val His His Leu Ala Ser Gly Val Gly Pro
                85                  90                  95

Val Leu Asp Trp Thr Thr Ala Arg Ala Met Val Leu Ala Arg Leu Val
            100                 105                 110

Ala Ile Ala Gln Gly Ala Ser Gly Ala Ser Glu Gly Thr Ile Ala Arg
        115                 120                 125

Leu Ile Asp Leu Leu Asn Ser Glu Leu Ala Pro Ala Val Pro Met Arg
130                 135                 140

Gly Thr Val Gly Ala Ser Gly Asp Leu Thr Pro Leu Ala His Met Val
145                 150                 155                 160

Leu Cys Leu Gln Gly Arg Gly Asp Phe Leu Asp Arg Asp Gly Thr Arg
                165                 170                 175

Leu Asp Gly Ala Glu Gly Leu Arg Arg Gly Arg Leu Gln Pro Leu Asp
            180                 185                 190

Leu Ser His Arg Asp Ala Leu Ala Leu Val Asn Gly Thr Ser Ala Met
        195                 200                 205

Thr Gly Ile Ala Leu Val Asn Ala His Ala Cys Arg His Leu Gly Asn
    210                 215                 220

Trp Ala Val Ala Leu Thr Ala Leu Leu Ala Glu Cys Leu Gly Gly Arg
225                 230                 235                 240

Thr Glu Ala Trp Ala Ala Ala Leu Ser Asp Leu Arg Pro His Pro Gly
                245                 250                 255

Gln Lys Asp Ala Ala Ala Arg Leu Arg Ala Arg Val Asp Gly Ser Ala
            260                 265                 270

Arg Val Val Arg His Val Ile Ala Glu Arg Arg Leu Gly Ala Ser Asp
        275                 280                 285

Ile Gly Thr Glu Pro Glu Ala Gly Gln Asp Ala Tyr Ser Leu Arg Cys
    290                 295                 300
```

-continued

```
Ala Pro Gln Val Leu Gly Ala Gly Phe Asp Thr Leu Ala Trp His Asp
305                 310                 315                 320

Arg Val Leu Thr Ile Glu Leu Asn Ala Val Thr Asp Asn Pro Val Phe
            325                 330                 335

Pro Pro Asp Gly Ser Val Pro Ala Leu His Gly Gly Asn Phe Met Gly
        340                 345                 350

Gln His Val Ala Leu Thr Ser Asp Ala Leu Ala Thr Ala Val Thr Val
    355                 360                 365

Leu Ala Gly Leu Ala Glu Arg Gln Ile Ala Arg Leu Thr Asp Glu Arg
370                 375                 380

Leu Asn Arg Gly Leu Pro Pro Phe Leu His Arg Gly Pro Ala Gly Leu
385                 390                 395                 400

Asn Ser Gly Phe Met Gly Ala Gln Val Thr Ala Thr Ala Leu Leu Ala
                405                 410                 415

Glu Met Arg Ala Thr Gly Pro Ala Ser Ile His Ser Ile Ser Thr Asn
            420                 425                 430

Ala Ala Asn Gln Asp Val Val Ser Leu Gly Thr Ile Ala Ala Arg Leu
        435                 440                 445

Cys Arg Glu Lys Ile Asp Arg Trp Ala Glu Ile Leu Ala Ile Leu Ala
450                 455                 460

Leu Cys Leu Ala Gln Ala Ala Glu Leu Arg Cys Gly Ser Gly Leu Asp
465                 470                 475                 480

Gly Val Ser Pro Ala Gly Lys Lys Leu Val Gln Ala Leu Arg Glu Gln
                485                 490                 495

Phe Pro Pro Leu Glu Thr Asp Arg Pro Leu Gly Gln Glu Ile Ala Ala
            500                 505                 510

Leu Ala Thr His Leu Leu Gln Gln Ser Pro Val
            515                 520

<210> SEQ ID NO 44
<211> LENGTH: 510
<212> TYPE: PRT
<213> ORGANISM: Saccharothrix espanaensis

<400> SEQUENCE: 44

Met Thr Gln Val Val Glu Arg Gln Ala Asp Arg Leu Ser Ser Arg Glu
1               5                   10                  15

Tyr Leu Ala Arg Val Val Arg Ser Ala Gly Trp Asp Ala Gly Leu Thr
            20                  25                  30

Ser Cys Thr Asp Glu Glu Ile Val Arg Met Gly Ala Ser Ala Arg Thr
        35                  40                  45

Ile Glu Glu Tyr Leu Lys Ser Asp Lys Pro Ile Tyr Gly Leu Thr Gln
    50                  55                  60

Gly Phe Gly Pro Leu Val Leu Phe Asp Ala Asp Ser Glu Leu Glu Gln
65                  70                  75                  80

Gly Gly Ser Leu Ile Ser His Leu Gly Thr Gly Gln Gly Ala Pro Leu
                85                  90                  95

Ala Pro Glu Val Ser Arg Leu Ile Leu Trp Leu Arg Ile Gln Asn Met
            100                 105                 110

Arg Lys Gly Tyr Ser Ala Val Ser Pro Val Phe Trp Gln Lys Leu Ala
        115                 120                 125

Asp Leu Trp Asn Lys Gly Phe Thr Pro Ala Ile Pro Arg His Gly Thr
    130                 135                 140

Val Ser Ala Ser Gly Asp Leu Gln Pro Leu Ala His Ala Ala Leu Ala
```

-continued

```
            145                 150                 155                 160
        Phe Thr Gly Val Gly Glu Ala Trp Thr Arg Asp Ala Asp Gly Arg Trp
                        165                 170                 175
        Ser Thr Val Pro Ala Val Asp Ala Leu Ala Ala Leu Gly Ala Glu Pro
                        180                 185                 190
        Phe Asp Trp Pro Val Arg Glu Ala Leu Ala Phe Val Asn Gly Thr Gly
                        195                 200                 205
        Ala Ser Leu Ala Val Ala Val Leu Asn His Arg Ser Ala Leu Arg Leu
                        210                 215                 220
        Val Arg Ala Cys Ala Val Leu Ser Ala Arg Leu Ala Thr Leu Leu Gly
        225                 230                 235                 240
        Ala Asn Pro Glu His Tyr Asp Val Gly His Gly Val Ala Arg Gly Gln
                        245                 250                 255
        Val Gly Gln Leu Thr Ala Ala Glu Trp Ile Arg Gln Gly Leu Pro Arg
                        260                 265                 270
        Gly Met Val Arg Asp Gly Ser Arg Pro Leu Gln Glu Pro Tyr Ser Leu
                        275                 280                 285
        Arg Cys Ala Pro Gln Val Leu Gly Ala Val Leu Asp Gln Leu Asp Gly
                        290                 295                 300
        Ala Gly Asp Val Leu Ala Arg Glu Val Asp Gly Cys Gln Asp Asn Pro
        305                 310                 315                 320
        Ile Thr Tyr Glu Gly Glu Leu Leu His Gly Gly Asn Phe His Ala Met
                        325                 330                 335
        Pro Val Gly Phe Ala Ser Asp Gln Ile Gly Leu Ala Met His Met Ala
                        340                 345                 350
        Ala Tyr Leu Ala Glu Arg Gln Leu Gly Leu Leu Val Ser Pro Val Thr
                        355                 360                 365
        Asn Gly Asp Leu Pro Pro Met Leu Thr Pro Arg Ala Gly Arg Gly Ala
                        370                 375                 380
        Gly Leu Ala Gly Val Gln Ile Ser Ala Thr Ser Phe Val Ser Arg Ile
        385                 390                 395                 400
        Arg Gln Leu Val Phe Pro Ala Ser Leu Thr Thr Leu Pro Thr Asn Gly
                        405                 410                 415
        Trp Asn Gln Asp His Val Pro Met Ala Leu Asn Gly Ala Asn Ser Val
                        420                 425                 430
        Phe Glu Ala Leu Glu Leu Gly Trp Leu Thr Val Gly Ser Leu Ala Val
                        435                 440                 445
        Gly Val Ala Gln Leu Ala Ala Met Thr Gly His Ala Ala Glu Gly Val
                        450                 455                 460
        Trp Ala Glu Leu Ala Gly Ile Cys Pro Pro Leu Asp Ala Asp Arg Pro
        465                 470                 475                 480
        Leu Gly Ala Glu Val Arg Ala Ala Arg Asp Leu Leu Ser Ala His Ala
                        485                 490                 495
        Asp Gln Leu Leu Val Asp Glu Ala Asp Gly Lys Asp Phe Gly
                        500                 505                 510

<210> SEQ ID NO 45
<211> LENGTH: 519
<212> TYPE: PRT
<213> ORGANISM: Rheinheimera sp. A13L

<400> SEQUENCE: 45

Met Arg Ser Glu Gln Leu Thr Leu Glu Asp Val Glu Ala Ile Ala Leu
1               5                   10                  15
```

```
Gly Arg Gln Thr Leu Val Val Thr Glu Lys Gln Met His Ala Val Glu
             20                  25                  30

Asn Ala His Lys Phe Leu Cys Arg Ala Ile Ser Asp Arg Lys Arg Ile
             35                  40                  45

Tyr Gly Val Thr Thr Gly Tyr Gly Pro Leu Ala Thr Thr Glu Val Asp
 50                  55                  60

Pro Arg Gln Ser Ala Leu Leu Gln Gln Asn Leu Val His His Leu Cys
 65                  70                  75                  80

Ser Gly Val Gly Asp Pro Leu Thr His Pro Gln Val Arg Ala Met Met
             85                  90                  95

Val Ala Arg Leu Ile Ser Leu Leu Ser Gly His Ser Gly Ala Asn Pro
            100                 105                 110

Leu Leu Ile Lys Arg Met Gln Glu Trp Leu Asp Ala Asp Ile Val Pro
            115                 120                 125

Phe Ile Pro Cys Arg Gly Thr Val Gly Ala Ser Gly Asp Leu Thr Pro
            130                 135                 140

Leu Ala His Leu Ala Arg Ala Leu Ser Gly Gly Gly Lys Val Ser Ile
145                 150                 155                 160

Lys Gly Gly Leu Trp Ile Glu Ser Arg Asp Ala His Gln Gln Leu Gly
            165                 170                 175

Trp Gln Pro Leu Val Leu Lys Gly Lys Asp Ala Ile Ser Leu Val Asn
            180                 185                 190

Gly Thr Ser Ala Thr Val Gly Ile Ala Ala Leu Asn Ala Thr Ala Ala
            195                 200                 205

Glu Arg Ala Leu Lys Leu Ser Thr Leu Leu Val Leu Leu Tyr Ala Glu
210                 215                 220

Leu Leu Asn Gly His Arg Glu Ala Phe His Pro Ala Ile Gly Gln Leu
225                 230                 235                 240

Arg Pro His Pro Gly Gln Lys Leu His Ser Trp Leu Trp Ser Leu
            245                 250                 255

Ser Ala Ser Ser Asp Ala Leu Val Pro Trp Cys Ala Glu Ser Arg Asn
            260                 265                 270

Leu Asn Leu Met Gly Glu Asp Ile Gln Gln Asn Gln Pro Leu Leu Gln
            275                 280                 285

Asp Ala Tyr Thr Leu Arg Cys Ala Pro Gln Ala Leu Gly Ala Ala Leu
            290                 295                 300

Asp Val Ile Ser Gln His Ala Thr Thr Val Lys Ile Glu Leu Ser Ala
305                 310                 315                 320

Val Thr Asp Asn Pro Leu Leu Phe Ala Glu Asp Glu Leu Ile Leu His
            325                 330                 335

Gly Gly Asn Phe Phe Gly Gln His Leu Ala Phe Ala Ser Asp His Leu
            340                 345                 350

Asn Asn Ala Leu Ile Gln Met Ala Leu Tyr Ser Glu Arg Arg Ile Ala
            355                 360                 365

Arg Ile Thr Asp Pro Leu Arg Asn Lys Gly Leu Pro Ala Phe Met Gln
            370                 375                 380

Pro Leu Asp Thr Gly Leu His Ser Gly Phe Met Gly Ala Gln Val Cys
385                 390                 395                 400

Ala Thr Ser Leu Val Ala Glu Leu Arg Ser Gln Ala Met Pro Ala Ser
            405                 410                 415

Ile Gln Ser Ile Pro Thr Asn Ala Asp Asn Gln Asp Ile Val Pro Leu
            420                 425                 430

Gly Thr Ile Ala Ala Arg Arg Ala Ser Thr Ser Leu Thr Gln Leu Tyr
```

```
            435                 440                 445
Gln Ile Leu Ala Ile Glu Ala Leu Val Leu Val Gln Gly Ala Glu Leu
    450                 455                 460
Lys Asn Thr His Ser Phe Ser His Ser Ser Gln Val Val Cys Ala Trp
465                 470                 475                 480
Leu Arg Gln Tyr Ala Leu Pro Leu Lys Glu Asp Arg Ala Leu Ser Glu
                485                 490                 495
Asp Ile Thr Arg Val Ala Glu Ala Leu Ile Asp Pro Asp Lys Val Lys
            500                 505                 510
Ser Leu Ile Glu Leu Leu Ala
            515

<210> SEQ ID NO 46
<211> LENGTH: 713
<212> TYPE: PRT
<213> ORGANISM: Rhodotorula mucilaginosa

<400> SEQUENCE: 46

Met Ala Pro Ser Val Asp Ser Ile Ala Thr Ser Val Ala Asn Ser Leu
1               5                   10                  15
Ser Asn Gly Leu His Ala Ala Ala Ala Asn Gly Gly Asp Val His
            20                  25                  30
Lys Lys Thr Ala Gly Ala Gly Ser Leu Leu Pro Thr Thr Glu Thr Thr
        35                  40                  45
Gln Leu Asp Ile Val Glu Arg Ile Leu Ala Asp Ala Gly Ala Thr Asp
    50                  55                  60
Gln Ile Lys Leu Asp Gly Tyr Thr Leu Thr Leu Gly Asp Val Val Gly
65                  70                  75                  80
Ala Ala Arg Arg Gly Arg Ser Val Lys Val Ala Asp Ser Pro His Ile
                85                  90                  95
Arg Glu Lys Ile Asp Ala Ser Val Glu Phe Leu Arg Thr Gln Leu Asp
            100                 105                 110
Asn Ser Val Tyr Gly Val Thr Thr Gly Phe Gly Gly Ser Ala Asp Thr
        115                 120                 125
Arg Thr Glu Asp Ala Ile Ser Leu Gln Lys Ala Leu Leu Glu His Gln
    130                 135                 140
Leu Cys Gly Val Leu Pro Thr Ser Met Asp Gly Phe Ala Leu Gly Arg
145                 150                 155                 160
Gly Leu Glu Asn Ser Leu Pro Leu Glu Val Val Arg Gly Ala Met Thr
                165                 170                 175
Ile Arg Val Asn Ser Leu Thr Arg Gly His Ser Ala Val Arg Ile Val
            180                 185                 190
Val Leu Glu Ala Leu Thr Asn Phe Leu Asn His Gly Ile Thr Pro Ile
        195                 200                 205
Val Pro Leu Arg Gly Thr Ile Ser Ala Ser Gly Asp Leu Ser Pro Leu
    210                 215                 220
Ser Tyr Ile Ala Ala Ser Ile Thr Gly His Pro Asp Ser Lys Val His
225                 230                 235                 240
Val Asp Gly Lys Ile Met Ser Ala Gln Glu Ala Ile Ala Leu Lys Gly
                245                 250                 255
Leu Gln Pro Val Val Leu Gly Pro Lys Glu Gly Leu Gly Leu Val Asn
            260                 265                 270
Gly Thr Ala Val Ser Ala Ser Met Ala Thr Leu Ala Leu Thr Asp Ala
        275                 280                 285
```

```
-continued

His Val Leu Ser Leu Leu Ala Gln Ala Leu Thr Ala Leu Thr Val Glu
    290                 295                 300
Ala Met Val Gly His Ala Gly Ser Phe His Pro Phe Leu His Asp Val
305                 310                 315                 320
Thr Arg Pro His Pro Thr Gln Ile Glu Val Ala Arg Asn Ile Arg Thr
                325                 330                 335
Leu Leu Glu Gly Ser Lys Tyr Ala Val His His Glu Thr Glu Val Lys
            340                 345                 350
Val Lys Asp Asp Glu Gly Ile Leu Arg Gln Asp Arg Tyr Pro Leu Arg
        355                 360                 365
Cys Ser Pro Gln Trp Leu Gly Pro Leu Val Ser Asp Met Ile His Ala
370                 375                 380
His Ala Val Leu Ser Leu Glu Ala Gly Gln Ser Thr Thr Asp Asn Pro
385                 390                 395                 400
Leu Ile Asp Leu Glu Asn Lys Met Thr His His Gly Gly Ala Phe Met
                405                 410                 415
Ala Ser Ser Val Gly Asn Thr Met Glu Lys Thr Arg Leu Ala Val Ala
            420                 425                 430
Leu Met Gly Lys Val Ser Phe Thr Gln Leu Thr Glu Met Leu Asn Ala
        435                 440                 445
Gly Met Asn Arg Ala Leu Pro Ser Cys Leu Ala Ala Glu Asp Pro Ser
450                 455                 460
Leu Ser Tyr His Cys Lys Gly Leu Asp Ile Ala Ala Ala Tyr Thr
465                 470                 475                 480
Ser Glu Leu Gly His Leu Ala Asn Pro Val Ser Thr His Val Gln Pro
                485                 490                 495
Ala Glu Met Gly Asn Gln Ala Ile Asn Ser Leu Ala Leu Ile Ser Ala
            500                 505                 510
Arg Arg Thr Ala Glu Ala Asn Asp Val Leu Ser Leu Leu Leu Ala Thr
        515                 520                 525
His Leu Tyr Cys Val Leu Gln Ala Val Asp Leu Arg Ala Met Glu Phe
        530                 535                 540
Glu His Thr Lys Ala Phe Glu Pro Met Val Thr Glu Leu Leu Lys Gln
545                 550                 555                 560
His Phe Gly Ala Leu Ala Thr Ala Glu Val Glu Asp Lys Val Arg Lys
                565                 570                 575
Ser Ile Tyr Lys Arg Leu Gln Gln Asn Asn Ser Tyr Asp Leu Glu Gln
            580                 585                 590
Arg Trp His Asp Thr Phe Ser Val Ala Thr Gly Ala Val Val Glu Ala
        595                 600                 605
Leu Ala Gly Gln Glu Val Ser Leu Ala Ser Leu Asn Ala Trp Lys Val
610                 615                 620
Ala Cys Ala Glu Lys Ala Ile Ala Leu Thr Arg Ser Val Arg Asp Ser
625                 630                 635                 640
Phe Trp Ala Ala Pro Ser Ser Ser Pro Ala Leu Lys Tyr Leu Ser
                645                 650                 655
Pro Arg Thr Arg Val Leu Tyr Ser Phe Val Arg Glu Glu Val Gly Val
            660                 665                 670
Lys Ala Arg Arg Gly Asp Val Tyr Leu Gly Lys Gln Glu Val Thr Ile
        675                 680                 685
Gly Thr Asn Val Ser Arg Ile Tyr Glu Ala Ile Lys Ser Gly Cys Ile
690                 695                 700
Ala Pro Val Leu Val Lys Met Met Ala
```

```
705                710
```

<210> SEQ ID NO 47
<211> LENGTH: 689
<212> TYPE: PRT
<213> ORGANISM: Trichosporon cutaneum

<400> SEQUENCE: 47

```
Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
            20                  25                  30

Ala His Ser Gln Ala Thr Lys Thr Val Ser Ile Asp Gly His Thr Met
        35                  40                  45

Lys Val Gly Asp Val Val Ala Val Ala Arg His Gly Ala Lys Val Glu
    50                  55                  60

Leu Ala Ala Ser Val Ala Gly Pro Val Arg Ala Ser Val Asp Phe Lys
65                  70                  75                  80

Glu Ser Lys Lys His Thr Ser Ile Tyr Gly Val Thr Thr Gly Phe Gly
                85                  90                  95

Gly Ser Ala Asp Thr Arg Thr Ser Asp Thr Glu Ala Leu Gln Ile Ser
            100                 105                 110

Leu Leu Glu His Gln Leu Cys Gly Phe Leu Pro Thr Asp Ala Thr Tyr
        115                 120                 125

Glu Gly Met Leu Leu Ala Ala Met Pro Ile Pro Ile Val Arg Gly Ala
    130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Arg Gly Leu Val
                165                 170                 175

Pro Cys Val Pro Leu Arg Gly Thr Ile Ser Ala Ser Gly Asp Leu Ser
            180                 185                 190

Pro Leu Ser Tyr Ile Ala Gly Ala Ile Cys Gly His Pro Asp Val Lys
        195                 200                 205

Val Phe Asp Thr Ala Ala Ser Pro Pro Thr Val Leu Thr Ser Pro Glu
    210                 215                 220

Ala Ile Ala Lys Tyr Gly Leu Lys Thr Val Lys Leu Ala Ser Lys Glu
225                 230                 235                 240

Gly Leu Gly Leu Val Asn Gly Thr Ala Val Ser Ala Ala Gly Ala
                245                 250                 255

Leu Ala Leu Tyr Asp Ala Glu Cys Leu Ala Ile Met Ser Gln Thr Asn
            260                 265                 270

Thr Val Leu Thr Val Glu Ala Leu Asp Gly His Val Gly Ser Phe Ala
        275                 280                 285

Pro Phe Ile Gln Glu Ile Arg Pro His Ala Gly Gln Ile Glu Ala Ala
    290                 295                 300

Arg Asn Ile Arg His Met Leu Gly Gly Ser Lys Leu Ala Val His Glu
305                 310                 315                 320

Glu Ser Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Ala Leu Gly Leu Ala Arg Gln Gln Ile Glu Thr Glu Leu Asn Ser Thr
        355                 360                 365
```

```
Thr Asp Asn Pro Leu Ile Asp Val Glu Gly Gly Met Phe His His Gly
    370                 375                 380
Gly Asn Phe Gln Ala Met Ala Val Thr Ser Ala Met Asp Ser Ala Arg
385                 390                 395                 400
Ile Val Leu Gln Asn Leu Gly Lys Leu Ser Phe Ala Gln Val Thr Glu
                405                 410                 415
Leu Ile Asn Cys Glu Met Asn His Gly Leu Pro Ser Asn Leu Ala Gly
            420                 425                 430
Ser Glu Pro Ser Thr Asn Tyr His Cys Lys Gly Leu Asp Ile His Cys
        435                 440                 445
Gly Ala Tyr Cys Ala Glu Leu Gly Phe Leu Ala Asn Pro Met Ser Asn
    450                 455                 460
His Val Gln Ser Thr Glu Met His Asn Gln Ser Val Asn Ser Met Ala
465                 470                 475                 480
Phe Ala Ser Ala Arg Arg Thr Met Glu Ala Asn Glu Val Leu Ser Leu
                485                 490                 495
Leu Leu Gly Ser Gln Met Tyr Cys Ala Thr Gln Ala Leu Asp Leu Arg
            500                 505                 510
Val Met Glu Val Lys Phe Lys Met Ala Ile Val Lys Leu Leu Asn Glu
        515                 520                 525
Thr Leu Thr Lys His Phe Ala Ala Phe Leu Thr Pro Glu Gln Leu Ala
    530                 535                 540
Lys Leu Asn Thr His Ala Ala Ile Thr Leu Tyr Lys Arg Leu Asn Gln
545                 550                 555                 560
Thr Pro Ser Trp Asp Ser Ala Pro Arg Phe Glu Asp Ala Ala Lys His
                565                 570                 575
Leu Val Gly Val Ile Met Asp Ala Leu Met Val Asn Asp Asp Ile Thr
            580                 585                 590
Asp Leu Thr Asn Leu Pro Lys Trp Lys Lys Glu Phe Ala Lys Glu Ala
        595                 600                 605
Gly Asn Leu Tyr Arg Ser Ile Leu Val Ala Thr Thr Ala Asp Gly Arg
    610                 615                 620
Asn Asp Leu Glu Pro Ala Glu Tyr Leu Gly Gln Thr Arg Ala Val Tyr
625                 630                 635                 640
Glu Ala Val Arg Ser Glu Leu Gly Val Lys Val Arg Arg Gly Asp Val
                645                 650                 655
Ala Glu Gly Lys Ser Gly Lys Ser Ile Gly Ser Ser Val Ala Lys Ile
            660                 665                 670
Val Glu Ala Met Arg Asp Gly Arg Leu Met Gly Ala Val Gly Lys Met
        675                 680                 685
Phe

<210> SEQ ID NO 48
<211> LENGTH: 716
<212> TYPE: PRT
<213> ORGANISM: Rhodosporidium toruloides

<400> SEQUENCE: 48

Met Ala Pro Ser Leu Asp Ser Ile Ser His Ser Phe Ala Asn Gly Val
1               5                   10                  15
Ala Ser Ala Lys Gln Ala Val Asn Gly Ala Ser Thr Asn Leu Ala Val
                20                  25                  30
Ala Gly Ser His Leu Pro Thr Thr Gln Val Thr Gln Val Asp Ile Val
            35                  40                  45
```

```
Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
    195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
            275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
            435                 440                 445

Asn Arg Gly Leu Pro Ser Cys Leu Ala Ala Glu Asp Pro Ser Leu Ser
450                 455                 460

Tyr His Cys Lys Gly Leu Asp Ile Ala Ala Ala Ala Tyr Thr Ser Glu
```

```
                465                 470                 475                 480
Leu Gly His Leu Ala Asn Pro Val Thr Thr His Val Gln Pro Ala Glu
                    485                 490                 495
Met Ala Asn Gln Ala Val Asn Ser Leu Ala Leu Ile Ser Ala Arg Arg
                500                 505                 510
Thr Thr Glu Ser Asn Asp Val Leu Ser Leu Leu Ala Thr His Leu
            515                 520                 525
Tyr Cys Val Leu Gln Ala Ile Asp Leu Arg Ala Ile Glu Phe Glu Phe
            530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
                580                 585                 590
Leu Val Pro Arg Trp His Asp Ala Phe Ser Phe Ala Ala Gly Thr Val
            595                 600                 605
Val Glu Val Leu Ser Ser Thr Ser Leu Ser Leu Ala Ala Val Asn Ala
        610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
                660                 665                 670
Leu Gly Val Lys Ala Arg Arg Gly Asp Val Phe Leu Gly Lys Gln Glu
            675                 680                 685
Val Thr Ile Gly Ser Asn Val Ser Lys Ile Tyr Glu Ala Ile Lys Ser
        690                 695                 700
Gly Arg Ile Asn Asn Val Leu Leu Lys Met Leu Ala
705                 710                 715

<210> SEQ ID NO 49
<211> LENGTH: 737
<212> TYPE: PRT
<213> ORGANISM: Phanerochaete chrysosporium

<400> SEQUENCE: 49

Met Pro Ser Arg Ile Asp Tyr Tyr Thr Ser Gly Asn Gly Tyr Ala
1               5                   10                  15
Gln Ser Arg Lys Ser Ser Ala Ile Tyr Pro Ala Ser Ala Ser Thr Gly
                20                  25                  30
His Ala Ala Pro Ser Thr Glu Arg Lys Pro Glu Leu Leu Asp Lys Phe
            35                  40                  45
Val Glu Ala Tyr Asp Glu Leu Gln Ser Tyr Arg Glu Gly Lys Pro Val
        50                  55                  60
Ile Val Asp Gly His Asn Leu Ser Ile Pro Ala Val Ala Ala Thr Ala
65                  70                  75                  80
Arg Phe Gly Ala Ala Val Val Leu Asp Glu Asn Pro Glu Thr His Glu
                85                  90                  95
Arg Val Leu Gln Ser Arg Arg Val Ile Val Asp Lys Val Ser Thr Gln
            100                 105                 110
Arg Ser Val Tyr Gly Val Ser Thr Gly Phe Gly Gly Ser Ala Asp Thr
        115                 120                 125
```

```
Arg Thr Ser Asp Pro Leu Gln Leu Gly His Ala Leu Leu Gln His Gln
    130                 135                 140

His Val Gly Val Leu Pro Thr Gln Thr Glu Ser Pro Leu Pro Ala Leu
145                 150                 155                 160

Pro Leu Gly Asp Pro Leu Ala Thr Thr Ser Met Pro Glu Ala Trp Val
                165                 170                 175

Arg Gly Ala Ile Leu Ile Arg Met Asn Ser Leu Ile Arg Gly His Ser
            180                 185                 190

Gly Val Arg Trp Glu Leu Ile Glu Lys Met Gly Glu Leu Leu Arg Glu
        195                 200                 205

Asn Ile Thr Pro Leu Val Pro Leu Arg Gly Ser Ile Ser Ala Ser Gly
210                 215                 220

Asp Leu Ser Pro Leu Ser Tyr Ile Ala Gly Thr Leu Ile Gly Ser Pro
225                 230                 235                 240

Ala Ile Arg Val Phe Asp Gly Pro Ala Ser Tyr Gly Ala Arg Arg Ile
                245                 250                 255

Leu Pro Ser Asn Ile Ala Leu Ala Asn His Gly Val Ala Pro Ile Pro
            260                 265                 270

Leu Ser Ser Lys Glu His Leu Gly Ile Leu Asn Gly Thr Ala Phe Ser
        275                 280                 285

Ala Ser Val Gly Ala Leu Ala Leu Asn Glu Ala Val His Leu Ser Leu
290                 295                 300

Leu Ala Gln Val Cys Thr Ala Met Gly Thr Glu Ala Met Ile Gly Ala
305                 310                 315                 320

Val Gly Ser Phe Asp Ala Phe Ile His Asp Thr Ala Arg Pro His Pro
                325                 330                 335

Gly Gln Val Glu Val Ala Arg Asn Val Arg Thr Leu Leu Glu Asp Ser
            340                 345                 350

Gln Met Ala Val Lys Ala Glu Asp Glu Val His Ile Ala Glu Asp Glu
        355                 360                 365

Gly Glu Leu Arg Gln Asp Arg Tyr Pro Leu Arg Thr Ala Ala Gln Phe
370                 375                 380

Leu Gly Pro Gln Ile Glu Asp Ile Leu Ser Ala His Glu Thr Val Thr
385                 390                 395                 400

Leu Glu Cys Asn Ser Thr Thr Asp Asn Pro Leu Ile Asp Gly Glu Thr
                405                 410                 415

Gly Thr Val His His Gly Gly Asn Phe Gln Ala Met Ala Val Thr Asn
            420                 425                 430

Ala Met Glu Lys Thr Arg Leu Ala Ile His His Ile Gly Lys Leu Leu
        435                 440                 445

Phe Ala Gln Ala Thr Glu Leu Ile Asn Pro Met Met Asn Arg Gly Leu
450                 455                 460

Pro Pro Asn Leu Ala Ala Thr Asp Pro Ser His Asn Tyr Phe Ala Lys
465                 470                 475                 480

Gly Val Asp Ile His Leu Ala Ala Tyr Val Gly Glu Leu Gly Phe Leu
                485                 490                 495

Ala Ser Pro Val Ser Ser His Ile Gln Ser Ala Glu Met His Asn Gln
            500                 505                 510

Ala Val Asn Ser Leu Ala Leu Val Ser Ala Arg Tyr Thr Ile Ser Ala
        515                 520                 525

Leu Asp Val Leu Ser Leu Leu Thr Ala Ala Tyr Leu Tyr Val Leu Cys
530                 535                 540

Gln Ala Leu Asp Leu Arg Ala Met His Asn Asp Leu Gln Ser Ser Leu
```

```
                545                 550                 555                 560
Ser Ala Ile Val Arg Glu Leu Leu Pro Lys His Phe Pro Ser Ala Ala
                    565                 570                 575

Lys Arg Ala Asp Ala Leu Leu Pro Ile Leu Glu Arg Thr Ile Phe Arg
                580                 585                 590

Ala Leu Asn Ser Ser Ser Ala Asp Cys Lys Ala Arg Met Val Ser
                595                 600                 605

Val Ala Ala Ser Thr Thr Thr Pro Leu Val Asp Phe Leu Ser Ala Asp
    610                 615                 620

Ala Ala Leu Ala Ser Glu Leu Ala Asn Ile Thr Ala Phe Arg Thr Glu
625                 630                 635                 640

Leu Ala Thr Arg Ala Ala Asp Ala Leu Thr Thr Leu Arg Thr Gln Tyr
                    645                 650                 655

Leu Glu Gly Ala Arg Gly Ala Ala Pro Ala Ser Lys Tyr Leu Gly Lys
                660                 665                 670

Thr Arg Pro Val Tyr Glu Phe Val Arg Val Thr Leu Asn Val Pro Met
                675                 680                 685

His Gly Arg Glu Asn Leu His Asn Phe Glu Met Gly Pro Gly Val Glu
                690                 695                 700

Asp Gly Ile Ile Gly Asn Asn Ile Ser Thr Ile Tyr Glu Ala Ile Arg
705                 710                 715                 720

Asp Gly Lys Met Gln Asn Val Val Met Gln Leu Val Lys Ser Ile Lys
                    725                 730                 735

Ala

<210> SEQ ID NO 50
<211> LENGTH: 540
<212> TYPE: PRT
<213> ORGANISM: Rhodobacter capsulatus

<400> SEQUENCE: 50

Met Leu Asp Ala Thr Ile Gly Arg Lys Arg Met Thr Leu Gln Ser Gln
1               5                   10                  15

Thr Ala Lys Asp Cys Leu Ala Leu Asp Gly Ala Leu Thr Leu Val Gln
                20                  25                  30

Cys Glu Ala Ile Ala Thr His Arg Ser Arg Ile Ser Val Thr Pro Ala
            35                  40                  45

Leu Arg Glu Arg Cys Ala Arg Ala His Ala Arg Leu Glu His Ala Ile
    50                  55                  60

Ala Glu Gln Arg His Ile Tyr Gly Ile Thr Thr Gly Phe Gly Pro Leu
65                  70                  75                  80

Ala Asn Arg Leu Ile Gly Ala Asp Gln Gly Ala Glu Leu Gln Gln Asn
                85                  90                  95

Leu Ile Tyr His Leu Ala Thr Gly Val Gly Pro Lys Leu Ser Trp Ala
                100                 105                 110

Glu Ala Arg Ala Leu Met Leu Ala Arg Leu Asn Ser Ile Leu Gln Gly
                115                 120                 125

Ala Ser Gly Ala Ser Pro Glu Thr Ile Asp Arg Ile Val Ala Val Leu
            130                 135                 140

Asn Ala Gly Phe Ala Pro Glu Val Pro Ala Gln Gly Thr Val Gly Ala
145                 150                 155                 160

Ser Gly Asp Leu Thr Pro Leu Ala His Met Val Leu Ala Leu Gln Gly
                165                 170                 175

Arg Gly Arg Met Ile Asp Pro Ser Gly Arg Val Gln Glu Ala Gly Ala
```

```
            180                 185                 190
    Val Met Asp Arg Leu Cys Gly Gly Pro Leu Thr Leu Ala Ala Arg Asp
            195                 200                 205
    Gly Leu Ala Leu Val Asn Gly Thr Ser Ala Met Thr Ala Ile Ala Ala
            210                 215                 220
    Leu Thr Gly Val Glu Ala Arg Ala Ile Asp Ala Ala Leu Arg His
225                 230                 235                 240
    Ser Ala Val Leu Met Glu Val Leu Ser Gly His Ala Glu Ala Trp His
                        245                 250                 255
    Pro Ala Phe Ala Glu Leu Arg Pro His Pro Gly Gln Leu Arg Ala Thr
                260                 265                 270
    Glu Arg Leu Ala Gln Ala Leu Asp Gly Ala Gly Arg Val Cys Arg Thr
                275                 280                 285
    Leu Thr Ala Ala Arg Arg Leu Thr Ala Ala Asp Leu Arg Pro Glu Asp
                290                 295                 300
    His Pro Ala Gln Asp Ala Tyr Ser Leu Arg Val Val Pro Gln Leu Val
305                 310                 315                 320
    Gly Ala Val Trp Asp Thr Leu Asp Trp His Asp Arg Val Val Thr Cys
                        325                 330                 335
    Glu Leu Asn Ser Val Thr Asp Asn Pro Ile Phe Pro Glu Gly Cys Ala
                340                 345                 350
    Val Pro Ala Leu His Gly Gly Asn Phe Met Gly Val His Val Ala Leu
                355                 360                 365
    Ala Ser Asp Ala Leu Asn Ala Ala Leu Val Thr Leu Ala Gly Leu Val
                370                 375                 380
    Glu Arg Gln Ile Ala Arg Leu Thr Asp Glu Lys Leu Asn Lys Gly Leu
385                 390                 395                 400
    Pro Ala Phe Leu His Gly Gly Gln Ala Gly Leu Gln Ser Gly Phe Met
                        405                 410                 415
    Gly Ala Gln Val Thr Ala Thr Ala Leu Leu Ala Glu Met Arg Ala Asn
                420                 425                 430
    Ala Thr Pro Val Ser Val Gln Ser Leu Ser Thr Asn Gly Ala Asn Gln
                435                 440                 445
    Asp Val Val Ser Met Gly Thr Ile Ala Ala Arg Arg Ala Arg Ala Gln
                450                 455                 460
    Leu Leu Pro Leu Ser Gln Ile Gln Ala Ile Leu Ala Leu Ala Leu Ala
465                 470                 475                 480
    Gln Ala Met Asp Leu Leu Asp Asp Pro Glu Gly Gln Ala Gly Trp Ser
                        485                 490                 495
    Leu Thr Ala Arg Asp Leu Arg Asp Arg Ile Arg Ala Val Ser Pro Gly
                500                 505                 510
    Leu Arg Ala Asp Arg Pro Leu Ala Gly Asp Ile Glu Ala Val Ala Gln
                515                 520                 525
    Gly Leu Arg His Pro Ser Ala Ala Asp Pro Pro Ala
                530                 535                 540

<210> SEQ ID NO 51
<211> LENGTH: 1620
<212> TYPE: DNA
<213> ORGANISM: Rhodobacter capsulatus

<400> SEQUENCE: 51
atgctggatg caaccattgg tcgtaaacgt atgaccctgc agagccagac cgcaaaagat      60
tgtctggcac tggatggtgc actgaccctg gttcagtgtg aagcaattgc aacccatcgt     120
```

```
agccgtatta gcgttacacc ggcactgcgt gaacgttgtg cacgtgccca tgcacgtctg        180
gaacatgcaa ttgccgaaca gcgtcatatt tatggtatta ccaccggttt tggtccgctg        240
gcaaatcgtc tgattggtgc agatcagggt gcagaactgc agcagaatct gatttatcat        300
ctggcaaccg gtgtgggtcc gaaactgagc tgggctgaag cccgtgcact gatgctggca        360
cgtctgaata gcatcctgca gggtgcaagc ggtgcaagtc cggaaaccat tgatcgcatt        420
gttgccgttc tgaatgcagg ttttgcaccg gaagttccgg cacagggcac cgttggtgcc        480
agcggtgatc tgactccgct ggcccatatg gttctggccc tgcaaggtcg tggtcgtatg        540
attgatccga cggtcgtgt tcaagaggca ggcgcagtta tggatcgtct gtgtggcggt        600
ccgctgacac tggcagcacg tgatggtctg gcgctggtta atggcaccag cgcaatgacc        660
gcaattgcag cactgaccgg tgttgaagcc gcacgtgcaa ttgatgcagc cctgcgtcat        720
agcgcagttc tgatggaagt tctgagcggt catgcagaag catggcatcc ggcatttgcg        780
gaactgcgtc cgcatccggg tcagctgcgt gcaaccgaac gtctggcaca ggccctggat        840
ggcgcaggtc gtgtttgtcg taccctgacc gcagcacgtc gtctgacagc agccgatctg        900
cgtccggaag atcatcctgc acaggatgca atagcctgc gtgttgttcc gcagctggtt        960
ggtgcagttt gggatacct ggattggcat gatcgtgttg ttacctgtga actgaatagc       1020
gttaccgata tccgattt tccggaaggt tgtgcagttc ctgccctgca tggtggcaat       1080
tttatgggtg ttcatgttgc actggcaagt gatgcactga atgccgcact ggttaccctg       1140
gcaggtctgg ttgaacgtca gattgcccgt ctgaccgatg aaaaactgaa taaaggtctg       1200
cctgcctttc tgcatggcgg tcaggctggt ctgcagagcg gttttatggg agcacaggtt       1260
accgcaaccg cactgctggc agaaatgcgt gcaaatgcga caccggttag cgttcagagc       1320
ctgagcacca atggtgcgaa tcaggatgtt gttagcatgg gtacaattgc cgcacgtcgt       1380
gcgcgtgcac agctgctgcc gctgagccag attcaggcaa tcctggccct ggctctggcc       1440
caggcaatgg atctgctgga tgatccggaa ggccaggcag gttggagtct gaccgcacgt       1500
gatctgcgtg atcgtattcg tgcagttagt ccgggtctgc gtgcagatcg tcctctggca       1560
ggcgatattg aagcagttgc acagggactg cgtcatccga gcgcagcgga tcctccggca       1620
```

<210> SEQ ID NO 52
<211> LENGTH: 1518
<212> TYPE: DNA
<213> ORGANISM: Flavobacterium johnsoniae

<400> SEQUENCE: 52

```
atgaacacca tcaacgaata tctgagcctg aagaatttg aagccattat ctttggcaat         60
cagaaagtga ccattagtga tgttgttgtg aatcgcgtta acgagagctt taactttctg        120
aaagaattta gcggcaacaa agtgatctat ggtgtgaata ccggttttgg tccgatggca        180
cagtatcgta ttaaagaaag cgatcagatt cagctgcagt ataatctgat tcgtagccat        240
agcagcggca ccggtaaacc gctgagtccg gtttgtgcaa aagcagcaat tctggcacgt        300
ctgaataccc tgagtctggg taatagcggt gttcatccga gcgttattaa tctgatgagc        360
gaactgatca acaaagatat actaccgctg atttttgaac atggtggtgt tggtgcaagc        420
ggtgatctgg ttcagctgag ccatctggca ctggttctga ttggtgaagg tgaagttttc        480
tataaaggtg aacgtcgtcc gacaccggaa gttttttgaaa ttgaaggtct gaaaccgatc        540
caggtggaaa ttcgcgaagg tctggccctg attaatggca ccagcgttat gaccggtatt        600
```

```
ggtgttgtta atgtgtacca tgcaaaaaaa ctgctggatt ggagcctgaa aagcagctgt    660
gcaattaatg aactggttca ggcatatgat gatcacttta gcgcagaact gaatcagacc    720
aaacgtcata aaggtcagca agaaattgca ctgaaaatgc gtcagaatct gagcgatagc    780
accctgattc gcaaacgtga agatcatctg tatagcggtg aaaacaccga agaaatcttc    840
aaagaaaaag tgcaagagta ttatagcctg cgttgtgttc cgcagattct gggtccggtt    900
ctggaaacca ttaacaatgt tgcaagcatt ctggaagatg aatttaacag cgcaaacgat    960
aacccgatca tcgatgttaa aaaccagcat gtttatcacg gtggcaattt tcatggtgat   1020
tatatcagcc tggaaatgga taaactgaaa atcgtgatta ccaaactgac catgctggca   1080
gaacgtcagc tgaattatct gctgaatagc aaaattaacg aactgctgcc tccgtttgtt   1140
aatctgggca ccctgggttt taactttggt atgcagggtg ttcagtttac cgcaaccagc   1200
accaccgcag aaagccagat gctgagcaat ccgatgtatg ttcatagcat tccgaacaat   1260
aatgataacc aggatattgt tagcatgggc accaatagcg cagttattac cagcaaagtt   1320
atcgaaaatg cctttgaagt tctggccatt gaaatgatta ccattgttca ggcgattgat   1380
tatctgggcc agaaagataa aatcagcagc gttagcaaaa atggtatga tgaaatccgc    1440 aacatcatcc cgacctttaa agaagatcag gtgatgtatc cgttcgtgca gaaagtaaaa   1500
gaccacctga ttaacaat                                                 1518

<210> SEQ ID NO 53
<211> LENGTH: 1569
<212> TYPE: DNA
<213> ORGANISM: Rhodobacter sphaeroides

<400> SEQUENCE: 53
atgctggcaa tgagccctcc gaaaccggca gttgaactgg atcgtcatat tgatctggat     60
gaagcacata gcgttgcaag cggtggtgca cgtattgttc tggcaccgcc tgcacgtgat    120
cgttgtcgtg caagcgaagc acgtctgggt gcagttattc gtgaagcccg tcatgtttat    180
ggtctgacca ccggttttgg tccgctggca aatcgtctgg ttagcggtga aaatgttcgt    240
accctgcagg caaatctggt tcatcatctg gccagcggtg tgggtccggt tctggattgg    300
accaccgcac gtgcaatggt gctggcacgc ctggttgcaa ttgcccaggg tgcgagcggt    360
gcaagtgaag gtacaattgc acgtctgatt gatctgctga atagcgaact ggcaccggca    420
gtgccgatgc gtggcaccgt tggtgcatca ggtgatctga ctccgctggc ccatatggtt    480
ctgtgtctgc agggtcgtgg tgattttctg gatcgtgatg caccgtct gatggtgcc     540 gaaggtctgc gtcgtggtcg tctgcagccg ctggatctga ccatcgtga tgcactggca    600 ctggttaatg gcaccagcgc aatgacaggt attgcactgg tgaatgcaca tgcctgtcgt    660
catctgggta attgggcagt tgcactgacc gcactgctgg ccgaatgtct gggtggtcgt    720
accgaagcat gggcagcagc actgagcgat ctgcgtccgc atccgggtca gaaagatgca    780
gcagcccgtc tgcgtgcacg tgttgatggt agcgcacgtg tggttcgtca tgttattgca    840
gaacgtcgcc tgggtgccag cgatattggc accgaaccgg aagcaggtca ggatgcatat    900
agcctgcgtt gtgcaccgca ggttctgggt gccggttttg ataccctggc atggcatgat    960
cgtgttctga ccattgaact gaatgcagtt accgataatc cggttttttcc tccggatggt   1020 agtgttccgg cactgcatgg tgcaattttt atgggtcagc atgttgccct gacctcagat   1080
gccctggcaa ccgcagtgac cgttctggca ggtctggccg aacgtcagat tgcccgtctg   1140
accgatgaac gtctgaatcg tggtctgcct ccgtttctgc accgtggtcc ggcaggcctg   1200
```

```
aatagtggct ttatgggtgc acaggttacc gcaacagccc tgctggcaga aatgcgtgca    1260
accggtccgg caagcattca tagcattagc accaatgcag caaatcagga tgttgttagc    1320
ctgggtacga ttgccgcacg tctgtgtcgt gaaaaaattg atcgttgggc agaaattctg    1380
gccattctgg cactgtgtct ggcacaggca gcagaactgc gttgcggtag tggcctggat    1440
ggcgtttcac cggcaggtaa aaaactggtt caggcactgc gcgaacagtt ccgcctctg     1500 gaaaccgatc gtccgctggg tcaagaaatt gcagcactgg caacccatct gctgcaacag    1560
agtccggtt                                                            1569
```

<210> SEQ ID NO 54
<211> LENGTH: 58
<212> TYPE: DNA
<213> ORGANISM: Artificial Sequence
<220> FEATURE:
<223> OTHER INFORMATION: Primer CBJP472

<400> SEQUENCE: 54

```
tagaaataat tttgtttaac tttaagaagg agatatacca tggagttctc ccgtccac     58
```

<210> SEQ ID NO 55
<211> LENGTH: 49
<212> TYPE: DNA
<213> ORGANISM: Artificial Sequence
<220> FEATURE:
<223> OTHER INFORMATION: Primer CBJP473

<400> SEQUENCE: 55

```
taagcattat gcggccgcaa gcttgtcata gttcacaacg aaacttgaa               49
```

<210> SEQ ID NO 56
<211> LENGTH: 62
<212> TYPE: DNA
<213> ORGANISM: Artificial Sequence
<220> FEATURE:
<223> OTHER INFORMATION: Primer CBJP470

<400> SEQUENCE: 56

```
tagaaataat tttgtttaac tttaagaagg agatatacca tggaactgat tcaggatacc    60
ag                                                                   62
```

<210> SEQ ID NO 57
<211> LENGTH: 47
<212> TYPE: DNA
<213> ORGANISM: Artificial Sequence
<220> FEATURE:
<223> OTHER INFORMATION: Primer CBJP471

<400> SEQUENCE: 57

```
taagcattat gcggccgcaa gcttgttaca gttcgctacg aaagctc                 47
```

<210> SEQ ID NO 58
<211> LENGTH: 60
<212> TYPE: DNA
<213> ORGANISM: Artificial Sequence
<220> FEATURE:
<223> OTHER INFORMATION: Primer CBJP499

<400> SEQUENCE: 58

```
tagaaataat tttgtttaac tttaagaagg agatatacca tggagctgat ccaggacacc    60
```

<210> SEQ ID NO 59

<211> LENGTH: 45
<212> TYPE: DNA
<213> ORGANISM: Artificial Sequence
<220> FEATURE:
<223> OTHER INFORMATION: Primer CBJP500

<400> SEQUENCE: 59
taagcattat gcggccgcaa gcttgtcaca cctctgagcg gaagc                45

<210> SEQ ID NO 60
<211> LENGTH: 57
<212> TYPE: DNA
<213> ORGANISM: Artificial Sequence
<220> FEATURE:
<223> OTHER INFORMATION: Primer CBJP505

<400> SEQUENCE: 60
tagaaataat tttgtttaac tttaagaagg agatatacca tggagccggt ccaggac    57

<210> SEQ ID NO 61
<211> LENGTH: 45
<212> TYPE: DNA
<213> ORGANISM: Artificial Sequence
<220> FEATURE:
<223> OTHER INFORMATION: Primer CBJP506

<400> SEQUENCE: 61
taagcattat gcggccgcaa gcttgtcaca gctcagagcg gaagc                45

<210> SEQ ID NO 62
<211> LENGTH: 57
<212> TYPE: DNA
<213> ORGANISM: Artificial Sequence
<220> FEATURE:
<223> OTHER INFORMATION: Primer CBJP503

<400> SEQUENCE: 62
tagaaataat tttgtttaac tttaagaagg agatatacca tggaggacat tcccgac    57

<210> SEQ ID NO 63
<211> LENGTH: 45
<212> TYPE: DNA
<213> ORGANISM: Artificial Sequence
<220> FEATURE:
<223> OTHER INFORMATION: Primer CBJP504

<400> SEQUENCE: 63
taagcattat gcggccgcaa gcttgtcaca gctgtgtgcg gaagc                45

<210> SEQ ID NO 64
<211> LENGTH: 62
<212> TYPE: DNA
<213> ORGANISM: Artificial Sequence
<220> FEATURE:
<223> OTHER INFORMATION: Primer CBJP501

<400> SEQUENCE: 64
tagaaataat tttgtttaac tttaagaagg agatatacca tggggaatga tgaggtgatc    60
ag                                                                   62

<210> SEQ ID NO 65
<211> LENGTH: 54
<212> TYPE: DNA
<213> ORGANISM: Artificial Sequence
<220> FEATURE:
<223> OTHER INFORMATION: Primer CBJP502

```
<400> SEQUENCE: 65
taagcattat gcggccgcaa gcttgttact ctgtctattg caatttatta cagg          54

<210> SEQ ID NO 66
<211> LENGTH: 65
<212> TYPE: DNA
<213> ORGANISM: Artificial Sequence
<220> FEATURE:
<223> OTHER INFORMATION: Primer CBJP491

<400> SEQUENCE: 66
catcttagta tattagttaa gtataagaag gagatataca tatggatcaa atacgactta    60
ctcac                                                               65

<210> SEQ ID NO 67
<211> LENGTH: 46
<212> TYPE: DNA
<213> ORGANISM: Artificial Sequence
<220> FEATURE:
<223> OTHER INFORMATION: Primer CBJP492

<400> SEQUENCE: 67
tggccggccg atatccaatt gatcaggatc tgataatatc gttctg                   46

<210> SEQ ID NO 68
<211> LENGTH: 24
<212> TYPE: DNA
<213> ORGANISM: Artificial Sequence
<220> FEATURE:
<223> OTHER INFORMATION: Primer CBJP497

<400> SEQUENCE: 68
tcaggatctg ataatatcgt tctg                                           24

<210> SEQ ID NO 69
<211> LENGTH: 59
<212> TYPE: DNA
<213> ORGANISM: Artificial Sequence
<220> FEATURE:
<223> OTHER INFORMATION: Primer CBJP498

<400> SEQUENCE: 69
cagaacgata ttatcagatc ctgataagtt aacaccgctc acagagacga ggtggagaa     59

<210> SEQ ID NO 70
<211> LENGTH: 46
<212> TYPE: DNA
<213> ORGANISM: Artificial Sequence
<220> FEATURE:
<223> OTHER INFORMATION: Primer CBJP496

<400> SEQUENCE: 70
tggccggccg atatccaatt gattagtaaa tagacactct gaaccc                   46

<210> SEQ ID NO 71
<211> LENGTH: 62
<212> TYPE: DNA
<213> ORGANISM: Artificial Sequence
<220> FEATURE:
<223> OTHER INFORMATION: Primer CBJP487

<400> SEQUENCE: 71
catcttagta tattagttaa gtataagaag gagatataca tatggcaccg agcgttgata    60
```

<210> SEQ ID NO 72
<211> LENGTH: 47
<212> TYPE: DNA
<213> ORGANISM: Artificial Sequence
<220> FEATURE:
<223> OTHER INFORMATION: Primer CBJP488

<400> SEQUENCE: 72
tggccggccg atatccaatt gattaggcca tcattttaac cagaacc    47

<210> SEQ ID NO 73
<211> LENGTH: 59
<212> TYPE: DNA
<213> ORGANISM: Artificial Sequence
<220> FEATURE:
<223> OTHER INFORMATION: Primer CBJP483

<400> SEQUENCE: 73
catcttagta tattagttaa gtataagaag gagatataca tatgctggca atgagccct    59

<210> SEQ ID NO 74
<211> LENGTH: 41
<212> TYPE: DNA
<213> ORGANISM: Artificial Sequence
<220> FEATURE:
<223> OTHER INFORMATION: Primer CBJP484

<400> SEQUENCE: 74
tggccggccg atatccaatt gattaaaccg gactctgttg c    41

<210> SEQ ID NO 75
<211> LENGTH: 65
<212> TYPE: DNA
<213> ORGANISM: Artificial Sequence
<220> FEATURE:
<223> OTHER INFORMATION: Primer CBJP555

<400> SEQUENCE: 75
catcttagta tattagttaa gtataagaag gagatataca tatgaacacc atcaacgaat    60
atctg    65

<210> SEQ ID NO 76
<211> LENGTH: 55
<212> TYPE: DNA
<213> ORGANISM: Artificial Sequence
<220> FEATURE:
<223> OTHER INFORMATION: Primer CBJP556

<400> SEQUENCE: 76
tggccggccg atatccaatt gattaattgt taatcaggtg gtcttttact ttctg    55

<210> SEQ ID NO 77
<211> LENGTH: 61
<212> TYPE: DNA
<213> ORGANISM: Artificial Sequence
<220> FEATURE:
<223> OTHER INFORMATION: Primer CBJP745

<400> SEQUENCE: 77
catcttagta tattagttaa gtataagaag gagatataca tatgctggat gcaaccattg    60
g    61

```
<210> SEQ ID NO 78
<211> LENGTH: 41
<212> TYPE: DNA
<213> ORGANISM: Artificial Sequence
<220> FEATURE:
<223> OTHER INFORMATION: Primer CBJP746

<400> SEQUENCE: 78
tggccggccg atatccaatt gattatgccg gaggatccgc t          41

<210> SEQ ID NO 79
<211> LENGTH: 33
<212> TYPE: DNA
<213> ORGANISM: Artificial Sequence
<220> FEATURE:
<223> OTHER INFORMATION: Primer CBJP633

<400> SEQUENCE: 79
agtgcaggua aaacaatgga gttctcccgt cca                   33

<210> SEQ ID NO 80
<211> LENGTH: 30
<212> TYPE: DNA
<213> ORGANISM: Artificial Sequence
<220> FEATURE:
<223> OTHER INFORMATION: Primer CBJP634

<400> SEQUENCE: 80
cgtgcgautc atagttcaca acgaaacttg                       30

<210> SEQ ID NO 81
<211> LENGTH: 34
<212> TYPE: DNA
<213> ORGANISM: Artificial Sequence
<220> FEATURE:
<223> OTHER INFORMATION: Primer CBJP635

<400> SEQUENCE: 81
atctgtcaua aaacaatgga attttcacgt ccgc                  34

<210> SEQ ID NO 82
<211> LENGTH: 32
<212> TYPE: DNA
<213> ORGANISM: Artificial Sequence
<220> FEATURE:
<223> OTHER INFORMATION: Primer CBJP636

<400> SEQUENCE: 82
cacgcgautc acagttcaca acgaaatttg aa                    32

<210> SEQ ID NO 83
<211> LENGTH: 25
<212> TYPE: DNA
<213> ORGANISM: Artificial Sequence
<220> FEATURE:
<223> OTHER INFORMATION: Primer PTEF1_fw

<400> SEQUENCE: 83
cacgcgaugc acacaccata gcttc                            25

<210> SEQ ID NO 84
<211> LENGTH: 25
<212> TYPE: DNA
<213> ORGANISM: Artificial Sequence
<220> FEATURE:
<223> OTHER INFORMATION: Primer PTEF1_rv
```

```
<400> SEQUENCE: 84
cgtgcgaugg aagtaccttc aaaga                                         25

<210> SEQ ID NO 85
<211> LENGTH: 58
<212> TYPE: DNA
<213> ORGANISM: Artificial Sequence
<220> FEATURE:
<223> OTHER INFORMATION: Primer CBJP517

<400> SEQUENCE: 85
tagaaataat tttgtttaac tttaagaagg agatatacca tggccctgga taaaatgg    58

<210> SEQ ID NO 86
<211> LENGTH: 49
<212> TYPE: DNA
<213> ORGANISM: Artificial Sequence
<220> FEATURE:
<223> OTHER INFORMATION: Primer CBJP518

<400> SEQUENCE: 86
taagcattat gcggccgcaa gcttgtcaca attccatgcg aaaaactag              49

<210> SEQ ID NO 87
<211> LENGTH: 56
<212> TYPE: DNA
<213> ORGANISM: Artificial Sequence
<220> FEATURE:
<223> OTHER INFORMATION: Primer CBJP533

<400> SEQUENCE: 87
tagaaataat tttgtttaac tttaagaagg agatatacca tggaattttc acgtcc      56

<210> SEQ ID NO 88
<211> LENGTH: 47
<212> TYPE: DNA
<213> ORGANISM: Artificial Sequence
<220> FEATURE:
<223> OTHER INFORMATION: Primer CBJP534

<400> SEQUENCE: 88
taagcattat gcggccgcaa gcttgttaca gttcacaacg aaatttg                47

<210> SEQ ID NO 89
<211> LENGTH: 35
<212> TYPE: DNA
<213> ORGANISM: Artificial Sequence
<220> FEATURE:
<223> OTHER INFORMATION: Primer

<400> SEQUENCE: 89
ttaaaagctt gggattggtc aaaaggagct catcc                             35

<210> SEQ ID NO 90
<211> LENGTH: 35
<212> TYPE: DNA
<213> ORGANISM: Artificial Sequence
<220> FEATURE:
<223> OTHER INFORMATION: Primer

<400> SEQUENCE: 90
aatagcggcc gcttaccgcc acatcgcgtg tttat                             35

<210> SEQ ID NO 91
<211> LENGTH: 40
```

```
<212> TYPE: DNA
<213> ORGANISM: Artificial Sequence
<220> FEATURE:
<223> OTHER INFORMATION: Primer

<400> SEQUENCE: 91
ttaaaagctt agaaagtcat taaatttata agggtgcgca                            40

<210> SEQ ID NO 92
<211> LENGTH: 33
<212> TYPE: DNA
<213> ORGANISM: Artificial Sequence
<220> FEATURE:
<223> OTHER INFORMATION: Primer

<400> SEQUENCE: 92
aatagcggcc gctcaggcgc tttgtgcgag agc                                   33

<210> SEQ ID NO 93
<211> LENGTH: 19
<212> TYPE: DNA
<213> ORGANISM: Artificial Sequence
<220> FEATURE:
<223> OTHER INFORMATION: Primer

<400> SEQUENCE: 93
ggatctcgac gctctccct                                                   19

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gattatgcgg ccgtgtacaa                                                  20

<210> SEQ ID NO 95
<211> LENGTH: 595
<212> TYPE: PRT
<213> ORGANISM: Rhodobacter capsulatus

<400> SEQUENCE: 95
```

Met Ile Asp Leu Gly Leu Gly Ala Ala Gln Ala Trp Leu Ser Ile
1               5                   10                  15

Ala Ile Val Leu Gly Met Phe Val Leu Phe Val Arg Glu Lys Asp Pro
            20                  25                  30

Pro Glu Val Ile Ala Ile Gly Gly Ala Ala Leu Met Leu Val Leu Gly
        35                  40                  45

Leu Val Pro Tyr Lys Glu Ala Val Gly Ala Leu Ser Asn Ser Ala Pro
    50                  55                  60

Trp Thr Ile Ala Phe Met Phe Leu Ile Met Gly Ala Leu Val Arg Thr
65                  70                  75                  80

Gly Ala Leu Asp Arg Ala Thr Arg Ala Val Glu Ser Gln Ile Asp Glu
                85                  90                  95

Arg Pro Ala Thr Thr Thr Ala Leu Leu Phe Ala Ile Val Met Gly Ala
            100                 105                 110

Ser Ala Phe Met Asn Asn Thr Pro Val Val Ala Val Met Ile Pro Ile
        115                 120                 125

Phe Met Gln Ala Ala Arg Lys Leu Asn Val Pro Pro Ser Arg Leu Leu
    130                 135                 140

```
Met Pro Leu Ser Tyr Phe Thr Ile Met Gly Gly Met Ile Thr Leu Ile
145                 150                 155                 160

Gly Thr Ser Thr Asn Ile Leu Val Asp Gly Val Arg Lys Asp Gly
                165                 170                 175

Met Ala Pro Phe Ser Ile Phe Glu Ile Ala Pro Val Gly Leu Ala Ile
                180                 185                 190

Cys Leu Ala Gly Ser Leu Phe Met Ala Leu Phe Ser Arg Arg Leu Val
                195                 200                 205

Pro Asp Arg Val Ser Met Ala Ala Thr Leu Gly Gly Arg Pro Lys
    210                 215                 220

Met Lys Tyr Phe Thr Glu Val Ala Ile Pro Glu Ser Asn Leu Ile
225                 230                 235                 240

Gly Lys Gly Val Leu Glu Ile Asp Ile Phe Lys Arg Thr Gly Val Arg
                245                 250                 255

Val Ile Asp Val Leu Arg Gly Asp Ala Ser Leu Arg Arg Asp Leu Thr
                260                 265                 270

Ala Ala Val Leu Glu Ala Gly Asp Arg Val Val Leu Arg Thr Glu Val
                275                 280                 285

Ser Glu Leu Leu Gly Met Gln Ala Asn Lys Asp Val Arg Val Val Asp
                290                 295                 300

Lys Leu Ser Ser Val Ala Thr Glu Thr Val Glu Val Leu Ile Ser Pro
305                 310                 315                 320

Gly Cys Arg Met Ile Gly Arg Ser Leu Gly Asp Leu Arg Leu Arg Arg
                325                 330                 335

Arg Tyr Gly Val Tyr Val Leu Ala Ala His Arg Arg Asn Gln Asn Ile
                340                 345                 350

Gly Arg Lys Leu Asp Asp Leu Val Val Val Gly Asp Thr Leu Leu
                355                 360                 365

Leu Glu Gly Ala Pro Glu Asp Ile Ala Arg Leu Ala Gln Asp Met Asp
370                 375                 380

Leu Val Asp Val Ser Arg Pro Thr Ala Arg Ala Phe Arg Arg Gly Lys
385                 390                 395                 400

Met Pro Ile Ala Val Leu Ala Leu Leu Ala Val Val Gly Leu Ser Ala
                405                 410                 415

Leu Asp Val Ala Pro Ile Met Glu Leu Ala Met Val Ala Val Ala Val
                420                 425                 430

Ile Leu Leu Thr Arg Cys Ile Asp Ala Asp Glu Ala Phe Ser Tyr Val
                435                 440                 445

Asp Gly Arg Leu Leu Ala Met Ile Phe Ala Met Leu Val Val Gly Glu
                450                 455                 460

Gly Leu Asp Ala Ser Gly Ala Val Ala Leu Ile Val Asp Ala Val Ala
465                 470                 475                 480

Pro Leu Met Gln Asp Leu Pro Pro Ile Ala Ala Leu Ala Ala Val Tyr
                485                 490                 495

Phe Leu Gly Leu Ala Met Thr Glu Leu Leu Ser Asn Asn Ala Val Ala
                500                 505                 510

Val Ile Phe Thr Pro Ile Ala Ile Gln Leu Ala His Thr Leu Gly Leu
                515                 520                 525

Asp Pro Arg Pro Phe Ala Val Ala Val Met Phe Ser Ala Ser Val Ala
                530                 535                 540

Phe Ala Thr Pro Ile Gly Tyr Gln Thr His Met Met Val Tyr Gly Pro
545                 550                 555                 560
```

Gly Gly Tyr Lys Phe Ser Asp Phe Leu Arg Leu Gly Ile Pro Leu Asp
            565                 570                 575

Ile Leu Thr Gly Ile Val Ala Val Leu Val Ile Pro Leu Val Trp Pro
            580                 585                 590

Leu Val Pro
        595

<210> SEQ ID NO 96
<211> LENGTH: 59
<212> TYPE: DNA
<213> ORGANISM: Artificial Sequence
<220> FEATURE:
<223> OTHER INFORMATION: Forward primer

<400> SEQUENCE: 96
tagaaataat tttgtttaac tttaagaagg agatatacca tgccccagtc gagcttctt        59

<210> SEQ ID NO 97
<211> LENGTH: 46
<212> TYPE: DNA
<213> ORGANISM: Artificial Sequence
<220> FEATURE:
<223> OTHER INFORMATION: Reverse primer

<400> SEQUENCE: 97
taagcattat gcggccgcaa gcttgttacg tggacgcaaa cttgct                      46

<210> SEQ ID NO 98
<211> LENGTH: 1017
<212> TYPE: DNA
<213> ORGANISM: Drosophila melanogaster

<400> SEQUENCE: 98
atgccccagt cgagcttctt tgccaagagc gtgcccttcg agcagatcga caagctggcc        60
atcagtggcg gctactcctc gatcttcgcc agcagcaagc cgtcggtgcc ggtggtcggg       120
aactgggagc agcgtttctg ccgcctagcg gacactttcc agccggtcct ggatcgggtg       180
tacgacttcg aggtgcggga cgacgatgtg tggattgtca cgctgccaaa atgcggcacc       240
acctggatgc aggagctggc ctggctggtg atcaatgagt gtgattttga acggccaag        300 agcgtggatc tcacgcatcg atcgcccttc cttgaattca atggcgtggt tcccaatgta       360
ccacacgaca ccatagccgc agcgaatgcc ctgccatcgc cgcgcctgat caagtcccat       420
ctgcccgcct ggatgctgcc gaggcagatc tggagcaaga gccaagat catttatgtg       480 taccgcaacc cgaaggacgc ggccatctcg tacttccacc actggcgtgg aatggtgggc       540
taccagggca ccaagtcgga cttcatgcac tcctttatcg acggctatgt gaacttcacg       600
ccctgctggc cgcacatcct ggactttttgg cagctgcgcc acgagcccaa catcttcttc       660
accagctacg agcggatgaa gggccagctg gccaggtta tctcggaggt ggcccagttc       720
ctggagcgca gtgtcagcca ggagcagatc cagcagatgc agcgacacct ctccttcgag       780
agcatgcgcg acaatcccgc ctgcaaccac gtcaaggagt cgagagcat gaaggcggct       840 gccggcaggg aggtggagga gttcaggttc gttcgccgcg gagtcgtggg cagccacaag       900
gatgagctca ccgccgacat catccgggaa ttcgatctct ggtccgatag taatctgcgg       960
gatttcaaat tgaacatgga tgactttgcc aactacagca gtttgcgtc cacgtga        1017

<210> SEQ ID NO 99
<211> LENGTH: 338
<212> TYPE: PRT

<213> ORGANISM: Drosophila melanogaster

<400> SEQUENCE: 99

Met Pro Gln Ser Ser Phe Phe Ala Lys Ser Val Pro Phe Glu Gln Ile
1               5                   10                  15

Asp Lys Leu Ala Ile Ser Gly Gly Tyr Ser Ser Ile Phe Ala Ser Ser
            20                  25                  30

Lys Pro Ser Val Pro Val Val Gly Asn Trp Glu Gln Arg Phe Cys Arg
        35                  40                  45

Leu Ala Asp Thr Phe Gln Pro Val Leu Asp Arg Val Tyr Asp Phe Glu
    50                  55                  60

Val Arg Asp Asp Asp Val Trp Ile Val Thr Leu Pro Lys Cys Gly Thr
65                  70                  75                  80

Thr Trp Met Gln Glu Leu Ala Trp Leu Val Ile Asn Glu Cys Asp Phe
                85                  90                  95

Glu Thr Ala Lys Ser Val Asp Leu Thr His Arg Ser Pro Phe Leu Glu
            100                 105                 110

Phe Asn Gly Val Val Pro Asn Val Pro His Asp Thr Ile Ala Ala Ala
        115                 120                 125

Asn Ala Leu Pro Ser Pro Arg Leu Ile Lys Ser His Leu Pro Ala Trp
    130                 135                 140

Met Leu Pro Arg Gln Ile Trp Ser Lys Arg Pro Lys Ile Ile Tyr Val
145                 150                 155                 160

Tyr Arg Asn Pro Lys Asp Ala Ala Ile Ser Tyr Phe His His Trp Arg
                165                 170                 175

Gly Met Val Gly Tyr Gln Gly Thr Lys Ser Asp Phe Met His Ser Phe
            180                 185                 190

Ile Asp Gly Tyr Val Asn Phe Thr Pro Cys Trp Pro His Ile Leu Asp
        195                 200                 205

Phe Trp Gln Leu Arg His Glu Pro Asn Ile Phe Phe Thr Ser Tyr Glu
    210                 215                 220

Arg Met Lys Gly Gln Leu Gly Gln Val Ile Ser Glu Val Ala Gln Phe
225                 230                 235                 240

Leu Glu Arg Ser Val Ser Gly Glu Gln Ile Gln Gln Met Gln Arg His
                245                 250                 255

Leu Ser Phe Glu Ser Met Arg Asp Asn Pro Ala Cys Asn His Val Lys
            260                 265                 270

Glu Phe Glu Ser Met Lys Ala Ala Gly Arg Glu Val Glu Glu Phe
        275                 280                 285

Arg Phe Val Arg Arg Gly Val Val Gly Ser His Lys Asp Glu Leu Thr
    290                 295                 300

Ala Asp Ile Ile Arg Glu Phe Asp Leu Trp Ser Asp Ser Asn Leu Arg
305                 310                 315                 320

Asp Phe Lys Leu Asn Met Asp Asp Phe Ala Asn Tyr Ser Lys Phe Ala
                325                 330                 335

Ser Thr

<210> SEQ ID NO 100
<211> LENGTH: 925
<212> TYPE: DNA
<213> ORGANISM: Danio rerio

<400> SEQUENCE: 100
atggacatcc cggatttag cagcattagc agccgtccga ccattttga atttgaaggt    60

```
attagcatga tcaaccactt taccgaaaac tgggagaaag tgaaaaactt tcaggcacgt    120
ccggatgata ttctgattgc aacctatccg aaagcaggca ccacctgggt tagctatatt    180
ctggatctgc tgtattttgg tgaaaacgca ccggaagaac ataccagcca gccgatttat    240
atgcgtgttc cgtttctgga aagctgcttt aaagttattg caagcggcac cgaactggca    300
gataatatga ccaccagtcc gcgtctgatt aaaacccatc tgccggttca gctgattccg    360
aaaagttttt gggaacagaa tagccgtgtt gtttatgttg cacgtaatgc caaagataac    420
gtggtgagct atttttcattt tgatcgcatg aatatcgttg aaccggatcc tggtgattgg    480
aatacctttc tgcatcgttt tatggatggc aaaagcgttt ttggtccgtg gtatgatcac    540
gttaatggct attgggaaaa aaaacagacc tatagcaacc tgctgtacct gttttatgaa    600
gatctggttg aagataccgg tcgtgaagtt gatcgtctgt gtagctttct gggtctgagc    660
accagcgtta gcgatcgtga aaaaatcacc aaagatgttc agttcgatgc catgaaacag    720
aacaaaatga ccaattatag caccctgccg gtgatggatt tcaaaatttc accgtttatg    780
cgcaaaggca agttggcga ttggaaaaat cattttaccg tggcacagaa cgaacagttt    840
gatgaggtgt acaaagaaaa aatgaaaaac gccaccgtga aatttcgcac gaaatctaa     900
caagcttgcg gccgcataat gctta                                          925
```

<210> SEQ ID NO 101
<211> LENGTH: 299
<212> TYPE: PRT
<213> ORGANISM: Danio rerio

<400> SEQUENCE: 101

```
Met Asp Ile Pro Asp Phe Ser Ser Ile Ser Ser Arg Pro Thr Ile Phe
1               5                   10                  15

Glu Phe Glu Gly Ile Ser Met Ile Asn His Phe Thr Glu Asn Trp Glu
            20                  25                  30

Lys Val Lys Asn Phe Gln Ala Arg Pro Asp Asp Ile Leu Ile Ala Thr
        35                  40                  45

Tyr Pro Lys Ala Gly Thr Thr Trp Val Ser Tyr Ile Leu Asp Leu Leu
    50                  55                  60

Tyr Phe Gly Glu Asn Ala Pro Glu Glu His Thr Ser Gln Pro Ile Tyr
65                  70                  75                  80

Met Arg Val Pro Phe Leu Glu Ser Cys Phe Lys Val Ile Ala Ser Gly
                85                  90                  95

Thr Glu Leu Ala Asp Asn Met Thr Thr Ser Pro Arg Leu Ile Lys Thr
            100                 105                 110

His Leu Pro Val Gln Leu Ile Pro Lys Ser Phe Trp Glu Gln Asn Ser
        115                 120                 125

Arg Val Val Tyr Val Ala Arg Asn Ala Lys Asp Asn Val Val Ser Tyr
    130                 135                 140

Phe His Phe Asp Arg Met Asn Ile Val Glu Pro Asp Pro Gly Asp Trp
145                 150                 155                 160

Asn Thr Phe Leu His Arg Phe Met Asp Gly Lys Ser Val Phe Gly Pro
                165                 170                 175

Trp Tyr Asp His Val Asn Gly Tyr Trp Glu Lys Lys Gln Thr Tyr Ser
            180                 185                 190

Asn Leu Leu Tyr Leu Phe Tyr Glu Asp Leu Val Glu Asp Thr Gly Arg
        195                 200                 205

Glu Val Asp Arg Leu Cys Ser Phe Leu Gly Leu Ser Thr Ser Val Ser
    210                 215                 220
```

Asp Arg Glu Lys Ile Thr Lys Asp Val Gln Phe Asp Ala Met Lys Gln
225                 230                 235                 240

Asn Lys Met Thr Asn Tyr Ser Thr Leu Pro Val Met Asp Phe Lys Ile
            245                 250                 255

Ser Pro Phe Met Arg Lys Gly Lys Val Gly Asp Trp Lys Asn His Phe
        260                 265                 270

Thr Val Ala Gln Asn Glu Gln Phe Asp Glu Val Tyr Lys Glu Lys Met
    275                 280                 285

Lys Asn Ala Thr Val Lys Phe Arg Thr Glu Ile
        290                 295

<210> SEQ ID NO 102
<211> LENGTH: 916
<212> TYPE: DNA
<213> ORGANISM: Danio rerio

<400> SEQUENCE: 102

| | | | | |
|---|---|---|---|---|
| atgagccaga | tgaaaagccg | tatggaaacc | gcagcaaaaa | tgaaagatga ggataaactg | 60 |
| tatcgccgtg | atggtattct | gtatagcacc | gttctgagcc | ctccggaaac cctggacaaa | 120 |
| ctgaaagatc | tgcaggcacg | tgaagatgat | ctgattctgg | ttgcatatcc gaatgcggt | 180 |
| tttaattgga | tggttgcagt | tctgcgcaaa | atcattaatg | caagcaccgg caaagatgaa | 240 |
| aaaccgcctg | aacgtccgcc | tctggttgaa | tttctgcctc | cgaccgttca agaagaaatg | 300 |
| gcccagatgc | tccgcctcg | tctgctgggc | acccatctgc | atccggataa tatgcctgca | 360 |
| acctttttta | ccaaaaaacc | gaaaatcctg | gtggtgtttc | gtaatccgaa agataccctg | 420 |
| gttagctatt | atcactttat | gaacaaaaat | ccggttctgc | cgaatgcaga aagctgggat | 480 |
| aaattcttta | gcgatttat | gaccggtgat | gttagctggg | gtagctattt tgatcatgca | 540 |
| ctggcatggg | aaaaacgtat | tgatgatccg | aatgtgatga | tcgtgatgta tgaagatctg | 600 |
| aaacagaatc | tgccggaagg | cgtgaaaaaa | atcagcgaat | ttttcagcct gccgctgacc | 660 |
| gatgaacagg | ttagcagcat | tgcaggtcag | agcacccttta | gcgcaatggt tgaaaattca | 720 |
| cagaaaagcc | atggtaactt | tggcagcatc | ttttttcgta | aggtgaagt gggtgattgg | 780 |
| aaaaaccatt | ttagcgaagc | acagagcaaa | caaatggatg | agctgtatca tagcaaactg | 840 |
| gcaggtacaa | aactggctgc | acgtatgaat | tatgatctgt | attgccagta acaagcttgc | 900 |
| ggccgcataa | tgctta | | | | 916 |

<210> SEQ ID NO 103
<211> LENGTH: 296
<212> TYPE: PRT
<213> ORGANISM: Danio rerio

<400> SEQUENCE: 103

Met Ser Gln Met Lys Ser Arg Met Glu Thr Ala Ala Lys Met Lys Asp
1               5                   10                  15

Glu Asp Lys Leu Tyr Arg Arg Asp Gly Ile Leu Tyr Ser Thr Val Leu
            20                  25                  30

Ser Pro Pro Glu Thr Leu Asp Lys Leu Lys Asp Leu Gln Ala Arg Glu
        35                  40                  45

Asp Asp Leu Ile Leu Val Ala Tyr Pro Lys Cys Gly Phe Asn Trp Met
    50                  55                  60

Val Ala Val Leu Arg Lys Ile Ile Asn Ala Ser Thr Gly Lys Asp Glu
65                  70                  75                  80

Lys Pro Pro Glu Arg Pro Pro Leu Val Glu Phe Leu Pro Pro Thr Val
                85                  90                  95

Gln Glu Glu Met Ala Gln Met Pro Pro Arg Leu Leu Gly Thr His
            100                 105                 110

Leu His Pro Asp Asn Met Pro Ala Thr Phe Phe Thr Lys Lys Pro Lys
        115                 120                 125

Ile Leu Val Val Phe Arg Asn Pro Lys Asp Thr Leu Val Ser Tyr Tyr
130                 135                 140

His Phe Met Asn Lys Asn Pro Val Leu Pro Asn Ala Glu Ser Trp Asp
145                 150                 155                 160

Lys Phe Phe Ser Asp Phe Met Thr Gly Asp Val Ser Trp Gly Ser Tyr
                165                 170                 175

Phe Asp His Ala Leu Ala Trp Glu Lys Arg Ile Asp Asp Pro Asn Val
            180                 185                 190

Met Ile Val Met Tyr Glu Asp Leu Lys Gln Asn Leu Pro Glu Gly Val
        195                 200                 205

Lys Lys Ile Ser Glu Phe Phe Ser Leu Pro Leu Thr Asp Glu Gln Val
210                 215                 220

Ser Ser Ile Ala Gly Gln Ser Thr Phe Ser Ala Met Val Glu Asn Ser
225                 230                 235                 240

Gln Lys Ser His Gly Asn Phe Gly Ser Ile Phe Phe Arg Lys Gly Glu
                245                 250                 255

Val Gly Asp Trp Lys Asn His Phe Ser Glu Ala Gln Ser Lys Gln Met
            260                 265                 270

Asp Glu Leu Tyr His Ser Lys Leu Ala Gly Thr Lys Leu Ala Ala Arg
        275                 280                 285

Met Asn Tyr Asp Leu Tyr Cys Gln
    290                 295

<210> SEQ ID NO 104
<211> LENGTH: 667
<212> TYPE: DNA
<213> ORGANISM: Haliangium ochraceum

<400> SEQUENCE: 104
atgagcatgg atattattgg tgcaggtatg gtcgtaccg gcaccctgag cctgaaacat      60
gcactggaac gtctgggttt tgatccgtgt tatcatatga ccaccctgct ggaacatccg     120
gaacatgcaa gcacctgggc agcagcagca cgtggtgaac aggttgattg gaataccgca     180
ctgggtagct tcgtgcaac cgttgatcat ccgggttgta acttctataa agatctgatg     240
gcaaaatatc cggaagccaa agttattctg agcgttcgtg atccgggtaa atggtatgat     300
agcgcacgtg aaaccattta tcgtgcaagc cgtgcagcaa ttgcagccgg tgcacgtgaa     360
ggtgcaccgg aaattatgcg tgttgcaaat agcctggttt gggaaaaaca gtttgatggt     420
cgttttgaag atcgcgaata tgccattagc gttttgaac agcataacga agaagtgaaa     480
cgtaccgttc cggcagaacg tctgctggtt tttgaagcac gtcagggttg gaaccgctg      540 tgtgcatttc tgggtgttga tgtgccggat gaaccgtatc cgcgtgttaa tagccgtgaa     600
gaattcaaaa aaatgatcgc cgaaatggaa ggcgaagcct aacaagcttg cggccgcata     660
atgctta                                                              667

<210> SEQ ID NO 105
<211> LENGTH: 213
<212> TYPE: PRT
<213> ORGANISM: Haliangium ochraceum

```
<400> SEQUENCE: 105

Met Ser Met Asp Ile Ile Gly Ala Gly Met Gly Arg Thr Gly Thr Leu
1               5                   10                  15

Ser Leu Lys His Ala Leu Glu Arg Leu Gly Phe Asp Pro Cys Tyr His
            20                  25                  30

Met Thr Thr Leu Leu Glu His Pro Glu His Ala Ser Thr Trp Ala Ala
        35                  40                  45

Ala Ala Arg Gly Glu Gln Val Asp Trp Asn Thr Ala Leu Gly Ser Phe
    50                  55                  60

Arg Ala Thr Val Asp His Pro Gly Cys Asn Phe Tyr Lys Asp Leu Met
65                  70                  75                  80

Ala Lys Tyr Pro Glu Ala Lys Val Ile Leu Ser Val Arg Asp Pro Gly
                85                  90                  95

Lys Trp Tyr Asp Ser Ala Arg Glu Thr Ile Tyr Arg Ala Ser Arg Ala
            100                 105                 110

Ala Ile Ala Ala Gly Ala Arg Glu Gly Ala Pro Glu Ile Met Arg Val
            115                 120                 125

Ala Asn Ser Leu Val Trp Glu Lys Gln Phe Asp Gly Arg Phe Glu Asp
    130                 135                 140

Arg Glu Tyr Ala Ile Ser Val Phe Glu Gln His Asn Glu Glu Val Lys
145                 150                 155                 160

Arg Thr Val Pro Ala Glu Arg Leu Leu Val Phe Glu Ala Arg Gln Gly
                165                 170                 175

Trp Glu Pro Leu Cys Ala Phe Leu Gly Val Asp Val Pro Asp Glu Pro
            180                 185                 190

Tyr Pro Arg Val Asn Ser Arg Glu Glu Phe Lys Lys Met Ile Ala Glu
            195                 200                 205

Met Glu Gly Glu Ala
    210
```

US 10,954,536 B2

MODIFIED ESCHERICHIA COLI HAVING AN INCREASED EXPRESSION OF A CYSP TRANSPORTER, AN ATP SULFURYLASE, AN APS KINASE AND A PAP PHOSPHATASE

CROSS REFERENCE TO RELATED APPLICATIONS

This application is a U.S. National Phase Application of PCT International Application Number PCT/EP2017/054346, filed on Feb. 24, 2017, designating the United States of America and published in the English language, which is an International Application of and claims the benefit of priority to European Patent Application No. 16157231.8, filed on Feb. 24, 2016. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ZACCO44-023APC.txt, the date of creation of the ASCII text file is Aug. 17, 2018, and the size of the ASCII text file is 202 KB.

TECHNICAL FIELD OF THE INVENTION

The present invention generally relates to the field of biotechnology as it applies to the production of aryl sulfates using recombinant host cells. More particularly, the present invention pertains to recombinant host cells comprising (e.g., expressing) a polypeptide having aryl sulfotransferase activity, the use of such recombinant host cells in the production of aryl sulfates, and processes for the production of aryl sulfates, such as zosteric acid, employing such recombinant host cells.

BACKGROUND OF THE INVENTION

A range of phenolic compounds are of great interest to the biotech industry since they are building blocks for polymeric compounds. Examples of such phenolic compounds include p-coumaric acid (pHCA) or other hydroxycinnamic acids which form the basis for many secondary metabolites including flavonoids and stilbenes. However, many of these phenolic compounds are toxic to producing organisms, and thus limit the productivity during fermentation. Hence, there is a need for large scale production processes, and especially for biological large scale production processes allowing improved productivity.

Moreover, a range of phenolic compounds, and especially those used as drugs or food additives such as resveratrol or vanillin, show poor solubility in water which makes it difficult for these compounds to be uptaken by the body. Hence, there is also a need for providing such phenolic compounds in a form which improves the solubility, and hence bioavailablility, preferably by using biological large scale production processes.

SUMMARY OF THE INVENTION

The object of the present invention is to provide a method for large scale production of aryl sulfates. Furthermore, it is an object to provide a biological process for the large scale production of phenols. The inventors have developed a biological process that solves both objects.

The present invention thus provides in a first aspect a process for the production of a sulfated phenolic compound comprising:
(i') contacting a medium comprising a phenolic compound, such as p-coumaric acid, with a first recombinant host cell; wherein the first recombinant host cell comprises (e.g., expresses) a heterologous polypeptide having an aryl sulfotransferase activity; or
(i") contacting a medium comprising a fermentable carbon substrate with a first recombinant host cell; wherein the first recombinant host cell comprises (e.g., expresses) a heterologous polypeptide having an aryl sulfotransferase activity; or
(i'") contacting a medium comprising a precursor of a phenolic compound with a first recombinant host cell; wherein the first recombinant host cell comprises (e.g., expresses) a heterologous polypeptide having an aryl sulfotransferase activity.

Particularly, the present invention provides a process for the production of a sulfated phenolic compound comprising:
(i') contacting a medium comprising a phenolic compound with a first recombinant host cell; wherein the first recombinant host cell comprises (e.g., expresses) a heterologous polypeptide having an aryl sulfotransferase activity, and wherein the first recombinant host cell has been modified to have an increased uptake of sulfate compared to an identical host cell that does not carry said modification; or
(i") contacting a medium comprising a fermentable carbon substrate with a first recombinant host cell; wherein the first recombinant host cell comprises (e.g., expresses) a heterologous polypeptide having an aryl sulfotransferase activity, and wherein the first recombinant host cell has been modified to have an increased uptake of sulfate compared to an identical host cell that does not carry said modification; or
(i'") contacting a medium comprising a precursor of a phenolic compound with a first recombinant host cell; wherein the first recombinant host cell comprises (e.g., expresses) a heterologous polypeptide having an aryl sulfotransferase activity, and wherein the first recombinant host cell has been modified to have an increased uptake of sulfate compared to an identical host cell that does not carry said modification.

The present invention provides in a further aspect a recombinant host cell comprising (e.g. expressing) a heterologous polypeptide having an aryl sulfotransferase activity.

Particularly, the present invention provides a recombinant host cell comprising (e.g. expressing) a heterologous polypeptide having an aryl sulfotransferase activity, wherein the recombinant host cell has been modified to have an increased uptake of sulfate compared to an identical host cell that does not carry said modification.

The present invention can be further summarized by the following items:
1. A process for the production of a sulfated phenolic compound comprising:
(i') contacting a medium comprising a phenolic compound with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification; or
(i") contacting a medium comprising a fermentable carbon substrate with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification; or (i''') contacting a medium comprising a precursor of a phenolic compound with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification.

2. The process according to item 1, further comprising:
(ii) culturing the first recombinant host cell under suitable conditions for the production of the corresponding sulfated phenolic compound; and
(iii) optionally, recovering said sulfated phenolic compound.

3. The process according to item 1 or 2, wherein the heterologous polypeptide having an aryl sulfotransferase activity is a sulfotransferase 1A1 enzyme.

4. The process according to any one of items 1-3, wherein the heterologous polypeptide having an aryl sulfotransferase activity is selected from the group consisting of:
1a) a polypeptide comprising an amino acid sequence set forth in SEQ ID NO: 1, 2, 3, 4, 5, 6, 7, 8, 9, 10, 11, 12 or 13 (e.g., SEQ ID NO: 1);
1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1); or
1c) a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

5. The process according to any one of items 1-4, wherein the heterologous polypeptide is selected from the group consisting of:
1a) a polypeptide comprising an amino acid sequence set forth in SEQ ID NO: 1;
1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1; or
1c) a polypeptide comprising an amino acid sequence set forth in SEQ ID NO: 1, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

6. The process according to any one of items 1-5, wherein the first recombinant host cell comprises an exogenous nucleic acid molecule comprising a nucleotide sequence encoding said heterologous polypeptide.

7. The process according to item 6, wherein the exogenous nucleic acid molecule further comprises a promoter that is functional in the host cell to cause the production of an mRNA molecule and that is operably linked to the nucleotide sequence encoding said heterologous polypeptide.

8. The process according to item 6 or 7, wherein the exogenous nucleic acid molecule is a vector.

9. The process according to item 6 or 7, wherein the exogenous nucleic acid molecule is stably integrated into the genome of said first recombinant host cell.

10. The process according to any one of items 1-9, wherein said first recombinant host cell has been modified to an have increased protein expression of a sulfate transporter compared to the identical host cell that does not carry said modification.

11. The process according to item 10, wherein the increase in protein expression of the sulfate transporter is achieved by increasing the number of copies of a gene or genes encoding said sulfate transporter.

12. The process according to item 11, wherein the increase in the number of copies of the gene or genes is achieved by introducing into said first recombinant host cell one or more exogenous nucleic acid molecules (such as one or more vectors) comprising the gene or genes operably linked to a promoter that is functional in the host cell to cause the production of an mRNA molecule.

13. The process according to any one of items 1-10, wherein said first recombinant host cell comprises an exogenous nucleic acid molecule (such as a vector) comprising one or more nucleotide sequences encoding a sulfate transporter.

14. The process according to item 12, wherein the exogenous nucleic acid molecule further comprises a promoter that is functional in the host cell to cause the production of an mRNA molecule and that is operably linked to the one or more nucleotide sequences encoding said sulfate transporter.

15. The process according to any one of items 12-14, wherein the exogenous nucleic acid molecule is a vector.

16. The process according to any one of items 12-14, wherein the exogenous nucleic acid molecule is stably integrated into the genome of said first recombinant host cell.

17. The process according to item 10, wherein the increase in protein expression is achieved by modifying the ribosome binding site.

18. The process according to any one of item 10, wherein the increase in protein expression is achieved by increasing the strength of the promoter(s) operably linked to the gene or genes encoding said sulfate transporter.

19. The process according to any one of items 10-18, wherein the sulfate transporter is a bacterial sulfate transporter.

20. The process according to any one of items 10-19, wherein the sulfate transporter is a selected from the group consisting of: members of the CysZ family, members of the SulT (cysPTWA) family, members of the SulP family, CysP transporters belonging to the phosphate inorganic transporter (PiT) family, and oxyanion permeases (PerO).

21. The process according to any one of items 10-20, wherein the sulfate transporter is a member of the CysZ family.

22. The process according to any one of items 10-21, wherein the sulfate transporter is a CysZ protein.

23. The process according to any one of items 10-22, wherein the sulfate transporter is a polypeptide selected from the group consisting of:
2a) a polypeptide comprising an amino acid sequence set forth in SEQ ID NO: 14;
2b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 14; or 2c) a polypeptide comprising an amino acid sequence set forth in SEQ ID NO: 14, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

24. The process according to any one of items 10-22, wherein the sulfate transporter is a polypeptide selected from the group consisting of:
3a) a polypeptide comprising an amino acid sequence set forth in SEQ ID NO: 15;
3b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15; or
3c) a polypeptide comprising an amino acid sequence set forth in SEQ ID NO: 15, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

25. The process according to any one of items 10-20, wherein the sulfate transporter is a sulfate-transporting ATPase.

26. The process according to any one of items 10-20, wherein the sulfate transporter is a member of the SulT (cysPTWA) family.

27. The process according to any one of items 10-20, wherein the sulfate transporter comprises a first membrane subunit (CysT), a second membrane subunit (CysW), an ATP binding subunit (CysA) and a periplasmic binding protein (CysP or Sbp).

28. The process according to any one of items 25 to 27, where the sulfate transporter is encoded by an operon comprising a nucleotide sequence encoding a first membrane subunit (CysT), a nucleotide sequence encoding a second membrane subunit (CysW), a nucleotide sequence encoding an ATP binding subunit (CysA) and a nucleotide sequence encoding a periplasmic binding protein (CysP or Sbp).

29. The process according to item 27 or 28, wherein the first membrane subunit is a polypeptide selected from the group consisting of:
4a) a polypeptide comprising an amino acid sequence set forth in SEQ ID NO: 16;
4b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16; or
4c) a polypeptide comprising an amino acid sequence set forth in SEQ ID NO: 16, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

30. The process according to any one of items 27 to 29, wherein the second membrane subunit is a polypeptide selected from the group consisting of:
5a) a polypeptide comprising an amino acid sequence set forth in SEQ ID NO: 17;
5b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17; or
5c) a polypeptide comprising an amino acid sequence set forth in SEQ ID NO: 17, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

31. The process according to any one of items 27 to 30, wherein the ATP binding subunit is a polypeptide selected from the group consisting of:
6a) a polypeptide comprising an amino acid sequence set forth in SEQ ID NO: 18;
6b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18; or
6c) a polypeptide comprising an amino acid sequence set forth in SEQ ID NO: 18, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

32. The process according to any one of items 27 to 31, wherein the periplasmic binding protein is CysP.

33. The process according to any one of items 27 to 31, wherein the periplasmic binding protein is a polypeptide selected from the group consisting of:
7a) a polypeptide comprising an amino acid sequence set forth in SEQ ID NO: 19;
7b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 19; or
7c) a polypeptide comprising an amino acid sequence set forth in SEQ ID NO: 19, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

34. The process according to any one of items 27 to 31, wherein the periplasmic binding protein is Sbp.

35. The process according to any one of items 27 to 31, wherein the periplasmic protein is a polypeptide selected from the group consisting of:
8a) a polypeptide comprising an amino acid sequence set forth in SEQ ID NO: 20;
8b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 20; or
8c) a polypeptide comprising an amino acid sequence set forth in SEQ ID NO: 20, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

36. The process according to any one of items 10-20, wherein the sulfate transporter is a member of the SulP family.

37. The process according to any one of items 10-20, wherein the sulfate transporter is a polypeptide selected from the group consisting of:
9a) a polypeptide comprising an amino acid sequence set forth in SEQ ID NO: 26;
9b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 26; or 9c) a polypeptide comprising an amino acid sequence set forth in SEQ ID NO: 26, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

38. The process according to any one of items 10-20, wherein the sulfate transporter is a CysP transporter belonging to the phosphate inorganic transporter (PiT) family.

39. The process according to any one of items 10-20, wherein the sulfate transporter is selected from the group consisting of:

10a) a polypeptide comprising an amino acid sequence set forth in SEQ ID NO: 27;

10b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 27; or 10c) a polypeptide comprising an amino acid sequence set forth in SEQ ID NO: 27, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

40. The process according to any one of items 1-39, wherein the first recombinant host cell has been further modified to have an increased protein expression of an ATP sulfurylase compared to an identical host cell that does not carry said modification.

41. The process according to item 40, wherein the ATP sulfurylase is encoded by the genes cysD and cysN.

42. The process according to item 40 or 41, wherein the ATP sulfurylase comprises a polypeptide comprising an amino acid sequence set forth in SEQ ID NO: 28 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 28, and iii) a polypeptide comprising an amino acid sequence set forth in SEQ ID NO: 29 or iv) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 29.

43. The process according to any one of items 1-42, wherein said first recombinant host cell has been further modified to have an increased protein expression of an APS kinase compared to an identical host cell that does not carry said modification.

44. The process according to item 43, wherein the APS kinase is encoded by the gene cysC.

45. The process according to item 43 or 44, wherein the APS kinase is a polypeptide comprising an amino acid sequence set forth in SEQ ID NO: 32 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 32.

46. The process according to any one of items 1-45, wherein said first recombinant host cell has been further modified to have an increased protein expression of a PAP phosphatase compared to an identical host cell that does not carry said modification.

47. The process according to item 46, wherein said PAP phosphatase is encoded by the gene cycQ.

48. The process according to item 46 or 47, wherein the PAP phosphatase is a polypeptide comprising an amino acid sequence set forth in SEQ ID NO: 37 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 37.

49. The process according to any one of items 40-48, wherein the increase in protein expression is achieved by increasing the number of copies of the encoding gene or genes.

50. The process according to item 49 wherein the increase in the number of copies of the gene or genes is achieved by introducing into said first recombinant host cell one or more exogenous nucleic acid molecules (such as one or more vectors) comprising the gene or genes operably linked to a promoter that is functional in the host cell to cause the production of an mRNA molecule.

51. The process according to any one of items 40-50, wherein the increase in protein expression is achieved by modifying the ribosome binding site.

52. The process according to any one of items 40-51, wherein the increase in protein expression is achieved by increasing the strength of the promoter(s) operably linked to the gene or genes.

53. The process according to any one of items 1-52, wherein said first recombinant host cell further comprises a heterologous polypeptide having a tyrosine ammonia lyase activity.

54. The process according to any one of items 1-53, wherein in step (i'), (i") or (i''') the medium is further contacted with a second recombinant host cell comprising a heterologous polypeptide having a tyrosine ammonia lyase activity.

55. The process according to item 53 or 54, wherein the heterologous polypeptide having a tyrosine ammonia lyase activity is selected from the group consisting of:

11a) a polypeptide comprising an amino acid sequence set forth in SEQ ID NO: 40, 41, 42, 43, 44, 45, 46, 47, 48, 49 or 50 (e.g., SEQ ID NO: 40);

11b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 40, 41, 42, 43, 44, 45, 46, 47, 48, 49 or 50 (e.g., SEQ ID NO: 40); or 11c) a polypeptide comprising an amino acid sequence set forth in SEQ ID NO: 40, 41, 42, 43, 44, 45, 46, 47, 48, 49 or 50 (e.g., SEQ ID NO: 40), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

56. The process according to any one of items 53 to 55, wherein the first and/or second recombinant host cell comprises an exogenous nucleic acid molecule comprising a nucleotide sequence encoding said heterologous polypeptide having a tyrosine ammonia lyase activity.

57. The process according to item 56, wherein the exogenous nucleic acid molecule further comprises a promoter that is functional in the host cell to cause the production of an mRNA molecule and that is operably linked to the nucleotide sequence encoding said heterologous polypeptide.
58. The process according to item 56 or 57, wherein the exogenous nucleic acid molecule is a vector.
59. The process according to item 56 or 57, wherein the exogenous nucleic acid is stably integrated into the genome of the first and/or second recombinant host cell.
60. The process according to any one of items 1 to 59, wherein the first recombinant host cell and the second recombinant host cell are independently selected from the group consisting of bacteria, yeasts, fungi, algae and plant cells.
61. The process according to any one of items 1 to 60, wherein the first recombinant host cell is a bacterium.
62. The process according to item 61, wherein the bacterium is a bacterium of the genus Bacillus, Lactococcus, Lactobacillus, Clostridium, Corynebacterium, Geobacillus, Thermoanaerobacterium, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus, or Yersinia.
63. The process according to item 61, wherein the bacterium is a bacterium of the genus Bacillus.
64. The process according to item 63, wherein the bacterium is Bacillus subtilis.
65. The process according to item 61, wherein the bacterium is a bacterium of the genus Lactococcus.
66. The process according to item 65, wherein the bacterium is Lactococcus lactis.
67. The process according to item 61, wherein the bacterium is a bacterium of the genus Pseudomonas.
68. The process according to item 67, wherein the bacterium is Pseudomonas putida.
69. The process according to item 61, wherein the bacterium is a bacterium of the genus Corynebacterium.
70. The process according to item 69, wherein the bacterium is Corynebacterium glutamicum.
71. The process according to item 61, wherein the bacterium is a bacterium of the genus Escherichia.
72. The process according to item 71, wherein the bacterium is Escherichia coli.
73. The process according to any one of item 1-60, wherein the first recombinant host cell is a yeast.
74. The process according to item 73, wherein the yeast is of the genus Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula, or Trichosporon.
75. The process according to any one of items 1-60, wherein the first recombinant host cell is a fungus.
76. The process according to item 75, wherein the fungus is a fungus of the genus Aspergillus.
77. The process according to any one of items 1-60, wherein the first recombinant host cell is an algae cell.
78. The process according to item 77, wherein the algae cells is an algae cell of the genus Haematococcus, Phaedactylum, Volvox or Dunaliella.
79. The process according to any one of items 1-60, wherein the first recombinant host cell is a plant cell.
80. The process according to item 79, wherein the plant cell is selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.
81. The process according to any one of items 1-80, wherein the phenolic compound is represented by the general formula (I):

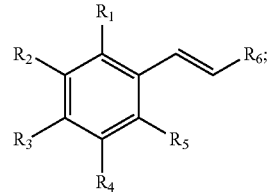

Formula (I)

wherein at least one of $R_1$, $R_2$, $R_3$, $R_4$, and $R_5$ being an hydroxyl group (—OH);
wherein $R_1$, $R_2$, $R_3$, $R_4$, $R_5$ and $R_6$ are independently selected from the group consisting of halide, hydrogen, hydroxyl (—OH), —$OR_7$, —$OCOR_7$, —$NR_7R_8$, —$COR_7$, —$COOR_7$, —$SR_7$, —$OSO_3R_7$, —$OCSR_7$, —$POR_7R_8$, alkyl, alkenyl, alkynyl, aryl, and heteroaryl; wherein $R_7$, and $R_8$ are independently selected from the group consisting of hydrogen, alkyl, alkenyl, alkynyl, aryl, and heteroaryl;
wherein $R_1$, $R_2$, $R_3$, $R_4$, $R_5$ and $R_6$, are optionally linked with a bridge member $Y_n$, thereby forming one or more rings, $Y_n$ being a bond or a $C_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, $S(O)_{1-2}$ and carbonyl, and wherein n is an integer between 1 and 12.
82. A process according to any one of the items 1-81, wherein the phenolic compound is represented by the general formula (II):

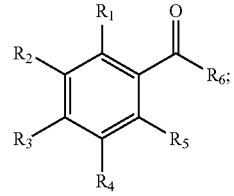

Formula (II)

wherein at least one of $R_1$, $R_2$, $R_3$, $R_4$, and $R_5$ being an hydroxyl group (—OH);
wherein $R_1$, $R_2$, $R_3$, $R_4$, $R_5$ and $R_6$ are independently selected from the group consisting of halide, hydrogen, hydroxyl (—OH), —$OR_7$, —$OCOR_7$, —$NR_7R_8$, —$COR_7$, —$COOR_7$, —$SR_7$, —$OSO_3R_7$, —$OCSR_7$, —$POR_7R_8$, alkyl, alkenyl, alkynyl, aryl, and heteroaryl; wherein $R_7$, and $R_8$ are independently selected from the group consisting of hydrogen, alkyl, alkenyl, alkynyl, aryl, and heteroaryl;
wherein $R_1$, $R_2$, $R_3$, $R_4$, $R_5$ and $R_6$, are optionally linked with a bridge member $Y_n$, thereby forming one or more rings, $Y_n$ being a bond or a $C_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ and carbonyl, and wherein n is an integer between 1 and 12.

83. The process according to any one of items 1-82, wherein the precursor of a phenolic compound in step (i''') is a compound of the general Formula (p-I):

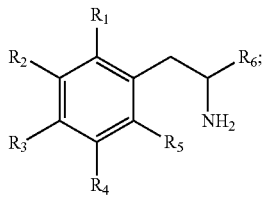

Formula (p-I)

wherein at least one of R$_1$, R$_2$, R$_3$, R$_4$, and R$_5$ being an hydroxyl group (—OH);
wherein R$_1$, R$_2$, R$_3$, R$_4$, R$_5$ and R$_6$ are independently selected from the group consisting of halide, hydrogen, hydroxyl (—OH), —OR$_7$, —OCOR$_7$, —NR$_7$R$_8$, —COR$_7$, —COOR$_7$, —SR$_7$, —OSO$_3$R$_7$, —OCSR$_7$, —POR$_7$R$_8$, alkyl, alkenyl, alkynyl, aryl, and heteroaryl; wherein R$_7$, and R$_8$ are independently selected from the group consisting of hydrogen, alkyl, alkenyl, alkynyl, aryl, and heteroaryl;
wherein R$_1$, R$_2$, R$_3$, R$_4$, R$_5$ and R$_6$, are optionally linked with a bridge member Y$_n$, thereby forming one or more rings, Y$_n$ being a bond or a C$_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ and carbonyl, and wherein n is an integer between 1 and 12.

84. The process according to any one of items 81-83, wherein R$_6$ is —COOR$_7$, wherein R$_7$ is selected from the group consisting of hydrogen, alkyl, alkenyl, alkynyl, aryl, and heteroaryl.

85. The process according to item 84, wherein R$_7$ is hydrogen.

86. The process according to any one of items 81-85, wherein R$_3$ is hydroxyl (—OH).

87. The process according to any one of items 81-86, wherein each of R$_1$, R$_2$, R$_4$ and R$_5$ is hydrogen.

88. The process according to any one of items 81-86, wherein R$_4$ is hydroxyl (—OH).

89. The process according to item 88, wherein each of R$_1$, R$_2$, and R$_5$ is hydrogen.

90. The process according to any one of items 81-83, wherein each of R$_1$, R$_3$ and R$_5$ is hydrogen, each of R$_2$ and R$_4$ is hydroxyl (—OH), and R$_6$ is p-hydroxyphenyl.

91. A recombinant host cell comprising a heterologous polypeptide having aryl sulfotransferase activity, such as a polypeptide selected from the group consisting of:
1a) a polypeptide comprising an amino acid sequence set forth in SEQ ID NO: 1, 2, 3, 4, 5, 6, 7, 8, 9, 10, 11, 12 or 13 (e.g., SEQ ID NO: 1);
1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1); or
1c) a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted;
wherein the recombinant host cell has been modified to have an increased uptake of sulfate compared to an identical host cell that does not carry said modification.

92. The recombinant host cell according to item 91, wherein the heterologous polypeptide having an aryl sulfotransferase activity is a sulfotransferase 1A1 enzyme.

93. The recombinant host cell according to item 91, wherein the heterologous polypeptide is selected from the group consisting of:
1a) a polypeptide comprising an amino acid sequence set forth in SEQ ID NO: 1;
1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1; or
1c) a polypeptide comprising an amino acid sequence set forth in SEQ ID NO: 1, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

94. The recombinant host cell according to item 91 to 93, wherein the polypeptide according to 1b) or 1c) has aryl sulfotransferase activity.

95. The recombinant host cells according to any one of items 91-94, the host cell comprises an exogenous nucleic acid molecule comprising a nucleotide sequence encoding said heterologous polypeptide having aryl sulfotransferase activity.

96. The recombinant host cell according to item 95, wherein the exogenous nucleic acid molecule further comprises a promoter that is functional in the host cell to cause the production of an mRNA molecule and that is operably linked to the nucleotide sequence encoding said heterologous polypeptide having aryl sulfotransferase activity.

97. The recombinant host cell according to item 96, wherein the exogenous nucleic acid molecule further comprises at least one regulatory element selected from a 5' untranslated region (5'UTR) and 3' untranslated region (3' UTR).

98. The recombinant host cell according to any one of items 95-97, wherein the exogenous nucleic acid is a vector.

99. The recombinant host cell according to any one of items 95-97, wherein the exogenous nucleic acid is stably integrated into the genome of the host cell.

100. The recombinant host cell according to any one of items 91-99, wherein said recombinant host cell has been modified to an have increased protein expression of a sulfate transporter compared to the identical host cell that does not carry said modification.

101. The recombinant host cell according to item 100, wherein the increase in protein expression of the sulfate transporter is achieved by increasing the number of copies of a gene or genes encoding said sulfate transporter.

102. The recombinant host cell according to item 101, wherein the increase in the number of copies of the gene or genes is achieved by introducing into said recombinant host cell one or more exogenous nucleic acid molecules (such as one or more vectors) comprising the gene or genes operably linked to a promoter that is functional in the host cell to cause the production of an mRNA molecule.

103. The recombinant host cell according to any one of items 91-100, wherein said recombinant host cell comprises an exogenous nucleic acid molecule (such as a vector) comprising one or more nucleotide sequences encoding a sulfate transporter.

104. The recombinant host cell according to item 102, wherein the exogenous nucleic acid molecule further comprises a promoter that is functional in the host cell to cause the production of an mRNA molecule and that is operably linked to the one or more nucleotide sequences encoding said sulfate transporter.

105. The recombinant host cell according to any one of items 102-104, wherein the exogenous nucleic acid molecule is a vector.

106. The recombinant host cell according to any one of items 102-104, wherein the exogenous nucleic acid molecule is stably integrated into the genome of said recombinant host cell.

107. The recombinant host cell according to item 100, wherein the increase in protein expression is achieved by modifying the ribosome binding site.

108. The recombinant host cell according to any one of item 100, wherein the increase in protein expression is achieved by increasing the strength of the promoter(s) operably linked to the gene or genes encoding said sulfate transporter.

109. The recombinant host cell according to any one of items 100-108, wherein the sulfate transporter is a bacterial sulfate transporter.

110. The recombinant host cell according to any one of items 100-109, wherein the sulfate transporter is a selected from the group consisting of: members of the CysZ family, members of the SulT (cysPTWA) family, members of the SulP family, CysP transporters belonging to the phosphate inorganic transporter (PiT) family, and oxyanion permeases (PerO).

111. The recombinant host cell according to any one of items 100-110, wherein the sulfate transporter is a member of the CysZ family.

112. The recombinant host cell according to any one of items 100-111, wherein the sulfate transporter is a CysZ protein.

113. The recombinant host cell according to any one of items 100-112, wherein the sulfate transporter is a polypeptide selected from the group consisting of:
2a) a polypeptide comprising an amino acid sequence set forth in SEQ ID NO: 14;
2b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 14; or
2c) a polypeptide comprising an amino acid sequence set forth in SEQ ID NO: 14, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

114. The recombinant host cell according to any one of items 100-112, wherein the sulfate transporter is a polypeptide selected from the group consisting of:
3a) a polypeptide comprising an amino acid sequence set forth in SEQ ID NO: 15;
3b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15; or
3c) a polypeptide comprising an amino acid sequence set forth in SEQ ID NO: 15, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

115. The recombinant host cell according to any one of items 100-110, wherein the sulfate transporter is a sulfate-transporting ATPase.

116. The recombinant host cell according to any one of items 100-110, wherein the sulfate transporter is a member of the SulT (cysPTWA) family.

117. The recombinant host cell according to any one of items 100-110, wherein the sulfate transporter comprises a first membrane subunit (CysT), a second membrane subunit (CysW), an ATP binding subunit (CysA) and a periplasmic binding protein (CysP or Sbp).

118. The recombinant host cell according to any one of items 115 to 117, where the sulfate transporter is encoded by an operon comprising a nucleotide sequence encoding a first membrane subunit (CysT), a nucleotide sequence encoding a second membrane subunit (CysW), a nucleotide sequence encoding an ATP binding subunit (CysA) and a nucleotide sequence encoding a periplasmic binding protein (CysP or Sbp).

119. The recombinant host cell according to item 117 or 118, wherein the first membrane subunit is a polypeptide selected from the group consisting of:
4a) a polypeptide comprising an amino acid sequence set forth in SEQ ID NO: 16;
4b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16; or
4c) a polypeptide comprising an amino acid sequence set forth in SEQ ID NO: 16, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

120. The recombinant host cell according to any one of items 117 to 119, wherein the second membrane subunit is a polypeptide selected from the group consisting of:
5a) a polypeptide comprising an amino acid sequence set forth in SEQ ID NO: 17;
5b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17; or
5c) a polypeptide comprising an amino acid sequence set forth in SEQ ID NO: 17, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

121. The recombinant host cell according to any one of items 117 to 120, wherein the ATP binding subunit is a polypeptide selected from the group consisting of:
6a) a polypeptide comprising an amino acid sequence set forth in SEQ ID NO: 18;
6b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18 or 23; or
6c) a polypeptide comprising an amino acid sequence set forth in SEQ ID NO: 18, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

122. The recombinant host cell according to any one of items 117 to 121, wherein the periplasmic binding protein is CysP.

123. The recombinant host cell according to any one of items 117 to 121, wherein the periplasmic binding protein is a polypeptide selected from the group consisting of:

7a) a polypeptide comprising an amino acid sequence set forth in SEQ ID NO: 19;

7b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 19; or 7c) a polypeptide comprising an amino acid sequence set forth in SEQ ID NO: 19, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

124. The recombinant host cell according to any one of items 117 to 121, wherein the periplasmic binding protein is Sbp.

125. The recombinant host cell according to any one of items 117 to 121, wherein the periplasmic protein is a polypeptide selected from the group consisting of:

8a) a polypeptide comprising an amino acid sequence set forth in SEQ ID NO: 20;

8b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 20; or 8c) a polypeptide comprising an amino acid sequence set forth in SEQ ID NO: 20, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

126. The recombinant host cell according to any one of items 100-110, wherein the sulfate transporter is a member of the SulP family.

127. The recombinant host cell according to any one of items 100-110, wherein the sulfate transporter is a polypeptide selected from the group consisting of:

9a) a polypeptide comprising an amino acid sequence set forth in SEQ ID NO: 26;

9b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 26; or 9c) a polypeptide comprising an amino acid sequence set forth in SEQ ID NO: 26, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

128. The recombinant host cell according to any one of items 100-110, wherein the sulfate transporter is a CysP transporter belonging to the phosphate inorganic transporter (PiT) family.

129. The recombinant host cell according to any one of items 100-110, wherein the sulfate transporter is selected from the group consisting of:

10a) a polypeptide comprising an amino acid sequence set forth in SEQ ID NO: 27;

10b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 27; or 10c) a polypeptide comprising an amino acid sequence set forth in SEQ ID NO: 27, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

130. The recombinant host cell according to any one of items 91-129, wherein the recombinant host cell has further been modified to have an increased protein expression of an ATP sulfurylase compared to an identical host cell that does not carry said modification.

131. The recombinant host cell according to item 130, wherein said ATP sulfurylase is encoded by the genes cysD and cysN.

132. The recombinant host cell according to item 130 or 131, wherein the ATP sulfurylase comprises a polypeptide comprising an amino acid sequence set forth in SEQ ID NO: 28 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 28, and iii) a polypeptide comprising an amino acid sequence set forth in SEQ ID NO: 29 or iv) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 29.

133. The recombinant host cell according to any one of items 91-132, wherein the recombinant host cell has further been modified to have an increased protein expression of an APS kinase compared to an identical host cell that does not carry said modification.

134. The recombinant host cell according to item 133, wherein said APS kinase is encoded by the gene cysC.

135. The process according to item 133 or 134, wherein the APS kinase is a polypeptide comprising an amino acid sequence set forth in SEQ ID NO: 32 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 32.

136. The recombinant host cell according to any one of items 91-135, wherein the recombinant host cell has further been modified to have an increased protein expression of a PAP phosphatase compared to an identical host cell that does not carry said modification.

137. The recombinant host cell according to item 136, wherein said PAP phosphatase is encoded by the gene cycQ.

138. The process according to item 136 or 137, wherein the PAP phosphatase is a polypeptide comprising an amino acid sequence set forth in SEQ ID NO: 37 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 37.

139. The recombinant host cell according to any one of items 91-138, wherein the increase in gene expression has been achieved by an increased number of copies of the gene or genes.
140. The recombinant host cell according to item 139, wherein the increase in the number of copies of the gene or genes is achieved by having introduced into said first recombinant host cell one or more exogenous nucleic acid molecules (such as one or more vectors) comprising the gene or genes operably linked to a promoter that is functional in the host cell to cause the production of an mRNA molecule.
141. The recombinant host cell according to any one of item 130-138, wherein the increase in protein expression is achieved by modifying the ribosome binding site.
142. The recombinant host cell according to any one of items 130-138, wherein the increase in gene expression has been achieved by increasing the strength of the promoter(s) operably linked to the gene or genes.
143. The recombinant host cell according to any one of items 91-142, further comprising a heterologous polypeptide having tyrosine ammonia lyase activity, such as a polypeptide selected from the group consisting of:
11a) a polypeptide comprising an amino acid sequence set forth in SEQ ID NO: 40, 41, 42, 43, 44, 45, 46, 47, 48, 49 or 50 (e.g., SEQ ID NO: 40);
11b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 40, 41, 42, 43, 44, 45, 46, 47, 48, 49 or 50 (e.g., SEQ ID NO: 40); or
11c) a polypeptide comprising an amino acid sequence set forth in SEQ ID NO: 40, 41, 42, 43, 44, 45, 46, 47, 48, 49 or 50 (e.g., SEQ ID NO: 40), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.
144. The recombinant host cell according to item 143, wherein the heterologous polypeptide according to 10b) or 10c) has tyrosine ammonia lyase activity.
145. The recombinant host cell according to item 143 or 144, wherein the recombinant host cell comprises an exogenous nucleic acid molecule comprising a nucleotide sequence encoding said heterologous polypeptide having tyrosine ammonia lyase activity.
146. The recombinant host cell according to item 145, wherein the exogenous nucleic acid molecule further comprises a promoter that is functional in the host cell to cause the production of an mRNA molecule and that is operably linked to the nucleotide sequence encoding said heterologous polypeptide having tyrosine ammonia lyase activity.
147. The recombinant host cell according to item 145 or 146, wherein the exogenous nucleic acid molecule is a vector.
148. The recombinant host cell according to item 145 or 146, wherein the exogenous nucleic acid is stably integrated into the genome of the recombinant host cell.
149. The recombinant host cell according to any one of items 91-148, wherein the recombinant host cell is selected from the group consisting of bacteria, yeasts, fungi, algae and plant cells.
150. The recombinant host cell according to any one of items 910-149, wherein the recombinant host cell is a bacterium.
151. The recombinant host cell according to item 150, wherein the bacterium is a bacterium of the genus *Bacillus*, *Lactococcus*, *Lactobacillus*, *Clostridium*, *Corynebacterium*, *Geobacillus*, *Streptococcus*, *Pseudomonas*, *Streptomyces*, *Escherichia*, *Shigella*, *Acinetobacter*, *Citrobacter*, *Salmonella*, *Klebsiella*, *Enterobacter*, *Erwinia*, *Kluyvera*, *Serratia*, *Cedecea*, *Morganella*, *Hafnia*, *Edwardsiella*, *Providencia*, *Proteus*, or *Yersinia*.
152. The recombinant host cell according to item 150, wherein the bacterium is a bacterium of the genus *Bacillus*.
153. The recombinant host cell according to item 152, wherein the bacterium is *Bacillus subtilis*.
154. The recombinant host cell according to item 150, wherein the bacterium is a bacterium of the genus *Lactococcus*.
155. The recombinant host cell according to item 154, wherein the bacterium is *Lactococcus lactis*.
156. The recombinant host cell according to item 150, wherein the bacterium is a bacterium of the genus *Pseudomonas*.
157. The recombinant host cell according to item 156, wherein the bacterium is *Pseudomonas putida*.
158. The recombinant host cell according to item 150, wherein the bacterium is a bacterium of the genus *Corynebacterium*.
159. The recombinant host cell according to item 158, wherein the bacterium is *Corynebacterium glutamicum*.
160. The recombinant host cell according to item 150, wherein the bacterium is a bacterium of the genus *Escherichia*.
161. The recombinant host cell according to item 160, wherein the bacterium is *Escherichia coll*.
162. The recombinant host cell according to any one of items 91-149, wherein the recombinant host cell is a yeast.
162. The recombinant host cell according to item 162, wherein the yeast is of the genus *Saccharomyces*, *Pichia*, *Schizosacharomyces*, *Zygosaccharomyces*, *Hansenula*, *Pachyosolen*, *Kluyveromyces*, *Debaryomyces*, *Yarrowia*, *Candida*, *Cryptococcus*, *Komagataella*, *Lipomyces*, *Rhodospiridium*, *Rhodotorula*, or *Trichosporon*.
163. The recombinant host cell according to any one of items 91-149, wherein the recombinant host cell is a fungus.
164. The recombinant host cell according to item 163, wherein the fungus is a fungus of the genus *Aspergillus*.
165. The recombinant host cell according to any one of items 91-149, wherein the recombinant host cell is an algae cell.
166. The recombinant host cell according to item 165, wherein the algae cells is an algae cell of the genus *Haematococcus*, *Phaedactylum*, *Volvox* or *Dunaliella*.
167. The recombinant host cell according to any one of items 91-149, wherein the recombinant host cell is a plant cell.
168. The recombinant host cell according to item 167, wherein the plant cell is selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.
169. The recombinant host cell according to any one of items 91-168, which is employed as first recombinant host cell in the process according to any one of items 1-90.
170. Use of the recombinant host cell according to any one of items 91-169 in the production of a sulfated phenolic compound, e.g., in the production of zosteric acid.
171. Use according to item 170, wherein the sulfated phenolic compound is derived from a phenolic compound of general formula (I) or (II) as defined herein.

DETAILED DESCRIPTION OF THE INVENTION

Figure 1:
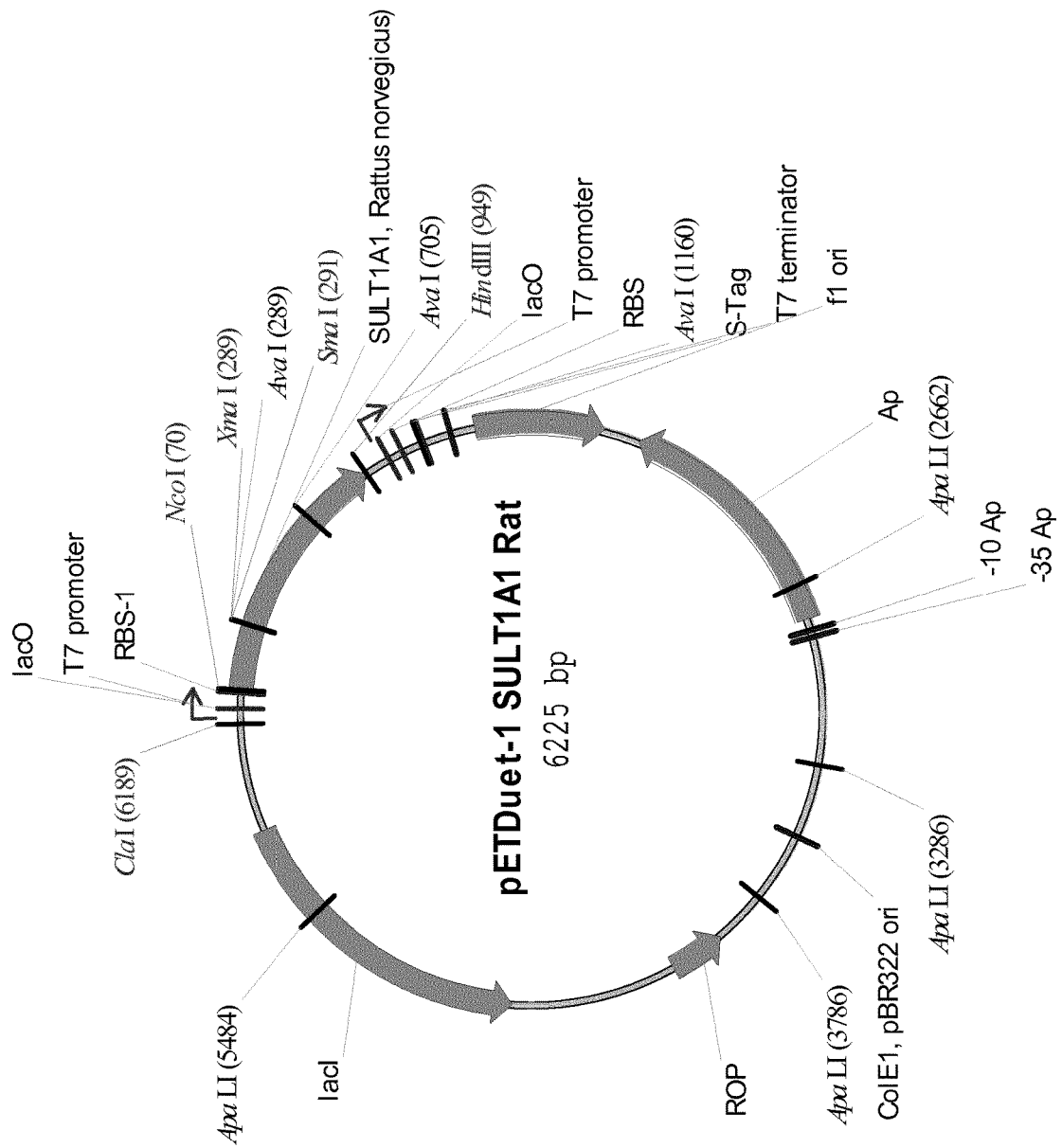
FIG. 1: Map of plasmid for expression of SULT1A1 from *Rattus norvegicus* in *Escherichia coli*

Unless specifically defined herein, all technical and scientific terms used have the same meaning as commonly understood by a skilled artisan in the fields of biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Recombinant Host Cells of the Invention

In one aspect, the present invention provides a recombinant host cell comprising (e.g., expressing) a heterologous polypeptide having an aryl sulfotransferase activity. More particularly, the present invention provides a recombinant host cell comprising (e.g., expressing) a heterologous polypeptide having an aryl sulfotransferase activity, wherein the recombinant host cell has been modified to have an increased uptake of sulfate compared to an identical host cell that does not carry said modification.

Generally, the polypeptide having an aryl sulfotransferase activity employed according to the invention will be heterologous to the host cells, which means that said polypeptide is normally not found in or made (i.e. expressed) by the host cells, but derived from a different species. Aryl sulfotransferases (EC:2.8.2.1) are a well-defined class of enyzmes catalyzing the transfer of a sulfate group from a donor molecule to an aryl acceptor molecule. This makes them particularly suitable for the sulfation of phenolic compounds such as p-coumaric acid and derivatives thereof (e.g., caffeic acid, ferulic acid or sinapic acid), or resveratrol.

The polypeptide having aryl sulfotransferase activity may be a sulfotransferase 1A1 enzyme, a sulfotransferase 1A2 enzyme, a sulfotransferase 1A3 enzyme, a sulfotransferase 1B1 enzyme, a sulfotransferase 1C1 enzyme, a sulfotransferase 1C2 enzyme, a sulfotransferase 1C4 enzyme, or a sulfotransferase 1E1 enzyme.

According to certain embodiments, the polypeptide having aryl sulfotransferase activity is a sulfotransferase 1A1 enzyme. According to certain other embodiments, the polypeptide having aryl sulfotransferase activity is a sulfotransferase 1A2 enzyme. According to certain embodiments, the polypeptide having aryl sulfotransferase activity is a sulfotransferase 1B1 enzyme. According to certain embodiments, the polypeptide having aryl sulfotransferase activity is a sulfotransferase 1C1 enzyme. According to certain embodiments, the polypeptide having aryl sulfotransferase activity is a sulfotransferase 1C2 enzyme. According to certain embodiments, the polypeptide having aryl sulfotransferase activity is a sulfotransferase 1C4 enzyme. According to other certain embodiments, the polypeptide having aryl sulfotransferase activity is a sulfotransferase 1E1 enzyme (estrogen sulfotransferase), such as the sulfotransferase 1E1 from *Gallus gallus domesticus*.

According to certain embodiments, the polypeptide having aryl sulfotransferase activity is a mammalian aryl sulfotransferase, such as a mammalian sulfotransferase 1A1 enzyme.

According to certain embodiments, the polypeptide having aryl sulfotransferase activity is an aryl sulfotransferase from *Rattus norvegicus* or a variant thereof. Such variant may have at least about 70%, such as at least about 75%, at least about 80%, at least about 85%, at least about 90%, at least about 93%, at least 95%, at least 96%, at least 97%, at least 98%, or at least 99%, sequence identity to the amino acid sequence of the aryl sulfotransferase from *Rattus norvegicus*. Such variant may also have an amino acid sequence of the sulfotransferase from *Rattus norvegicus*, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

It is understood that the foregoing values generally define the total number of alterations to the reference aryl sulfotransferase. The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

According to certain embodiments, the polypeptide having aryl sulfotransferase activity may be a polypeptide selected from the group consisting of:

1a) a polypeptide comprising an amino acid sequence set forth in SEQ ID NO: 1, 2, 3, 4, 5, 6, 7, 8, 9, 10, 11, 12, 13, 99, 101, 103 or 105 (e.g., SEQ ID NO: 1);

1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12, 13, 99, 101, 103 or 105 (e.g., SEQ ID NO: 1); or 1c) a polypeptide comprising an amino acid sequence set forth in SEQ ID NO: 1, 2, 3, 4, 5, 6, 7, 8, 9, 10, 11, 12, 13, 99, 101, 103 or 105 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the polypeptide having aryl sulfotransferase activity may be a polypeptide selected from the group consisting of:

1a) a polypeptide comprising an amino acid sequence set forth in SEQ ID NO: 1, 2, 3, 4, 5, 6, 7, 8, 9, 10, 11, 12 or 13 (e.g., SEQ ID NO: 1);

1b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1); or 1c) a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the polypeptide having aryl sulfotransferase activity is a polypeptide according to 1a). Accordingly, the polypeptide having aryl sulfotransferase activity may be a polypeptide comprising an amino acid sequence set forth in SEQ ID NO: 1, 2, 3, 4, 5, 6, 7, 8, 9, 10, 11, 12 or 13 (e.g., SEQ ID NO: 1). According to particular embodiments, the polypeptide according to a) comprises an amino acid sequence set forth in SEQ ID NO: 1. According other particular embodiments, a polypeptide according to 1a) comprises an amino acid sequence set forth in SEQ ID NO: 2. According to yet other particular embodiments, a polypeptide according to a) comprises an amino acid sequence set forth in SEQ ID NO: 3. According to yet other particular embodiments, a polypeptide according to 1a) comprises an amino acid sequence set forth in SEQ ID NO: 4. According to yet other particular embodiments, a polypeptide according to 1a) comprises an amino acid sequence set forth in SEQ ID NO: 5. According other particular embodiments, a polypeptide according to a) comprises an amino acid sequence set forth in SEQ ID NO: 6. According other particular embodiments, a polypeptide according to 1a) comprises an amino acid sequence set forth in SEQ ID NO: 7. According other particular embodiments, a polypeptide according to a) comprises an amino acid sequence set forth in SEQ ID NO: 8. According other particular embodiments, a polypeptide according to 1a) comprises an amino acid sequence set forth in SEQ ID NO: 9. According other particular embodiments, a polypeptide according to a) comprises an amino acid sequence set forth in SEQ ID NO: 10. According other particular embodiments, a polypeptide according to 1a) comprises an amino acid sequence set forth in SEQ ID NO: 11. According other particular embodiments, a polypeptide according to a) comprises an amino acid sequence set forth in SEQ ID NO: 12.

According other particular embodiments, a polypeptide according to 1a) comprises an amino acid sequence set forth in SEQ ID NO: 13.

According to other certain embodiments, the polypeptide having aryl sulfotransferase activity is a polypeptide according to 1b). Accordingly, a polypeptide having aryl sulfotransferase activity may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to particular embodiments, a polypeptide according to 1b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to 1b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to 1b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to 1b) comprises an amino acid sequence which has at least about 95%, such as at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1).

According to particular embodiments, a polypeptide according to 1b) comprises an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1. According to more particular embodiments, a polypeptide according to 1b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to 1b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to 1b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to 1b) comprises an amino acid sequence which has at least about 95%, such as at least about 96%, at least about 97%, at least about 98%, or at least about 99%, sequence identity to the amino acid sequence set forth in SEQ ID NO: 1.

Preferably, a polypeptide according to 1b) has aryl sulfotransferase activity. More preferably, a polypeptide according to 1b) has a aryl sulfotransferase activity similar to that of the polypeptide comprising an amino acid sequence set forth in SEQ ID NO: 1, 2, 3, 4, 5, 6, 7, 8, 9, 10, 11, 12 or 13 (e.g., SEQ ID NO: 1).

According to certain embodiment, a polypeptide according to 1b) has aryl sulfotransferase activity similar to that of the polypeptide comprising the amino acid sequence set forth in SEQ ID NO: 1. According to certain other embodiments, a polypeptide according to 1b) has aryl sulfotransferase activity similar to that of the polypeptide comprising the amino acid sequence set forth in SEQ ID NO: 2. According to certain other embodiments, a polypeptide according to 1b) has aryl sulfotransferase activity similar to that of the polypeptide comprising the amino acid sequence set forth in SEQ ID NO: 3. According to certain other embodiments, a polypeptide according to 1b) has aryl sulfotransferase activity similar to that of the polypeptide comprising the amino acid sequence set forth in SEQ ID NO: 4. According to certain other embodiments, a polypeptide according to 1b) has aryl sulfotransferase activity similar to that of the polypeptide comprising the amino acid sequence set forth in SEQ ID NO: 5. According to certain other embodiments, a polypeptide according to 1b) has aryl sulfotransferase activity similar to that of the polypeptide comprising the amino acid sequence set forth in SEQ ID NO: 6. According to certain other embodiments, a polypeptide according to 1b) has aryl sulfotransferase activity similar to that of the polypeptide comprising the amino acid sequence set forth in SEQ ID NO: 7. According to certain other embodiments, a polypeptide according to 1b) has aryl sulfotransferase activity similar to that of the polypeptide comprising the amino acid sequence set forth in SEQ ID NO: 8. According to certain other embodiments, a polypeptide according to 1b) has aryl sulfotransferase activity similar to that of the polypeptide comprising the amino acid sequence set forth in SEQ ID NO: 9. According to certain other embodiments, a polypeptide according to 1b) has aryl sulfotransferase activity similar to that of the polypeptide comprising the amino acid sequence set forth in SEQ ID NO: 10. According to certain other embodiments, a polypeptide according to 1b) has aryl sulfotransferase activity similar to that of the polypeptide comprising the amino acid sequence set forth in SEQ ID NO: 11. According to certain other embodiments, a polypeptide according to 1b) has aryl sulfotransferase activity similar to that of the polypeptide comprising the amino acid sequence set forth in SEQ ID NO: 12. According to certain other embodiments, a polypeptide according to 1b) has aryl sulfotransferase activity similar to that of the polypeptide comprising the amino acid sequence set forth in SEQ ID NO: 13. According to certain other embodiments, a polypeptide according to 1b) has aryl sulfotransferase activity similar to that of the polypeptide comprising the amino acid sequence set forth in SEQ ID NO: 99. According to certain other embodiments, a polypeptide according to 1b) has aryl sulfotransferase activity similar to that of the polypeptide comprising the amino acid sequence set forth in SEQ ID NO: 101. According to certain other embodiments, a polypeptide according to 1b) has aryl sulfotransferase activity similar to that of the polypeptide comprising the amino acid sequence set forth in SEQ ID NO: 103. According to certain other embodiments, a polypeptide according to 1b) has aryl sulfotransferase activity similar to that of the polypeptide comprising the amino acid sequence set forth in SEQ ID NO: 105.

With "similar" aryl sulfotransferase activity, it is meant that the polypeptide according to 1b) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the aryl sulfotransferase activity of the reference polypeptide (e.g., SEQ ID NO: 1).

The aryl sulfotransferase activity may for instance be determined in accordance to the following method: Aryl sulfotransferase activity may be determined by the reaction of radioactively sulfur labelled PAPS, [$^{35}$S]PAPS, with the substrate in presence of the polypeptide of interest. This is described previously, for example by Hattori et al (Biosci Biotechnol Biochem. 2008; 72(2):540-7). The reaction takes place in a buffer such as 250 µL 50 mM sodium phosphate pH 6.8 with 1 µM [$^{35}$S]PAPS (3.7 kBq) with 100 µM accepting compound for a period of 30 min at 30° C. The reaction is stopped by addition of 100 µL of a 1:1 mixture of 0.1 M barium acetate and barium hydroxide. 50 µL of 0.1 M zinc sulfate is added, followed by centrifugation at 1,200×g for 5 min. 3004 of the supernatant is then transferred to a new container and 50 µL of an equal volume of 0.1 M barium hydroxide and 0.1 M zinc sulfate is added. The mixture is then centrifuged at 13,000×g for 5 min, and 300-4 aliquots of the supernatant are mixed with 2.5 mL of Cleasol I (Nacalai Tesque, Kyoto, Japan). The radioactivity is then measured by scintillation.

Alternatively, the activity of a sulfotransferase may be detected by direct measurement of the product by analytical methods such as high performance liquid chromatography (HPLC) or liquid chromatography in combination with mass spectrometry (LC-MS).

According to other certain embodiments, the polypeptide having aryl sulfotransferase activity is a polypeptide according to 1c). Accordingly, the polypeptide having aryl sulfotransferase activity may be a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 or more, such as 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more, 90 or more, 100 or more, 110 or more, 120 or more, 130 or more, 140 or more, or 150 or more, amino acid residues are substituted, deleted, and/or inserted. According to particular embodiments, a polypeptide according to 1c) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 1c) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 1c) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 1c) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 25, such as about 1 to about 20, about 1 to about 15, about 1 to about 10, about 1 to about 5, or about 1 to about 3, amino acid residues are substituted, deleted and/or inserted.

According to particular embodiments, a polypeptide according to 1c) comprises an amino acid sequence set forth in SEQ ID NO: 1, wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 1c) comprises an amino acid sequence set forth in SEQ ID NO: 1, wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 1c) comprises an amino acid sequence set forth in SEQ ID NO: 1, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 1c) comprises an amino acid sequence set forth in SEQ ID NO: 1, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (e.g., SEQ ID NO: 1). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 1c) has aryl sulfotransferase activity. More preferably, a polypeptide according to 1c) has a aryl sulfotransferase activity similar to that of the polypeptide comprising an amino acid sequence set forth in SEQ ID NO: 1, 2, 3, 4, 5, 6, 7, 8, 9, 10, 11, 12 or 13 (e.g., SEQ ID NO: 1).

According to certain embodiment, a polypeptide according to 1c) has aryl sulfotransferase activity similar to that of the polypeptide comprising the amino acid sequence set forth in SEQ ID NO: 1. According to certain other embodiments, a polypeptide according to 1c) has aryl sulfotransferase activity similar to that of the polypeptide comprising the amino acid sequence set forth in SEQ ID NO: 2. According to certain other embodiments, a polypeptide according to 1c) has aryl sulfotransferase activity similar to that of the polypeptide comprising the amino acid sequence set forth in SEQ ID NO: 3. According to certain other embodiments, a polypeptide according to 1c) has aryl sulfotransferase activity similar to that of the polypeptide comprising the amino acid sequence set forth in SEQ ID NO: 4. According to certain other embodiments, a polypeptide according to 1c) has aryl sulfotransferase activity similar to that of the polypeptide comprising the amino acid sequence set forth in SEQ ID NO: 5. According to certain other embodiments, a polypeptide according to 1c) has aryl sulfotransferase activity similar to that of the polypeptide comprising the amino acid sequence set forth in SEQ ID NO: 6. According to certain other embodiments, a polypeptide according to 1c) has aryl sulfotransferase activity similar to that of the polypeptide comprising the amino acid sequence set forth in SEQ ID NO: 7. According to certain other embodiments, a polypeptide according to 1c) has aryl sulfotransferase activity similar to that of the polypeptide comprising the amino acid sequence set forth in SEQ ID NO: 8. According to certain other embodiments, a polypeptide according to 1c) has aryl sulfotransferase activity similar to that of the polypeptide comprising the amino acid sequence set forth in SEQ ID NO: 9. According to certain other embodiments, a polypeptide according to 1c) has aryl sulfotransferase activity similar to that of the polypeptide comprising the amino acid sequence set forth in SEQ ID NO: 10. According to certain other embodiments, a polypeptide according to 1c) has aryl sulfotransferase activity similar to that of the polypeptide comprising the amino acid sequence set forth in SEQ ID NO: 11. According to certain other embodiments, a polypeptide according to 1c) has aryl sulfotransferase activity similar to that of the polypeptide comprising the amino acid sequence set forth in SEQ ID NO: 12. According to certain other embodiments, a polypeptide according to 1c) has aryl sulfotransferase activity similar to that of the polypeptide comprising the amino acid sequence set forth in SEQ ID NO: 13. According to certain other embodiments, a polypeptide according to 1c) has aryl sulfotransferase activity similar to that of the polypeptide comprising the amino acid sequence set forth in SEQ ID NO: 99. According to certain other embodiments, a polypeptide according to 1c) has aryl sulfotransferase activity similar to that of the polypeptide comprising the amino acid sequence set forth in SEQ ID NO: 101. According to certain other embodiments, a polypeptide according to 1c) has aryl sulfotransferase activity similar to that of the polypeptide comprising the amino acid sequence set forth in SEQ ID NO: 103. According to certain other embodiments, a polypeptide according to 1c) has aryl sulfotransferase activity similar to that of the polypeptide comprising the amino acid sequence set forth in SEQ ID NO: 105.

With "similar" aryl sulfotransferase activity it is meant that the polypeptide according to 1c) has at least about 10%, such as at least about 20%, at least about 30%, at least about 40%, at least about 50%, at least about 60%, at least about 75%, at least about 80%, at least about 90%, at least about 95%, at least about 100%, at least about 200%, at least about 300%, at least about 400%, at least about 500%, at least about 800%, at least about 1000% or at least about 2000%, of the aryl sulfotransferase activity of the reference polypeptide (e.g., SEQ ID NO: 1).

The aryl sulfotransferase activity may for instance be determined in accordance to the following method: Aryl sulfotransferase activity may be determined by the reaction of radioactively sulfur labelled PAPS, [$^{35}$S]PAPS, with the substrate in presence of the polypeptide of interest. This is described previously, for example by Hattori et al (Biosci Biotechnol Biochem. 2008; 72(2):540-7). The reaction takes place in a buffer such as 250 μL 50 mM sodium phosphate pH 6.8 with 1 μM [$^{35}$S]PAPS (3.7 kBq) with 100 μM accepting compound for a period of 30 min at 30° C. The reaction is stopped by addition of 100 μL of a 1:1 mixture of 0.1 M barium acetate and barium hydroxide. 50 μL of 0.1 M zinc sulfate is added, followed by centrifugation at 1,200×g for 5 min. 300 μL of the supernatant is then transferred to a new container and 50 μL of an equal volume of 0.1 M barium hydroxide and 0.1 M zinc sulfate is added. The mixture is then centrifuged at 13,000×g for 5 min, and 300-4 aliquots of the supernatant are mixed with 2.5 mL of Cleasol I (Nacalai Tesque, Kyoto, Japan). The radioactivity is then measured by scintillation.

Alternatively, the activity of a sulfotransferase may be detected by direct measurement of the product by analytical methods such as high performance liquid chromatography (HPLC) or liquid chromatography in combination with mass spectrometry (LC-MS).

Sulfate supply may be a limiting factor in an enzymatic sulfation reaction, and hence in the production of sulfated phenolic compounds, such as zosteric acid. Here, the present inventors have demonstrated that the production of sulfated phenolic compounds can be significantly increased if the sulfate uptake by the recombinant host cell is increased.

Therefore, a recombinant host cell according to the invention may be one which has been modified to have an increased uptake of sulfate compared to an identical host cell that does not carry said modification.

Sulfate uptake by a given cell may be determined by a S$^{35}$-sulfate based method as described, e.g., by Mansilla and Mendoza (Microbiology, 2000, 146, 815-821). Generally, cells are first grown in a defined minimal medium, such as M9 minimal medium, supplemented with glutathione as sulphur source to exponential phase. Cells are collected, washed and then resuspended in minimal medium. The measurement of sulfate uptake is performed by incubating for 5 min at 30° C. the cell suspension containing 10$^8$ cells ml$^{-1}$, 0.01 mM sodium sulfate and approximately 10$^6$ cpm $^{35}$SO$_4^{2-}$ ml$^{-1}$ (1050 Ci mmol$^{-1}$). The incubation period is terminated by filtering the cell suspension through a 0.45 μm Millipore filter, followed by washing the filters with 5 ml minimal medium containing 2 mM magnesium sulfate and 2 mM sodium thiosulfate. Filters are transferred to polyethylene vials containing 2 ml Optiphase 'HiSafe 3' scintillation fluid (Wallac) and the radioactivity counted in an LKB Primo liquid scintillation counter. Uptake rates are expressed in nmol sulfate min$^{-1}$ (g cellular protein)$^{-1}$.

More particularly, a recombinant host cell according to the present invention may be modified to have an increased protein expression of sulfate transporter compared to the identical host cell that does not carry said modification. By "increased protein expression" it is meant that the amount of the sulfate transporter protein produced by the thus modified host cell is increased compared an identical host cell that does not carry said modification. More particularly, by "increased expression" it is meant that the amount of the sulfate transporter protein produced by the thus modified host cell is increased by at least 10%, such as at least 20%, at least 30%, at least 40%, at least 50% at least 60%, at least 70%, at least 80%, at least 90%, at least 100%, at least 150%, at least 200%, at least 300%, at least 400%, at least 500%, at least 600%, at least 700% at least 800%, at least about 900%, at least about 1000%, at least about 2000%, at least about 3000%, at least about 4000%, at least about 5000%, at least about 6000%, at least about 7000%, at least about 8000% at least about 9000% or at least about 10000%, compared an identical host cell that does not carry said modification. The amount of protein in a given cell can be determined by any suitable quantification technique known in the art, such as ELISA, Immunohistochemistry or Western Blotting.

An increase in protein expression may be achieved by any suitable means well-know to those skilled in the art. For example, an increase in protein expression may be achieved by increasing the number of copies of the gene or genes encoding the sulfate transporter in the host cell, such as by introducing into the host cell a exogenous nucleic acid, such as a vector, comprising the gene or genes encoding the sulfate transporter operably linked to a promoter that is functional in the host cell to cause the production of an mRNA molecule. An increase in protein expression may also be achieved by integration of at least a second copy of the gene or genes encoding the sulfate transporter into the genome of the host cell. An increase in protein expression may also be achieved by increasing the strength of the promoter(s) operably linked to the gene or genes encoding the sulfate transporter. An increase in protein expression may also be achieved by modifying the ribosome binding site on the mRNA molecule encoding the sulfate transporter. By modifying the sequence of the ribosome binding site the translation initiation rate may be increased, thus increasing the translation efficiency.

According to certain embodiments, the increase in the number of copies of the gene or genes is achieved by introducing into the recombinant host cell one or more (such as two or three) exogenous nucleic acid molecules (such as one or more vectors) comprising the gene or genes operably linked to a promoter that is functional in the host cell to cause the production of an mRNA molecule.

According to certain embodiments, a recombinant host cell is provided which comprises an exogenous nucleic acid molecule (such as a vector) comprising one or more (such as two, three or four) nucleotide sequences encoding a sulfate transporter. Suitably, the exogenous nucleic acid molecule further comprises a promoter that is functional in the host cell to cause the production of an mRNA molecule and that is operably linked to the one or more nucleotide sequences encoding said sulfate transporter.

According to certain embodiments, the exogenous nucleic acid molecule is stably integrated into the genome of the recombinant host cell.

The sulfate transporter may be derived from the same species as the recombinant host cell in which it is expressed or may be derived from a species different to the one in which it is expressed (i.e. it is heterologous). According to certain embodiments, the sulfate transporter is derived from the same species as the recombinant host cell in which it is expressed. According to certain other embodiments, the sulfate transporter is derived from a species different to the one in which it is expressed (i.e. it is heterologous).

According to certain embodiments, the sulfate transporter is a bacterial sulfate transporter. With "bacterial sulfate transporter" it is meant that the sulfate transporter is naturally derived from a bacterium, such as *Escherichia coli*.

The sulfate transporter employed in accordance of the invention may be any suitable sulfate transporter which is functional in the respective host cell.

According to certain embodiments, the sulfate transporter is a selected from the group consisting of: members of the CysZ family, members of the SuIT (cysPTWA) family, members of the SuIP family, CysP transporters belonging to the phosphate inorganic transporter (PiT) family, and oxyanion permeases (PerO).

According to certain embodiments, the sulfate transporter is a bacterial sulfate transporter selected from the group consisting of: members of the CysZ family, members of the SuIT (cysPTWA) family, members of the SuIP family, CysP transporters belonging to the phosphate inorganic transporter (PiT) family, and oxyanion permeases (PerO).

According to particular embodiments, the sulfate transporter is a CysZ protein.

Members of the CysZ family (TCDB 2.A.121) are high affinity, high specificity proton-dependent sulfate transporters which mediates sulfate uptake. Non-limiting examples of CysZ proteins are those found in bacteria, such as *E. coli* (NCBI: NP_416908.1) *S. typhimurium* (NCBI: NP_456966.1), *K. pneumoniae* (NCBI: CD015722.1), *P. fluorescens* (NCBI: AEV64873.1), *S. sonnei* (NCBI: AAZ89133.1), *V. anguillarum* (NCBI: AEH33702.1), *B. japonicum* (NCBI: KOY11972.1) and *C. glutamicum* (NCBI: CAF20834.1) to only name a few.

Accordingly, a sulfate transporter for use according to the invention may for instance be the CysZ protein from *Escherichia coli* (SEQ ID NO: 14). Further information regarding CysZ of *Escherichia coli* is available at EcoCyc (www.biocyc.org) under Accession number EG10003. See also NCBI Reference Sequence Database under NCBI Reference Sequence: NP_416908.1.

According to certain embodiments, the sulfate transporter is a polypeptide selected from the group consisting of:

2a) a polypeptide comprising an amino acid sequence set forth in SEQ ID NO: 14;

2b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 14; or 2c) a polypeptide comprising an amino acid sequence set forth in SEQ ID NO: 14, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the sulfate transporter is a polypeptide according to 2a).

According to other certain embodiments, the sulfate transporter is a polypeptide according to 2b). Accordingly, a sulfate transporter employed according to the present invention is a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 14. According to particular embodiments, a polypeptide according to 2b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 14. According to other particular embodiments, a polypeptide according to 2b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 14. According to other particular embodiments, a polypeptide according to 2b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 14. According to other particular embodiments, a polypeptide according to 2b) comprises an amino acid sequence which has at least about 95%, such as at least about 96%, at least about 97%, at least about 98%, or at least about 99%, sequence identity to the amino acid sequence set forth in SEQ ID NO: 14.

According to other certain embodiments, the sulfate transporter is a polypeptide according to 2c). According to particular embodiments, a polypeptide according to 2c) comprises an amino acid sequence set forth in SEQ ID NO: 14, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 2c) comprises an amino acid sequence set forth in SEQ ID NO: 14, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 2c) comprises an amino acid sequence set forth in SEQ ID NO: 14, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 14). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 2b) or 2c) has sulfate transporter activity. More preferably, a polypeptide according to 2b) or 2c) has a sulfate transporter activity similar to that of the polypeptide comprising an amino acid sequence set forth in SEQ ID NO: 14. With "similar" sulfate transporter activity it is meant that the polypeptide according to 2b) or 2c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the sulfate transporter activity of the reference polypeptide (i.e., SEQ ID NO: 14).

Another suitable sulfate transporter for use according to the invention may for instance be the CysZ protein from *Corynebacterium glutamicum* (SEQ ID NO: 15). Further information regarding CysZ of *C. glutamicum* is available at NCBI under accession number CAF20834.1.

According to certain embodiments, the sulfate transporter is a polypeptide selected from the group consisting of:

3a) a polypeptide comprising an amino acid sequence set forth in SEQ ID NO: 15;

3b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15; or 3c) a polypeptide comprising an amino acid sequence set forth in SEQ ID NO: 15, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the sulfate transporter is a polypeptide according to 3a).

According to other certain embodiments, the sulfate transporter is a polypeptide according to 3b). Accordingly, a sulfate transporter employed according to the present invention is a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15. According to particular embodiments, a polypeptide according to 3b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 15. According to other particular embodiments, a polypeptide according to 3b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 15. According to other particular embodiments, a polypeptide according to 3b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 15. According to other particular embodiments, a polypeptide according to 3b) comprises an amino acid sequence which has at least about 95%, such as at least about 96%, at least about 97%, at least about 98%, or at least about 99%, sequence identity to the amino acid sequence set forth in SEQ ID NO: 15.

According to other certain embodiments, the sulfate transporter is a polypeptide according to 3c). According to particular embodiments, a polypeptide according to 3c) comprises an amino acid sequence set forth in SEQ ID NO: 15, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 3c) comprises an amino acid sequence set forth in SEQ ID NO: 15, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 3c) comprises an amino acid sequence set forth in SEQ ID NO: 15, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 15). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 3b) or 3c) has sulfate transporter activity. More preferably, a polypeptide according to 3b) or 3c) has a sulfate transporter activity similar to that of the polypeptide comprising an amino acid sequence set forth in SEQ ID NO: 15. With "similar" sulfate transporter activity it is meant that the polypeptide according to 3b) or 3c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the sulfate transporter activity of the reference polypeptide (i.e., SEQ ID NO: 15).

According to certain embodiments, the sulfate transporter is a sulfate-transporting ATPase, such as a member of the SuIT (cysPTWA) family.

According to particular embodiments, the sulfate transporter is bacterial sulfate transporter of the SuIT (cysPTWA) family.

Sulfate transporters of the SuIT (cysPTWA) family from proteobacteria (TCDB 3.A.1.6.1), such as *E. coli*, are generally constituted by: (i) one of two periplasmic proteins, SbP, the sulfate binding protein, or CysP, the thiosulfate-binding protein; (ii) membrane proteins CysT (synonym: CysU) and CysW; and (iii) the ATP-binding protein CysA. The SuIT subunits are encoded by the cysPTWA operon and by the sbp gene, located either in another chromosomal region or instead of cysP in the same operon. Non-limiting examples of sulfate transporters of the SuIT (cysPTWA) family are those found in *Escherichia coli, Salmonella typhimurium* and *Rhodobacter capsulatus*.

CysT, CysW, CysA, CysP and Sbp of *Escherichia coli* are set forth in SEQ ID NO: 16 to 20, respectively. Further information regarding CysT, CysW, CysA, CysP and Sbp of *Escherichia coli* is available at EcoCyc (www.biocyc.org) under Accession numbers EG10197, EG10198, EG10183, EG10195 and EG10929, respectively.

CysT, CysW, CysA, CysP and Sbp of *Salmonella typhimurium* are set forth in SEQ ID NO: 21 to 25, respectively.

According to certain embodiments, the sulfate transporter comprises a first membrane subunit (CysT), a second membrane subunit (CysW), an ATP binding subunit (CysA) and a periplasmic binding protein (CysP or Sbp).

According to certain embodiments, the sulfate transporter is encoded by an operon comprising a nucleotide sequence encoding a first membrane subunit (CysT), a nucleotide sequence encoding a second membrane subunit (CysW), a nucleotide sequence encoding an ATP binding subunit (CysA) and a nucleotide sequence encoding a periplasmic binding protein (CysP or Sbp).

According to certain embodiments, the first membrane subunit is a polypeptide selected from the group consisting of:

4a) a polypeptide comprising an amino acid sequence set forth in SEQ ID NO: 16 or 21;
4b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16 or 21; or
4c) a polypeptide comprising an amino acid sequence set forth in SEQ ID NO: 16 or 21, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the first membrane subunit is a polypeptide according to 4a). According to particular embodiments, the first membrane subunit is a polypeptide comprising an amino acid sequence set forth in SEQ ID NO: 16. According to other particular embodiments, the first membrane subunit is a polypeptide comprising an amino acid sequence set forth in SEQ ID NO: 21.

According to other certain embodiments, the first membrane subunit is a polypeptide according to 4b). Accordingly, a first membrane subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16. According to particular embodiments, a polypeptide according to 4b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 16. According to other particular embodiments, a polypeptide according to 4b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 16. According to other particular embodiments, a polypeptide according to 4b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 16. According to other particular embodiments, a polypeptide according to 4b) comprises an amino acid sequence which has at least about 95%, such as at least about 96%, at least about 97%, at least about 98%, or at least about 99%, sequence identity to the amino acid sequence set forth in SEQ ID NO: 16.

Alternatively, a first membrane subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 21. According to particular embodiments, a polypeptide according to 4b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 21. According to other particular embodiments, a polypeptide according to 4b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 21. According to other particular embodiments, a polypeptide according to 4b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 21. According to other particular embodiments, a polypeptide according to 4b) comprises an amino acid sequence which has at least about 95%, such as at least about 96%, at least about 97%, at least about 98%, or at least about 99%, sequence identity to the amino acid sequence set forth in SEQ ID NO: 21.

According to other certain embodiments, the first membrane subunit is a polypeptide according to 4c). According to particular embodiments, a polypeptide according to 4c) comprises an amino acid sequence set forth in SEQ ID NO: 16, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 4c) comprises an amino acid sequence set forth in SEQ ID NO: 16, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 4c) comprises an amino acid sequence set forth in SEQ ID NO: 16, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to 4c) comprises an amino acid sequence set forth in SEQ ID NO: 21, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 4c) comprises an amino acid sequence set forth in SEQ ID NO: 21, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 4c) comprises an amino acid sequence set forth in SEQ ID NO: 21, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 16 or 21). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, the polypeptide according to 4b) or 4c) assembles with the proteins CysW, CysA and CysP/Sbp to form a sulfate-transporting ATPase which transports sulfate into the host cell.

According to certain embodiments, the second membrane subunit is a polypeptide selected from the group consisting of:
5a) a polypeptide comprising an amino acid sequence set forth in SEQ ID NO: 17 or 22;
5b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17 or 22; or
5c) a polypeptide comprising an amino acid sequence set forth in SEQ ID NO: 17 or 22, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the second membrane subunit is a polypeptide according to 5a). According to particular embodiments, the second membrane subunit is a polypeptide comprising an amino acid sequence set forth in SEQ ID NO: 17. According to other particular embodiments, the second membrane subunit is a polypeptide comprising an amino acid sequence set forth in SEQ ID NO: 22.

According to other certain embodiments, the second membrane subunit is a polypeptide according to 5b). Accordingly, a second membrane subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17. According to particular embodiments, a polypeptide according to 5b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 17. According to other particular embodiments, a polypeptide according to 5b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 17. According to other particular embodiments, a polypeptide according to 5b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 17. According to other particular embodiments, a polypeptide according to 5b) comprises an amino acid sequence which has at least about 95%, such as at least about 96%, at least about 97%, at least about 98%, or at least about 99%, sequence identity to the amino acid sequence set forth in SEQ ID NO: 17.

Alternatively, a second membrane subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 22. According to particular embodiments, a polypeptide according to 5b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 22. According to other particular embodiments, a polypeptide according to 5b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 22. According to other particular embodiments, a polypeptide according to 5b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 22. According to other particular embodiments, a polypeptide according to 5b) comprises an amino acid sequence which has at least about 95%, such as at least about 96%, at least about 97%, at least about 98%, or at least about 99%, sequence identity to the amino acid sequence set forth in SEQ ID NO: 22.

According to other certain embodiments, the second membrane subunit is a polypeptide according to 5c). According to particular embodiments, a polypeptide according to 5c) comprises an amino acid sequence set forth in SEQ ID NO: 17, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 5c) comprises an amino acid sequence set forth in SEQ ID NO: 17, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 5c) comprises an amino acid sequence set forth in SEQ ID NO: 17, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to 5c) comprises an amino acid sequence set forth in SEQ ID NO: 22, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 5c) comprises an amino acid sequence set forth in SEQ ID NO: 22, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 5c) comprises an amino acid sequence set forth in SEQ ID NO: 22, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 17 or 22). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, the polypeptide according to 5b) or 5c) assembles with the proteins CysT, CysA and CysP/Sbp to form a sulfate-transporting ATPase which tranports sulfate into the host cell.

According to certain embodiments, the ATP binding subunit is a polypeptide selected from the group consisting of:
6a) a polypeptide comprising an amino acid sequence set forth in SEQ ID NO: 18 or 23;
6b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18 or 23; or
6c) a polypeptide comprising an amino acid sequence set forth in SEQ ID NO: 18 or 23, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the ATP binding subunit is a polypeptide according to 6a). According to particular embodiments, the ATP binding subunit is a polypeptide comprising an amino acid sequence set forth in SEQ ID NO: 18. According to other particular embodiments, the ATP binding subunit is a polypeptide comprising an amino acid sequence set forth in SEQ ID NO: 23.

According to other certain embodiments, the ATP binding subunit is a polypeptide according to 6b). Accordingly, a ATP binding subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18. According to particular embodiments, a polypeptide according to 6b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 18. According to other particular embodiments, a polypeptide according to 6b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 18. According to other particular embodiments, a polypeptide according to 6b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 18. According to other particular embodiments, a polypeptide according to 6b) comprises an amino acid sequence which has at least about 95%, such as at least about 96%, at least about 97%, at least about 98%, or at least about 99%, sequence identity to the amino acid sequence set forth in SEQ ID NO: 18.

Alternatively, a ATP binding subunit may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 23. According to particular embodiments, a polypeptide according to 6b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 23. According to other particular embodiments, a polypeptide according to 6b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 23. According to other particular embodiments, a polypeptide according to 6b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 23. According to other particular embodiments, a polypeptide according to 6b) comprises an amino acid sequence which has at least about 95%, such as at least about 96%, at least about 97%, at least about 98%, or at least about 99%, sequence identity to the amino acid sequence set forth in SEQ ID NO: 23.

According to other certain embodiments, the ATP binding subunit is a polypeptide according to 6c). According to particular embodiments, a polypeptide according to 6c) comprises an amino acid sequence set forth in SEQ ID NO: 18, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 6c) comprises an amino acid sequence set forth in SEQ ID NO: 18, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 6c) comprises an amino acid sequence set forth in SEQ ID NO: 18, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to 6c) comprises an amino acid sequence set forth in SEQ ID NO: 23, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 6c) comprises an amino acid sequence set forth in SEQ ID NO: 23, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 6c) comprises an amino acid sequence set forth in SEQ ID NO: 23, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 18 or 23). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, the polypeptide according to 6b) or 6c) assembles with the proteins CysT, CysW and CysP/Sbp to form a sulfate-transporting ATPase which transports sulfate into the host cell.

According to certain embodiments, the periplasmic binding protein is CysP.

According to certain embodiments, the periplasmic binding protein is a polypeptide selected from the group consisting of:

7a) a polypeptide comprising an amino acid sequence set forth in SEQ ID NO: 19 or 24;

7b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 19 or 24; or 7c) a polypeptide comprising an amino acid sequence set forth in SEQ ID NO: 19 or 24, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the periplasmic binding protein is a polypeptide according to 7a). According to particular embodiments the periplasmic binding protein is a polypeptide comprising an amino acid sequence set forth in SEQ ID NO: 19. According to other particular embodiments, the periplasmic binding protein is a polypeptide comprising an amino acid sequence set forth in SEQ ID NO: 24.

According to other certain embodiments, the periplasmic binding protein is a polypeptide according to 7b). Accordingly, a periplasmic binding protein may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 19. According to particular embodiments, a polypeptide according to 7b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 19. According to other particular embodiments, a polypeptide according to 7b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 19. According to other particular embodiments, a polypeptide according to 7b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 19. According to other particular embodiments, a polypeptide according to 7b) comprises an amino acid sequence which has at least about 95%, such as at least about 96%, at least about 97%, at least about 98%, or at least about 99%, sequence identity to the amino acid sequence set forth in SEQ ID NO: 19.

Accordingly, a periplasmic binding protein may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 24. According to particular embodiments, a polypeptide according to 7b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 24. According to other particular embodiments, a polypeptide according to 7b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 24. According to other particular embodiments, a polypeptide according to 7b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 24. According to other particular embodiments, a polypeptide according to 7b) comprises an amino acid sequence which has at least about 95%, such as at least about 96%, at least about 97%, at least about 98%, or at least about 99%, sequence identity to the amino acid sequence set forth in SEQ ID NO: 24.

According to other certain embodiments, the periplasmic binding protein is a polypeptide according to 7c). According to particular embodiments, a polypeptide according to 7c) comprises an amino acid sequence set forth in SEQ ID NO: 19, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 7c) comprises an amino acid sequence set forth in SEQ ID NO: 19, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 7c) comprises an amino acid sequence set forth in SEQ ID NO: 19, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to 7c) comprises an amino acid sequence set forth in SEQ ID NO: 24, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 7c) comprises an amino acid sequence set forth in SEQ ID NO: 24, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 7c) comprises an amino acid sequence set forth in SEQ ID NO: 24, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 19 or 24). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, the polypeptide according to 7b) or 7c) assembles with the proteins CysT, CysW and CysA to form a sulfate-transporting ATPase which transports sulfate into the host cell.

According to certain embodiments, the periplasmic binding protein is Sbp.

According to certain embodiments, the periplasmic protein is a polypeptide selected from the group consisting of:
8a) a polypeptide comprising an amino acid sequence set forth in SEQ ID NO: 20 or 25;
8b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 20 or 25; or
8c) a polypeptide comprising an amino acid sequence set forth in SEQ ID NO: 20 or 25, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the periplasmic binding protein is a polypeptide according to 8a). According to particular embodiments the periplasmic binding protein is a polypeptide comprising an amino acid sequence set forth in SEQ ID NO: 20. According to other particular embodiments, the periplasmic binding protein is a polypeptide comprising an amino acid sequence set forth in SEQ ID NO: 25.

According to other certain embodiments, the periplasmic binding protein is a polypeptide according to 8b). Accordingly, a periplasmic binding protein may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 20. According to particular embodiments, a polypeptide according to 8b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 20. According to other particular embodiments, a polypeptide according to 8b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 20. According to other particular embodiments, a polypeptide according to 8b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 20. According to other particular embodiments, a polypeptide according to 8b) comprises an amino acid sequence which has at least about 95%, such as at least about 96%, at least about 97%, at least about 98%, or at least about 99%, sequence identity to the amino acid sequence set forth in SEQ ID NO: 20.

Alternatively, a periplasmic binding protein may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 25. According to particular embodiments, a polypeptide according to 8b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 25. According to other particular embodiments, a polypeptide according to 8b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 25. According to other particular embodiments, a polypeptide according to 8b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 25. According to other particular embodiments, a polypeptide according to 8b) comprises an amino acid sequence which has at least about 95%, such as at least about 96%, at least about 97%, at least about 98%, or at least about 99%, sequence identity to the amino acid sequence set forth in SEQ ID NO: 25.

According to other certain embodiments, the periplasmic binding protein is a polypeptide according to 8c). According to particular embodiments, a polypeptide according to 8c) comprises an amino acid sequence set forth in SEQ ID NO: 20, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 8c) comprises an amino acid sequence set forth in SEQ ID NO: 20, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 8c) comprises an amino acid sequence set forth in SEQ ID NO: 20, wherein about 1 to about 25, such as about 1 to about 20, about 1 to about 15, about 1 to about 10, about 1 to about 5, or about 1 to about 3, amino acid residues are substituted, deleted and/or inserted.

According to other particular embodiments, a polypeptide according to 8c) comprises an amino acid sequence set forth in SEQ ID NO: 25, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 8c) comprises an amino acid sequence set forth in SEQ ID NO: 25, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 8c) comprises an amino acid sequence set forth in SEQ ID NO: 25, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 20 or 25). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, the polypeptide according to 8b) or 8c) assembles with the proteins CysT, CysW and CysA to form a sulfate-transporting ATPase which transports sulfate into the host cell.

According to certain embodiments, the sulfate transporter is a member of the SulP family.

The sulfate transporter SulP family (TCDB 2.A.53) is a large and ubiquitous family with members derived from archaea, bacteria, fungi, plants and animals. Many organisms including *Bacillus subtilis, Synechocystis* sp, *Saccharomyces cerevisiae, Arabidopsis thaliana* and *Caenorhabditis elegans* possess multiple SulP family paralogues. Many of these proteins are functionally characterized, and most are inorganic anion uptake transporters or anion:anion exchange transporters. A non-limiting example of a sulfate transporter of the SulP family is that found in *Mycobacterium tuberculosis* (SEQ ID NO: 26; NCBI: NP_216255.1). Zolotarev et al. (Comp Biochem Physiol A Mol Integr Physiol. 2008 March; 149(3):255-66) have demonstrate that the overexpression of SulP protein Rv1739c from *M. tuberculosis* in *E. coli* increases sulfate uptake. Another non-limiting example is a SulP protein found in multiple species (NCBI: WP_012536065.1).

According to certain embodiments, the sulfate transporter is a polypeptide selected from the group consisting of:
9a) a polypeptide comprising an amino acid sequence set forth in SEQ ID NO: 26;
9b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 26; or
9c) a polypeptide comprising an amino acid sequence set forth in SEQ ID NO: 26, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the sulfate transporter is a polypeptide according to 9a).

According to other certain embodiments, the sulfate transporter is a polypeptide according to 9b). Accordingly, a sulfate transporter employed according to the present invention is a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 26. According to particular embodiments, a polypeptide according to 9b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 26. According to other particular embodiments, a polypeptide according to 9b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 26. According to other particular embodiments, a polypeptide according to 9b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 26. According to other particular embodiments, a polypeptide according to 9b) comprises an amino acid sequence which has at least about 95%, such as at least about 96%, at least about 97%, at least about 98%, or at least about 99%, sequence identity to the amino acid sequence set forth in SEQ ID NO: 26.

According to other certain embodiments, the sulfate transporter is a polypeptide according to 9c). According to particular embodiments, a polypeptide according to 9c) comprises an amino acid sequence set forth in SEQ ID NO: 26, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 9c) comprises an amino acid sequence set forth in SEQ ID NO: 26, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 9c) comprises an amino acid sequence set forth in SEQ ID NO: 26, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 26). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 9b) or 9c) has sulfate transporter activity. More preferably, a polypeptide according to 9b) or 9c) has a sulfate transporter activity similar to that of the polypeptide comprising an amino acid sequence set forth in SEQ ID NO: 26. With "similar" sulfate transporter activity it is meant that the polypeptide according to 9b) or 9c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the sulfate transporter activity of the reference polypeptide (i.e., SEQ ID NO: 26).

According to certain embodiments, the sulfate transporter is a CysP transporter belonging to the phosphate inorganic transporter (PiT) family.

Genes encoding PiT family transporters are widespread throughout the three life domains. A non-limiting example of a CysP transporter of the PiT family is that found in *Bacillus subtilis* (SEQ ID NO: 27; GenBank: CAB13432.1). Another non-limiting example of a CysP transporter of the PiT family is that found in *Halobacterium salinarum* (GenBank: CAP13497.1).

According to certain embodiments, the sulfate transporter is selected from the group consisting of:

10a) a polypeptide comprising an amino acid sequence set forth in SEQ ID NO: 27;

10b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 27; or 10c) a polypeptide comprising an amino acid sequence set forth in SEQ ID NO: 27, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the sulfate transporter is a polypeptide according to 10a).

According to other certain embodiments, the sulfate transporter is a polypeptide according to 10b). Accordingly, a sulfate transporter employed according to the present invention is a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 27. According to particular embodiments, a polypeptide according to 10b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 27. According to other particular embodiments, a polypeptide according to 10b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 27. According to other particular embodiments, a polypeptide according to 10b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 27. According to other particular embodiments, a polypeptide according to 10b) comprises an amino acid sequence which has at least about 95%, such as at least about 96%, at least about 97%, at least about 98%, or at least about 99%, sequence identity to the amino acid sequence set forth in SEQ ID NO: 27.

According to other certain embodiments, the sulfate transporter is a polypeptide according to 10c). According to particular embodiments, a polypeptide according to 10c) comprises an amino acid sequence set forth in SEQ ID NO: 27, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 10c) comprises an amino acid sequence set forth in SEQ ID NO: 27, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 10c) comprises an amino acid sequence set forth in SEQ ID NO: 27, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 27). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 10b) or 10c) has sulfate transporter activity. More preferably, a polypeptide according to 10b) or 10c) has a sulfate transporter activity similar to that of the polypeptide comprising an amino acid sequence set forth in SEQ ID NO: 27. With "similar" sulfate transporter activity it is meant that the polypeptide according to 10b) or 10c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the sulfate transporter activity of the reference polypeptide (i.e., SEQ ID NO: 27).

According to certain embodiments, the sulfate transporter is an oxyanion permease (PerO).

Oxyanion permeases act as a general oxyanion importer of molybdate, sulfate, tungstate, and vanadate. A non-limiting example of an oxyanion permease is that found in *Rhodobacter capsulatus* (SEQ DI NO: 95).

According to certain embodiments, the sulfate transporter is selected from the group consisting of:

12a) a polypeptide comprising an amino acid sequence set forth in SEQ ID NO: 95;

12b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 95; or 12c) a polypeptide comprising an amino acid sequence set forth in SEQ ID NO: 95, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, the sulfate transporter is a polypeptide according to 12a).

According to other certain embodiments, the sulfate transporter is a polypeptide according to 12b). Accordingly, a sulfate transporter employed according to the present invention is a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 95. According to particular embodiments, a polypeptide according to 12b) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 95. According to other particular embodiments, a polypeptide according to 12b) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 95. According to other particular embodiments, a polypeptide according to 12b) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 95. According to other particular embodiments, a polypeptide according to 12b) comprises an amino acid sequence which has at least about 95%, such as at least about 96%, at least about 97%, at least about 98%, or at least about 99%, sequence identity to the amino acid sequence set forth in SEQ ID NO: 95.

According to other certain embodiments, the sulfate transporter is a polypeptide according to 12c). According to particular embodiments, a polypeptide according to 12c) comprises an amino acid sequence set forth in SEQ ID NO: 95, wherein about 1 to about 50, such as about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to 12c) comprises an amino acid sequence set forth in SEQ ID NO: 95, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to 12c) comprises an amino acid sequence set forth in SEQ ID NO: 95, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (i.e., SEQ ID NO: 95). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 12b) or 12c) has sulfate transporter activity. More preferably, a polypeptide according to 12b) or 12c) has a sulfate transporter activity similar to that of the polypeptide comprising an amino acid sequence set forth in SEQ ID NO: 95. With "similar" sulfate transporter activity it is meant that the polypeptide according to 12b) or 12c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the sulfate transporter activity of the reference polypeptide (i.e., SEQ ID NO: 95).

Besides external sulfate supply, the sulfation reaction may further depend on the supply of sulfate from 3'-phosphoadenosine 5'-phosphosulfate (PAPS) or transferred from another sulfated compound. The inventors have shown that the sulfation reaction can further be enhanced by improving the supply of PAPS (3'-phosphoadenosine 5'-phosphosulfate) and, in addition, by the removal of the product 3'-phosphoadenosine 5'-phosphate (PAP). The improved supply is obtained by deregulation, mutation or overexpression of enzymes that increase PAPS concentration or similarly reduce PAP concentration. This is exemplified in Example 2, where an increased production of zosteric acid in *Escherichia coli* is obtained by increasing the expression of the genes cysD, cysN, and cysC which are responsible for production of PAPS. Without being bound to a specific theory, it is believed that an adenylyl moiety (AMP) of ATP is transferred to sulfate to form activated sulfate, or APS (adenosine 5'-phosphosulfate). This extremely unfavorable reaction is kinetically and energetically linked to the hydrolysis of GTP by the enzyme ATP sulfurylase, which is composed of two types of subunits: an adenylyl transferase (cysD) and a GTPase (cysN). APS is then phosphorylated at the 3'-hydroxyl to form PAPS (3'-phosphoadenosine 5'-phosphosulfate) in a reaction catalysed by APS kinase, which is encoded by cysC. Furthermore, the inventors have enhanced the production of zosteric acid even more by increasing the expression of the gene cysQ encoding a PAP phosphatase which is responsible for the removal of PAP.

Therefore, in order to further improve the production of a sulfated phenolic compound, such as zosteric acid, a recombinant host cell according to the present invention may be further modified to have an increased protein expression of an ATP sulfurylase compared to an identical host cell that does not carry said modification; may be further modified to have an increased protein expression of an APS kinase compared to an identical host cell that does not carry said modification; and/or may be further modified to have an increased protein expression of a PAP phosphatase compared to an identical host cell that does not carry said modification. By "increased protein expression" it is meant that the amount of the respective protein produced by the thus modified host cell is increased compared an identical host cell that does not carry said modification. More particularly, by "increase expression" it is meant that the amount of respective protein produced by the thus modified host cell is increased by at least 10%, such as at least 20%, at least 30%, at least 40%, at least 50% at least 60%, at least 70%, at least 80%, at least 90%, at least 100%, at least 150%, at least 200%, at least 300%, at least 400%, at least 500%, at least 600%, at least 700% at least 800%, at least about 900%, at least about 1000%, at least about 2000%, at least about 3000%, at least about 4000%, at least about 5000%, at least about 6000%, at least about 7000%, at least about 8000% at least about 9000% or at least about 10000%, compared an identical host cell that does not carry said modification. The amount of protein in a given cell can be determined by any suitable quantification technique known in the art, such as ELISA, Immunohistochemistry or Western Blotting.

According to certain embodiments, a recombinant host cell according to the invention has further been modified to have an increased protein expression an ATP sulfurylase compared to an identical host cell that does not carry said modification.

According to certain embodiments, a recombinant host cell according to the invention has further been modified to have an increased protein expression of an APS kinase compared to an identical host cell that does not carry said modification.

According to certain embodiments, a recombinant host cell according to the invention has further been modified to have an increased protein expression of a PAP phosphatase compared to an identical host cell that does not carry said modification.

An increase in protein expression may be achieved by any suitable means well-know to those skilled in the art. For example, an increase in protein expression may be achieved by increasing the number of copies of the gene or genes encoding the respective protein (e.g., ATP sulfurylase, APS kinase and/or PAP phosphatase) in the host cell, such as by using (e.g., introducing into the host cell) a vectors comprising the gene or genes operably linked to a promoter that is functional in the host cell to cause the production of an mRNA molecule. An increase in protein expression may also be achieved by integration of at least a second copy of the gene or genes encoding the respective protein into the genome of the host cell. An increase in protein expression may also be achieved by increasing the strength of the promoter(s) operably linked to the gene or genes. An increase in protein expression may also be achieved by modifying the ribosome binding site on the mRNA molecule encoding the respective protein (e.g., ATP sulfurylase, APS kinase and/or PAP phosphatase). By modifying the sequence of the ribosome binding site the translation initiation rate may be increased, thus increasing the translation efficiency.

ATP sulfurylase encoding genes for use according to the invention may for instance be the cysD and cysN genes from *Escherichia coli* (encoding SEQ ID NO: 28 and 29, respectively). Alternative ATP sulfurylase encoding genes include the *Arabidopsis thaliana* ATP sulfurylase ASAL gene (Gen Bank Accession No. U40715, Logan et al. (1996) J Biol Chem 271:12227); the *Allium cepa* ATP-sulfurylase gene (GenBank Accession No AF21154); the *Lotus japonicus* ATP sulfurylase gene (GenBank Accession No. AW164083); the *Arabidopsis thaliana* met3-1 ATP sulfurylase gene (GenBank Accession No. X79210).

According to certain embodiments, a recombinant host cell according to the invention comprises an exogenous nucleic acid molecule (such as a vector) comprising one or more nucleotide sequences encoding a ATP sulfurylase.

The ATP sulfurylase may be derived from the same species as the recombinant host cell in which it is expressed or may be derived from a species different to the one in which it is expressed (i.e. it is heterologous). According to certain embodiments, the ATP sulfurylase is derived from the same species as the recombinant host cell in which it is expressed. According to certain other embodiments, the ATP sulfurylase is derived from a species different to the one in which it is expressed (i.e. it is heterologous).

According to certain embodiments, the ATP sulfurylase is a protein constituted by two polypeptides, which are exemplified by the amino acid sequence set forth in SEQ ID NO: 28 and 29, respectively.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 28 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 28, and a nucleotide sequence encoding iii) a polypeptide comprising an amino acid sequence set forth in SEQ ID NO: 29 or iv) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 29. Preferably, the polypeptides assemble to form a protein having ATP sulfurylase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 28 and a nucleotide sequence encoding a polypeptide comprising an amino acid sequence set forth in SEQ ID NO: 29.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 28 and a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 29. Preferably, the polypeptides assemble to form a protein having ATP sulfurylase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 28 and a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 29. Preferably, the polypeptides assemble to form a protein having ATP sulfurylase activity.

An alternative ATP sulfurylase encoding gene for use according to the invention may for instance be the MET3 gene from *Saccharomyces cerevisiae* (encoding SEQ ID NO: 30).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 30 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 30. Preferably, the polypeptide according to ii) has ATP sulfurylase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 30.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 30. Preferably, the polypeptide has ATP sulfurylase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 30. Preferably, the polypeptide has ATP sulfurylase activity.

An alternative ATP sulfurylase encoding gene for use according to the invention may for instance be the ATP sulfurylase encoding gene from *Bacillus subtilis* (encoding SEQ ID NO: 31).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 31 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 31. Preferably, the polypeptide according to ii) has ATP sulfurylase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 31.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 31. Preferably, the polypeptide has ATP sulfurylase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 31. Preferably, the polypeptide has ATP sulfurylase activity.

Techniques for determining ATP sulfurylase activity are well known to the skilled person. Exemplary methods have been described, e.g. by Reuveny and Filner (Anal Biochem, 1976, 75(2), 410-428) or Hommes and Moss (Anal Biochem, 1986, 154(1), 100-103).

An APS kinase encoding gene for use according to the invention may for instance be the cysC gene from *Escherichia coli* (encoding SEQ ID NO: 32).

In certain instances a single polypeptide has been shown to possess both an ATP sulfurylase and a 5'-adenylylsulfate kinase activity. For example, an ATP sulfurylase/APS kinase encoding gene has been isolated from mouse (GenBank Accession No. U34883, Li et al. (1995) J Biol Chem) 70:1945), and human (GenBank Accession No. AF033026, Yanagisawa (1998) Biosci Biotechnol Biochem 62:1037) sources. Other examples of such bifunctional enzyme include 3'-phosphoadenosine 5'-phosphosulfate synthase enzymes (PAPSS) from rat (*Rattus norvegicus*) (SEQ ID NO: 33 or 34).

According to certain embodiments, a recombinant host cell according to the invention comprises an exogenous nucleic acid molecule (such as a vector) comprising a nucleotide sequence encoding an APS kinase.

The APS kinase may be derived from the same species as the recombinant host cell in which it is expressed or may be derived from a species different to the one in which it is expressed (i.e. it is heterologous). According to certain embodiments, the APS kinase is derived from the same species as the recombinant host cell in which it is expressed. According to certain other embodiments, the APS kinase is derived from a species different to the one in which it is expressed (i.e. it is heterologous).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 32 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 32. Preferably, said polypeptide according to ii) has APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 32.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 32. Preferably, said polypeptide has APS kinase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 32. Preferably, said polypeptide has APS kinase activity.

An alternative APS kinase encoding gene for use according to the invention may for instance be the MET14 gene from *Saccharomyces cerevisiae* (encoding SEQ ID NO: 35).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 35 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 35. Preferably, said polypeptide according to ii) has APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 35.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 35. Preferably, said polypeptide has APS kinase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 35. Preferably, said polypeptide has APS kinase activity.

An alternative APS kinase encoding gene for use according to the invention may for instance be the APS kinase encoding gene from *Bacillus subtilis* (encoding SEQ ID NO: 36).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 36 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 36. Preferably, said polypeptide according to ii) has APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 36.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 36. Preferably, said polypeptide has APS kinase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 36. Preferably, said polypeptide has APS kinase activity.

Alternatively, a polypeptide having both an ATP sulfurylase and a APS kinase activity can be used, such as a 3'-phosphoadenosine 5'-phosphosulfate synthase (PAPSS).

According to certain embodiments, a recombinant host cell according to the invention comprises an exogenous nucleic acid molecule (such as a vector) comprising a nucleotide sequence encoding an 3'-phosphoadenosine 5'-phosphosulfate synthase.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 33 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 33. Preferably, said polypeptide according to ii) has both an ATP sulfurylase and a APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 33.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 33. Preferably, said polypeptide has both an ATP sulfurylase and a APS kinase activity.

According to particular embodiments, a recombinant host cell according to the invention comprises an exogenous nucleic acid molecule (such as a vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 33. Preferably, said polypeptide has both an ATP sulfurylase and a APS kinase activity.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 34 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 34. Preferably, said polypeptide according to ii) has both an ATP sulfurylase and a APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 34.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 34. Preferably, said polypeptide has both an ATP sulfurylase and APS kinase activity.

According to particular embodiments, a recombinant host cell according to the invention comprises an exogenous nucleic acid molecule (such as a vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 34. Preferably, said polypeptide has both an ATP sulfurylase and a APS kinase activity.

Techniques for determining APS kinase activity are well known to the skilled person. An exemplary method has been described, e.g. by Burnell and Whatley (Anal Biochem, 1975, 68(1), 281-288).

A PAP phosphatase encoding gene for use according to the invention may for instance be the cysQ gene from *Escherichia coli* (encoding SEQ ID NO: 37).

According to certain embodiments, a recombinant host cell according to the invention comprises an exogenous nucleic acid molecule (such as a vector) comprising a nucleotide sequence encoding an PAP phosphatase.

The PAP phosphatase may be derived from the same species as the recombinant host cell in which it is expressed or may be derived from a species different to the one in which it is expressed (i.e. it is heterologous). According to certain embodiments, the PAP phosphatase is derived from the same species as the recombinant host cell in which it is expressed. According to certain other embodiments, the PAP phosphatase is derived from a species different to the one in which it is expressed (i.e. it is heterologous).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 37 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 37. Preferably, said polypeptide according to ii) has PAP phosphatase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 37.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 37. Preferably, said polypeptide has PAP phosphatase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 37. Preferably, said polypeptide has PAP phosphatase activity.

An alternative PAP phosphatase encoding gene for use according to the invention may for instance be the MET22 gene from *Saccharomyces cerevisiae* (encoding SEQ ID NO: 38).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 38 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 38. Preferably, said polypeptide according to ii) has PAP phosphatase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 38.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 38. Preferably, said polypeptide has PAP phosphatase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 38. Preferably, said polypeptide has PAP phosphatase activity.

An alternative PAP phosphatase encoding gene for use according to the invention may for instance be the PAP phosphatase encoding gene from *Bacillus subtilis* (encoding SEQ ID NO: 39).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 39 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 39. Preferably, said polypeptide according to ii) has PAP phosphatase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 39.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 39. Preferably, said polypeptide has PAP phosphatase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 39. Preferably, said polypeptide has PAP phosphatase activity.

Techniques for determining PAP phosphatase activity are well known to the skilled person. An exemplary method has been described, e.g. by Fukuda et al. (Appl Environ Microbiol, 2007, 73(17), 5447-5452).

According to certain embodiments, the nucleotide sequences coding for an ATP sulfurylase, an APS kinase and an PAP phosphatase, respectively, are part of an operon. Accordingly, a recombinant host cell according to the invention may comprise an exogenous nucleic acid molecule (such as vector) which comprises an operon comprising a nucleotide sequence or nucleotide sequences encoding an ATP sulfurylase, a nucleotide sequence encoding an APS kinase, and optionally a nucleotide sequence encoding an PAP phosphatase.

Contemplated by the present invention is the production of a sulfated phenolic compound from a precursor thereof, and in particular from a precursor of the general formula (p-I) as described in more detail below. In this case, it may be suitable to employ (e.g. to express by a host cell of the invention) a polypeptide which has tyrosine ammonia lyase activity.

Tyrosine ammonia lyases suitable for use according to the present invention have been described in, e.g., WO 2016/008886 A1.

Therefore, a recombinant host cell provided and utilized in accordance with the present invention may comprise a hetereologus polypeptide having tyrosine ammonia lyase activity. According to certain embodiments, a recombinant host cell according to the invention comprises a heterologous polypeptide selected from the group consisting of:

11a) a polypeptide comprising an amino acid sequence set forth in SEQ ID NO: 40, 41, 42, 43, 44, 45, 46, 47, 48, 49 or 50 (e.g., SEQ ID NO: 40);

11b) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 40, 41, 42, 43, 44, 45, 46, 47, 48, 49 or 50 (e.g., SEQ ID NO: 40); or 11c) a polypeptide comprising an amino acid sequence set forth in SEQ ID NO: 40, 41, 42, 43, 44, 45, 46, 47, 48, 49 or 50 (e.g., SEQ ID NO: 40), wherein 1 or more, such as about 1 to about 50, about 1 to about 40, about 1 to about 35, 1 to 30, 1 to 25, 1 to 20, 1 to 15, 1 to 10, 1 to 5, 1 to 3, amino acid residues are substituted, deleted and/or inserted.

According to certain embodiments, the polypeptide having tyrosine ammonia lyase activity is a polypeptide according to 11a). Accordingly, a polypeptide having tyrosine ammonia lyase activity may be a polypeptide comprising an amino acid sequence set forth in SEQ ID NO: 40, 41, 42, 43, 44, 45, 46, 47, 48, 49 or 50 (e.g., SEQ ID NO: 40).

According to certain embodiments, the polypeptide having tyrosine ammonia lyase activity is a polypeptide according to 11b). Accordingly, a polypeptide having tyrosine ammonia lyase activity may be a polypeptide comprising an amino acid sequence which has at least about 70%, such as at least about 75%, sequence identity to the amino acid sequence set forth in SEQ ID NO: 40, 41, 42, 43, 44, 45, 46, 47, 48, 49 or 50 (e.g., SEQ ID NO: 40).

According to other particular embodiments, a polypeptide according to 11b) comprises an amino acid sequence which has at least about 85%, such as at least about 90%, sequence identity to the amino acid sequence set forth in SEQ ID NO: 40, 41, 42, 43, 44, 45, 46, 47, 48, 49 or 50 (e.g., SEQ ID NO: 40). According to other particular embodiments, a polypeptide according to 11b) comprises an amino acid sequence which has at least about 95%, such as at least about 98%, or at least about 99%, sequence identity to the amino acid sequence set forth in SEQ ID NO: 40, 41, 42, 43, 44, 45, 46, 47, 48, 49 or 50 (e.g., SEQ ID NO: 40).

According to certain embodiments, the polypeptide having tyrosine ammonia lyase activity is a polypeptide according to 11c). Accordingly, a polypeptide having tyrosine ammonia lyase activity may be a polypeptide comprising an amino acid sequence set forth in SEQ ID NO: 40, 41, 42, 43, 44, 45, 46, 47, 48, 49 or 50 (e.g., SEQ ID NO: 40), wherein 1 or more, such as 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more, 90 or more, 100 or more, 110 or more, 120 or more, 130 or more, 140 or more, or 150 or more, amino acid residues are substituted, deleted, and/or inserted.

According to particular embodiments, a polypeptide according to 11c) comprises an amino acid sequence set forth in SEQ ID NO: 40, 41, 42, 43, 44, 45, 46, 47, 48, 49 or 50 (e.g., SEQ ID NO: 40), wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (e.g., SEQ ID NO: 40). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to 11b) or 11c) has tyrosine ammonia lyase activity. More preferably, a polypeptide according to 11b) or 11c) has a tyrosine ammonia lyase activity similar to that of the polypeptide comprising an amino acid sequence set forth in SEQ ID NO: 40, 41, 42, 43, 44, 45, 46, 47, 48, 49 or 50 (e.g., SEQ ID NO: 40). According to certain embodiment, a polypeptide according to 11b) or 11c) has tyrosine ammonia lyase activity similar to that of the polypeptide comprising the amino acid sequence set forth in SEQ ID NO: 40. With "similar" tyrosine ammonia lyase activity it is meant that the polypeptide according to 11b) or 11c) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the tyrosine ammonia lyase activity of the reference polypeptide (e.g., SEQ ID NO: 40). Tyrosine ammonia lyase activity may be determined according to the method described in WO 2016/008886 A1 (e.g., page 9, line 29 to page 10, line 2).

Alternatively, the heterologous polypeptide having aryl sulfotransferase activity may be comprised by a first recombinant host cell, and the heterologous polypeptide having tyrosine ammonia lyase activity may be comprised by a second recombinant host cell.

Further contemplated by the present invention is to employ a further (e.g., third) heterologous polypeptide which has phenylalanine ammonia lyase activity, such as a phenylalanine ammonia lyase (EC 4.3.1.24).

According to certain embodiments, a recombinant host cell comprises (e.g., expresses) a heterologous polypeptide having aryl sulfotransferase activity and a heterologous polypeptide having phenylalanine ammonia lyase activity.

Alternatively, the heterologous polypeptide having aryl sulfotransferase activity may be comprised by a first recombinant host cell, and the heterologous polypeptide having phenylalanine ammonia lyase activity may be comprised by a further recombinant host cell. Such further recombinant host cell may be a recombinant host cell also comprising a heterologous polypeptide having tyrosine ammonia lyase activity.

Recombinant host cells in accordance with the invention can be produced from any suitable host organism, including single-celled or multicellular microorganisms such as bacteria, yeast, fungi, algae and plant, and higher eukaryotic organisms including nematodes, insects, reptiles, birds, amphibians and mammals.

According to certain embodiments, a recombinant host cells in accordance with the invention is selected from the group consisting of bacteria, yeast, fungi, algae and plant.

According to certain other embodiments, a recombinant host cells in accordance with the invention is selected from the group consisting of bacteria, yeast, fungi, and algae.

According to certain other embodiments, a recombinant host cells in accordance with the invention is selected from the group consisting of bacteria, yeast and fungi.

According to certain other embodiments, a recombinant host cells in accordance with the invention is selected from the group consisting of bacteria and yeast.

According to certain embodiments, a recombinant host cells in accordance with the invention is not a plant cell.

Bacterial host cells are selected from Gram-positive and Gram-negative bacteria. Non-limiting examples for Gram-negative bacterial host cells include species from the genera *Escherichia*, *Erwinia*, *Klebsiella* and *Citrobacter*. Non-limiting examples of Gram-positive bacterial host cells include species from the genera *Bacillus*, *Lactococcus*, *Lactobacillus*, *Clostridium*, *Corynebacterium*, *Streptomyces*, *Streptococcus*, and *Cellulomonas*.

According to certain embodiment, the recombinant host cell is a bacterium of the family selected from the group consisting of Enterobacteriaceae, Bacillaceae, Lactobacillaceae and Corynebacteriaceae. According to certain embodiments, the recombinant host cell is a bacterium of the family Enterobacteriaceae.

According to certain embodiments, the recombinant host cell is a bacterium, which may be a bacterium of the genus *Bacillus*, *Lactococcus*, *Lactobacillus*, *Clostridium*, *Corynebacterium*, *Geobacillus*, *Thermoanaerobacterium*, *Streptococcus*, *Pseudomonas*, *Streptomyces*, *Escherichia*, *Shigella*, *Acinetobacter*, *Citrobacter*, *Salmonella*, *Klebsiella*, *Enterobacter*, *Erwinia*, *Kluyvera*, *Serratia*, *Cedecea*, *Morganella*, *Hafnia*, *Edwardsiella*, *Providencia*, *Proteus*, or *Yersinia*.

According to particular embodiments, the recombinant host cell is a bacterium of the genus *Bacillus*. Non-limiting examples of a bacteria of the genus *Bacillus* are *Bacillus subtilis*, *Bacillus amyloliquefaciens*, *Bacillus licheniformis*, and *Bacillus mojavensis*. According to more particular embodiments, the recombinant host cell is *Bacillus subtilis*. According to other more particular embodiments, the recombinant host cell is *Bacillus licheniformis*.

According to other particular embodiments, the recombinant host cell is a bacterium of the genus *Lactococcus*. A non-limiting example of a bacterium of the genus *Lactococcus* is *Lactococcus lactis*. According to more particular embodiments, the recombinant host cell is *Lactococcus lactis*.

According to other particular embodiments, the recombinant host cell is a bacterium of the genus *Corynebacterium*. A non-limiting example of a bacterium of the genus *Corynebacterium* is *Corynebacterium glutamicum*. According to more particular embodiments, the recombinant host cell is *Corynebacterium glutamicum*.

According to other particular embodiments, the recombinant host cell is a bacterium of the genus *Streptomyces*. A non-limiting examples of a bacterium of the genus *Streptomyces* are *Streptomyces lividans*, *Streptomyces coelicolor*, or *Streptomyces griseus*. According to more particular embodiments, the recombinant host cell is *Streptomyces lividans*. According to other more particular embodiments, the recombinant host cell is *Streptomyces coelicolor*.

According to other more particular embodiments, the recombinant host cell is *Streptomyces griseus*.

According to other particular embodiments, the recombinant host cell is a bacterium of the genus *Pseudomonas*. A non-limiting example of a bacterium of the genus *Pseudomonas* is *Pseudomonas putida*. According to more particular embodiments, the recombinant host cell is *Pseudomonas putida*.

According to other particular embodiments, the recombinant host cell is a bacterium of the genus *Geobacillus*. A non-limiting examples of a bacterium of the genus *Geobacillus* are *Geobacillus thermoglucosidasius* and *Geobacillus stearothermophilus*. According to more particular embodiments, the recombinant host cell is *Geobacillus thermoglucosidasius*.

According to other more particular embodiments, the recombinant host cell is *Geobacillus stearothermophilus*.

According to other particular embodiments, the recombinant host cell is a bacterium of the genus *Thermoanaerobacterium*. A non-limiting example of a bacterium of the genus *Thermoanaerobacterium* is *Thermoanaerobacterium thermosaccharolyticum*. According to more particular embodiments, the recombinant host cell is *Thermoanaerobacterium thermosaccharolyticum*.

According to other particular embodiments, the recombinant host cell is a bacterium of the genus *Escherichia*. A non-limiting example of a bacterium of the genus *Escherichia* is *Escherichia coli*. According to more particular embodiments, the recombinant host cell is *Escherichia coli*.

Yeast host cells may be derived from e.g., *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to certain embodiments, the recombinant host cell is a yeast, which may be a yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to particular embodiments, the recombinant host cell is a yeast of the genus *Saccharomyces*. A non-limiting example of a yeast of the genus *Saccharomyces* is *Saccharomyces cerevisiae*. According to more particular embodiments, the recombinant host cell is *Saccharomyces cerevisiae*.

According to particular embodiments, the recombinant host cell is a yeast of the genus *Pichia*. Non-limiting example of a yeast of the genus *Pichia* are *Pichia pastoris* and *Pichia kudriavzevii*. According to more particular embodiments, the recombinant host cell is *Pichia pastoris*. According to other more particular embodiments, the recombinant host cell is *Pichia kudriavzevii*.

Fungi host cells may be derived from, e.g., *Aspergillus*.

According to certain embodiments, the recombinant host cell is a fungus, such as a fungi of the genus *Aspergillus*. Non-limiting examples of a fungus of the genus *Aspergillus* are *Aspergillus Oryzae, Aspergillus niger* or *Aspergillus awamsii*. According to more particular embodiments, the recombinant host cell is *Aspergillus Oryzae*. According to other more particular embodiments, the recombinant host cell is *Aspergillus niger*. According to other more particular embodiments, the recombinant host cell is *Aspergillus awamsii*.

Algae host cells may be derived from, e.g., *Chlamydomonas, Haematococcus, Phaedactylum, Volvox* or *Dunaliella*.

According to certain embodiments, the recombinant host cell is an alga, which may be an algae of the genus *Chlamydomonas, Haematococcus, Phaedactylum, Volvox* or *Dunaliella*.

According to particular embodiments, the recombinant host cell is an alga cell of the genus *Chlamydomonas*. A non-limiting example of an alga of the genus *Chlamydomonas* is *Chlamydomonas reinhardtii*.

According to particular embodiments, the recombinant host cell is an alga cell of the genus *Haematococcus*. A non-limiting example of an alga of the genus *Haematococcus* is *Haematococcus pluvialis*.

According to other particular embodiments, the recombinant host cell is an alga cell of the genus *Phaedactylum*. A non-limiting example of an alga of the genus *Phaedactylum* is *Phaedactylum tricornatum*.

A plant host cell may be derived from, e.g., soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

According to certain embodiments, the recombinant host cell is a plant cell, such as a plant cell selected from the group consisting of soybean, rapeseed, sunflower, cotton, corn, tobacco, alfalfa, wheat, barley, oats, sorghum, lettuce, rice, broccoli, cauliflower, cabbage, parsnips, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

According to certain embodiments, a recombinant host cell according to the invention does not express an endogenous PAPS-dependent aryl sulfotransferase.

Generally, a recombinant host cell according to the invention has been genetically modified to express one or more polypeptides as detailed herein, which means that one or more exogenous nucleic acid molecules, such as DNA molecules, which comprise(s) a nucleotide sequence or nucleotide sequences encoding said polypeptide or polypeptides has been introduced in the host cell. Techniques for introducing exogenous nucleic acid molecule, such as a DNA molecule, into the various host cells are well-known to those of skill in the art, and include transformation (e.g., heat shock or natural transformation), transfection, conjugation, electroporation, microinjection and microparticle bombardment.

Accordingly, a recombinant host cell according to the invention comprises an exogenous nucleic acid molecule comprising a nucleotide sequence encoding a polypeptide as detailed herein.

In order to facilitate expression of a polypeptide in the host cell, the exogenous nucleic acid molecule may comprise suitable regulatory elements such as a promoter that is functional in the host cell to cause the production of an mRNA molecule and that is operably linked to the nucleotide sequence encoding said polypeptide.

Promoters useful in accordance with the invention are any known promoters that are functional in a given host cell to cause the production of an mRNA molecule. Many such promoters are known to the skilled person. Such promoters include promoters normally associated with other genes, and/or promoters isolated from any bacteria, yeast, fungi, alga or plant cell. The use of promoters for protein expression is generally known to those of skilled in the art of molecular biology, for example, see Sambrook et al., Molecular cloning: A Laboratory Manual, Cold Spring Harbor Laboratory, Cold Spring Harbor, N.Y., 1989. The promoter employed may be inducible. The term "inducible" used in the context of a promoter means that the promoter only directs transcription of an operably linked nucleotide sequence if a stimulus is present, such as a change in temperature or the presence of a chemical substance ("chemical inducer"). As used herein, "chemical induction" according to the present invention refers to the physical application of a exogenous or endogenous substance (incl. macromolecules, e.g., proteins or nucleic acids) to a host cell. This has the effect of causing the target promoter present in the host cell to increase the rate of transcription. Alternatively, the promoter employed may be constitutive. The term "constitutive" used in the context of a promoter means that the promoter is capable of directing transcription of an operably linked nucleotide sequence in the absence of stimulus (such as heat shock, chemicals etc.).

Non-limiting examples of promoters functional in bacteria, such as *Bacillus subtilis, Lactococcus lactis* or *Escherichia coli*, include both constitutive and inducible promoters such as T7 promoter, the beta-lactamase and lactose promoter systems; alkaline phosphatase (phoA) promoter, a tryptophan (trp) promoter system, tetracycline promoter, lambda-phage promoter, ribosomal protein promoters; and hybrid promoters such as the tac promoter. Other bacterial and synthetic promoters are also suitable.

Non-limiting examples of promoters functional in yeast, such as *Saccharomyces cerevisiae*, include xylose promoter, GAL1 and GAL10 promoters, TEF1 promoter, and pgk1 promoter.

Non-limiting examples of promoters functional in fungi, such as *Aspergillus Oryzae* or *Aspergillus niger*, include promotors derived from the gene encoding *Aspergillus oryzae* TAKA amylase, *Aspergillus niger* neutral α-amylase, *Aspergillus niger* acid stable α-amylase, *Aspergillus niger* or *Aspergillus awamsii* glucoamylase (gluA), *Aspergillus niger* acetamidase, *Aspergillus oryzae* alkaline protease, *Aspergillus oryzae* triose phosphatase isomerase, *Rhizopus meihei* aspartic proteinase, and *Rhizopus meihei* lipase.

Non-limiting examples of promoters functional in alga, such as *Haematococcus pluvialis*, include the CaMV35S promoter, the SV40 promoter, and promoter of the *Chlamydomonas reinhardtii* RBCS2 gene and the promoter of the *Volvox carteri* ARS gene.

Non-limiting examples of promoters functional in plant cells include the *Lactuca sative* psbA promoter, the tabacco psbA promoter, the tobacco rrn16 PEP+NEP promoter, the CaMV 35S promoter, the 19S promoter, the tomate E8 promoter, the nos promoter, the Mac promoter, and the pet E promoter or the ACT1 promoter.

Besides a promoter, the exogenous nucleic acid molecule may further comprise at least one regulatory element selected from a 5' untranslated region (5'UTR) and 3' untranslated region (3' UTR). Many such 5' UTRs and 3' UTRs derived from prokaryotes and eukaryotes are well known to the skilled person. Such regulatory elements include 5' UTRs and 3' UTRs normally associated with other genes, and/or 5' UTRs and 3' UTRs isolated from any bacteria, yeast, fungi, alga or plant cell.

If the host cell is a prokaryotic organism, the 5' UTR usually contains a ribosome binding site (RBS), also known as the Shine Dalgarno sequence which is usually 3-10 base pairs upstream from the initiation codon. Meanwhile, if the host cell is an eukaryotic organism the 5' UTR usually contains the Kozak consensus sequence. An eukaryotic 5' UTR may also contain cis-acting regulatory elements.

The exogenous nucleic acid molecule may be a vector or part of a vector, such as an expression vector. Normally, such a vector remains extrachromosomal within the host cell which means that it is found outside of the nucleus or nucleoid region of the host cell.

It is also contemplated by the present invention that the exogenous nucleic acid molecule is stably integrated into the genome of the host cell. Means for stable integration into the genome of a host cell, e.g., by homologous recombination, are well known to the skilled person.

It is understood that the details given herein with respect to a recombinant host cell apply to other aspects of the invention, in particular to the processes according to the invention, which are described in more detail below.

Methods and Uses

The present invention provides processes for the production of sulfated phenolic compounds. Particularly, a process for the production of a sulfated phenolic compound is provided comprising:

(i') contacting a medium comprising a phenolic compound with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification; or (i") contacting a medium comprising a fermentable carbon substrate with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification; or (i''') contacting a medium comprising a precursor of a phenolic compound with a first recombinant host cell; wherein the first recombinant host cell comprises a heterologous polypeptide having an aryl sulfotransferase activity and wherein the first recombinant host cell has been modified to have an increased uptake of sulfate compared to an identical host cell that does not carry said modification.

According to certain embodiments, the process for the production of a sulfated phenolic compound comprises:

(i') contacting a medium comprising a phenolic compound with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification.

According to other certain embodiments, the process for the production of a sulfated phenolic compound comprises:

(i") contacting a medium comprising a fermentable carbon substrate with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification.

According to other certain embodiments, the process for the production of a sulfated phenolic compound comprises:

(i''') contacting a medium comprising a precursor of a phenolic compound with a first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification.

The medium employed may be any conventional medium suitable for culturing the host cell in question, and may be composed according to the principles of the prior art. The medium will usually contain all nutrients necessary for the growth and survival of the respective host cell, such as carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains. Non-limiting standard medium well known to the skilled person include Luria Bertani (LB) broth, Sabouraud Dextrose (SD) broth, MS broth, Yeast Peptone Dextrose, BMMY, GMMY, or Yeast Malt Extract (YM) broth, which are all commercially available. A non-limiting example of suitable media for culturing bacterial cells, such as B. subtilis, L. lactis or E. coli cells, including minimal media and rich media such as Luria Broth (LB), M9 media, M17 media, SA media, MOPS media, Terrific Broth, YT and others. Suitable media for culturing eukaryotic cells, such as yeast cells, are RPMI 1640, MEM, DMEM, all of which may be supplemented with serum and/or growth factors as required by the particular host cell being cultured. The medium for culturing eukaryotic cells may also be any kind of minimal media such as Yeast minimal media.

The fermentable carbon substrate may be any suitable carbon substrate know in the art, and in particularly any carbon substrate commonly used in the cultivation of microorganisms and/or fermentation. Non-limiting examples of suitable fermentable carbon substates include carbohydrates (e.g., C5 sugars such as arabinose or xylose, or C6 sugars such as glucose), glycerol, glycerine, acetate, dihydroxyacetone, one-carbon source, methanol, methane, oils, animal fats, animal oils, plant oils, fatty acids, lipids, phospholipids, glycerolipids, monoglycerides, diglycerides, triglycerides, renewable carbon sources, polypeptides (e.g., a microbial or plant protein or peptide), yeast extract, component from a yeast extract, peptone, casaminoacids or any combination of two or more of the foregoing.

According to certain embodiments, the carbon substate is selected from the group consisting of C5 sugars (such as arabinose or xylose), C6 sugars (such as glucose or fructose), lactose, sucrose, glycerol, glycerine, acetate, Corn steep liquor, yeast extract, component from a yeast extract, peptone, casaminoacids or combinations thereof.

According to certain embodiments, the medium comprises glucose.

According to certain other embodiments, the medium comprises glycerol.

According to certain other embodiments, the medium comprises acetate.

It is also contemplated to use starch as a carbon substrate. Depending on the microorganism used, the metabolization of starch may require the supplementation of beta-glucosidase, such as the beta-glucosidase from Neurospora crassa, to the medium. Alternatively, a recombination host cell according to the invention may be further genetically modified to express a beta-glucosidase, such as the beta-glucosidase from Neurospora crassa.

When a fermentable carbon substrate is employed it is thus possible that the recombinant host cell produces the phenolic compound or a precursor thereof directly from such primary carbon substrate.

Therefore, according to certain embodiments, the process for the production of a sulfated phenolic compound comprises: (i″) contacting a medium comprising a fermentable carbon substrate with a first recombinant host cell, a phenolic compound being produced from the fermentable carbon substrate by the first recombinant host cell; wherein the first recombinant host cell comprises a heterologous polypeptide having an aryl sulfotransferase activity, and wherein the first recombinant host cell has been modified to have an increased uptake of sulfate compared to an identical host cell that does not carry said modification.

According to certain embodiments, the process further comprises:
(ii) culturing the first recombinant host cell under suitable conditions for the production of the corresponding sulfated phenolic compound.

Suitable conditions for culturing the respective host cell are well known to the skilled person. Typically, the recombinant host cell is cultured at a temperature ranging from about 23 to about 60° C., such as from about 25 to about 40° C., such as at about 37° C. The pH of the medium may range from pH 1.0 to pH 14.0, such as from about pH 1 to about pH 2, from about pH 4 to about pH 11, from about pH 5 to about pH 10, from about pH 6 to about pH 10, or from about pH 7 to about pH 9.5, e.g. at pH 6.0, pH 7.0, pH. 7.5, pH 8.0, pH 8.5, pH 9.0, pH 9.5, pH 10.0, pH 10.5 or pH 11.0.

The process may further comprise iii) recovering the sulfated phenolic compound. The sulfated phenolic compound may be recovered by conventional method for isolation and purification chemical compounds from a medium. Well-known purification procedures include centrifugation or filtration, precipitation, and chromatographic methods such as e.g. ion exchange chromatography, gel filtration chromatography, etc.

For the purpose of this specification and the appended claims, it should be understood that the phenolic compounds include those compounds in which a hydroxyl group is directly attached to a benzenoid carbon atom, and which compounds may or may not contain other substituent groups.

According to certain embodiments, the phenolic compound is a compound represented by the general formula (I):

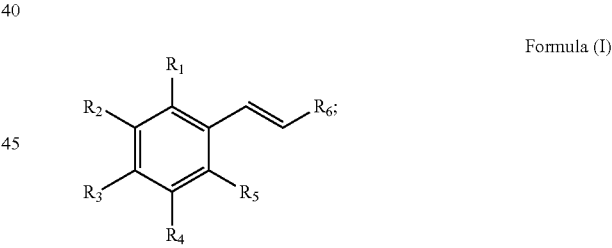

Formula (I)

wherein at least one of $R_1$, $R_2$, $R_3$, $R_4$, and $R_5$ being an hydroxyl group (—OH);
wherein $R_1$, $R_2$, $R_3$, $R_4$, $R_5$ and $R_6$ are independently selected from the group consisting of halide, hydrogen, hydroxyl (—OH), —$OR_7$, —$OCOR_7$, —$NR_7R_8$, —$COR_7$, —$COOR_7$, —$SR_7$, —$OSO_3R_7$, —$OCSR_7$, —$POR_7R_8$, alkyl, alkenyl, alkynyl, aryl, and heteroaryl; wherein $R_7$, and $R_8$ are independently selected from the group consisting of hydrogen, alkyl, alkenyl, alkynyl, aryl, and heteroaryl;
wherein $R_1$, $R_2$, $R_3$, $R_4$, $R_5$ and $R_6$, are optionally linked with a bridge member $Y_n$, thereby forming one or more rings, $Y_n$ being a bond or a $C_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, $S(O)_{1-2}$ and carbonyl, and wherein n is an integer between 1 and 12.

Specific examples of compounds of Formula I include, but are not limited to, reservatrol, o-, m-, and p-coumaric acid, caffeic acid, ferulic acid, sinapic acid, curcumin, rosmarinic acid, sinapyl alcohol, coniferyl alcohol, and salvianolic acid.

A precursor of a phenolic compound according to Formula I may be a compound represented by the general Formula (p-I):

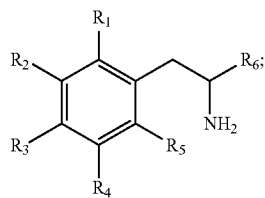

Formula (p-I)

wherein at least one of $R_1$, $R_2$, $R_3$, $R_4$, and $R_5$ being an hydroxyl group (—OH);
wherein $R_1$, $R_2$, $R_3$, $R_4$, $R_5$ and $R_6$ are independently selected from the group consisting of halide, hydrogen, hydroxyl (—OH), —$OR_7$, —$OCOR_7$, —$NR_7R_8$, —$COR_7$, —$COOR_7$, —$SR_7$, —$OSO_3R_7$, —$OCSR_7$, —$POR_7R_8$, alkyl, alkenyl, alkynyl, aryl, and heteroaryl; wherein $R_7$, and $R_8$ are independently selected from the group consisting of hydrogen, alkyl, alkenyl, alkynyl, aryl, and heteroaryl;
wherein $R_1$, $R_2$, $R_3$, $R_4$, $R_5$ and $R_6$, are optionally linked with a bridge member $Y_n$, thereby forming one or more rings, $Y_n$ being a bond or a $C_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, $S(O)_{1-2}$ and carbonyl, and wherein n is an integer between 1 and 12.

Such a precursor may be converted to the phenolic compound by a recombinant host cell according to the invention, comprising a polypeptide having tyrosine ammonia lyase activity. Such polypeptide will eliminate ammonia from the precursor of Formula (p-I) under the formation of the corresponding molecule of Formula I. Preferably, the p-I precursor is the L-isomer.

According to certain embodiments, the precursor of a phenolic compound as employed in step (i''') is a compound of the general Formula (p-I) as defined herein.

According to certain other embodiments, the phenolic compound is a compound represented by the general formula (II):

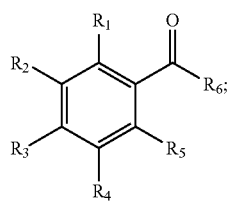

Formula (II)

wherein at least one of $R_1$, $R_2$, $R_3$, $R_4$, and $R_5$ being an hydroxyl group (—OH);
wherein $R_1$, $R_2$, $R_3$, $R_4$, $R_5$ and $R_6$ are independently selected from the group consisting of halide, hydrogen, hydroxyl (—OH), —$OR_7$, —$COOR_7$, —$NR_7R_8$, —$COR_7$, —$COOR_7$, —$SR_7$, —$OSO_3R_7$, —$OCSR_7$, —$POR_7R_8$, alkyl, alkenyl, alkynyl, aryl, and heteroaryl; wherein $R_7$, and $R_8$ are independently selected from the group consisting of hydrogen, alkyl, alkenyl, alkynyl, aryl, and heteroaryl;
wherein $R_1$, $R_2$, $R_3$, $R_4$, $R_5$ and $R_6$, are optionally linked with a bridge member $Y_n$, thereby forming one or more rings, $Y_n$ being a bond or a $C_{1-12}$ alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, $S(O)_{1-2}$ and carbonyl, and wherein n is an integer between 1 and 12.

According to certain embodiments, $R_6$ is —$COOR_7$.
According to certain embodiments, $R_7$ is hydrogen.
According to certain embodiments, $R_2$ is hydroxyl (—OH).
According to certain embodiments, $R_3$ is hydroxyl (—OH).
According to certain embodiments, $R_4$ is hydroxyl (—OH).
According to certain embodiments, each of $R_1$, $R_2$, $R_4$ and $R_5$ is hydrogen.
According to certain embodiments, each of $R_1$, $R_2$, and $R_5$ is hydrogen.
According to particular embodiments, the phenolic compound is p-coumaric acid (Formula I: $R_1$=H, $R_2$=H, $R_3$=OH, $R_4$=H, $R_5$=H, $R_6$=COOH).
According to other particular embodiments, the phenolic compound is caffeic acid (Formula I: $R_1$=H, $R_2$=H, $R_3$=OH, $R_4$=OH, $R_5$=H, $R_6$=COOH).
According to other particular embodiments, the phenolic acid is ferulic acid (Formula I: $R_1$=H, $R_2$=$OCH_3$, $R_3$=OH, $R_4$=H, $R_5$=H, $R_6$=COOH).
According to other particular embodiments, the phenolic acid is isoferulic acid (Formula I: R1=H, R2=OH, R3=$OCH_3$, R4=H, R5=H, R6=COOH).
According to other particular embodiments, the phenolic acid is sinapic acid (Formula I: $R_1$=H, $R_2$=$OCH_3$, $R_3$=OH, $R_4$=$OCH_3$, $R_5$=H, $R_6$=COOH).
According to other particular embodiments, the phenolic compound is resvератrol (Formula I: $R_1$=H, $R_2$=OH, $R_3$=H, $R_4$=OH, $R_5$=H, $R_6$=p-hydroxyphenyl).
According to other particular embodiments, the phenolic compound is vanillin (Formula II: $R_1$=H, $R_2$=H, $R_3$=OH, $R_4$=$OCH_3$, $R_5$=H, $R_6$=H).
According to other particular embodiments, the phenolic compound is vanillic acid (Formula II: R1=H, R2=H, R3=OH, R4=$OCH_3$, R5=H, R6=OH).
According to other particular embodiments, the phenolic compound is 4-vinylphenol (Formula I: $R_1$=H, $R_2$=H, $R_3$=OH, $R_4$=H, $R_5$=H, $R_6$=H).
According to other particular embodiments, the phenolic compound is 2-methoxy 4-vinylphenol (Formula I: $R_1$=H, $R_2$=$OCH_3$, $R_3$=OH, $R_4$=H, $R_5$=H, $R_6$=H).
According to certain embodiments, the phenolic compound is selected from the group consisting of:

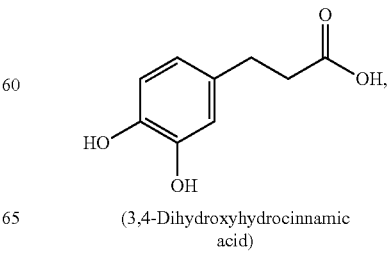

(3,4-Dihydroxyhydrocinnamic acid)

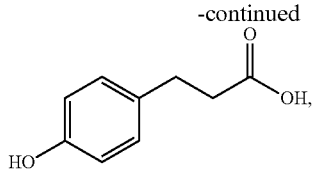
(3,4-Hydroxyphenyl(propionic acid)

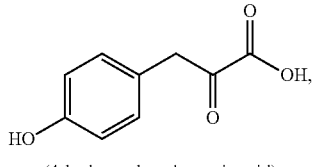
(4-hydroxyphenylpyruvic acid)

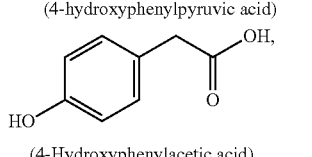
(4-Hydroxyphenylacetic acid)

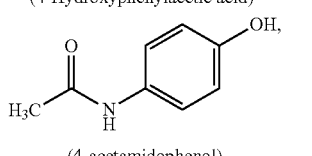
(4-acetamidophenol)

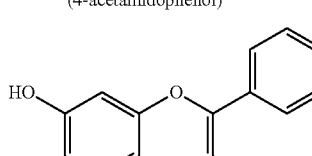
(Kaempferol)

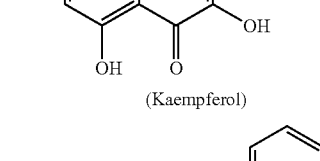
(Naringenin)

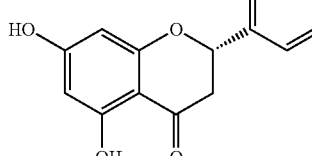
(4-nitrophenol)        (4-methylbelliferone)

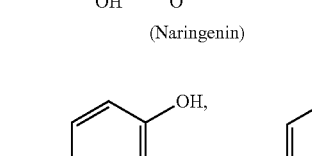
(4-ethylguaiacol)  , and  (4-ethylphenol)  .

According to particular embodiments, the phenolic compound is 3,4-Dihydroxyhydrocinnamic acid.

According to other particular embodiments, the phenolic compound is 3-(4-Hydroxyphenyl)propionic acid.

According to other particular embodiments, the phenolic compound is 4-hydroxyphenylpyruvic acid.

According to other particular embodiments, the phenolic compound is 4-Hydroxyphenylacetic acid.

According to other particular embodiments, the phenolic compound is 4-acetamidophenol.

According to other particular embodiments, the phenolic compound is Kaempferol.

According to other particular embodiments, the phenolic compound is Naringenin.

According to other particular embodiments, the phenolic compound is 4-nitrophenol.

According to other particular embodiments, the phenolic compound is 4-methylbelliferone.

According to other particular embodiments, the phenolic compound is 4-ethylguaiacol.

According to other particular embodiments, the phenolic compound is 4-ethylphenol.

According to other particular embodiments, the phenolic compound is Luteolin.

According to other particular embodiments, the phenolic compound is Apigenin.

According to other particular embodiments, the phenolic compound is fisetin.

According to other particular embodiments, the phenolic compound is Quercetin.

According to certain embodiments, the phenolic compound is a hydroxycinnamic acid.

According to certain embodiments, the phenolic compound is a compound represented by the general formula (I), wherein $R_1$ is hydrogen; $R_2$, $R_3$ and $R_4$ independently are selected from the group consisting of hydrogen (H), hydroxyl (—OH), $C_{1-6}$-alkyl and $C_{1-6}$-Alkoxy, provided that at least one of $R_2$, $R_3$ and $R_4$ is hydroxyl (—OH); $R_5$ is hydrogen, and $R_6$ is COOH.

According to certain embodiments, the precursor of a phenolic compound as employed in step (i''') is a compound of the general Formula (p-I), wherein $R_1$ is hydrogen; $R_2$, $R_3$ and $R_4$ independently are selected from the group consisting of hydrogen (H), hydroxyl (—OH), $C_{1-6}$-alkyl and $C_{1-6}$-Alkoxy, provided that at least one of $R_2$, $R_3$ and $R_4$ is hydroxyl (—OH); $R_5$ is hydrogen, and $R_6$ is COOH.

According to certain embodiment, the sulfated phenolic compound obtained in according to the present invention is zosteric acid.

Suitable sulfate donor molecules metabolized by a polypeptide having aryl sulfotransferase activity are well-known to one skilled in the art. Non-limiting examples include 3'-phosphoadenosine 5'-phosphosulfate (PAPS), para-nitrophenyl sulfate (pNPS) and 4-methylumbelliferyl sulfate (MUS). Such sulfate donor molecules may be employed to facilitate the sulfation of phenolic compounds in accordance with the invention.

The medium employed for culturing the recombinant host cell may be any conventional medium suitable for culturing the host cell in question, and may be composed according to the principles of the prior art. The medium will usually contain all nutrients necessary for the growth and survival of the respective host cell, such as carbon and nitrogen sources and other inorganic salts, such as sulfate salts. Suitable media, e.g. minimal or complex media, are available from commercial suppliers, or may be prepared according to published receipts, e.g. the American Type Culture Collection (ATCC) Catalogue of strains. Non-limiting standard medium well known to the skilled person include Luria Bertani (LB) broth, Sabouraud Dextrose (SD) broth, MS broth, Yeast Peptone Dextrose, BMMY, GMMY, or Yeast Malt Extract (YM) broth, which are all commercially available. A non-limiting example of suitable media for culturing bacterial cells, such as *B. subtilis*, *L. lactis* or *E. coli* cells, including minimal media and rich media such as Luria Broth (LB), M9 media, M17 media, SA media, MOPS media, Terrific Broth, YT and others. Suitable media for culturing eukaryotic cells, such as yeast cells, are RPMI 1640, MEM, DMEM, all of which may be supplemented with serum and/or growth factors as required by the particular host cell being cultured. The medium for culturing eukaryotic cells may also be any kind of minimal media such as Yeast minimal media.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the invention.

Certain Definitions

"Aryl sulfotransferase activity" as used herein refers to the ability of a polypeptide to catalyze the catalyze the transfer of a sulfate group from a donor molecule to an aryl acceptor molecule.

"Tyrosine ammonia lyase activity" as used herein refers to the ability of a polypeptide to catalysed the conversion of L-tyrosine into p-coumaric acid.

"Phenylalanine ammonia lyase activity" as used herein refers to the ability of a polypeptide to catalysed the conversion of L-phenylalanine into trans-cinnamic acid.

"Sulfate transporter" or "sulfate permease" are used herein interchangeably to refer to a protein or protein complex that mediates sulfate uptake by a cell.

"ATP sulfurylase" as used herein refers to an enzyme that catalyzes the reaction: ATP+sulfate=diphosphate+adenosine 5'-phosphosulfate (APS).

"APS kinase" as used herein refers to an enzyme that catalyzes the reaction: ATP+adenosine 5'-phosphosulfate (APS)=ADP+3'-phosphoadenosine 5'-phosphosulfate (PAPS).

"PAP phosphatase" as used herein refers to an enzyme that catalyzes the reaction: 3'-phosphoadenosine 5'-phosphate (PAP)+$H_2O$=AMP+phosphate.

"Polypeptide," or "protein" are used interchangeably herein to denote a polymer of at least two amino acids covalently linked by an amide bond, regardless of length or post-transiational modification (e.g., glycosylation, phosphorylation, lipidation, myristilation, ubiquitination, etc.). Included within this definition are D- and L-amino acids, and mixtures of D- and L-amino acids.

"Nucleic acid" or "polynucleotide" are used interchangeably herein to denote a polymer of at least two nucleic acid monomer units or bases (e.g., adenine, cytosine, guanine, thymine) covalently linked by a phosphodiester bond, regardless of length or base modification.

"Recombinant" or "non-naturally occurring" when used with reference to, e.g., a host cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant host cells expressing genes that are not found within the native (non-recombinant) form of the cell or express native genes that are otherwise expressed at a different level.

"Substitution" or "substituted" refers to modification of the polypeptide by replacing one amino acid residue with another, for instance the replacement of an Arginine residue with a Glutamine residue in a polypeptide sequence is an amino acid substitution.

"Conservative substitution" refers to a substitution of an amino acid residue with a different residue having a similar side chain, and thus typically involves substitution of the amino acid in the polypeptide with amino acids within the same or similar class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having an aromatic side chain is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" or "deleted" refers to modification of the polypeptide by removal of one or more amino acids in the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide, in various embodiments, the deletion can comprise a continuous segment or can be discontinuous.

"Insertion" or "inserted" refers to modification of the polypeptide by addition of one or more amino acids to the reference polypeptide. Insertions can comprise addition of 1 or more amino acids, 2 or more amino acids, 5 or more amino acids, 10 or more amino acids, 15 or more amino acids, or 20 or more amino acids. Insertions can be in the internal portions of the polypeptide, or to the carboxy or amino terminus. The insertion can be a contiguous segment of amino acids or separated by one or more of the amino acids in the reference polypeptide.

"Host cell" as used herein refers to a living cell or microorganism that is capable of reproducing its genetic material and along with it recombinant genetic material that has been introduced into it—e.g., via heterologous transformation.

"Expression" includes any step involved in the production of a polypeptide (e.g., encoded enzyme) including, but not limited to, transcription, post-transcriptional modification, translation, post-translational modification, and secretion.

As used herein, "vector" refers to a nucleic acid molecule capable of transporting another nucleic acid molecule to which it has been linked. One type of vector is a "plasmid", which refers to a circular double stranded nucleic acid loop into which additional nucleic acid segments can be ligated. Certain vectors are capable of directing the expression of genes to which they are operatively linked. Such vectors are referred to herein as "expression vectors". Certain other vectors are capable of facilitating the insertion of a exogenous nucleic acid molecule into a genome of a host cell. Such vectors are referred to herein as "transformation vectors". In general, vectors of utility in recombinant nucleic acid techniques are often in the form of plasmids. In the present specification, "plasmid" and "vector" can be used interchangeably as the plasmid is the most commonly used form of a vector. Large numbers of suitable vectors are known to those of skill in the art and commercially available.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A "promoter functional in a host cell" refers to a "promoter" which is capable of supporting the initiation of transcription in said cell, causing the production of an mRNA molecule.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence. A promoter sequence is "operably-linked" to a gene when it is in sufficient proximity to the transcription start site of a gene to regulate transcription of the gene.

As used herein, an operon is a functioning unit of DNA containing a cluster of genes under the control of a single promoter.

"Percentage of sequence identity," "% sequence identity" and "percent identity" are used herein to refer to comparisons between an amino acid sequence and a reference amino acid sequence. The "% sequence identify", as used herein, is calculated from the two amino acid sequences as follows: The sequences are aligned using Version 9 of the Genetic Computing Group's GAP (global alignment program), using the default BLOSUM62 matrix (see below) with a gap open penalty of −12 (for the first null of a gap) and a gap extension penalty of −4 (for each additional null in the gap). After alignment, percentage identity is calculated by expressing the number of matches as a percentage of the number of amino acids in the reference amino acid sequence.

The following BLOSUM62 matrix is used:

| Ala | 4 | | | | | | | | | | | | | | | | | | |
|---|---|---|---|---|---|---|---|---|---|---|---|---|---|---|---|---|---|---|---|
| Arg | −1 | 5 | | | | | | | | | | | | | | | | | |
| Asn | −2 | 0 | 6 | | | | | | | | | | | | | | | | |
| Asp | −2 | −2 | 1 | 6 | | | | | | | | | | | | | | | |
| Cys | 0 | −3 | −3 | −3 | 9 | | | | | | | | | | | | | | |
| Gln | −1 | 1 | 0 | 0 | −3 | 5 | | | | | | | | | | | | | |
| Glu | −1 | 0 | 0 | 2 | −4 | 2 | 5 | | | | | | | | | | | | |
| Gly | 0 | −2 | 0 | −1 | −3 | −2 | −2 | 6 | | | | | | | | | | | |
| His | −2 | 0 | 1 | −1 | −3 | 0 | 0 | −2 | 8 | | | | | | | | | | |
| Ile | −1 | −3 | −3 | −3 | −1 | −3 | −3 | −4 | −3 | 4 | | | | | | | | | |
| Leu | −1 | −2 | −3 | −4 | −1 | −2 | −3 | −4 | −3 | 2 | 4 | | | | | | | | |
| Lys | −1 | 2 | 0 | −1 | −3 | 1 | 1 | −2 | −1 | −3 | −2 | 5 | | | | | | | |
| Met | −1 | −1 | −2 | −3 | −1 | 0 | −2 | −3 | −2 | 1 | 2 | −1 | 5 | | | | | | |
| Phe | −2 | −3 | −3 | −3 | −2 | −3 | −3 | −3 | −1 | 0 | 0 | −3 | 0 | 6 | | | | | |
| Pro | −1 | −2 | −2 | −1 | −3 | −1 | −1 | −2 | −2 | −3 | −3 | −1 | −2 | −4 | 7 | | | | |
| Ser | 1 | −1 | 1 | 0 | −1 | 0 | 0 | 0 | −1 | −2 | −2 | 0 | −1 | −2 | −1 | 4 | | | |
| Thr | 0 | −1 | 0 | −1 | −1 | −1 | −1 | −2 | −2 | −1 | −1 | −1 | −1 | −2 | −1 | 1 | 5 | | |
| Trp | −3 | −3 | −4 | −4 | −2 | −2 | −3 | −2 | −2 | −3 | −2 | −3 | −1 | 1 | −4 | −3 | −2 | 11 | |
| Tyr | −2 | −2 | −2 | −3 | −2 | −1 | −2 | −3 | 2 | −1 | −1 | −2 | −1 | 3 | −3 | −2 | −2 | 2 | 7 |
| Val | 0 | −3 | −3 | −3 | −1 | −2 | −2 | −3 | −3 | 3 | 1 | −2 | 1 | −1 | −2 | −2 | 0 | −3 | −1 | 4 |
| | Ala | Arg | Asn | Asp | Cys | Gln | Glu | Gly | His | Ile | Leu | Lys | Met | Phe | Pro | Ser | Thr | Trp | Tyr | Val |

"Reference sequence" or "reference amino acid sequence" refers to a defined sequence to which another sequence is compared. In the context of the present invention a reference amino acid sequence may be any amino acid sequence set forth in SEQ ID NO: 1 to 50.

Aliphatic radicals/groups, as referred herein, are optionally mono- or polysubstituted and may be branched or unbranched, saturated or unsaturated. Unsaturated aliphatic groups, as defined in herein, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2R'$, NHR', NR'R" whereby R' and optionally R" for each substitutent independently represents a linear or branched $C_{1-6}$-alkyl group.

"Alkyl", "alkyl radical" or group as used herein means saturated, linear or branched hydrocarbons, which can be unsubstituted or mono- or polysubstituted. Thus, unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$CH_3$.

"$C_{1-12}$ alkyl" includes $C_{1-12}$ alkyl, $C_{1-3}$-alkyl, $C_{1-4}$ alkyl, and $C_{1-5}$-alkyl, $C_{1-6}$-alkyl, $C_{1-7}$-alkyl, $C_{1-8}$-alkyl, $C_{1-9}$-alkyl, $C_{1-10}$-alkyl, and $C_{1-11}$-alkyl. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl etc. The alkyl radicals may be methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethyl propyl, 1,2-dimethylpropyl, 2,2-dimethylpropyl, hexyl, 1-methylpentyl, if substituted also $CHF_2$, $CF_3$ or $CH_2OH$ etc. These alkyl, alkenyl or alkinyl radicals may optionally be mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, (C=O)R', SR', SOR', $SO_2R'$, NHR', NR'R" whereby R' and optionally R" for each substituent independently represents linear or branched $C_{1-6}$-alkyl group.

"Aryl" or "aryl radical" as herein is understood as meaning ring systems with at least one aromatic ring but without heteroatoms even in only one of the rings. These aryl radicals may optionally be mono- or polysubstituted by substitutents independently selected from a $C_{1-4}$ alkyl group, a linear or branched $C_{1-6}$ alkoxy group, an optionally at least mono-substituted phenyl group, F, Cl, I, Br, $CF_3$, $CH_2F$, $CHF_2$, CN, OH, SH, $NH_2$, oxo, (C=O)R', SR', SOR', $SO_2R'$, N(C=O)—OR', NHR', NR'R" whereby R' and optionally R" for each substitutent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

"Alkyl-aryl" or "alkyl-aryl radical" as used herein comprises a linear or branched, optionally at least mono-substituted alkyl chain which is bonded to an aryl group, as defined above. A preferred alkyl-aryl radical is a benzyl group, wherein the alkyl chain is optionally branched or substituted. Preferred substituents for alky-aryl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

"Heteroaryl" or "heteroaryl radical" as used herein is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-4}$ alkyl group, a linear or branched $C_{1-6}$ alkoxy group, F, Cl, I, Br, $CF_3$, $CH_2F$, $CHF_2$, CN, OH, SH, $NH_2$, oxo, (C=O)R', SR', SOR', $SO_2R'$, NHR', NR'R" whereby R' and optionally R" for each substitutent independently represents a linear or branched $C_1$-6-alkyl group. Preferred examples of heteroaryls include but are not restricted to furan, benzofuran, thiophene, benzothiophene, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidzole, carbazole and quinazoline.

"Alkoxy", "alkoxy radical" or group as used herein means an "alkyl" singular bonded to oxygen. "$C_{1-6}$-alkoxy" includes $C_{1-2}$-alkoxy, $C_{1-3}$-alkoxy, $C_{1-4}$-alkoxy, and $C_{1-5}$-alkoxy, as well as $C_{2-3}$-alkoxy, $C_{2-4}$-alkoxy, $C_{2-5}$-alkoxy, $C_{3-4}$-alkoxy, $C_{3-5}$-alkoxy, and $C_{4-5}$-alkoxy. In these radicals, $C_{1-2}$-alkoxy represents C1- or C2-alkoxy, $C_{1-3}$-alkoxy represents $C_1$-, $C_2$- or $C_3$-alkoxy, $C_{1-4}$-alkyl represents $C_1$-, $C_2$-, $C_3$- or $C_4$-alkoxy, $C_{1-5}$-alkoxy represents $C_1$-, $C_2$-, $C_3$-, $C_4$-, or $C_5$-alkoxy, $C_{1-6}$-alkoxy represents $C_1$-, $C_2$-, $C_3$-, $C_4$-, $C_5$- or $C_6$-alkoxy. The alkoxy radicals may be methoxy, ethoxy, propoxy, butoxy, pentyloxy or hexyloxy.

The term "precursor of a phenolic compound" refers to any compound that may be converted to a phenolic compound by a host cells as described herein.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1—Production of Zosteric Acid in *E. coli*

A range of aryl sulfotransferases including SULT1A1 *Rattus norvegicus* (SEQ ID NO: 1), SULT1A1 *Homo sapiens* (SEQ ID NO: 2), SULT1A1 *Equus caballus* (SEQ ID NO: 3), SULT1A1 *Sus scrofa domesticus* (SEQ ID NO: 4), SULT1A1 *Canis lupus familiaris* (SEQ ID NO: 5) and SULT1E1 *Gallus gallus domesticus* (SEQ ID NO: 6) were expressed in *Escherichia coli*. The respective genes encoding SEQ ID NO. 1, 3, 4, 5, and 6 were cloned amplified from liver tissue cDNA (Zyagen) by PCR using the primers listed in Table 1. The nucleotide sequence of the gene encoding SEQ ID NO: 2 was codon optimized for expression in *Escherichia coli* (GeneArt, Life Technologies) and amplified by PCR using the primers in Table 1. The pETDuet-1 plasmid was digested with restriction endonucleases NcoI and SalI. The PCR products were then individually cloned into the plasmid pETDuet-1 using the Gibson reaction (New England Biolabs). The resulting plasmids were transformed into BL21(DE3)pLysS (Life Technologies). FIG. 1 shows the plasmid map of the plasmid encoding SULT1A1 *Rattus norvegicus* (SEQ ID NO: 1).

TABLE 1

Overview of enzymes and primers for cloning aryl sulfotransferases

| SEQ ID NO | Name | Fwd Primer | Rev Primer |
|---|---|---|---|
| 1 | SULT1A1 *Rattus norvegicus* | CBJP472 | CBJP473 |
| 2 | SULT1A1 *Homo sapiens* | CBJP470 | CBJP471 |
| 3 | SULT1A1 *Equus caballus* | CBJP499 | CBJP500 |
| 4 | SULT1A1 *Sus scrofa domesticus* | CBJP505 | CBJP506 |
| 5 | SULT1A1 *Canis lupus familiaris* | CBJP503 | CBJP504 |
| 6 | SULT1E1 *Gallus gallus domesticus* | CBJP501 | CBJP502 |

The strains were grown in M9 minimal media containing glucose as a carbon source, and 0.1 mM IPTG for induction of gene expression as well as 0.1 mM p-coumaric acid (pHCA). After four days of growth, samples were withdrawn by filtration and analyzed by HPLC.

The concentration of p-courmaric acid (pHCA) and zosteric acid in the supernatant was quantified by high performance liquid chromatography (HPLC) and compared to chemical standards. HPLC was done on a Thermo setup using a HS-F5 column and mobile phases: 5 mM ammonium formate pH 4.0 (A) and acetonitrile (B) at 1.5 mL min-1, using a gradient elution starting at 5% B. From 0.5 min after injection to 7 min, the fraction of B increased linearly from 5% to 60%, and between 9.5 min and 9.6 the fraction of B decreased back to 5%, and remaining there until 12 min. pHCA and zosteric acid were quantified by measuring absorbance at 277 nm.

Table 2 shows the remaining pHCA and the produced zosteric acid in the culture media. Zosteric acid was formed with an aryl sulfotransferase heterologously expressed in a microorganism exemplified by *E. coli* supplied with the substrate.

TABLE 2

Production of zosteric acid in *E. coli* from pHCA through the heterologous expression of sulfotransferases.

| Enzyme | pHCA remaining (mM) | Zosteric acid formed (mM) |
|---|---|---|
| No enzyme | 0.10 | Not detectable |
| SULT1A1 *Rattus norvegicus* | 0.02 | 0.10 |
| SULT1A1 *Homo sapiens* | 0.08 | 0.02 |
| SULT1A1 *Equus caballus* | 0.09 | 0.01 |
| SULT1A1 *Sus scrofa domesticus* | 0.09 | 0.01 |
| SULT1A1 *Canis lupus familiaris* | 0.10 | 0.01 |
| SULT1E1 *Gallus gallus domesticus* | 0.08 | 0.01 |

Example 2—Increased Production of Zosteric Acid in *E. coli*

The addition of sulfated groups to targets is dependent on supply of the donor molecule 3'-Phosphoadenosine 5'-phosphosulfate (PAPS). We examined if we could increase the production of zosteric acid by overexpressing enzymes providing PAPS and an enzyme that removes the product 3'-Phosphoadenosine 5'-phosphate (PAP).

TABLE 3

Cloning of enzymes involved in activating sulfate and product removal.

| Genes | Fwd Primer | Rev Primer |
|---|---|---|
| cysDNC alone | CBJP491 | CBJP492 |
| cysDNC for artificial operon | CBJP491 | CBJP497 |
| cysQ for artificial operon | CBJP498 | CBJP496 |

In *E. coli*, the genes cysD and cysN encode the two subunits of ATP sulfurylase (EC:2.7.7.4), cysC encodes APS kinase (EC:2.7.1.25), and cysQ encode a PAP phosphatase.

Figure 2:
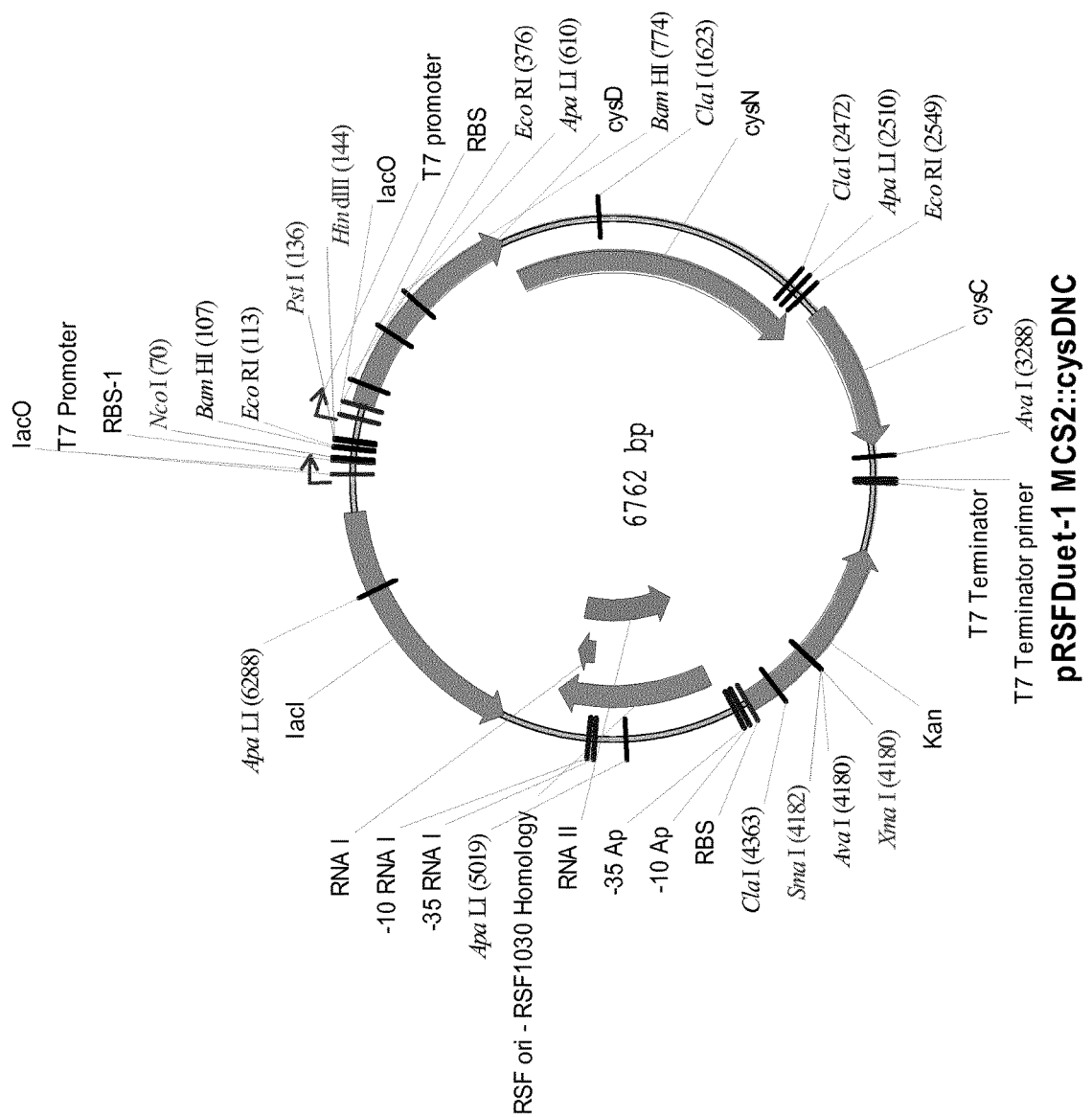
FIG. 2: Map of plasmid for over-expression of cysDNC in *E. coli*.
Figure 3:
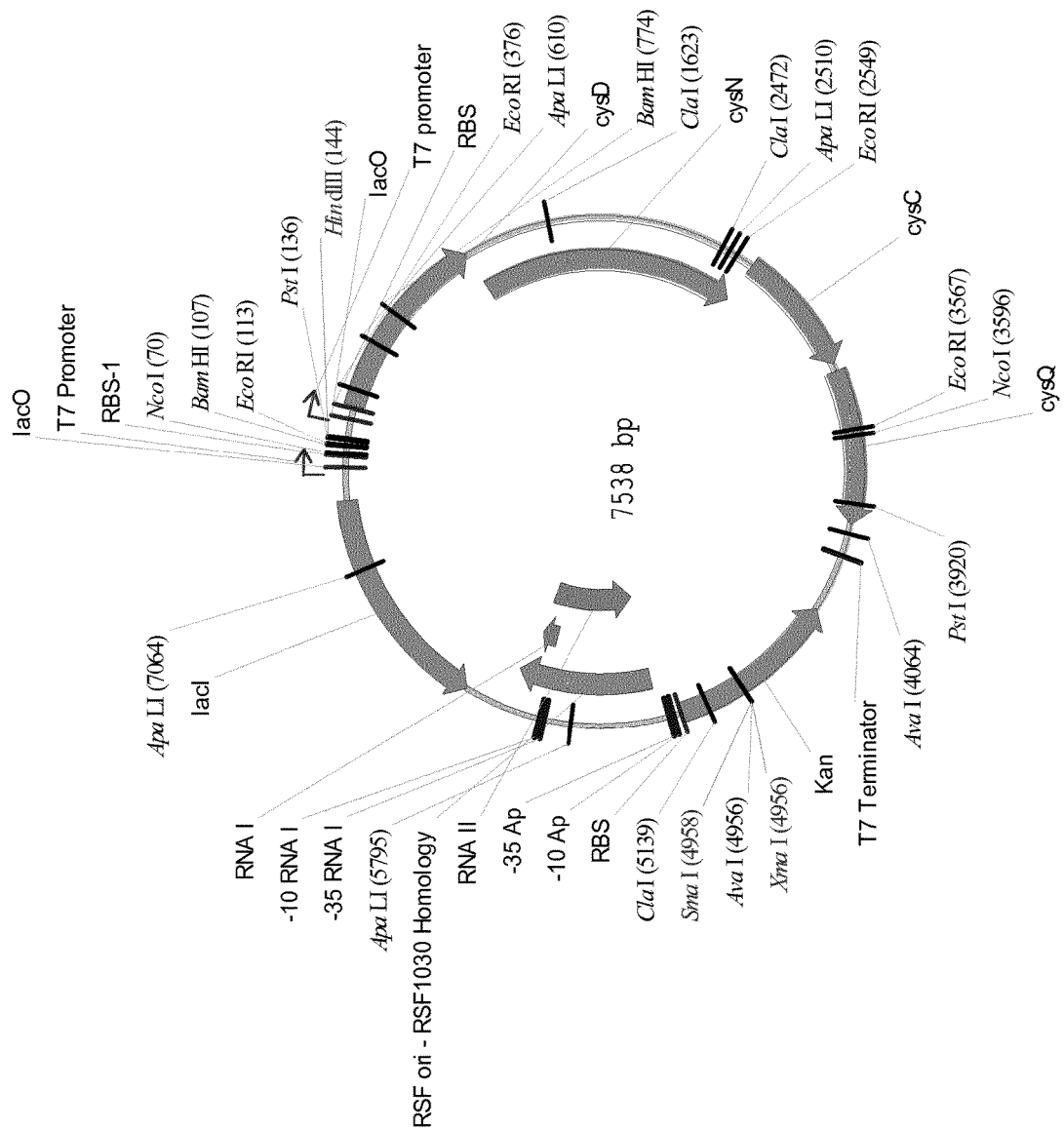
FIG. 3: Map of plasmid for over-expression of cysDNCQ in *E. coli*.

The cysDNC cluster was amplified by PCR from *E. coli* MG1655 chromosomal DNA using the primers shown in Table 3. The plasmid pRSFDuet-1 (Life Technologies) was digested by the restriction endonucleases NdeI and BglII. The gene cluster was inserted into the digested plasmid using the Gibson reaction (New England Biolabs). FIG. 2 shows the resulting plasmid. For the combined expression of cysDNC and cysQ in an artificial operon, cysDNCQ, the two parts were amplified by PCR from *E. coli* MG1655 chromosomal DNA using the primers shown in Table 3. Again the parts were inserted into the digested plasmid. FIG. 3 shows the resulting plasmids. The plasmid expressing SULT1A1 *Homo sapiens* (SEQ ID NO: 2) from example 1 was co-transformed into *E. coli* BL21(DE3)pLysS cells (Life Technologies) with either the plasmid expressing cysDNC or cysDNCQ.

Cells were grown as in Example 1 and the supernatants were analyzed for product formation as in example 1. The strain expressing SULT1A1 in combination with cysDNCQ was also grown without the addition of IPTIG for induction. Table 4 shows the concentrations of pHCA and zosteric acid.

TABLE 4

Concentrations of pHCA and zosteric acid in culture media with *E. coli* expressing an aryl sulfotransferase in combination with cysDNC and cysQ.

| Enzymes | Induction | pHCA remaining (mM) | Zosteric acid formed (mM) |
|---|---|---|---|
| SULT1A1 *Homo sapiens* | 0.1 mM IPTG | 0.08 | 0.02 |
| SULT1A1 *Homo sapiens*, CysDNC | 0.1 mM IPTG | 0.06 | 0.06 |
| SULT1A1 *Homo sapiens*, CysDNCQ | 0.1 mM IPTG | 0.04 | 0.09 |
| SULT1A1 *Homo sapiens*, CysDNCQ | None | 0.10 | Not detectable |

This shows that more of the pHCA is transformed into zosteric acid when the protein expression of cysDNC is increased. Even more zosteric acid is formed when the protein expression cysQ is additionally increased.

Example 3—A Sulfated Product can be Formed In Vivo by Co-Expression of an Heterologous Pathway and an Aryl Sulfotransferase The production of a sulfated product can be accomplished biologically by the expression of aryl sulfotransferase as shown in example 1. The substrate for sulfation may also be formed by a biological organism, and here it will be shown for an organism expressing both a heterologous pathway leading to a phenolic compound and expressing a sulfotransferase acting upon the phenolic compound.

The enzyme RmXAL from *Rhodotorula mucilaginosa/Rhodotorula rubra* (SEQ ID NO: 46) has tyrosine ammonia lyase activity, thus catalyzing the non-oxidative deamination of the amino acid tyrosine, releasing p-coumaric acid (pHCA) and ammonia. The gene encoding RmXAL was codon optimized using standard algorithms for expression in *E. coli* available by GeneArt (Life Technologies) and amplified by PCR using the primers shown in Table 5 and inserted into the pCDFDuet-1 vector (Novagen/Life Technologies), which had been digested by the restriction enzymes NdeI and BglII, using Gibson reaction (New England Biolabs).

TABLE 5

Primers used for cloning of tyrosine ammonialyase

| Genes | Fwd Primer | Rev Primer |
|---|---|---|
| RmXAL | CBJP487 | CBJP488 |

The resulting plasmid was co-transformed into *E. coli* BL21(DE3)pLysS cells (Life Technologies) alone or together with the plasmid expressing SULT1A1 from *Homo sapiens* (example 1). The resulting strains was grown in M9 media with glucose as a carbon source, with 0.1 mM IPTG for induction of gene expression. Samples were taken as described previously (example 1) for analysis of product formation. Table 6 shows the resulting concentrations of pHCA and zosteric acid. RmXAL allowed the production of pHCA without addition of any substrate, thus providing a heterologous pathway from the cells normal metabolism to a heterologous product. The additional expression of an aryl sulfotransferase, exemplified by SULT1A1 from *Homo sapiens*, allowed the in vivo conversion of pHCA to zosteric acid. Thus, an aryl sulfotransferase can act upon a compound produced in vivo and the cells can release the resulting sulfated product to the medium.

TABLE 6

Concentrations of pHCA and zosteric acid in culture media with *E. coli* expressing an aryl sulfotransferase in combination with a tyrosine ammonia lyase.

| Enzymes | pHCA (mM) | Zosteric acid formed (mM) |
|---|---|---|
| RmXAL | 0.04 | Not detectable |
| SULT1A1 *Homo sapiens*, RmXAL | 0.02 | 0.01 |

Example 4—Decreased Toxicity of Sulfated Product

Figure 4:
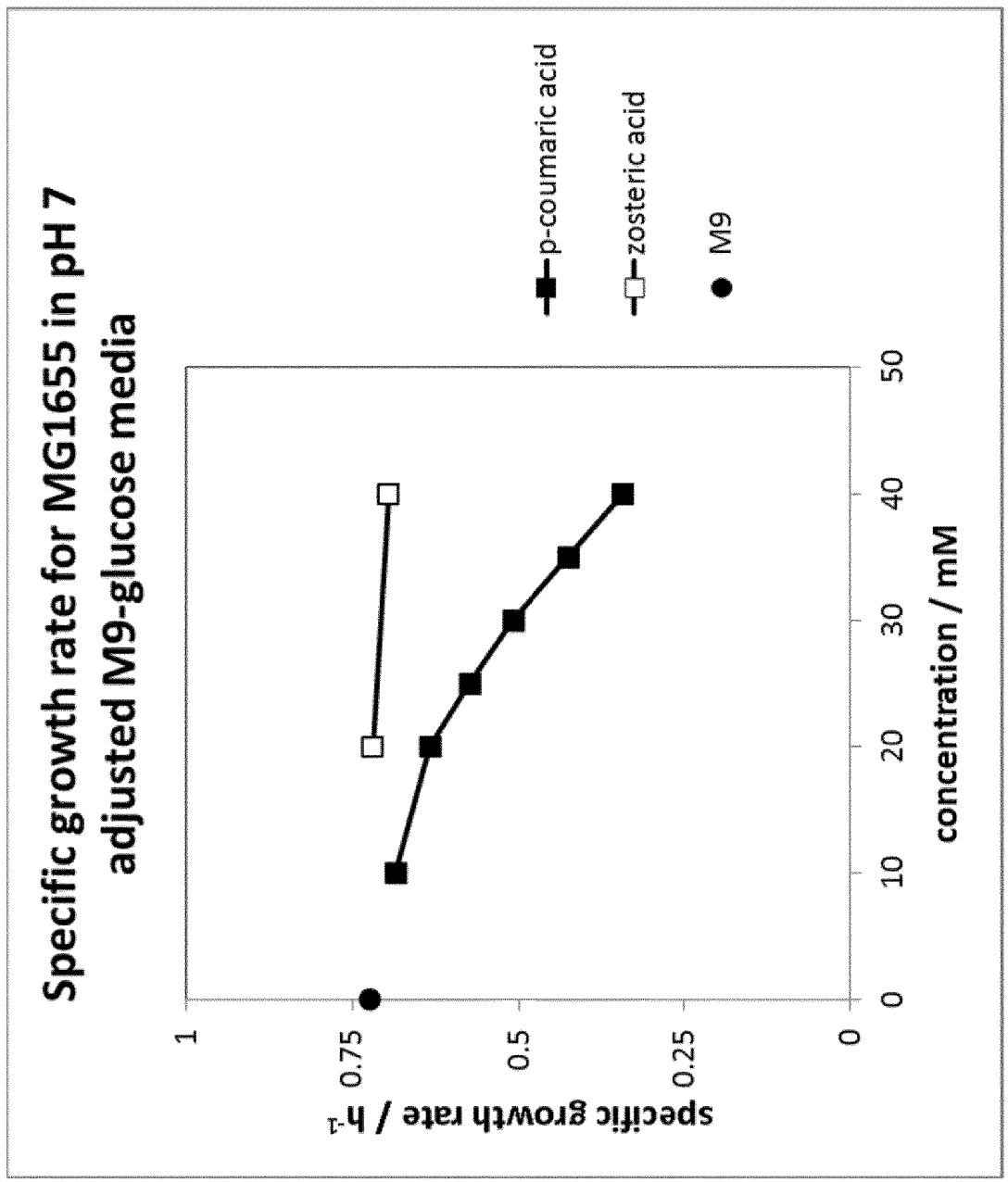
FIG. 4: Toxicity of unsulfated or sulfated products

*E. coli* MG1655 was grown in chemically defined M9 minimal media with 0.2% glucose as a carbon source without further addition or with the additions of either 10 mM, 20 mM, 25 mM, 30 mM, 35 mM or 40 mM p-coumaric acid (pHCA), or with 20 mM or 40 mM of the sulfate ester of pHCA (zosteric acid). All media preparations had been adjusted to pH 7. Cells were grown at 37° C. with 250 rpm shaking in an orbital shaker. The growth rates were examined by following the optical density at 600 nm. The resulting growth rates in exponential growth phase are shown in FIG. 4. Filled squares represent growth rates in media with pHCA. Open squares represent growth rates in media with zosteric acid. And the circle represents the growth rate in media without any of these additions. It is evident that the presence of pHCA is toxic to the cells, while the sulfate ester, zosteric acid is much less so.

Example 5—In Vivo Supply of Precursor of Sulfated Product

The substrate that is the subject for sulfation may be supplied to the medium void of such precursors or may be provided by microorganisms in the medium. Here we show that p-coumaric acid that is sulfated to generate zosteric acid, can be produced in vivo by the expression of a tyrosine ammonia-lyase.

The genes encoding the tyrosine ammonia-lyases RcTAL (from *Rhodobacter capsulatus*; SEQ ID NO: 50), RsTAL (from *Rhodobacter sphaeroides*; SEQ ID NO: 43) and FjTAL (from *Flavobacterium johnsoniae*; SEQ ID NO: 40) were cloned into expression vectors as follows. Genes (SEQ ID NO: 51, 52, and 53, respectively) were optimized for *E. coli* and synthesized by GeneArt, amplified by PCR using the oligonucleotides shown in the table below, and cloned into pCDFDuet-1 (Novagen): The plasmid was digested with NdeI and BglII and gel purified. The genes were inserted by isothermal assembly using Gibson Assembly Master Mix (New England Biolabs), and transformed into chemically competent DH5a (laboratory strain) or NEB5α (New England Biolabs), selecting for resistance to 50 µg mL$^{-1}$ spectinomycin in LB medium. Resulting plasmids pCBJ215 (RsTAL), pCBJ228 (FjTAL) and pCBJ297 (RcTAL) were co-transformed by electroporation into the *E. coli* expression strain BL21(DE3) (Invitrogen/Life Technologies) together with a pETDuet-1-based plasmid expressing SULT1A1 from rat (Example 1). Transformation cultures were plated on LB containing 50 µg mL$^{-1}$ spectinomycin and 100 µg mL$^{-1}$ ampicillin. A control strain carrying pCDFDuet-1 was also made.

TABLE 7

Primers

| Oligo-nucleotide | Gene | Direction | Sequence |
|---|---|---|---|
| CBJP483 | RsTAL | Forward | CATCTTAGTATATTAGTTAAGTATAAGAAGGAGATATACATATGCTGGCAATGAGCCCT |
| CBJP484 | RsTAL | Reverse | TGGCCGGCCGATATCCAATTGATTAAACCGGACTCTGTTGC |
| CBJP555 | FjTAL | Forward | CATCTTAGTATATTAGTTAAGTATAAGAAGGAGATATACATATGAACACCATCAACGAATATCTG |
| CBJP556 | FjTAL | Reverse | TGGCCGGCCGATATCCAATTGATTAATTGTTAATCAGGTGGTCTTTTACTTTCTG |
| CBJP745 | RcTAL | Forward | CATCTTAGTATATTAGTTAAGTATAAGAAGGAGATATACATATGCTGGATGCAACCATTGG |
| CBJP746 | RcTAL | Reverse | TGGCCGGCCGATATCCAATTGATTATGCCGGAGGATCCGCT |

Strains harboring recombinant plasmids were pre-cultured in 2×YT liquid medium with 100 µg mL$^{-1}$ ampicillin and 50 µg mL$^{-1}$ spectinomycin and incubated at 37° C. and 250 rpm overnight. The following day, each pre-culture was transferred into 5 ml of M9 minimal medium with 0.2% glucose, 2 mM tyrosine and 1 mM IPTG for induction of expression. Cultures were placed in an incubator at 37° C. with shaking at 250 rpm overnight. The supernatants were then collected by centrifugation twice and applied to HPLC analysis as described in example 1, and the titers of p-coumaric acid (pHCA) and zosteric acid (ZA) were quantified using chemical standards and are presented in the table below.

TABLE 8

Titers of p-coumaric acid (pHCA) and zosteric acid (ZA)

| Sulfotransferase | Tyrosine ammonia-lyase | µM pHCA | µM ZA |
|---|---|---|---|
| SULT1A1 rat | None | 0 | 0 |
| SULT1A1 rat | RsTAL | 78 | <1 |
| SULT1A1 rat | RcTAL | 20 | <1 |
| SULT1A1 rat | FjTAL | 398 | 16 |

Here, it is evident that the zosteric acid is formed when there is a supply of exogenous p-coumaric acid or if the cells are capable of producing p-coumaric acid. Conclusively, a sulfated product may be formed from an unsulfated precursor molecule, when this is produced in vivo.

Furthermore, the data surprisingly show that employing the tyrosine ammonia-lyase from *Flavobacterium johnsoniae* (FjTAL; SEQ ID NO: 40) results in a higher supply in unsulfated precursor molecule (here: p-coumaric acid), which in turn leads to a higher yield of sulfated product (here: zosteric acid) compare to other tyrosine ammonia-lyases.

Example 6—Production of Sulfated Products in Other Hosts

We have shown that zosteric acid can be produced in vivo in *Escherichia coli* by expression of an aryl sulfotransferase. To show that the reaction is possible in other microorganisms, we here show that the yeast *Saccharomyces cerevisiae* can also be used as a host for the production.

The gene encoding aryl sulfotransferase SULT1A (Example 1) was cloned after a TEF1 promoter into an episomal plasmid with a 2-micron origin of replication as follows. The gene was amplified by PCR using primers CBJP633 and CBJP634. Alternatively, the gene was codon-optimized for *E. coli* and synthesized by GeneArt and amplified by primers CBJP635 and CBJP636. The TEF1 promoter (Jensen et al., 2014, FEMS Yeast Res 14: 238-248) was amplified by PCR using the primers PTEF1_fw and PTEF1_rv. Plasmid pCfB132 (Jensen et al., supra) was digested by restriction enzymes AsiSI and Nt.BsmI. The three fragments—plasmid, TEF1 promotor and SULT1A1-encoding gene—were assembled using a uracil-excission cloning procedure, resulting in plasmids pCBJ283 and pCBJ284, which were subsequently transformed into the *Saccharomyces cerevisiae* strain CEN.PK102-5B selecting for growth on synthetic dropout media plates lacking uracil. A control strain was also made by transformation of pCfB132 into CEN.PK102-5B.

The strains were grown in modified Delft medium (Jensen et al., supra) with 20 mg/mL histidine and 60 mg/mL leucine and 10 mM p-coumaric acid overnight at 30° C. with aeration. The supernatant was then isolated and examined by HPLC as described in Example 1. The table below shows that zosteric acid (ZA) was produced by the strain expressing SULT1A1 and not the control strain lacking a sulfotransferase.

TABLE 10

Titers of zosteric acid

| Sulfotransferase | µM ZA (averages and standard deviations of replicate experiments) |
|---|---|
| None | 0 ± 0 |
| SULT1A1 rat (native) | 37.8 ± 5.7 |
| SULT1A1 rat (codon optimized for *E. coli*) | 46.2 ± 3.5 |

It is evident that zosteric acid is formed only when a sulfotransferase is expressed in yeast, and that the gene encoding this may be natural or encoded by a synthetic gene with a specific codon-optimization. Conclusively, the sulfation reactions shown to be catalyzed by sulfotransferases in *E. coli* are also catalyzed when the sulfotransferases are expressed in other organisms, as demonstrated here for the yeast *S. cerevisiae*. The efficacy of production may be affected by means such as the codon-usage of the genes encoding the sulfotransferase. Thus yeast expressing sulfotransferases may be able to detoxify aromatic compounds such as p-coumaric acid, and form sulfated products such as zosteric acid.

Example 7—A Range of Compounds are Substrates for Sulfation In Vivo

Here we show that the expression of an aryl sulfotransferase may be able to convert several substrates. Some of these are inhibitors that can be found in biomass hydrolyzate used as a substrate for cell growth and production in biotechnology. The compounds also include some that are of biotechnological interest as products of a cell culture or be some whose sulfate ester is of economic interest.

Different sulfotransferases were examined for their substrate specificities against three substrates. We tested the sulfotransferases mentioned in example 1, as well as additional ones. The genes encoding these were cloned as described in example 1 using the primers shown in the table

TABLE 9

Primers

| Oligo-nucleotide | Gene/promoter | Direction | Sequence |
|---|---|---|---|
| CBJP633 | SULT1A1 rat | Forward | AGTGCAGGUAAAACAATGgagttctcccgtcca |
| CBJP634 | SULT1A1 rat | Reverse | CGTGCGAUTCAtagttcacaacgaaacttg |
| CBJP635 | SULT1A1 rat (*E. coli*) | Forward | ATCTGTCAUAAAACAATGgaattttcacgtccgc |
| CBJP636 | SULT1A1 rat (*E. coli*) | Reverse | CACGCGAUTCAcagttcacaacgaaatttgaa |
| PTEF1_fw | PTEF1 | Forward | Cacgcgaugcacacaccatagcttc |
| PTEF1_rv | PTEF1 | Reverse | Cgtgcgauggaagtaccttcaaaga | below from cDNA libraries of the respective organisms, except for the SULT1A1 from rat (*Rattus norvegicus*) codon-optimized for *E. coli* (described above). The resulting vectors were transformed into BL21(DE3)pLysS.

TABLE 11

Primers

| Oligo-nucleotide | Gene | Direction | |
|---|---|---|---|
| C13.1P517 | SULT1C1 *Gallus gallus domesticus* | Forward | TAGAAATAATTTTGTTTAACTTTA AGAAGGAGATATACCatggccctgg ataaaatgg |
| CBJP518 | SULT1C1 *Gallus gallus domesticus* | Reverse | TAAGCATTATGCGGCCGCAAGCT TGtcacaattccatgcgaaaaactag |
| CBJP533 | SULT1A1 *Rattus norvegicus* (Codon-optimized for *E. coli*) | Forward | TAGAAATAATTTTGTTTAACTTTA AGAAGGAGATATACCatggaattttc acgtcc |
| CBJP534 | SULT1A1 *Rattus norvegicus* (Codon-optimized for *E. coli*) | Reverse | TAAGCATTATGCGGCCGCAAGCT TGttacagttcacaacgaaatttg |

The resulting strains were grown in M9 medium containing either 100 µM pHCA, 95 µM resveratrol or 87 µM kaempferol. The cultures were grown overnight at 37° C., 300 rpm. The following day the supernatants were isolated and examined by HPLC as described in example 1. BL21 (DE3)pLysS were used as a control strain and did not convert the substrates.

TABLE 12

Percent conversion of the various substrates

| Enzyme | pHCA 100 µM | resveratrol 95 µM | kaempferol 87 µM |
|---|---|---|---|
| SULT1A1 *Rattus norvegicus* | 93% | 93% | 95% |
| SULT1C1 *Gallus gallus domesticus* | 26% | 100% | 80% |
| SULT1A1 *Rattus norvegicus* (Codon-optimized for *E. coli*) | 73% | 58% | 38% |
| SULT1A1 human | 39% | 36% | 97% |
| SULT1A1 *Equus caballus* | 21% | 100% | 96% |
| SULT1E1 *Gallus gallus domesticus* | 17% | 100% | 47% |
| SULT1A1 *Canis lupus familiaris* | 34% | 61% | 60% |
| SULT1A1 *Sus scrofa domesticus* | 8% | 88% | 45% |

The table shows the percent conversion of the various substrates by cells expressing the different sulfotransferases. The results show that several sulfotransferases, and especially the aryl sulfotransferase from rat (*Rattus norvegicus*), may be employed in the sulfation of phenolic compounds.

To further test the range of substrates that can be sulfated, we used strains carrying plasmids expressing SULT1A1 from rat (*Rattus norvegicus*) and SULT1E1 from chicken (*Gallus gallus domesticus*) (Example 1) cloned into the expression vector pETDuet-1, and cysDNCQ from *E. coli* cloned into expression vector pRSFDuet-1 (Example 2). The plasmids were introduced into the *E. coli* expression strain BL21(DE3)pLysS as described previously, selecting for transformants with appropriate antibiotics, namely 34 µg mL$^{-1}$ chloramphenicol for pLysS, 100 µg mL$^{-1}$ ampicillin for pETDuet-1-based vectors, and 100 µg mL$^{-1}$ kanamycin for pRSFDuet-1-based vectors. The table below shows the combination of over-expressed genes on plasmids. A control strain without a sulfotransferase gene or cysDNCQ operon was also examined.

TABLE 13

Combination of over-expressed genes on plasmids

| *E. coli* strains | Sulfotransferase | Cys genes |
|---|---|---|
| Control strain | — | — |
| SULT1A1 rat | SULT1A1 rat | — |
| SULT1E1 chicken | SULT1E1 chicken | — |
| SULT1A1 rat + CysDNCQ | SULT1A1 rat | CysDNCQ |

The strains were precultured in 2×YT medium with appropriate antibiotics. 10 µL of these precultures were used to inoculate M9 media with 1 mM IPTG and none or a single substrate for sulfation. After overnight growth at 37° C., 300 rpm the supernatants were withdrawn and examined by HPLC as described in Example 1. The compounds were detected by UV absorbance. The table below shows the percent reduction in concentration in the strains expressing sulfotransferases alone or in combination with cysDNCQ genes when compared to the control strain.

TABLE 14

Percent reduction in concentration

| Compound | Start concentration in µM | SULT1A1 | SULT1E1 | SULT1A1 + CysDNCQ |
|---|---|---|---|---|
| Ferulic acid | 110 | 72% | 67% | 100% |
| Quercetin | 85 | 75% | 74% | 81% |

TABLE 14-continued

| | Percent reduction in concentration | | | |
|---|---|---|---|---|
| Compound | Start concentration in µM | SULT1A1 | SULT1E1 | SULT1A1 + CysDNCQ |
| 4-hydroxybenzoic acid | 287 | 5% | 4% | 6% |
| 4-acetamidophenol | 114 | 24% | 10% | 30% |
| 3-Hydroxy-4-methoxycinnamic acid | 132 | 51% | 24% | 62% |
| 4-Hydroxyphenylpyruvic acid | 255 | 47% | 100% | 64% |
| 3-(4-Hydroxyphenyl)propionic acid | 241 | 3% | 1% | 7% |
| Vanillic acid | 173 | 33% | 0% | 39% |
| Luteolin | 61 | 27% | 0% | 37% |
| Apigenin | 77 | 41% | 98% | 99% |
| fisetin | 81 | 98% | 98% | 100% |

Conclusively, a wide range of phenolic compounds are substrates for sulfotransferases. In the shown examples, the conversion is enhanced by the overexpression of cysDNCQ genes. Some of these compounds and their sulfate esters are of interest in biotechnology. Also, some of these compounds are inhibitors of cell growth and function, and thus conversion by sulfation is of interest for use in biological systems.

Example 8—Increasing Uptake of Sulfate

E. coli BL21(DE3)-derived strains expressing an aryl sulfotransferase and a sulfate transporter were constructed as follows.

Figure 5:
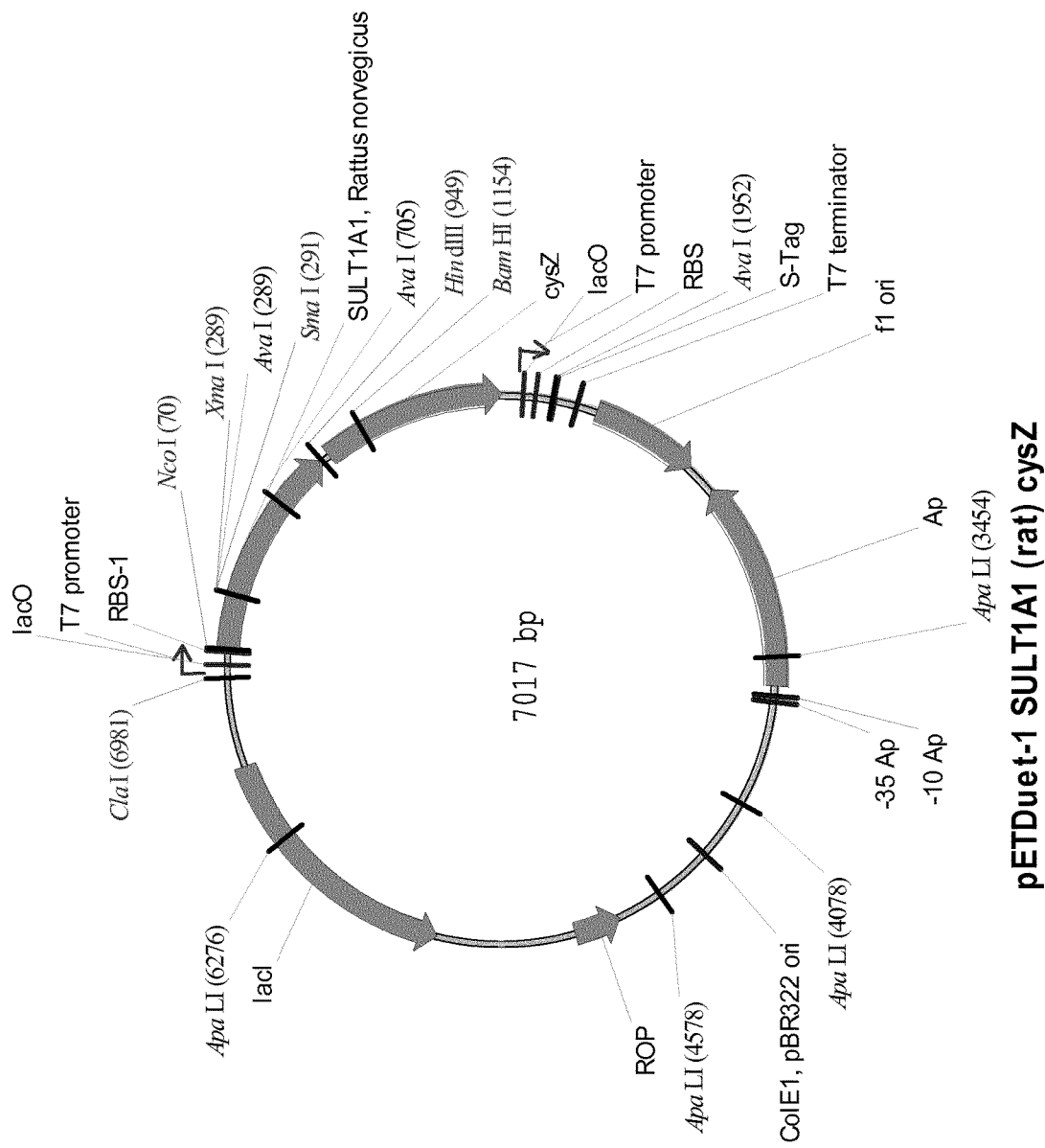
FIG. 5: Map of plasmid for over-expression of cysZ in *E. coli*

A plasmid (FIG. 5) was constructed for the over-expressing of the CysZ (NCBI reference sequence NP_416908.1) from E. coli by amplifying the cysZ gene from the chromosome of E. coli MG1655 by PCR using the primers in the table below. The resulting PCR product and the plasmid expressing SULT1A1 from rat mentioned in example 1 (FIG. 1) were digested using the restriction enzymes HindIII and NotI, purified by column purification and ligated together with T4 DNA polymerase, and the ligation reaction was used to transform the E. coli cloning strain NEB5a (New England Biolabs). Resulting colonies resistant to ampicillin were tested for correct insert by PCR using primers pET-Upstream (ATGCGTCCGGCGTAGA) and DuetDOWN1 (GATTATGCGGCCGTGTACAA). The correct plasmid was purified and transformed into E. coli BL21(DE3) (Life Technologies) together with the plasmid encoding CysDNCQ from example 2 (FIG. 3), selecting for both ampicillin and kanamycin.

Figure 6:
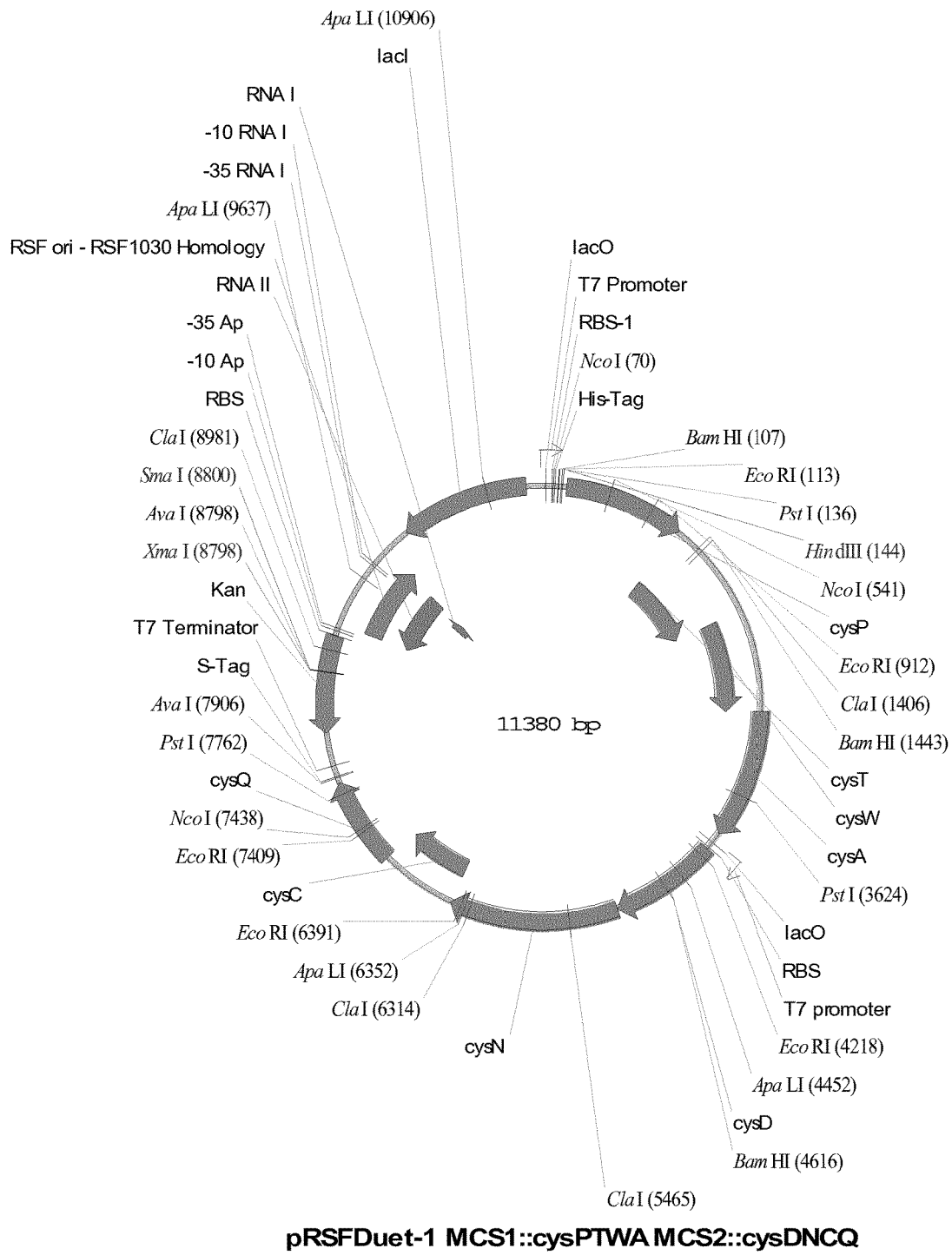
FIG. 6: Map of plasmid for over-expression of cysPTWA in *E. coli*

Similarly a plasmid (FIG. 6) was constructed for the over-expressing of the CysP (GenBank AAC75478.1), CysT (GenBank AAC75477.1, CysW (GenBank AAC75476.2) and CysA (Genbank AAC75475.1) from E. coli. The cysPTWA (also known as cysPUWA) operon was amplified from the chromosome of E. coli MG1655 by PCR using the primers in the table below. The resulting PCR product and the plasmid expressing CysDNCQ mentioned in example 2 (FIG. 3) were digested using restriction enzymes HindIII and NotI, purified by column purification and ligated together with T4 DNA polymerase, and the ligation reaction was used to transform the E. coli cloning strain NEB5a. Resulting colonies resistant to kanamycin were tested for correct insert by PCR using primers ACYCDuetUP1 (GGATCTCGACGCTCTCCCT) and DuetDOWN1 (GATTATGCGGCCGTGTACAA). The correct plasmid was purified and transformed into E. coli BL21(DE3) together with the plamid encoding SULT1A1 from rat mentioned in example 1 (FIG. 1), selecting for both ampicillin and kanamycin.

TABLE 15

| | | Primers | | |
|---|---|---|---|---|
| Oligo-nucleotide | Gene(s) | Direction | Sequence | Restriction site |
| CBJP891 | cysZ | Forward | ttaaaagcttgggattggtcaaaa ggagctcatcc | HindIII |
| CBJP892 | cysZ | Reverse | aatagcggccgcttaccgccacat cgcgtgtttat | NotI |
| CBJP893 | cysPTWA | Forward | ttaaaagcttagaaagtcattaaa tttataagggtgcgca | HindIII |
| CBJP894 | cysPTWA | Reverse | aatagcggccgctcaggcgctttg tgcgagagc | NotI |

Control strains carrying only the emotive plasmids pET-Duet-1 and pRSFDuet-1 (Life Technologies), carrying the plasmid encoding SULT1A1 from rat (FIG. 1) and pRSF-Duet-1, or carrying the plasmid encoding SULT1A1 from rat (FIG. 1) and the plasmid encoding cysDNCQ (FIG. 3) were used as controls for growth experiments.

The E. coli strains were propagated overnight in grown in M9 minimal medium containing 0.2% (w/v) glucose, 2 mM p-coumaric acid, 100 µg/mL ampicillin and 50 µg/mL kanamycin in wells of a 96-well deep-well plate (Enzy-Screen) shaking at 300 rpm in an orbital shaker at 37° C. From these cultures, 30 µL was used to inoculate 500 µL of M9 medium with 0.2% (w/v) glucose, 2 mM p-coumaric acid, 100 µg/mL ampicillin, 50 µg/mL kanamycin and further 200 µM IPTG in wells of a 96-well deep-well plate (EnzyScreen) that was left shaking at 300 rpm in an orbital shaker at 37° C. overnight. The cell density was then measured by the optical density at 600 nm, and the supernatant was sampled for production of zosteric acid, by two rounds of centrifugation. Zosteric acid in the supernatant was quantified by high performance liquid chromatography (HPLC) and compared to a chemical standard. HPLC was done on a Thermo setup using a HS-F5 column (3 µm) and mobile phases: 5 mM ammonium formate pH 4.0 (A) and acetonitrile (B) at 1.5 mL min-1, using a gradient elution starting at 5% B. From 0.5 min after injection to 7 min, the fraction of B increased linearly from 5% to 60%, and between 9.5 min and 9.6 the fraction of B decreased back to 5%, and remaining there until 12 min. Zosteric acid were quantified by measuring absorbance at 290 nm.

Figure 7:
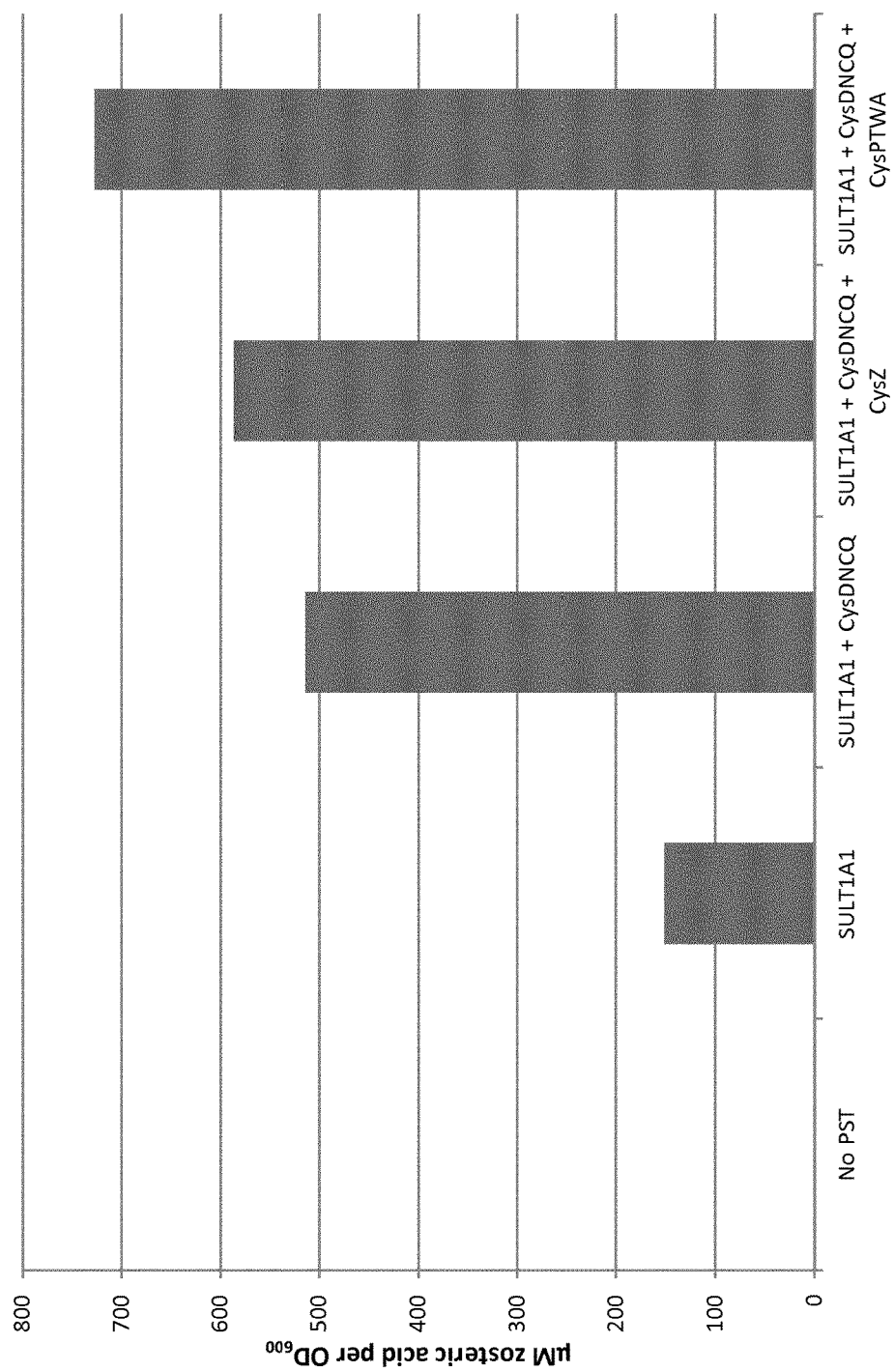
FIG. 7: Concentrations of zosteric acid in culture media with *E. coli* over-expressing SULT1A1 from *Rattus norvegicus*, either alone or in combination with over-expressing cysDNCQ and cysZ or cysPTWA

FIG. 7 shows that increased titers of zosteric acid were reached when overexpressing CysZ and CysPTWA.

It is clear that the additional expression of a sulfate transporter such as that encoded by cysZ (proton symporter) or by cysPTWA (ABC transporter) enhanced the sulfation catalyzed by a phenol sulfotransferase, optionally with increased expression of sulfate adenylyltransferase, APS kinase and adenosine-3',5'-bisphosphate nucleotidase. The sulfate transport activity may be optained by the activity of transporters belonging to several different families of transporters.

Example 9—Different Compounds as Substrates

Further compounds may be sulfated by sulfotransferases and cells heterologously expressing such, which is shown by the following experiment.

E. coli strain KRX (obtained from Promega) was transformed with either plasmids pETDuet-1 or the derived plasmid encoding SULT1A1 from Rattus norvegicus described in Example 1.

M9 medium containing 0.2% glucose, 0.1 mM IPTG, 0.1% rhamnose, and 100 µg/mL ampicillin was prepared. To aliquots of the medium, phenolic compounds (Table 14) were added from 10 mM stock solutions in 99.9% ethanol to a final concentration of the compounds of 50 µM.

The strains described above were grown in 2×YT medium with 100 µg/mL ampicillin overnight before their were used to inoculate the media by 50-fold dilution. The cultures were grown overnight with vigorous shaking at 37° C. The supernatants were isolated by centrifugation and subjected to HPLC analysis as described in example 1. The compounds were detected by UV absorbance except for 4-methylbelliferone, which was measured by fluorescence.

Table 16 shows that the phenolic compounds were all subject to sulfation, when a sulfotransferase is present in the medium. Additional peaks corresponding to more hydrophilic compounds were also the result of the activity of the sulfotransferase on each of the compounds.

TABLE 16

| | Percent reduction |
|---|---|
| Compound | SULT1A1 |
| Sinapic acid | 31% |
| Naringenin | 60% |
| 4-ethylphenol | 100% |
| 4-vinylphenol | 100% |
| 4-ethylguaiacol | 50% |
| 4-methylbelliferone | 100% |
| 4-nitrophenol | 30% |

Conclusively, a wide range of phenolic compounds are substrates for sulfotransferases. Some of these compounds and their sulfate esters are of interest in biotechnology or as markers of sulfation activity or as donors of sulfate in the reverse reaction. Also, some of these compounds are inhibitors of cell growth and function, and thus conversion by sulfation is of interest for use in biological systems. The example shows that the phenolic acceptor molecule for sulfation may differ by the position of the hydroxyl-group and still remains an active substrate. 4-vinylphenol is a degradation product of p-coumaric acid by decarboxylation, and it is still a substrate for sulfation by a sulfotransferase, showing that the side chain can vary significantly, and the compound remains an active substrate.

Example 10—Different Sulfotransferases are Active

The sulfotransferases may be of very different sequences. To show this, we tested the sulfotransferases with lower homology to the sequences presented in the examples above against three substrates.

The gene (sequence SEQ ID NO: 98) encoding dmST1 (sequence SEQ ID NO: 99) from Drosophila melanogaster was amplified from cDNA using primers listed in Table 17 similarly to the cloning of genes described in Example 1.

TABLE 17

| | Primers | | |
|---|---|---|---|
| Oligo-nucleotide | Gene | Direction | Sequence |
| CBJP474 | dmST1 Drosophila melanogaster | Forward | TAGAAATAATTTTGTTTAACTTTAA GAAGGAGATATAC C ATGCCCCAGTCGAGCTTCTT |
| CBJP475 | dmST1 Drosophila melanogaster | Reverse | TAAGCATTATGCGGCCGCAAGCTTG TTACGTGGACGCAAACTTGCT |

The gene (sequence SEQ ID NO: 100) encoding SULT1ST1 (sequence SEQ ID NO: 101) from Danio rerio was codon-optimized for E. coli and synthesized as in example 1.

The gene (sequence SEQ ID NO: 102) encoding SULT6B1 (sequence SEQ ID NO: 103) from *Danio rerio* was codon-optimized for *E. coli* and synthesized as in example 1.

The gene (sequence SEQ ID NO: 104) encoding Hoch_6098 (sequence SEQ ID NO: 105) from the bacterium *Haliangium ochraceum* DSM 14365 was codon-optimized for *E. coli* and synthesized as in example 1.

The genes were cloned into the vector pETDuet-1 as described in Example 1, and the resulting vectors were transformed into *E. coli* KRX (obtained from Promega). Strains were grown as described above in presence of either 100 µM resveratrol, 20 µM kaempferol or 50 µL 3-hydroxy-4-methoxycinnamic acid, and the supernatant were analyzed as described above, except that for kaempferol the cultures were mixed with an equal volume of methanol before isolation of the supernatants. Table 18 shows the reduction in the concentrations of compounds in the presence sulfotransferases (n.d.=not determined).

TABLE 18

| | Percent reduction | | |
|---|---|---|---|
| | Resveratrol | Kaempferol | 3-hydroxy-4-methoxycinnamic acid |
| *D. rerio* SULT1ST1 | 80% | n.d. | 12% |
| *D. rerio* SULT6B1 | n.d. | 44% | n.d. |
| *D. melanogaster* dmST1 | n.d. | n.d. | 12% |
| *H. ochraceum* DSM 14365 Hoch_6098 | 7% | 100% | n.d. |

The example shows that the sulfation reaction may occur in a medium with a cell expressing a heterologous sulfotransferase more distantly related to the sequences in the previous examples. It may even be of non-animal origin, exemplified with the bacterial sulfotransferase from *Haliangium ochraceum*.

The invention claimed is:

1. An *Escherichia coli* bacterium comprising a heterologous polypeptide having an aryl sulfotransferase activity; wherein the bacterium has been modified to have an increased protein expression of a CysP transporter, an ATP sulfurylase, an APS kinase and a PAP phosphatase compared to an identical bacterium that does not carry said modifications;
    wherein the polypeptide having an aryl sulfotransferase activity comprises an amino acid sequence which has at least 95% sequence identity with the amino acid sequence set forth in SEQ ID NO: 1, 6, 7, 8 or 13;
    wherein the CysP transporter comprises an amino acid sequence which has at least 95% sequence identity with the amino acid sequence set forth in SEQ ID NO: 27;
    wherein the ATP sulfurylase comprises i) a polypeptide comprising an amino acid sequence which has at least 95% sequence identity with the amino acid sequence set forth in SEQ ID NO: 28, and ii) a polypeptide comprising an amino acid sequence which has at least 95% sequence identity with the amino acid sequence set forth in SEQ ID NO: 29;
    wherein the APS kinase comprises an amino acid sequence which has at least 95% sequence identity with the amino acid sequence set forth in SEQ ID NO: 32; and
    wherein the PAP phosphatase comprises an amino acid sequence which has at least 95% sequence identity with the amino acid sequence set forth in SEQ ID NO: 37 and wherein said *Escherichia coli* bacterium is capable of enhanced sulfation of a phenolic compound compared to the identical *Escherichia coli* bacterium, which does not have an increased expression of said CysP transporter, ATP sulfurylase, APS kinase and a PAP phosphatase.

2. A process for the production of a sulfated phenolic compound comprising:
    (i') contacting a medium comprising a phenolic compound with a bacterium according to claim 1; or
    (i'') contacting a medium comprising a fermentable carbon substrate with a bacterium according to claim 1 such that a phenolic compound is produced from the fermentable carbon substrate by the bacterium; or
    (i''') contacting a medium comprising a precursor of a phenolic compound with a bacterium according to claim 1, the precursor being converted to the phenolic compound by the bacterium.

3. The bacterium according to claim 1, wherein the polypeptide having an aryl sulfotransferase activity comprises an amino acid sequence which has at least 95% sequence identity with the amino acid sequence set forth in SEQ ID NO: 1.

4. The bacterium according to claim 1, wherein the polypeptide having an aryl sulfotransferase activity comprises an amino acid sequence which has at least 95% sequence identity with the amino acid sequence set forth in SEQ ID NO: 6.

5. The bacterium according to claim 1, wherein the polypeptide having an aryl sulfotransferase activity comprises an amino acid sequence which has at least 95% sequence identity with the amino acid sequence set forth in SEQ ID NO: 7.

6. The bacterium according to claim 1, wherein the polypeptide having an aryl sulfotransferase activity comprises an amino acid sequence which has at least 95% sequence identity with the amino acid sequence set forth in SEQ ID NO: 8.

7. The bacterium according to claim 1, wherein the polypeptide having an aryl sulfotransferase activity comprises an amino acid sequence which has at least 95% sequence identity with the amino acid sequence set forth in SEQ ID NO: 13.

8. The bacterium according to claim 1, wherein the polypeptide having an aryl sulfotransferase activity comprises the amino acid sequence set forth in SEQ ID NO: 1, 6, 7, 8 or 13.

9. The bacterium according to claim 1, wherein the polypeptide having an aryl sulfotransferase activity comprises the amino acid sequence set forth in SEQ ID NO: 1.

10. The bacterium according to claim 1, wherein the polypeptide having an aryl sulfotransferase activity comprises the amino acid sequence set forth in SEQ ID NO: 6.

11. The bacterium according to claim 1, wherein the polypeptide having an aryl sulfotransferase activity comprises the amino acid sequence set forth in SEQ ID NO: 7.

12. The bacterium according to claim 1, wherein the polypeptide having an aryl sulfotransferase activity comprises the amino acid sequence set forth in SEQ ID NO: 8.

13. The bacterium according to claim 1, wherein the polypeptide having an aryl sulfotransferase activity comprises the amino acid sequence set forth in SEQ ID NO: 13.

14. The bacterium according to claim 1, wherein the CysP transporter comprises the amino acid sequence set forth in SEQ ID NO: 27.

15. The bacterium according to claim 1, wherein the ATP sulfurylase comprises i) a polypeptide comprising the amino acid sequence set forth in SEQ ID NO: 28, and ii) a polypeptide comprising the amino acid sequence set forth in SEQ ID NO: 29.

16. The bacterium according to claim 1, wherein the APS kinase comprises the amino acid sequence set forth in SEQ ID NO: 32.

17. The bacterium according to claim 1, wherein the PAP phosphatase comprises the amino acid sequence set forth in SEQ ID NO: 37.

18. The bacterium according to claim 1, wherein the phenolic compound is selected from p-coumaric acid, ferulic acid, quercetin, 4-hydroxybenzoic acid, 4-acetamidophenol, 3-hydroxy-4methoxycinnamic acid, 4-hydroxyphenylpyruvic acid, 3-(4-hydroxyphenyl)proprionic acid, vanillic acid, luteolin, apigenin, fisetin, sinapic acid, naringenin, 4-ethylphenol, 4-vinylphenol, 4-ethylguaiacol, 4-methylbelliferone, 4-nitrophenol, resveratrol, kaempferol, or methoxycinnamic acid.

* * * * *

UNITED STATES PATENT AND TRADEMARK OFFICE
CERTIFICATE OF CORRECTION

PATENT NO. : 10,954,536 B2  
APPLICATION NO. : 16/079502  
DATED : March 23, 2021  
INVENTOR(S) : Christian Bille Jendresen Page 1 of 6

It is certified that error appears in the above-identified patent and that said Letters Patent is hereby corrected as shown below:

On the Title Page

On page 2, in Column 1, item (56), Other Publications, Line 17, delete "SuIP" and insert --SulP--.

In the Drawings

In sheet 1 of 7, FIG. 1, Line 8, delete "norvegicus)" and insert --norvegicus--.

In the Specification

In Column 1, Line 60, delete "bioavailablility," and insert --bioavailability,--.

In Column 4, Line 2, delete "stabily" and insert --stably--.

In Column 4, Line 49, delete "SuIT" and insert --SulT--.

In Column 4, Line 49, delete "SuIP" and insert --SulP--.

In Column 5, Line 26, delete "SuIT" and insert --SulT--.

In Column 6, Line 59, delete "SuIP" and insert --SulP--.

In Column 9, Line 50, delete "Schizosacharomyces," and insert --Schizosaccharomyces,--.

In Column 9, Line 51, delete "Pachyosolen," and insert --Pachysolen,--.

In Column 9, Line 53, delete "Rhodospiridium," and insert --Rhodosporidium,--.

In Column 9, Line 62, delete "Phaedactylum," and insert --Phaeodactylum,--.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,954,536 B2

In Column 13, Line 30, delete "SuIT" and insert --SulT--.

In Column 13, Line 31, delete "SuIP" and insert --SulP--.

In Column 14, Line 9, delete "SuIT" and insert --SulT--.

In Column 15, Line 42, delete "SuIP" and insert --SulP--.

In Column 18, Line 28 approx., delete "coll." and insert --coli.--.

In Column 18, Line 32 approx., delete "Schizosacharomyces," and insert --Schizosaccharomyces,--.

In Column 18, Line 33 approx., delete "Pachyosolen," and insert --Pachysolen,--.

In Column 18, Lines 34-35, delete "Rhodospiridium," and insert --Rhodosporidium,--.

In Column 18, Line 44, delete "Phaedactylum," and insert --Phaeodactylum,--.

In Column 18, Line 67, delete "coli" and insert --coli.--.

In Column 19, Line 5, delete "products" and insert --products.--.

In Column 19, Line 7, delete "coli" and insert --coli.--.

In Column 19, Line 9, delete "coli" and insert --coli.--.

In Column 19, Line 13, delete "cysPTWA" and insert --cysPTWA.--.

In Column 20, Line 8, delete "enyzmes" and insert --enzymes--.

In Column 24, Line 28, delete "3004" and insert --300 μL--.

In Column 24, Line 31, delete "300-4" and insert --300 μL--.

In Column 27, Line 20, delete "300-4" and insert --300 μL--.

In Column 28, Line 16, delete "well-know" and insert --well-known--.

In Column 29, Line 6, delete "SuIT" and insert --SulT--.

In Column 29, Line 7, delete "SuIP" and insert --SulP--.

In Column 29, Line 13, delete "SuIT" and insert --SulT--.

In Column 29, Line 13, delete "SuIP" and insert --SulP--.

CERTIFICATE OF CORRECTION (continued)
U.S. Pat. No. 10,954,536 B2

In Column 29, Line 23, delete "CD015722.1)," and insert --CDO15722.1),--.

In Column 32, Line 30, delete "SuIT" and insert --SulT--.

In Column 32, Line 32, delete "SuIT" and insert --SulT--.

In Column 32, Line 34, delete "SuIT" and insert --SulT--.

In Column 32, Line 40, delete "SuIT" and insert --SulT--.

In Column 32, Line 43, delete "SuIT" and insert --SulT--.

In Column 37, Line 11 approx., delete "tranports" and insert --transport--.

In Column 43, Line 31, delete "SuIP" and insert --SulP--.

In Column 43, Line 32, delete "SuIP" and insert --SulP--.

In Column 43, Line 37, delete "SuIP" and insert --SulP--.

In Column 43, Line 41, delete "SuIP" and insert --SulP--.

In Column 43, Line 45, delete "SuIP" and insert --SulP--.

In Column 43, Line 47, delete "SuIP" and insert --SulP--.

In Column 49, Line 24, delete "well-know" and insert --well-known--.

In Column 49, Lines 48-49, delete "(Gen Bank" and insert --(GenBank--.

In Column 52, Line 27, delete "1945)," and insert --1945,--.

In Column 58, Line 9 approx., delete "hetereologus" and insert --heterologous--.

In Column 61, Line 31, delete "Schizosacharomyces," and insert --Schizosaccharomyces,--.

In Column 61, Line 32, delete "Pachyosolen," and insert --Pachysolen,--.

In Column 61, Line 34, delete "Rhodospiridium," and insert --Rhodosporidium,--.

In Column 61, Line 37, delete "Schizosacharomyces," and insert --Schizosaccharomyces,--.

In Column 61, Line 38, delete "Pachyosolen," and insert --Pachysolen,--.

In Column 61, Line 40, delete "Rhodospiridium," and insert --Rhodosporidium,--.

CERTIFICATE OF CORRECTION (continued)
U.S. Pat. No. 10,954,536 B2

In Column 61, Line 67, delete "Phaedactylum," and insert --Phaeodactylum,--.

In Column 62, Line 3, delete "Phaedactylum," and insert --Phaeodactylum,--.

In Column 62, Line 14, delete "Phaedactylum." and insert --Phaeodactylum.--.

In Column 62, Line 15, delete "Phaedactylum" and insert --Phaeodactylum--.

In Column 62, Line 16, delete "Phaedactylum tricornatum." and insert --Phaeodactylum tricornutum.--.

In Column 63, Line 39, delete "meihei" and insert --miehei--.

In Column 63, Line 40, delete "meihei" and insert --miehei--.

In Column 63, Line 47, delete "sative" and insert --sativa--.

In Column 63, Line 47, delete "tabacco" and insert --tobacco--.

In Column 63, Line 49, delete "tomate" and insert --tomato--.

In Column 65, Line 38, delete "casaminoacids" and insert --casamino acids--.

In Column 65, Line 45, delete "casaminoacids" and insert --casamino acids--.

In Column 66, Line 21 approx., delete "pH. 7.5," and insert --pH 7.5,--.

In Column 67, Line 2, delete "reservatrol," and insert --resveratrol,--.

In Column 67, Line 67, delete "-COOR$_7$," and insert -- -OCOR$_7$,--.

In Column 68, Lines 34-35 approx., delete "R1=H, R2=OH, R3=OCH3, R4=H, R5=H, R6" and insert --R$_1$=H, R$_2$=OH, R$_3$=OCH$_3$, R$_4$=H, R$_5$=H, R$_6$--.

In Column 68, Lines 46-47, delete "R1=H, R2=H, R3=OH, R4=OCH3 , R5=H, R6," and insert --R$_1$=H, R$_2$=H, R$_3$=OH, R$_4$=OCH$_3$, R$_5$=H, R$_6$--.

In Column 69, Line 53 approx., delete "(4-methylbelliferone)" and insert --(4-methylumbelliferone)--.

In Column 70, Line 14, delete "4-methylbelliferone." and insert --4-methylumbelliferone.--.

In Column 71, Line 50, delete "post-transiational" and insert --post-translational--.

In Column 71, Line 51, delete "myristilation," and insert --myristoylation,--.

In Column 74, Line 60, delete "substitutent" and insert --substituent--.

CERTIFICATE OF CORRECTION (continued)
U.S. Pat. No. 10,954,536 B2

In Column 75, Line 1, delete "$C_{1-12}$" and insert --$C_{1-12}$- --.

In Column 75, Line 1, delete "$C_{1-12}$" and insert --$C_{1-2}$- --.

In Column 75, Line 1, delete "$C_{1-4}$ alkyl," and insert --$C_{1-4}$ -alkyl,--.

In Column 75, Line 11, delete "dimethyl propyl," and insert --dimethylpropyl,--.

In Column 75, Line 14, delete "substitutents" and insert --substituents--.

In Column 75, Line 18, delete "substitutent" and insert --substituent--.

In Column 75, Line 25, delete "substitutents" and insert -- - substituents--.

In Column 75, Line 30, delete "substitutent" and insert --substituent--.

In Column 75, Line 50, delete "substitutents" and insert --substituents--.

In Column 75, Line 54, delete "substitutent" and insert --substituent--.

In Column 75, Line 67, delete "C1- or C2" and insert --$C_1$- or $C_2$--.

In Column 76, Line 61, delete "p-courmaric" and insert --p-coumaric--.

In Column 78, Table 5, Line 1, delete "ammonialyase" and insert --ammonia lyase--.

In Column 80, Line 17, delete "DH5a" and insert --DH5α--.

In Column 81, Line 31 approx., delete "SULT1A" and insert --SULT1A1--.

In Column 81, Line 43, delete "uracil-excission" and insert --uracil-excision--.

In Column 83, Table 11, Line 4, delete "C13.1P517" and insert --CBJP517--.

In Column 85, Line 57, delete "NEB5a" and insert --NEB5α--.

In Column 86, Line 17 approx., delete "AAC75477.1," and insert --AAC75477.1),--.

In Column 86, Line 26 approx., delete "NEB5a." and insert --NEB5α.--.

In Column 86, Line 32 approx., delete "plamid" and insert --plasmid--.

In Column 86, Line 53, delete "emotive" and insert --emptive--.

In Column 87, Line 27, delete "optaned" and insert --obtained--.

CERTIFICATE OF CORRECTION (continued)
U.S. Pat. No. 10,954,536 B2

In Column 87, Lines 66-67, delete "4-methylbelliferone" and insert --4-methylumbelliferone--.

In Column 88, Line 18, delete "4-methylbelliferone" and insert --4-methylumbelliferone--.

In the Claims

In Column 228, Line 25 approx., Claim 18, delete "3-hydroxy-4methoxycinnamic" and insert --3-hydroxy-4-methoxycinnamic--.

In Column 228, Line 26 approx., Claim 18, delete "proprionic acid," and insert --propionic acid,--.

In Column 228, Lines 28-29 approx., Claim 18, delete "4-methylbelliferone," and insert --4-methylumbelliferone,--.